United States Patent
Showe et al.

(10) Patent No.: US 11,661,632 B2
(45) Date of Patent: May 30, 2023

(54) COMPOSITIONS AND METHODS FOR DIAGNOSING LUNG CANCERS USING GENE EXPRESSION PROFILES

(71) Applicant: The Wistar Institute of Anatomy and Biology, Philadelphia, PA (US)

(72) Inventors: Michael Showe, Media, PA (US); Louise C. Showe, Media, PA (US); Andrei V. Kossenkov, Huntingdon Valley, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 403 days.

(21) Appl. No.: 16/312,036

(22) PCT Filed: Jun. 21, 2017

(86) PCT No.: PCT/US2017/038571
§ 371 (c)(1),
(2) Date: Dec. 20, 2018

(87) PCT Pub. No.: WO2017/223216
PCT Pub. Date: Dec. 28, 2017

(65) Prior Publication Data
US 2020/0123613 A1    Apr. 23, 2020

Related U.S. Application Data

(60) Provisional application No. 62/352,865, filed on Jun. 21, 2016.

(51) Int. Cl.
*C12Q 1/68* (2018.01)
*C12Q 1/6886* (2018.01)

(52) U.S. Cl.
CPC ...... *C12Q 1/6886* (2013.01); *C12Q 2600/112* (2013.01); *C12Q 2600/158* (2013.01)

(58) Field of Classification Search
CPC .................................................. C12Q 1/68
See application file for complete search history.

(56) References Cited

U.S. PATENT DOCUMENTS

| | | | |
|---|---|---|---|
| 6,582,908 B2 * | 6/2003 | Fodor | B01J 19/0046 435/288.3 |
| 7,081,340 B2 | 7/2006 | Baker et al. | |
| 2009/0317392 A1 | 12/2009 | Nakamura et al. | |
| 2011/0201517 A1 | 8/2011 | Kolman et al. | |
| 2012/0021946 A1 | 1/2012 | Nakamura et al. | |
| 2014/0005065 A1 | 1/2014 | Showe et al. | |
| 2015/0315643 A1 | 11/2015 | O'Garra et al. | |
| 2021/0079479 A1 | 3/2021 | Showe et al. | |

FOREIGN PATENT DOCUMENTS

| | | | |
|---|---|---|---|
| WO | WO-2007/141004 | 12/2007 | |
| WO | WO-2009/075799 | 6/2009 | |
| WO | WO-2010/03 0697 | 3/2010 | |
| WO | WO 2012/006632 A2 | 1/2012 | |
| WO | WO-2012/150275 | 11/2012 | |
| WO | WO-2012/150275 A1 | 11/2012 | |
| WO | WO-2012150275 A1 * | 11/2012 | ........... C12Q 1/6886 |
| WO | WO-2013/153130 | 10/2013 | |
| WO | WO-2016/011068 A1 | 1/2016 | |

OTHER PUBLICATIONS

NCBI (2009) "PREDICTED: *Homo sapiens* similar to CG10103 (LOC728533), miscRNA" (Year: 2009).*
NEB catalog (1998/1999), pp. 121, 284 (Year: 1999).*
Geiss et al., "Direct multiplexed measurement of gene expression with color-coded probe pairs", (2008) Nature Biotechnology 26(3): 317-325 (Year: 2008).*
Ahern, "Biochemical, reagent kits offer scientists good return on investment", (1995) The Scientist 9(15): 1-5 (Year: 1995).*
Silvestri et al., A Bronchial Genomic Classifier for the Diagnostic Evaluation of Lung Cancer, N Engl J Med., vol. 373(3): 243-251, Jul. 2015.
Velculescu et al., Characterization of the yeast transcriptome, Cell, vol. 88(2):243-51, Jan. 1997.
Geiss et al., Direct multiplexed measurement of gene expression with color-coded probe pairs, NatBiotechnol., vol. 26(3):317-25, Mar. 2008 (Epub Feb. 17, 2008).
Velculescu et al., Serial analysis of gene expression, Science, vol. 270(523 5):484-487, 1995.
Brenner et al., Gene expression analysis by massively parallel signature sequencing (MPSS) on microbead arrays, Nature Biotechnology, vol. 18(6):630-634, Jun. 2000.
International Search Report and Written Opinion issued on International Patent Application No. PCT/US2017/038571, dated Nov. 30, 2017.
GA Accession No. GPL96, Mar. 2002.
Rooney et al., AACR 104th Annual Meeting Abstract 2407: Expression profiling of FGF-receptor pathway genes in squamous NSCLC tissue by Nanostring, Cancer Research, vol. 73(8):6-10, Apr. 2013.
Extended Search Report issued in corresponding European Patent Application No. 17816148,5, dated Jan. 21, 2020.
Search Report and Written Opinion issued in corresponding Singapore Patent Application No. 11201810914V, dated Apr. 18, 2020.

* cited by examiner

*Primary Examiner* — Juliet C Switzer
(74) *Attorney, Agent, or Firm* — Howson & Howson LLP; Colleen M. Schaller

(57) ABSTRACT

Methods and compositions are provided for diagnosing lung cancer in a mammalian subject by use of 10 or more selected genes, e.g., a gene expression profile, from the blood of the subject which is characteristic of disease. The gene expression profile includes 10 or more genes of Table I or Table II herein.

8 Claims, 6 Drawing Sheets
Specification includes a Sequence Listing.

Fig. 1

| Variable | Value | N samples/average | | | p | odds ratio or difference | comment |
|---|---|---|---|---|---|---|---|
| | | Cancer | Nodule | Total | | | |
| All | | 73^ | 77^^ | 150 | | | |
| Gender | Female | 34 | 40 | 74 | 0.5106 | 0.895 | |
| | Male | 39 | 37 | 76 | 0.5106 | 1.117 | |
| Smoking | Never | 4 | 3 | 7 | 0.1208 | | |
| | Quit | 52 | 42 | 94 | 0.6459 | 1.184 | |
| | Smoker | 17 | 31 | 48 | 0.0347 | 1.475 | more quit-smokers among cancers |
| | Unknown | 0 | 1 | 1 | 0.0259 | 0.645 | more smokers among nodules |
| | | | | | 0.3286 | na | |
| Race | Black | 14 | 7 | 21 | 0.1541 | | |
| | White | 57 | 67 | 124 | 0.0751 | 1.458 | more black patients among cancers |
| | Hispanic | 1 | 0 | 1 | 0.1487 | 0.747 | |
| | Indian | 1 | 0 | 1 | 0.3028 | 2.069 | |
| | Hispanic/White | 0 | 2 | 2 | 0.3028 | 2.069 | |
| | Asian | 0 | 1 | 1 | 0.1657 | 0.000 | |
| | | | | | 0.3286 | 0.000 | |
| Hospital | Temple | 2 | 4 | 6 | 1E-05 | 0.676 | |
| | Christiana | 34 | 13 | 47 | 0.4431 | 1.444 | more cancers in Christiana |
| | UPENN | 22 | 16 | 38 | 9E-05 | 1.271 | |
| | NYU | 15 | 44 | 59 | 0.1878 | 0.399 | more nodules in NYU |
| Age* | | 67 | 63.0658 | | 5E-06 | 3.940 | patients with cancer are 4 years older |
| Pack Years* | | 40 | 38 | | 0.0211 | 2 | |
| | | | | | 0.9251 | | |

*continuous variables; medians are reported and p-values are calculated by Wilcoxon rank sum test
^ +1 extra, ^^ +5 extra

| Size | Cancers | | Nodules | |
|---|---|---|---|---|
| | Total | Sensitivity | Total | Specificity |
| ≤5mm | 2 | 100.0% | 126 | 81.7% |
| >5,≤8mm | 13 | 38.5% | 100 | 80.0% |
| >8,≤12mm | 30 | 53.3% | 52 | 67.3% |
| >12,≤16mm | 34 | 76.5% | 25 | 64.0% |
| >16mm | 125 | 76.8% | 28 | 50.0% |
| Total | 204 | 71.1% | 331 | 74.9% |

Cancers

Nodules

Small Nodules (≤10mm) vs. Cancer

Large Nodules (>10mm) vs. Cancer

SEQUENCE LISTING

<160> NUMBER OF SEQ ID NOS: 559

<210> SEQ ID NO 1
<211> LENGTH: 100
<212> TYPE: DNA
<213> ORGANISM: Homo sapiens

<400> SEQUENCE: 1
aaggaagact gtgtgtagaa tcttacgtaa tagtctgatt ctttgactct gtggctagaa    60
tgacagttat ctatggaggt ggtagaatta agccatacct                          100

<210> SEQ ID NO 2
<211> LENGTH: 100
<212> TYPE: DNA
<213> ORGANISM: Homo sapiens

<400> SEQUENCE: 2
cctaaacaaa caagaggtga ccaccttatt gtgaggttcc atccagccaa gtttatgtgg    60
cctattgtct caggactctc atcactcaga agcctgcctc                          100

<210> SEQ ID NO 3
<211> LENGTH: 100
<212> TYPE: DNA
<213> ORGANISM: Homo sapiens

<400> SEQUENCE: 3
ctcactgtga cccatcctta ctctacttgg ccaggccaca gtaaaacaag tgaccttcag    60
agcagctgcc acaactggcc atgccctgcc attgaaacag                          100

<210> SEQ ID NO 4
<211> LENGTH: 100
<212> TYPE: DNA
<213> ORGANISM: Homo sapiens

<400> SEQUENCE: 4
agccaatagt gatttgtttg catatcacct aatgtgaaaa gtgctcatct gtgaactcta    60
cagcaaatta tattttagaa aatactttgt gaggccgggc                          100

<210> SEQ ID NO 5
<211> LENGTH: 100
<212> TYPE: DNA
<213> ORGANISM: Homo sapiens

<400> SEQUENCE: 5
ctatcactca tgtcaatcat atctatgaga caaatgtctc cgatgctctt ctgcgtaaat    60
taaattgtgt actgaaggga aaagtttgat cataccaaac                          100

<210> SEQ ID NO 6
<211> LENGTH: 100

```
<212> TYPE: DNA
<213> ORGANISM: Homo sapiens

<400> SEQUENCE: 6
ttctagagtg agatttgtgt tttctgccct tttcctctcc agccgatggg ctggagctgg    60
gagaggtgct gagctaacag tgccaacaag tgctccttaa                         100

<210> SEQ ID NO 7
<211> LENGTH: 100
<212> TYPE: DNA
<213> ORGANISM: Homo sapiens

<400> SEQUENCE: 7
gccagtactc gggacagact aagggcgctt gtcccatcct ggacttttcc tctcatgtct    60
ttgctgcaga actgaagaga ctaggcgctg gggctcagct                         100

<210> SEQ ID NO 8
<211> LENGTH: 100
<212> TYPE: DNA
<213> ORGANISM: Homo sapiens

<400> SEQUENCE: 8
ctaccacccg tccagtttga ctggagtagc agtggcctta ctaacccttt agatggtgtg    60
gatccggagt tgtatgagtt aacaacttct aagctggaaa                         100

<210> SEQ ID NO 9
<211> LENGTH: 100
<212> TYPE: DNA
<213> ORGANISM: Homo sapiens

<400> SEQUENCE: 9
ctacccggca ggtaggttag atgtgggtgg tgcatgttaa tttcccttag aagttccaag    60
ccctgtttcc tgcgtaaagg tggtatgtcc agttcagaga                         100

<210> SEQ ID NO 10
<211> LENGTH: 100
<212> TYPE: DNA
<213> ORGANISM: Homo sapiens

<400> SEQUENCE: 10
aatgaaatta ctgtagagtc agcaaagaag tagagaagaa aaaacaccaa gaatgaggag    60
aacctagcaa gggcaggctt ttggaagcaa gaggtagata                         100

<210> SEQ ID NO 11
<211> LENGTH: 100
<212> TYPE: DNA
<213> ORGANISM: Homo sapiens

<400> SEQUENCE: 11
agaatttctt ggtagcttta caccgaaaaa tgcgtgtaac taaataccag acatcttgac    60
cattcagcta gaaccctggc agcaacagag ctatttaatt                         100

<210> SEQ ID NO 12
<211> LENGTH: 100
<212> TYPE: DNA
<213> ORGANISM: Homo sapiens
```

```
<400> SEQUENCE: 12 ccctccagc cagccctgcg tggttgtggc cccactgcag aaacgcctcc gcttaacact      60
ccagcctctc ttctattcgg tcaggccaca gctgctgact                          100

<210> SEQ ID NO 13
<211> LENGTH: 100
<212> TYPE: DNA
<213> ORGANISM: Homo sapiens

<400> SEQUENCE: 13
gtacctggta gaaattgtgt cttggaatga cccttttcgag ttattgacat ggctctgatg    60
aatagaacat gagccccaaa actaaatcca aaaggaattt                          100

<210> SEQ ID NO 14
<211> LENGTH: 100
<212> TYPE: DNA
<213> ORGANISM: Homo sapiens

<400> SEQUENCE: 14
cttattgatt agtgaatgta gcttaagcct ttgtatgtgt cctcaggggg cagaccgact    60
ttaagaggga ccagataacg tttgaatgga gggattatat                          100

<210> SEQ ID NO 15
<211> LENGTH: 100
<212> TYPE: DNA
<213> ORGANISM: Homo sapiens

<400> SEQUENCE: 15
ctgtaagtgt cctcaactgg cttctcagtg atctccagaa gtatgccttg ggtttccaac    60
atgcactgag cccctcaacc tctacctgta aacataaagt                          100

<210> SEQ ID NO 16
<211> LENGTH: 100
<212> TYPE: DNA
<213> ORGANISM: Homo sapiens

<400> SEQUENCE: 16
gaggacgtct ctatgccggt gactggacat atcacctcta cttaaatccg tcctgtttag    60
cgacttcagt caactacagc tgagtccata ggccagaaag                          100

<210> SEQ ID NO 17
<211> LENGTH: 100
<212> TYPE: DNA
<213> ORGANISM: Homo sapiens

<400> SEQUENCE: 17
ggggatcggg atggagtcat gccaaaaatg gacatcattt ctggaacact tggcaaagcc    60
tttggttgtg ttggagggta catcgccagc acgagttctc                          100

<210> SEQ ID NO 18
<211> LENGTH: 100
<212> TYPE: DNA
<213> ORGANISM: Homo sapiens

<400> SEQUENCE: 18
accaccctct tgctgaaagc actggttccc ctgttgaagc ttgctaggga ttacagtggg    60
tttgactcaa ttcaaagctt cttttattct cgtaagaatt                          100
```

<210> SEQ ID NO 19
<211> LENGTH: 100
<212> TYPE: DNA
<213> ORGANISM: Homo sapiens

<400> SEQUENCE: 19
gtgatgctca ggggctgtca aagtgactgc gttcatcagt tttacactgg ggctgctaca    60
taatattttc atttgaacga agaacttcaa aaagcacagg                         100

<210> SEQ ID NO 20
<211> LENGTH: 100
<212> TYPE: DNA
<213> ORGANISM: Homo sapiens

<400> SEQUENCE: 20
cttggaaccc tatgataaaa gttatccaaa attcaactga atgcactgat gcccagcaga    60
tttggcctgg cacgtgggca cctcatattg gaaacatgca                         100

<210> SEQ ID NO 21
<211> LENGTH: 100
<212> TYPE: DNA
<213> ORGANISM: Homo sapiens

<400> SEQUENCE: 21
caccttggaa cctttgaaaa agttagaatg tctgaaaagc ctggacctct ttaactgtga    60
ggttaccaac ctgaatgact accgagagag tgtcttcaag                         100

<210> SEQ ID NO 22
<211> LENGTH: 100
<212> TYPE: DNA
<213> ORGANISM: Homo sapiens

<400> SEQUENCE: 22
gaaatcagag acattaacag ggtctacaga gaggaactga agagagatct ggccaaagac    60
ataacctcag acacatctgg agattttcgg aacgctttgc                         100

<210> SEQ ID NO 23
<211> LENGTH: 100
<212> TYPE: DNA
<213> ORGANISM: Homo sapiens

<400> SEQUENCE: 23
tggatgaaac caaaggagat tatgagaaaa tcctggtggc tctttgtgga ggaaactaaa    60
cattcccttg atggtctcaa gctatgatca gaagacttta                         100

<210> SEQ ID NO 24
<211> LENGTH: 100
<212> TYPE: DNA
<213> ORGANISM: Homo sapiens

<400> SEQUENCE: 24
cgagtaaccg tgccgttgtc gtgtgatgcc ataagcgtct gtgcgtggag tccccaataa    60
acctgtggtc ctgcctggcc ttgccgtcaa aaaaaaaaaa                         100

<210> SEQ ID NO 25
<211> LENGTH: 100
<212> TYPE: DNA
<213> ORGANISM: Homo sapiens

```
<400> SEQUENCE: 25
aaactccaga acagcagaaa gcgggtgctg tagaggagca ctcagctcac ggggagggag     60
ctcttggctg agcttctaca gggctgagag ctgcgctttg                          100

<210> SEQ ID NO 26
<211> LENGTH: 100
<212> TYPE: DNA
<213> ORGANISM: Homo sapiens

<400> SEQUENCE: 26
cacttttagc tggttgaaaa gtaccactcc cactctgaac atctggccgt ccctgcaaag     60
agtgtactgt gcttgaagca gagcactcac acataaatgg                          100

<210> SEQ ID NO 27
<211> LENGTH: 100
<212> TYPE: DNA
<213> ORGANISM: Homo sapiens

<400> SEQUENCE: 27
aaggaactaa aaggaaagat tcccgatgtg ccaggattct cctgggtgac tccctgtata     60
tctgccaagg atattgtgta tattggcttg agagacgtgg                          100

<210> SEQ ID NO 28
<211> LENGTH: 100
<212> TYPE: DNA
<213> ORGANISM: Homo sapiens

<400> SEQUENCE: 28
ttcggacttg ctcgggaggg taatcacaag cctattgact accttaaccc acctaagtaa     60
atgtggaaac atccgatata aatctcatag ttaatggcat                          100

<210> SEQ ID NO 29
<211> LENGTH: 100
<212> TYPE: DNA
<213> ORGANISM: Homo sapiens

<400> SEQUENCE: 29
catgtatggt ctgtgtctcc ccagtcccct cagaaccatg cccatggatg gtgactgctg     60
gctctgtcac ctcatcaaac tggatgtgac ccatgccgcc                          100

<210> SEQ ID NO 30
<211> LENGTH: 100
<212> TYPE: DNA
<213> ORGANISM: Homo sapiens

<400> SEQUENCE: 30
tttttgacca aaaagataac aaataccagg tatggcaagt tgtgaagaca gcacattaaa     60
acatacctaa tttcacagta ttcctgtcac gacagaatgt                          100

<210> SEQ ID NO 31
<211> LENGTH: 100
<212> TYPE: DNA
<213> ORGANISM: Homo sapiens

<400> SEQUENCE: 31
tccctgagct ttcccagtag cctccagttt cctttgtaag acccagggat cacttagcca     60
tagcctgaat cttttagggg tattaaggtc agcctctcac                          100
```

<210> SEQ ID NO 32
<211> LENGTH: 100
<212> TYPE: DNA
<213> ORGANISM: Homo sapiens

<400> SEQUENCE: 32
gattacaaca tttcctcact gcgggatatt tctgacccgc tttagaactt aagacctgat    60
tctagcaata aacgtgtccg agatgagcgg tgaaaaaaaa                         100

<210> SEQ ID NO 33
<211> LENGTH: 100
<212> TYPE: DNA
<213> ORGANISM: Homo sapiens

<400> SEQUENCE: 33
gaatgtgtct cctccacagt ggctcccaga ggttccacac actctctgaa gctccttctc    60
ccacactgca cctactcctt gaggctgaac tggtcacaga                         100

<210> SEQ ID NO 34
<211> LENGTH: 100
<212> TYPE: DNA
<213> ORGANISM: Homo sapiens

<400> SEQUENCE: 34
gggggaccat tggggcctga gccaaggaac tttccttcta ctgccttata gtgcttaaac    60
attctccgcc tccagggtgc agattcagag ctggccagag                         100

<210> SEQ ID NO 35
<211> LENGTH: 100
<212> TYPE: DNA
<213> ORGANISM: Homo sapiens

<400> SEQUENCE: 35
accattacaa agaatgtggc aacttgcttg tgcctaaaag gaggaattgg aactagaatg    60
tgtgactctg tggggactgc ataggtttgt taattgacct                         100

<210> SEQ ID NO 36
<211> LENGTH: 100
<212> TYPE: DNA
<213> ORGANISM: Homo sapiens

<400> SEQUENCE: 36
acggggaaga cgttttcatc ccgctaatct tgggaataag aggaggaagc ggctggcaac    60
tgaaggctgg aacacttgct actggataat cgtagctttt                         100

<210> SEQ ID NO 37
<211> LENGTH: 100
<212> TYPE: DNA
<213> ORGANISM: Homo sapiens

<400> SEQUENCE: 37
ctgtctccgg gccagggtca gggaccctct gcctctggca gccttaacct gtcctctgct    60
aggaccaggg tgatttcaag ccagggaagc aactgggacc                         100

<210> SEQ ID NO 38
<211> LENGTH: 100
<212> TYPE: DNA
<213> ORGANISM: Homo sapiens

<400> SEQUENCE: 38
ggacgcagct actctgacct acgacactct ccgtttgct gagtttgaag attttcctga    60
gacctcagag cccgtttgga tactgggtag aaaatacagc                         100

<210> SEQ ID NO 39
<211> LENGTH: 100
<212> TYPE: DNA
<213> ORGANISM: Homo sapiens

<400> SEQUENCE: 39
tgcagtggct gagtgaacat ctgagctacc cggataattt tcttcatatt agtatcatcc    60
cacagccaac agattgaagg atcaactatt tgcctgaaca                         100

<210> SEQ ID NO 40
<211> LENGTH: 100
<212> TYPE: DNA
<213> ORGANISM: Homo sapiens

<400> SEQUENCE: 40
acgctaagtc gctggccatt ggtggacatg gcgcaggcgc gtttgctccg acgggccgaa    60
tgttttgggg cagtgttttg agcgcggaga ccgcgtgata                         100

<210> SEQ ID NO 41
<211> LENGTH: 100
<212> TYPE: DNA
<213> ORGANISM: Homo sapiens

<400> SEQUENCE: 41
taaaaagtcc ccaaacccaa acaaatggtt tatgaaccag agtatatgtg gaagattctt    60
tgctggtctt gctctgtgtg catctgaagc ttctttggcc                         100

<210> SEQ ID NO 42
<211> LENGTH: 100
<212> TYPE: DNA
<213> ORGANISM: Homo sapiens

<400> SEQUENCE: 42
ctatatggtg ggacccattg aagaagctgt ggcaaaagct gataagctgg ctgaagagca    60
ttcatcgtga ggggtctttg tcctctgtac tgtctctctc                         100

<210> SEQ ID NO 43
<211> LENGTH: 100
<212> TYPE: DNA
<213> ORGANISM: Homo sapiens

<400> SEQUENCE: 43
ttgccagaga attggcagaa gatgacagca tattaaagtg agtgaccctg cgacccactc    60
tttggaccag cagcggatga ataaagcttc ctgtgttgtg                         100

<210> SEQ ID NO 44
<211> LENGTH: 100
<212> TYPE: DNA
<213> ORGANISM: Homo sapiens

<400> SEQUENCE: 44
gctggcatgc tacgtgctct ttagctactc cttttcctac aagcatctca agcacgagcg    60
gctccgcaaa taccactgaa gaggacacac tctgcacccc                         100

<210> SEQ ID NO 45
<211> LENGTH: 100
<212> TYPE: DNA
<213> ORGANISM: Homo sapiens

<400> SEQUENCE: 45
gggacggggt cctgcagcgg gtccttccgg cgggtgacat tcagccggcg gttcggggcg    60
acggactctc cattccagaa ccatggccca atttgtccgt                        100

<210> SEQ ID NO 46
<211> LENGTH: 100
<212> TYPE: DNA
<213> ORGANISM: Homo sapiens

<400> SEQUENCE: 46
agcagaaggc aggggagtcc acacagggca agcagcaacc aggcttctga ggacaggaaa    60
ggagggagca tctggtggga agctggcgag gaggggctgg                        100

<210> SEQ ID NO 47
<211> LENGTH: 100
<212> TYPE: DNA
<213> ORGANISM: Homo sapiens

<400> SEQUENCE: 47
gatatctcac acacggaata atcattaaga aacaaccact gttgagcaaa gttgataggc    60
agtaaggaaa taaagtggac ataaacacag cagtactaat                        100

<210> SEQ ID NO 48
<211> LENGTH: 100
<212> TYPE: DNA
<213> ORGANISM: Homo sapiens

<400> SEQUENCE: 48
gaattggtgt cagatgctgg aatttattct gaccaatgaa cacagctgac tcaggggagt    60
acaatctcct gccaagtaat agaaccaaac ccaatatgca                        100

<210> SEQ ID NO 49
<211> LENGTH: 100
<212> TYPE: DNA
<213> ORGANISM: Homo sapiens

<400> SEQUENCE: 49
tccagaacca gtctgatgca agtgcacctc taatatatgc cttacaaact ccagaggcca    60
tattcaaaac agggtcttct cagtgtatgc aaggggctgc                        100

<210> SEQ ID NO 50
<211> LENGTH: 100
<212> TYPE: DNA
<213> ORGANISM: Homo sapiens

<400> SEQUENCE: 50
ccccaccacc tgttagctgt ggttgtgcac tgtcttttgt agctctggac tggaggggta    60
gatggggagt caattaccca tcacataaat atgaaacatt                        100

<210> SEQ ID NO 51
<211> LENGTH: 100
<212> TYPE: DNA
<213> ORGANISM: Homo sapiens

```
<400> SEQUENCE: 51 ggagccctttt gctgtgtgct ctgtccagtg tcatgaggca ggtgtttgca aagccagctc      60
tcggttccga tggggtattg ctgacctact tttctagggg                              100

<210> SEQ ID NO 52
<211> LENGTH: 100
<212> TYPE: DNA
<213> ORGANISM: Homo sapiens

<400> SEQUENCE: 52
cctggcaaac aggactcatc tgatgatgtg agaagagttc agaggaggga gaaaaatcgt       60
attgccgccc agaagagccg acagaggcag acacagaagg                              100

<210> SEQ ID NO 53
<211> LENGTH: 100
<212> TYPE: DNA
<213> ORGANISM: Homo sapiens

<400> SEQUENCE: 53
tgaaaatacc atcttctctt caactacact tcccagacct ggggacccag gggctcctcc       60
tttgccacca gatctacagt tagaagaaga aggaacttgt                              100

<210> SEQ ID NO 54
<211> LENGTH: 100
<212> TYPE: DNA
<213> ORGANISM: Homo sapiens

<400> SEQUENCE: 54
cctcacggtg ccttttttca cggaagtttt caatgatggg cgagcgtgca ccatcccttt       60
ttgaagtgta ggcagacaca gggacttgaa gttgttacta                              100

<210> SEQ ID NO 55
<211> LENGTH: 100
<212> TYPE: DNA
<213> ORGANISM: Homo sapiens

<400> SEQUENCE: 55
atacaaagct ctgatgacag gccatgactg tagagtggtc agaactgtgt ggttggtttg       60
agggagcgaa ttcggggaag gcacttggtg atataacttt                              100

<210> SEQ ID NO 56
<211> LENGTH: 100
<212> TYPE: DNA
<213> ORGANISM: Homo sapiens

<400> SEQUENCE: 56
tgtatttctg tgcaatgaga gaggctcttt atggtggtgc tacaaacaag ctcatctttg       60
gaactggcac tctgcttgct gtccagccaa atatccagaa                              100

<210> SEQ ID NO 57
<211> LENGTH: 100
<212> TYPE: DNA
<213> ORGANISM: Homo sapiens

<400> SEQUENCE: 57
aagcacgaca gtggatgctg ggtccatatc acacacattg ctgtgaacag gaaactcctg       60
tgaccacaac atgaggccac tggagacgca tatgagtaag                              100
```

<210> SEQ ID NO 58
<211> LENGTH: 100
<212> TYPE: DNA
<213> ORGANISM: Homo sapiens

<400> SEQUENCE: 58
cagcggccct ggcgggtgcc ctggctacca tggaccatcc tgctggtcag cactgcggct    60
gcttcgcaga atcaagaacg gctatgtgcg tttaaagatc                         100

<210> SEQ ID NO 59
<211> LENGTH: 100
<212> TYPE: DNA
<213> ORGANISM: Homo sapiens

<400> SEQUENCE: 59
gctggagtga ttggccctga tgaccatgga gaaagagag tagggagaac agtataacca    60
gaagtcaggg gggtctcctg gaatccctcc tcacaatacc                         100

<210> SEQ ID NO 60
<211> LENGTH: 100
<212> TYPE: DNA
<213> ORGANISM: Homo sapiens

<400> SEQUENCE: 60
ccctgtgggc cttgcaggcc agtccaggca ggtctttcac actgttgtcc cacataacag    60
aaaaagctga gcagacaggg taggaaacac acttgcatct                         100

<210> SEQ ID NO 61
<211> LENGTH: 100
<212> TYPE: DNA
<213> ORGANISM: Homo sapiens

<400> SEQUENCE: 61
ttaagcaact tgctccagtg acgcagctgg taagcagcag agctgggatt aaaacccagg    60
cattctgatt ccaccaccta cacacttagc cattccgccc                         100

<210> SEQ ID NO 62
<211> LENGTH: 100
<212> TYPE: DNA
<213> ORGANISM: Homo sapiens

<400> SEQUENCE: 62
atttagggtg agagcttcac agctgaaaat ctcctttaaa gaaaacgcgg cccaaatgtg    60
ctgggaggag aagccagtgg atctaggagg gggcccggcg                         100

<210> SEQ ID NO 63
<211> LENGTH: 100
<212> TYPE: DNA
<213> ORGANISM: Homo sapiens

<400> SEQUENCE: 63
atattttgga gagggaagtt ggctcactgt tgtagaggac ctgaacaagg tgttcccacc    60
cgaggtcgct gtgtttgagc catcagaagc agagatctcc                         100

<210> SEQ ID NO 64
<211> LENGTH: 100
<212> TYPE: DNA

<400> SEQUENCE: 64
atgcagacaa tttgcctgtg agatgaggaa aattctctgg aagatttagg ccctgagagc        60
tgaaaaggga ccctaaacat tacctggtga caactgccct                              100

<210> SEQ ID NO 65
<211> LENGTH: 100
<212> TYPE: DNA
<213> ORGANISM: Homo sapiens

<400> SEQUENCE: 65
cctgagcttt taacgtgagg gtctttattg gataggacta ctccctattt cttgcctaga        60
gaacacacat gggctttgga gcccgacaga cctgggcttg                              100

<210> SEQ ID NO 66
<211> LENGTH: 100
<212> TYPE: DNA
<213> ORGANISM: Homo sapiens

<400> SEQUENCE: 66
aaggatgggg gtggattgac caagctgggc cagaggtgcg aggagctgat ctgcgagccc        60
tgtgtgcctg tgagtcctgg cggagtggcc gtgcgtggtg                              100

<210> SEQ ID NO 67
<211> LENGTH: 100
<212> TYPE: DNA
<213> ORGANISM: Homo sapiens

<400> SEQUENCE: 67
catctacctg gacaaggtct cacactctga ggatgactgt ctagctttca aagttcacca        60
atactttaat gtagagctta ccagcctgg agcagtcaag                               100

<210> SEQ ID NO 68
<211> LENGTH: 100
<212> TYPE: DNA
<213> ORGANISM: Homo sapiens

<400> SEQUENCE: 68
gagtccaggg tgcactacac cgtgtgcatc tggcggaacg gcaaggtggg gctgtctggc        60
atggccatcg cggacgtcac cctcctgagt ggattccacg                              100

<210> SEQ ID NO 69
<211> LENGTH: 100
<212> TYPE: DNA
<213> ORGANISM: Homo sapiens

<400> SEQUENCE: 69
gaaccgtgaa gatgaaacag agagataaga aagttgtgac aaagaccttt catggtgcag        60
gcttggttgt tccagtagat aaaaatgatg ttgggtaccg                              100

<210> SEQ ID NO 70
<211> LENGTH: 100
<212> TYPE: DNA
<213> ORGANISM: Homo sapiens

<400> SEQUENCE: 70
taaaagatga agttcaccca gaggtgaagt gtgttggctc cgtagccctg actgccttgg        60
tgactgtatc ctcagaagaa tttgaagaca agtggttcag                              100

<210> SEQ ID NO 71
<211> LENGTH: 100
<212> TYPE: DNA
<213> ORGANISM: Homo sapiens

<400> SEQUENCE: 71
cgctggccat ggggaagcca cctccagggc agtcccaggg actgaattgg aagttgtccc    60
aagtcacttc aggtccaact gggacagcag aggtaacccc                         100

<210> SEQ ID NO 72
<211> LENGTH: 100
<212> TYPE: DNA
<213> ORGANISM: Homo sapiens

<400> SEQUENCE: 72
ttgtccagag aatcaaggat tttttgcgga atcttgtacc caggacagag tcctagtgtg    60
tgccctaccc tggctcaggc ttctgggctc tgagaaataa                         100

<210> SEQ ID NO 73
<211> LENGTH: 100
<212> TYPE: DNA
<213> ORGANISM: Homo sapiens

<400> SEQUENCE: 73
atttatccaa taatggacaa gtcaagccgc acacgtcttg ctctcattat ctgcaatgaa    60
gaatttgaca gtattcctag aagaactgga gctgaggttg                         100

<210> SEQ ID NO 74
<211> LENGTH: 100
<212> TYPE: DNA
<213> ORGANISM: Homo sapiens

<400> SEQUENCE: 74
cccaccactc ttgactcagg tggtgtcctt cttcctcaag tcttgacaat tcccgggccc    60
ttcagtccct gagcagtcta cttctgtgtc tgtcaccaca                         100

<210> SEQ ID NO 75
<211> LENGTH: 100
<212> TYPE: DNA
<213> ORGANISM: Homo sapiens

<400> SEQUENCE: 75
actccacagc acctggttat tattcttggc gaaattcaaa ggatggctcc tggttcatcc    60
agtcgctttg tgccatgctg aaacagtatg ccgacaagct                         100

<210> SEQ ID NO 76
<211> LENGTH: 100
<212> TYPE: DNA
<213> ORGANISM: Homo sapiens

<400> SEQUENCE: 76
atgaggggga aaaaaactta tgtgtagtca atcttttaag ctttgactgt tttgggaagg    60
aagagtacct cttatcgagg tagtataaaa cacatagggt                         100

<210> SEQ ID NO 77
<211> LENGTH: 100
<212> TYPE: DNA
<213> ORGANISM: Homo sapiens

<400> SEQUENCE: 77
ttgcataagc acagctcaag aactgagctt tgtatgtgtc cttttggggg ataacagggc    60
tggaccatgc ttccctgccc ttaaacgcag agcttttagt                          100

<210> SEQ ID NO 78
<211> LENGTH: 100
<212> TYPE: DNA
<213> ORGANISM: Homo sapiens

<400> SEQUENCE: 78
gggagagggc ccacacagtc tcctcgccgg caccggcctc ctccattttt ccgggccttg    60
cgtggagggt tttggcggat gttttttgaac gaaggaatgt                         100

<210> SEQ ID NO 79
<211> LENGTH: 100
<212> TYPE: DNA
<213> ORGANISM: Homo sapiens

<400> SEQUENCE: 79
atccagagtg agacagcatt ggagggacaa gtgtgcatgc agatgtcctc agacgggaag    60
gtttgagaag ggtcagatgg taggcgggcc taacaagggc                          100

<210> SEQ ID NO 80
<211> LENGTH: 100
<212> TYPE: DNA
<213> ORGANISM: Homo sapiens

<400> SEQUENCE: 80
cagttctctg catcacttgc tgctgacacg ccgaccgcct gctgcttcag ctacacctcc    60
cggcagattc cacagaattt catagctgac tactttgaga                          100

<210> SEQ ID NO 81
<211> LENGTH: 100
<212> TYPE: DNA
<213> ORGANISM: Homo sapiens

<400> SEQUENCE: 81
ggagcctgag ccttgggaac atgcgtgtga cctctacagc tacctcttct atggactggt    60
tattgccaaa cagccacact gtgggactct tcttaactta                          100

<210> SEQ ID NO 82
<211> LENGTH: 100
<212> TYPE: DNA
<213> ORGANISM: Homo sapiens

<400> SEQUENCE: 82
ggggaggagc aggagcctga gccttgggaa catgcgtgtg acctccacag ctacctcttc    60
tatggactgg ttattgccaa acagccacac tgtgggactc                          100

<210> SEQ ID NO 83
<211> LENGTH: 100
<212> TYPE: DNA
<213> ORGANISM: Homo sapiens

<400> SEQUENCE: 83
ttctgcagcc tcacctctga gaaaacctct tgccaccaa taccatgaag ctctgcgtga    60
ctgtcctgtc tctcctcatg ctagtagctg ccttctgctc                          100

<210> SEQ ID NO 84
<211> LENGTH: 100
<212> TYPE: DNA
<213> ORGANISM: Homo sapiens

<400> SEQUENCE: 84
ggccagccat gtctgcattt cggtggctag tcaagctcct cctccctgca tctgaccagc      60
agcgcctttc ccaactctag ctgggggtgg gccaggctga                            100

<210> SEQ ID NO 85
<211> LENGTH: 100
<212> TYPE: DNA
<213> ORGANISM: Homo sapiens

<400> SEQUENCE: 85
catcatttgg gccctggcca tcttggcttc catgccaggc ttatactttt ccaagaccca      60
atgggaattc actcaccaca cctgcagcct tcactttcct                            100

<210> SEQ ID NO 86
<211> LENGTH: 100
<212> TYPE: DNA
<213> ORGANISM: Homo sapiens

<400> SEQUENCE: 86
ctttaactgc gggatgctgc tcctgacttg cattagcatg gaccggtaca tcgccattgt      60
acaggcgact aagtcattcc ggctccgatc cagaacacta                            100

<210> SEQ ID NO 87
<211> LENGTH: 100
<212> TYPE: DNA
<213> ORGANISM: Homo sapiens

<400> SEQUENCE: 87
ccctgttctc tatgttttg tgggtgagag attccgccgg gatctcgtga aaaccctgaa       60
gaacttgggt tgcatcagcc aggcccagtg ggtttcattt                            100

<210> SEQ ID NO 88
<211> LENGTH: 100
<212> TYPE: DNA
<213> ORGANISM: Homo sapiens

<400> SEQUENCE: 88
gcccaagggc accatgaaga tgctcgtttc tggcgctgga gacatcaaac ttactaaaga      60
cggcaatgtg ctgcttcacg aaatgcaaat tcaacaccca                            100

<210> SEQ ID NO 89
<211> LENGTH: 100
<212> TYPE: DNA
<213> ORGANISM: Homo sapiens

<400> SEQUENCE: 89
gcccaagcac actcgcctgc cttttcctgc gaacaggttc gcgccttccc ggcccttacc      60
agcctagacc tgtctgacaa tcctggactg ggcgaacgcg                            100

<210> SEQ ID NO 90
<211> LENGTH: 100
<212> TYPE: DNA
<213> ORGANISM: Homo sapiens

```
<400> SEQUENCE: 90
ttgatgttca ccataagcca agtcacaccg ttgcacagtg ggacctacca gtgttgtgcc      60
agaagccaga agtcaggtat ccgccttcag ggccattttt                            100

<210> SEQ ID NO 91
<211> LENGTH: 100
<212> TYPE: DNA
<213> ORGANISM: Homo sapiens

<400> SEQUENCE: 91
aaaggaagac agccagatcc agtgattgac ttggcatgaa aatgagaaaa tgcagacaga      60
cctcaacatt caacaacatc catacagcac tgctggagga                            100

<210> SEQ ID NO 92
<211> LENGTH: 100
<212> TYPE: DNA
<213> ORGANISM: Homo sapiens

<400> SEQUENCE: 92
cctgttttag atatccctta ctccagaggg ccttccctga cttacaagtg ggaagcagtc      60
tcttcctggt ctgaactccc gccacatttt agccgtactt                            100

<210> SEQ ID NO 93
<211> LENGTH: 100
<212> TYPE: DNA
<213> ORGANISM: Homo sapiens

<400> SEQUENCE: 93
taaagaatct gaagaggaac tatattgtgc ctattctttg gcttaatgag actgggacca      60
ttggtgatga gaaggcaaac atgttcagaa gtcaagtaac                            100

<210> SEQ ID NO 94
<211> LENGTH: 100
<212> TYPE: DNA
<213> ORGANISM: Homo sapiens

<400> SEQUENCE: 94
aatttaaagg cagggtcaga cttgatcctc agagtggcgc actgtacatc tctaaggtcc      60
agaaagagga caacagcacc tacatcatga gggtgttgaa                            100

<210> SEQ ID NO 95
<211> LENGTH: 100
<212> TYPE: DNA
<213> ORGANISM: Homo sapiens

<400> SEQUENCE: 95
tatacagtgt cttacagaga aaagacataa gcaaagacta tgaggaatat ttgcaagaca      60
tagaatagtg ttggaaaatg tgcaatatgt gatgtggcaa                            100

<210> SEQ ID NO 96
<211> LENGTH: 100
<212> TYPE: DNA
<213> ORGANISM: Homo sapiens

<400> SEQUENCE: 96
cctatgggtg cgtcctgcgg gctgctttgg tcccattggt cgcgggcttg gtgatctgcc      60
tcgtggtgtg catccagcgc ttcgcacagg ctcagcagca                            100
```

<210> SEQ ID NO 97
<211> LENGTH: 100
<212> TYPE: DNA
<213> ORGANISM: Homo sapiens

<400> SEQUENCE: 97
tgaagatgaa aacctttatg aaggcctgaa cctggacgac tgctccatgt atgaggacat    60 ctcccgggc ctccagggca cctaccagga tgtgggcagc                          100

<210> SEQ ID NO 98
<211> LENGTH: 100
<212> TYPE: DNA
<213> ORGANISM: Homo sapiens

<400> SEQUENCE: 98
gaagctggaa aagggccgca tggaagagtc ccagaacgaa tctctcgcca ccctcaccat    60
ccaaggcatc cggtttgagg acaatggcat ctacttctgt                         100

<210> SEQ ID NO 99
<211> LENGTH: 100
<212> TYPE: DNA
<213> ORGANISM: Homo sapiens

<400> SEQUENCE: 99
agggctttgt ggaggacagg ccttgccctc aagaacgtcg tacctgacgc tgagcctgtc    60
atgagaatgc aacaggagca aaccaagtgt tgctgtgaca                         100

<210> SEQ ID NO 100
<211> LENGTH: 100
<212> TYPE: DNA
<213> ORGANISM: Homo sapiens

<400> SEQUENCE: 100 tctcccttc tctgcctcac ctggtcgcca atccatgctc tctttctttt ctctgtctac     60
tccttatccc ttggtttaga ggaacccaag atgtggcctt                         100

<210> SEQ ID NO 101
<211> LENGTH: 100
<212> TYPE: DNA
<213> ORGANISM: Homo sapiens

<400> SEQUENCE: 101
catgtgtcct ggttcccgtt tctccaccta gactgtaaac ctctcgaggg cagggaccac    60
accctgtact gttctgtgtc tttcacagct cctcccacaa                         100

<210> SEQ ID NO 102
<211> LENGTH: 100
<212> TYPE: DNA
<213> ORGANISM: Homo sapiens

<400> SEQUENCE: 102
ctggttggtc tttattgagc acctactata tgcagaaggg gaggccgagg tgggaggatc    60
attggatctc aggagttcga gatcagcatg ggccacgtag                         100

<210> SEQ ID NO 103
<211> LENGTH: 100
<212> TYPE: DNA
<213> ORGANISM: Homo sapiens

```
<400> SEQUENCE: 103
tccaccctaa caaagtagga tggggttggg ggctaaatta attggagtgg ggcgaggaga      60
gagccagaaa acatagatcc gagggcagca gtgctgggtg                          100

<210> SEQ ID NO 104
<211> LENGTH: 100
<212> TYPE: DNA
<213> ORGANISM: Homo sapiens

<400> SEQUENCE: 104
cgccgctccc tcatgctgcc cgggcccttc ctccaagacc ctacagagcc tgaggggcac      60
cttggcttcc gcctgtgcta gctttgccat gtcatctgga                          100

<210> SEQ ID NO 105
<211> LENGTH: 100
<212> TYPE: DNA
<213> ORGANISM: Homo sapiens

<400> SEQUENCE: 105
actaaggaaa tggaatctta aaagtctatg acagtgtaac tctacagtct caaaatgacc      60
tgataaattg ataagacaaa gatgagatta ttggggctgt                          100

<210> SEQ ID NO 106
<211> LENGTH: 100
<212> TYPE: DNA
<213> ORGANISM: Homo sapiens

<400> SEQUENCE: 106
gcatgtcttg taaagagagg ggatgtgcat ttgtgtgtga tgttggatag tcatccacgc      60
tcagtttgga ccattggagg aacttagtgt cacgcacaaa                          100

<210> SEQ ID NO 107
<211> LENGTH: 100
<212> TYPE: DNA
<213> ORGANISM: Homo sapiens

<400> SEQUENCE: 107
agacttggtg tccaacagag tctaggctgg gttcattaca tgattcatga gccagaacca      60
catattcttc tctttagacg acctcttcca aaagatcaac                          100

<210> SEQ ID NO 108
<211> LENGTH: 100
<212> TYPE: DNA
<213> ORGANISM: Homo sapiens

<400> SEQUENCE: 108
atttctactg aatcagcatc ttggcaagac agtgagaagg actgtgctag aatggaggct      60
cacctgctgg tgataaacac tcaagaagag caggatttca                          100

<210> SEQ ID NO 109
<211> LENGTH: 100
<212> TYPE: DNA
<213> ORGANISM: Homo sapiens

<400> SEQUENCE: 109
tacgagagta tcaacagtat catccaagcc tgacctgcgt catggaagga aaggacatag      60
aagattggag ctgctgccca accccttgga cttcatttca                          100
```

<210> SEQ ID NO 110
<211> LENGTH: 100
<212> TYPE: DNA
<213> ORGANISM: Homo sapiens

<400> SEQUENCE: 110
ccccatccaa cccttagact cacgaacaaa tccacctgag atcagcagag ccaccctaga    60
tcagctgaaa ctctaagcac aaaaataaaa acttatcact                        100

<210> SEQ ID NO 111
<211> LENGTH: 100
<212> TYPE: DNA
<213> ORGANISM: Homo sapiens

<400> SEQUENCE: 111
cgtacgccgc tacctggaca gcgcgatgca ggagaaagag ttcaaataca cgtgtccgca    60
cagcgccgag atcctggcgg cctaccggcc cgccgtgcac                        100

<210> SEQ ID NO 112
<211> LENGTH: 100
<212> TYPE: DNA
<213> ORGANISM: Homo sapiens

<400> SEQUENCE: 112
gattatagcc gggatcgggg agatgcctac tatgacacag actatcggca ttcctatgaa    60
tatcagcggg agaacagcag ttaccgcagc cagcgcagca                        100

<210> SEQ ID NO 113
<211> LENGTH: 100
<212> TYPE: DNA
<213> ORGANISM: Homo sapiens

<400> SEQUENCE: 113
ggcgccagag ctgggctctt caacacggca tttagcgcag aaagtcgtgg ttcaggcagt    60
atgggccgct gtgacaaaac acctaagact gggtagttta                        100

<210> SEQ ID NO 114
<211> LENGTH: 100
<212> TYPE: DNA
<213> ORGANISM: Homo sapiens

<400> SEQUENCE: 114
tctgtgtttc cagccatctc gccctgccag cccagcacca ctgggaatca tggtgaagct    60
gatgcagcgt tgccgagggg gtgggttggg cgggggtggg                        100

<210> SEQ ID NO 115
<211> LENGTH: 100
<212> TYPE: DNA
<213> ORGANISM: Homo sapiens

<400> SEQUENCE: 115
ttgaatactg ttctgtgacc ctgactgcta gttctgagga cactggtggc tgtgctatgt    60
gtggccatcc tccatgtccc gtccctgtag ctgctctgtt                        100

<210> SEQ ID NO 116
<211> LENGTH: 100
<212> TYPE: DNA
<213> ORGANISM: Homo sapiens

<400> SEQUENCE: 116
aggaaactaa gacatggaaa ggttaggtaa cttgcccaag gtcgcacagc tagtaagtgg    60
cagacatcca gagtctctgc tctgctctta actctcacca                         100

<210> SEQ ID NO 117
<211> LENGTH: 100
<212> TYPE: DNA
<213> ORGANISM: Homo sapiens

<400> SEQUENCE: 117
aatgactgaa gctggagaag ccgtggttga agtcagccta cactacagtg cacagttgag    60
gagccagaga cttcttaaat catccttaga accgtgacca                         100

<210> SEQ ID NO 118
<211> LENGTH: 100
<212> TYPE: DNA
<213> ORGANISM: Homo sapiens

<400> SEQUENCE: 118
ttgcagtaag cgaacagatc tttgtgacca tgccctgcac atatcgcatg atgagctatg    60
aaccactgga gcagcccaca ctggcttgat ggatcacccc                         100

<210> SEQ ID NO 119
<211> LENGTH: 100
<212> TYPE: DNA
<213> ORGANISM: Homo sapiens

<400> SEQUENCE: 119
acacaagcca ggctatccag cgaatcaaga acgactttca aaatctgcag caggtttttc    60
ttcaagccaa gaaggacacg gattggctga aggagaaagt                         100

<210> SEQ ID NO 120
<211> LENGTH: 100
<212> TYPE: DNA
<213> ORGANISM: Homo sapiens

<400> SEQUENCE: 120
ctgtgtgcca ggcctcacag actcccagtt gggttgaaga atggttgact gagtttgatt    60
cttcctgtac cctcggtcgt ctgagctgtg tgcggacaac                         100

<210> SEQ ID NO 121
<211> LENGTH: 100
<212> TYPE: DNA
<213> ORGANISM: Homo sapiens

<400> SEQUENCE: 121
ctctcgagtc cgggccgcaa gtcccagacg ctgcccatgg aggcgtccag cgagccgccg    60
ctggatgcta agtccgatgt caccaaccag cttgtagatt                         100

<210> SEQ ID NO 122
<211> LENGTH: 100
<212> TYPE: DNA
<213> ORGANISM: Homo sapiens

<400> SEQUENCE: 122
aagtaaagtt gttgatggtg gtgaaacacc gtagggcatg tggttcaaag agaagcagga    60
gggcaaggga aagttaccct gatcttagtt tgtagcttat                         100

<210> SEQ ID NO 123
<211> LENGTH: 100
<212> TYPE: DNA
<213> ORGANISM: Homo sapiens

<400> SEQUENCE: 123
gaagttttgc caaaacctcg gatgcgtggc cttctggcca ggcgtctgcg aaatcatatg      60
gctgtagcat tcgtgctatc cctgggggtt gcagctttgt                          100

<210> SEQ ID NO 124
<211> LENGTH: 100
<212> TYPE: DNA
<213> ORGANISM: Homo sapiens

<400> SEQUENCE: 124
cagagccacc agaaacgtac acctgatttt catgacaaat acggtaatgc tgtattagct      60
agtggagcca ctttctgtat tgttacatgg acatatgtag                          100

<210> SEQ ID NO 125
<211> LENGTH: 100
<212> TYPE: DNA
<213> ORGANISM: Homo sapiens

<400> SEQUENCE: 125
caaggtcgtg aaaaaaaagg tcttggtgag gtgccgccat ttcatctgtc ctcattctct      60
gcgcctttcg cagagcttcc agcagcggta tgttgggcca                          100

<210> SEQ ID NO 126
<211> LENGTH: 100
<212> TYPE: DNA
<213> ORGANISM: Homo sapiens

<400> SEQUENCE: 126
tgtatttgtt tctttacaac aggtgtaggt ataggaggtc aagaaaagga gttcggtaaa      60
gggcatagct aataacaacc acacattggg ccaggcacag                          100

<210> SEQ ID NO 127
<211> LENGTH: 100
<212> TYPE: DNA
<213> ORGANISM: Homo sapiens

<400> SEQUENCE: 127
ggtgtcaagc aaataatatg tgggggccga cacgactacc aacctgtgta agtgttttcc      60
ctctcgagtg tccagcactt cctatgatcc acaatggaca                          100

<210> SEQ ID NO 128
<211> LENGTH: 100
<212> TYPE: DNA
<213> ORGANISM: Homo sapiens

<400> SEQUENCE: 128
agcccagttt cactgccata tactcttcaa ggactttctg aagcctcact tatgagatgc      60
ctgaagccag gccatggcta taaacaatta catggctcta                          100

<210> SEQ ID NO 129
<211> LENGTH: 100
<212> TYPE: DNA
<213> ORGANISM: Homo sapiens

<400> SEQUENCE: 129
tttgatggta ggtcagcagc agtgctagtc tctgaaagca caataccagt caggcagcct    60
atcccatcag atgtcatctg gctgaagttt atctctgtct                         100

<210> SEQ ID NO 130
<211> LENGTH: 100
<212> TYPE: DNA
<213> ORGANISM: Homo sapiens

<400> SEQUENCE: 130
acctactcac ctttttccct tctaagttct gctaaatcac atctgcctca tagagaaagg    60
aatgttgcct ttgagaactg tcttggagaa cagataagct                         100

<210> SEQ ID NO 131
<211> LENGTH: 100
<212> TYPE: DNA
<213> ORGANISM: Homo sapiens

<400> SEQUENCE: 131
ttctaaagga gcagaaggac aggtctctga gacaggatcg ttgtccctac aggaggaaca    60
gtggccttgc ttcttagacg gtcttcactg tgtgttttaa                         100

<210> SEQ ID NO 132
<211> LENGTH: 100
<212> TYPE: DNA
<213> ORGANISM: Homo sapiens

<400> SEQUENCE: 132
cagctcaggt ggccctgagg gctccctcgg aacagtgcct caaatcctga cccaagggcc    60
agcatgggga agagatggtt gcaggcaaaa tgcactttat                         100

<210> SEQ ID NO 133
<211> LENGTH: 100
<212> TYPE: DNA
<213> ORGANISM: Homo sapiens

<400> SEQUENCE: 133
cctcctagca agacctgttg gttagctgga catgctttgg caattttttt atactaccaa    60
gtgaccataa aggcatggca tttgttgtga ctggcaccca                         100

<210> SEQ ID NO 134
<211> LENGTH: 100
<212> TYPE: DNA
<213> ORGANISM: Homo sapiens

<400> SEQUENCE: 134
tctagggacc cctcgcccca gcctcattcc ccattctgtg tcccatgtcc cgtgtctcct    60
cggtcgcccc gtgtttgcgc ttgaccatgt tgcactgttt                         100

<210> SEQ ID NO 135
<211> LENGTH: 100
<212> TYPE: DNA
<213> ORGANISM: Homo sapiens

<400> SEQUENCE: 135
caaccacacc ttgaagcaga ctctgagctg ctactctgaa gtctgggtcg tgccctggct    60
ccagcacttc gaggtgcctg ttctccgttg tcactgaccc                         100

<210> SEQ ID NO 136
<211> LENGTH: 100
<212> TYPE: DNA
<213> ORGANISM: Homo sapiens

<400> SEQUENCE: 136
gcggggccag ggggccggag agccgcctgc ttgagttcta cctcgccatg cctttcgcga    60
cacccatgga agcagagctg gcccgcagga gcctggccca                         100

<210> SEQ ID NO 137
<211> LENGTH: 100
<212> TYPE: DNA
<213> ORGANISM: Homo sapiens

<400> SEQUENCE: 137
gaggtcgggc cagctgcccc attcttttaa cgttgtaggg cctgcccatg gagcggaccc    60
tcctctttgg gcctcgtgag cttttttgct tatcatgttc                         100

<210> SEQ ID NO 138
<211> LENGTH: 100
<212> TYPE: DNA
<213> ORGANISM: Homo sapiens

<400> SEQUENCE: 138
tgcaccgagg gagcaatacc tgtggcatca ccaagttccc gctcactgcc cgtgtgcaga    60
aaccggatat gaagccccga gtctcctgcc ctccctgaac                         100

<210> SEQ ID NO 139
<211> LENGTH: 100
<212> TYPE: DNA
<213> ORGANISM: Homo sapiens

<400> SEQUENCE: 139
cactggctgc gagtgttcct gagagttgaa agtgggatga cttatgacac ttgcacagca    60
tggctctgcc tcacaatgat gcagtcagcc acctggtgaa                         100

<210> SEQ ID NO 140
<211> LENGTH: 100
<212> TYPE: DNA
<213> ORGANISM: Homo sapiens

<400> SEQUENCE: 140
agcaccacgg tgtgacgaaa tgcaacatca cgtgcagcaa gatgacatca aagatacctg    60
tagctttgct catccactat caacagaacc aggcatcatg                         100

<210> SEQ ID NO 141
<211> LENGTH: 100
<212> TYPE: DNA
<213> ORGANISM: Homo sapiens

<400> SEQUENCE: 141
atcacatgtc agccactgtg atagaggctg aggaatccaa gaaaatggcc agtgagatca    60
atgtgacggc agggaaatgt atgtgtgtct attttgtaac                         100

<210> SEQ ID NO 142
<211> LENGTH: 100
<212> TYPE: DNA
<213> ORGANISM: Homo sapiens

<400> SEQUENCE: 142
acctcaaaaa tggaagattt taacatggag agtgacagct ttgaagattt ctggaaaggt    60
gaagatctta gtaattacag ttacagctct accctgcccc                         100

<210> SEQ ID NO 143
<211> LENGTH: 100
<212> TYPE: DNA
<213> ORGANISM: Homo sapiens

<400> SEQUENCE: 143
acgtcccttt tttctctgag tatctcctcg caagctgggt aatcgatggg ggagtctgaa    60
gcagatgcaa agaggcaaga ggctggattt tgaattttct                         100

<210> SEQ ID NO 144
<211> LENGTH: 100
<212> TYPE: DNA
<213> ORGANISM: Homo sapiens

<400> SEQUENCE: 144
actggagagg gtacctcagt tataaggagt ctgagaatat tggccctttc taacctatgt    60
gcataattaa aaccagcttc atttgttgct ccgagagtgt                         100

<210> SEQ ID NO 145
<211> LENGTH: 100
<212> TYPE: DNA
<213> ORGANISM: Homo sapiens

<400> SEQUENCE: 145
cttacaccaa actactgaat gaagcagtat tttggtaacc aggccatttt tggtgggaat    60
ccaagattgg tctcccatat gcagaaatag acaaaaagta                         100

<210> SEQ ID NO 146
<211> LENGTH: 100
<212> TYPE: DNA
<213> ORGANISM: Homo sapiens

<400> SEQUENCE: 146
gttcttggtc tgtatgtgta ggtggaggga ggcaaagttg tggtaataaa gtgggaaggc    60
ccgggaagaa cagctaactg tatagggtg aaatgacgct                          100

<210> SEQ ID NO 147
<211> LENGTH: 100
<212> TYPE: DNA
<213> ORGANISM: Homo sapiens

<400> SEQUENCE: 147
cataaataca gaacggcccg ggatgttgga cttcacgggc aaggccaagt gggatgcctg    60
gaatgagctg aaagggactt ccaaggaaga tgccatgaaa                         100

<210> SEQ ID NO 148
<211> LENGTH: 100
<212> TYPE: DNA
<213> ORGANISM: Homo sapiens

<400> SEQUENCE: 148
ttaacactgt gctgtgaaac aactatgggg aatctccatt gaaggctact tcatgggcac    60
ctgaaagtgg agtgttatag ctatgacttt ctatttcttg                         100

```
<210> SEQ ID NO 149
<211> LENGTH: 100
<212> TYPE: DNA
<213> ORGANISM: Homo sapiens

<400> SEQUENCE: 149
gacctgttgt aggcagctat cttacagacg catgaatgta agagtaggaa ggggtgggtg      60
tcagggatca cttgggatct ttgacacttg aaaaattaca                          100

<210> SEQ ID NO 150
<211> LENGTH: 100
<212> TYPE: DNA
<213> ORGANISM: Homo sapiens

<400> SEQUENCE: 150
attgcactgg gccatcagct catgccaggc tatgggggca gccagttggc attgctcccc      60
agactgaaca gaaacctggc cgccggatgg gacctccttt                          100

<210> SEQ ID NO 151
<211> LENGTH: 100
<212> TYPE: DNA
<213> ORGANISM: Homo sapiens

<400> SEQUENCE: 151
acatcgagtg gcatatctat caggactggc attcttttct cctgtgggag tttgccagcc      60
ggatcacatt acatggcttc atctacctcc aggcttctcc                          100

<210> SEQ ID NO 152
<211> LENGTH: 100
<212> TYPE: DNA
<213> ORGANISM: Homo sapiens

<400> SEQUENCE: 152
ttgtaaagaa tctgtaacca ataccatgaa gttcaggctg tgatctgggc tccctgactt      60
tctgaagcta gaaaaatgtt gtgtctccca accacctttc                          100

<210> SEQ ID NO 153
<211> LENGTH: 100
<212> TYPE: DNA
<213> ORGANISM: Homo sapiens

<400> SEQUENCE: 153
cccgtgtcaa cttctttctc cctggcggtg accacctggt tctgctaaat gtttacacac      60
agtgggctga gagtggttac tcttcccagt ggtgctatga                          100

<210> SEQ ID NO 154
<211> LENGTH: 100
<212> TYPE: DNA
<213> ORGANISM: Homo sapiens

<400> SEQUENCE: 154
accaaagagt tcatgagaca ggtactggag attgagagca gttggcttct ggaggtggct      60
ccccattatt ataaggccaa ggagctagaa gatccccatg                          100

<210> SEQ ID NO 155
<211> LENGTH: 100
<212> TYPE: DNA
<213> ORGANISM: Homo sapiens
```

```
<400> SEQUENCE: 155
ctcctgcagc ttctgtgagc caagccccag cctgcaccgt cgctgcccct tccctgccta    60 acccttttcct gtctcgcctt ggaagcaccc atgtctccct                          100

<210> SEQ ID NO 156
<211> LENGTH: 100
<212> TYPE: DNA
<213> ORGANISM: Homo sapiens

<400> SEQUENCE: 156
cacaatggct ggctctccca caactgtggc catcatgaag acgctggtgt catctgctca    60
gcttcccagt cccagccgac acccagccca gacacttggc                          100

<210> SEQ ID NO 157
<211> LENGTH: 100
<212> TYPE: DNA
<213> ORGANISM: Homo sapiens

<400> SEQUENCE: 157
gacctctggc tccagtgaag ctgaatgtcc tcactttgtg ggtcacactc tttacatttc    60
tgtaaggcaa tcttggcaca cgtggggctt accagtggcc                          100

<210> SEQ ID NO 158
<211> LENGTH: 100
<212> TYPE: DNA
<213> ORGANISM: Homo sapiens

<400> SEQUENCE: 158
cttccctgca tgctccctcc cagtgacttt ccttcccttt cacatgagga tctgccgttc    60
atgttgcttt ctcctttgtc ctcttggact tgagggcatt                          100

<210> SEQ ID NO 159
<211> LENGTH: 100
<212> TYPE: DNA
<213> ORGANISM: Homo sapiens

<400> SEQUENCE: 159
aaagagattt ccatttctgc tgccagagct ggtatttgcc tgcctgattc tctgtgtttc    60
ctgtttcacc gccaccctttt caggagagaa ctacaccagt                         100

<210> SEQ ID NO 160
<211> LENGTH: 100
<212> TYPE: DNA
<213> ORGANISM: Homo sapiens

<400> SEQUENCE: 160
tctcagctca tggggaagcc acatagacat ccctttcttc ccttgcacgc tcgctagcag    60
ctggtaaggt cttcacaccc tgattcctca agttttctgc                          100

<210> SEQ ID NO 161
<211> LENGTH: 100
<212> TYPE: DNA
<213> ORGANISM: Homo sapiens

<400> SEQUENCE: 161
tttgggaact cggtggagga acctctttat tggacttaat cagcataccc atcacaggtg    60
acaccttacg gacgttttct cttgttctcg ttctggatct                          100
```

<210> SEQ ID NO 162
<211> LENGTH: 100
<212> TYPE: DNA
<213> ORGANISM: Homo sapiens

<400> SEQUENCE: 162
cccagtgtct tgcccagtag atacaagata aatattgcca gaatcagata tcaggaagta    60
gtaagaaaag gagttaatat gcaaactaaa tcactcgctc                         100

<210> SEQ ID NO 163
<211> LENGTH: 100
<212> TYPE: DNA
<213> ORGANISM: Homo sapiens

<400> SEQUENCE: 163
ggatacggaa ttaagaaact tcaaatacag tgtgtagttg aagatgataa agttggaaca    60
gatatgctgg aggagcagat cactgctttt gaggactatg                         100

<210> SEQ ID NO 164
<211> LENGTH: 80
<212> TYPE: DNA
<213> ORGANISM: Homo sapiens

<400> SEQUENCE: 164
agcagcatgg acgacctgat acgccactgt aacgggaagc tgggcagcta caaaatcaat    60
ggccggacga aagccatggt                                                80

<210> SEQ ID NO 165
<211> LENGTH: 100
<212> TYPE: DNA
<213> ORGANISM: Homo sapiens

<400> SEQUENCE: 165
gaggcatacc aagatccact tgcggcagaa ggacaagaaa gcagacaaaa gtgttgtggc    60
ctcttcggcc acctcctctc tctcttccta cccgtccccg                         100

<210> SEQ ID NO 166
<211> LENGTH: 100
<212> TYPE: DNA
<213> ORGANISM: Homo sapiens

<400> SEQUENCE: 166
tcaaacatta aatatcccga ggtctccttg gtgggtggca ggatttaaat tcaatcaaat    60
cctgtcctag tgtgtgcagt gtcttcggcc ctgtggacac                         100

<210> SEQ ID NO 167
<211> LENGTH: 100
<212> TYPE: DNA
<213> ORGANISM: Homo sapiens

<400> SEQUENCE: 167
gccagtttag ttaactcagt cattaggggg aatgcaaact ggaagggaat acggcaatgt    60
gcaattgaag gaggaagcac actccgaaat ggaaacagac                         100

<210> SEQ ID NO 168
<211> LENGTH: 100
<212> TYPE: DNA
<213> ORGANISM: Homo sapiens

```
<400> SEQUENCE: 168
gtctctaatg agctagatga ccctgatgat ctgcaatgta agcggggaga acatgttgcg    60
ctggctaact ggcagaacca cgcatccctm cggttgttga                         100

<210> SEQ ID NO 169
<211> LENGTH: 100
<212> TYPE: DNA
<213> ORGANISM: Homo sapiens

<400> SEQUENCE: 169
cacactgggc aggaccctgc ttcatctcgg gttggtttat gggcttttac tttggagcac    60
tctgtgtgaa gctgtttggt ggaacccatg catctggtgt                         100

<210> SEQ ID NO 170
<211> LENGTH: 100
<212> TYPE: DNA
<213> ORGANISM: Homo sapiens

<400> SEQUENCE: 170
gggaagacga ttggatcaat cattgcatac tcattcacca tcatcaacac ccttcaggga    60
gtgttgctct ttgtggtaca ctgtctcctt aatcgccagg                         100

<210> SEQ ID NO 171
<211> LENGTH: 100
<212> TYPE: DNA
<213> ORGANISM: Homo sapiens

<400> SEQUENCE: 171
ccagccaggc ccaacagagc agtcctggat taggtttgat aaatagcatg gtcaaaagcc    60
caatgacaca ggcaggcttg acttctccca acatggggat                         100

<210> SEQ ID NO 172
<211> LENGTH: 100
<212> TYPE: DNA
<213> ORGANISM: Homo sapiens

<400> SEQUENCE: 172
catccttcca cctgctgggg caccattctt agtatacaga ggtggcctta cacacatctt    60
gcatggatgg cagcattgtt ctgaaggggt ttgcagaaaa                         100

<210> SEQ ID NO 173
<211> LENGTH: 100
<212> TYPE: DNA
<213> ORGANISM: Homo sapiens

<400> SEQUENCE: 173
tgatggccct ggaggcgggg ctgaggaaca gggaaatgcc gctgtgaagt cttaaagcac    60
ttctgcttaa actcccatgt gtgaggagtg tgcctccctg                         100

<210> SEQ ID NO 174
<211> LENGTH: 100
<212> TYPE: DNA
<213> ORGANISM: Homo sapiens

<400> SEQUENCE: 174
tgacctcttg tcatctgtgg ctctgagtgg tactaatcat gaacatgacc agccggcaca    60
cttaacctta agggatgaca gtatacctgt aaatagaaat                         100
```

<210> SEQ ID NO 175
<211> LENGTH: 100
<212> TYPE: DNA
<213> ORGANISM: Homo sapiens

<400> SEQUENCE: 175
gagagagcta aactgtgtaa tttaatggta tcttccttgc tggatgtggc agaatccaca      60
ccagcttatc aaccaacaca gctaatttta gaatagatcc                          100

<210> SEQ ID NO 176
<211> LENGTH: 100
<212> TYPE: DNA
<213> ORGANISM: Homo sapiens

<400> SEQUENCE: 176
aaaaatggat aaaggcgagc accgtcagga gcgcagagat cggccctact agatgcagag      60
accccgcaga gctgcattga ctaccagatt tattttttaa                          100

<210> SEQ ID NO 177
<211> LENGTH: 100
<212> TYPE: DNA
<213> ORGANISM: Homo sapiens

<400> SEQUENCE: 177
gattcctggt taggaactgc attaaagtcc ttacttctca tccagtccag aaagaattgt      60
gtgaatgttc tgatcactac cacccagctg gttccagccc                          100

<210> SEQ ID NO 178
<211> LENGTH: 100
<212> TYPE: DNA
<213> ORGANISM: Homo sapiens

<400> SEQUENCE: 178
ttagaacaag tagaatggga aaggagtgac tgataaatct aagattcaaa atagtcccgt      60
cgaaacttaa aggccagatt attgctttgg agctttctat                          100

<210> SEQ ID NO 179
<211> LENGTH: 100
<212> TYPE: DNA
<213> ORGANISM: Homo sapiens

<400> SEQUENCE: 179
actcttagac tcagagtcct tgggaggcag ccgcaaggcc actgacagag gggtggcccc      60
tgacagcaag acaactggca gctcataccc ttttcagctg                          100

<210> SEQ ID NO 180
<211> LENGTH: 100
<212> TYPE: DNA
<213> ORGANISM: Homo sapiens

<400> SEQUENCE: 180
ccctgacttg tagccagctt gtgtaagatc ccttgcagaa cgagaaagtt aaaaacaagc      60
ccacccagta ctcacaccat caagtctgtt atagagtgta                          100

<210> SEQ ID NO 181
<211> LENGTH: 100
<212> TYPE: DNA
<213> ORGANISM: Homo sapiens

```
<400> SEQUENCE: 181 agaccctga aatgttgcca aattcttcaa ataactgttt gggggtggg gggagatgaa      60 agagagtcgc gttttgttta cagttaaaga catccaatat                         100

<210> SEQ ID NO 182
<211> LENGTH: 100
<212> TYPE: DNA
<213> ORGANISM: Homo sapiens

<400> SEQUENCE: 182
ttctgagtat tttagtgttg ccacctggat ttgctgcatt gctctgctga gctgtattga      60
aaccatgact gggcccactg tcagacagaa attagaatag                         100

<210> SEQ ID NO 183
<211> LENGTH: 100
<212> TYPE: DNA
<213> ORGANISM: Homo sapiens

<400> SEQUENCE: 183
caggctctag atcacatggc atcaggctgg ggcagaggca tagctattgt ctcgggcatc      60
cttcccaggg ttgggtctta cacaaataga aggctcttgc                         100

<210> SEQ ID NO 184
<211> LENGTH: 100
<212> TYPE: DNA
<213> ORGANISM: Homo sapiens

<400> SEQUENCE: 184
agaaacaagc cctttaagtt tatgctaggc aagcaggagg tgatccgagg ctgggaagaa      60
ggggttgccc agatgagtgt gggtcagaga gccaaactga                         100

<210> SEQ ID NO 185
<211> LENGTH: 100
<212> TYPE: DNA
<213> ORGANISM: Homo sapiens

<400> SEQUENCE: 185
cagacctgag ctggctttgg aatgaggtta aagtgtcagg gacgttgcct gagcccaaat      60
gtgtagtgtg gtctgggcag gcagacccttt aggttttgct                         100

<210> SEQ ID NO 186
<211> LENGTH: 100
<212> TYPE: DNA
<213> ORGANISM: Homo sapiens

<400> SEQUENCE: 186
tgtgtgttgc actaattcta aactttggag gcattttgct gtgtgaggcc gatcgccact      60
gtaaaggtcc tagagttgcc tgtttgtctc tggagatgga                          100

<210> SEQ ID NO 187
<211> LENGTH: 100
<212> TYPE: DNA
<213> ORGANISM: Homo sapiens

<400> SEQUENCE: 187 tttttttgccg taggcaccat tctgcatctt gaacccagac tgaagtgtgc ctctcacaga      60
tggaaggtgc acacgctcct gtctcctcct cactctgcca                          100
```

<210> SEQ ID NO 188
<211> LENGTH: 100
<212> TYPE: DNA
<213> ORGANISM: Homo sapiens

<400> SEQUENCE: 188
cttgtcctcc cagctgagct ttcttattcc acccttctg gtgtctatag gaatgcatga    60
gagaccctgg acgtttttct gctctcttct ggccctccat                        100

<210> SEQ ID NO 189
<211> LENGTH: 100
<212> TYPE: DNA
<213> ORGANISM: Homo sapiens

<400> SEQUENCE: 189
ggactcagag gccgccatca accgccagat caacctagag ctctgtgcct cctacgttta    60
cctgtccatg tcttactgct ttgaccgtga tgatgtggct                        100

<210> SEQ ID NO 190
<211> LENGTH: 100
<212> TYPE: DNA
<213> ORGANISM: Homo sapiens

<400> SEQUENCE: 190
gtccagttga ttgtacgtag ccacaggagc cctgctatga aggaataaa acctacacac    60 aaggttggag cttttgcaatt cttttggaa aagagctggg                        100

<210> SEQ ID NO 191
<211> LENGTH: 100
<212> TYPE: DNA
<213> ORGANISM: Homo sapiens

<400> SEQUENCE: 191
actcgcgctg gccggccggg ggaagggacc cgcacgccgg gctttgttgt ggaaatcccg    60
gttacctggc ttataaccca caccatggat aacttattgg                        100

<210> SEQ ID NO 192
<211> LENGTH: 100
<212> TYPE: DNA
<213> ORGANISM: Homo sapiens

<400> SEQUENCE: 192
aaagcatagt tggtcttggt gtcatatgga tcagaggcac aagtgcagag gctgtggtca    60
tgcggaacac tctgttattt aagatggcta tccagataat                        100

<210> SEQ ID NO 193
<211> LENGTH: 100
<212> TYPE: DNA
<213> ORGANISM: Homo sapiens

<400> SEQUENCE: 193
tacagcaggt gaacagtcta caaggtcttt tatcttggat aaaatcattg aagaggatga    60
tgcttatgac ttcagtacag attatgtgta acagaacaat                        100

<210> SEQ ID NO 194
<211> LENGTH: 100
<212> TYPE: DNA
<213> ORGANISM: Homo sapiens

```
<400> SEQUENCE: 194
cctgtgtttg catcctctgt tcctattctg cccttgctct gtgtcatctc agtcatttga      60
cttagaaagt gcccttcaaa aggaccctgt tcactgctgc                            100

<210> SEQ ID NO 195
<211> LENGTH: 100
<212> TYPE: DNA
<213> ORGANISM: Homo sapiens

<400> SEQUENCE: 195
ctcactgacc ggaaggtcca ggtgaatctc gtcataagtg atctcaggct ctcacaggat      60
ccggagggaa atgtgttaga gggtctggaa aattcagtgc                            100

<210> SEQ ID NO 196
<211> LENGTH: 100
<212> TYPE: DNA
<213> ORGANISM: Homo sapiens

<400> SEQUENCE: 196
agtctgggag cagcagtctt cgtggctggt tcagggtgtt ttgttccgag cctgcctgcc      60
tgccggttct atacctcagg ggcattttta caaaaagccc                            100

<210> SEQ ID NO 197
<211> LENGTH: 100
<212> TYPE: DNA
<213> ORGANISM: Homo sapiens

<400> SEQUENCE: 197
cagtgctcaa gtgacctctc acgacgcttc taccaatggg ctcatcaact tcatcaagca      60
gcagcgcgag gccagagtcc aataaactcg tgctcatctg                            100

<210> SEQ ID NO 198
<211> LENGTH: 100
<212> TYPE: DNA
<213> ORGANISM: Homo sapiens

<400> SEQUENCE: 198
tatgattttt ctcactcttt ctttggactc cagggtgtca gccatcaggt ctcctaattt      60
tgtgtaccgg tctccaacaa ccccagctac tgaatactgc                            100

<210> SEQ ID NO 199
<211> LENGTH: 100
<212> TYPE: DNA
<213> ORGANISM: Homo sapiens

<400> SEQUENCE: 199
agagctctac ttacagaaca gccctgaggc ctgtgactat gggctctgaa ggggcagga       60 gtcagcaata aagctatgtc tgatattttc cttcactaat                            100

<210> SEQ ID NO 200
<211> LENGTH: 100
<212> TYPE: DNA
<213> ORGANISM: Homo sapiens

<400> SEQUENCE: 200
ggtatcccca ctcagtagcc aagtcacaat gtttggaaaa cagcctgttt acttgagcaa      60
gactgatacc acctgcgtgt cccttcctcc ccgagtcagg                            100
```

<210> SEQ ID NO 201
<211> LENGTH: 100
<212> TYPE: DNA
<213> ORGANISM: Homo sapiens

<400> SEQUENCE: 201
gcctccgagg tggaagagac tcgtgcaatg gagattctgg aagcccttttg ttgtgcgagg      60 gtgttttccg aggggtcact tcctttggcc ttgaaaataa                           100

<210> SEQ ID NO 202
<211> LENGTH: 100
<212> TYPE: DNA
<213> ORGANISM: Homo sapiens

<400> SEQUENCE: 202
acactacaag aggtgaagat gacagtgcag gaagatcgaa agtgcgaatc tgacttacgc      60
cattattacg acagtaccat tgagttgtgc gtgggggacc                           100

<210> SEQ ID NO 203
<211> LENGTH: 100
<212> TYPE: DNA
<213> ORGANISM: Homo sapiens

<400> SEQUENCE: 203
ggcccctcgt gtgtaaggac gtagcccaag gtattctctc ctatggaaac aaaaaaggga      60
cacctccagg agtctacatc aaggtctcac acttcctgcc                           100

<210> SEQ ID NO 204
<211> LENGTH: 100
<212> TYPE: DNA
<213> ORGANISM: Homo sapiens

<400> SEQUENCE: 204
aaccaaatag aaataagcat gcaacatgaa cagctggaag agagttttca ggaactagtg      60
gaagattacc ggcgtgttat tgaacgactt gctcaagagt                           100

<210> SEQ ID NO 205
<211> LENGTH: 100
<212> TYPE: DNA
<213> ORGANISM: Homo sapiens

<400> SEQUENCE: 205
tatatgaagt ggaggagccc aatgagtatt attgctatgt cagcagcagg cagcaaccct      60
cacaaccttt gggttgtcgc tttgcaatgc catagatcca                           100

<210> SEQ ID NO 206
<211> LENGTH: 100
<212> TYPE: DNA
<213> ORGANISM: Homo sapiens

<400> SEQUENCE: 206
aagatgaaga gagagagatt tggaaggggc tctggctccc taacacctga atcccagatg      60
atgggaagta tgttttcaag tgtggggagg atatgaaaat                           100

<210> SEQ ID NO 207
<211> LENGTH: 100
<212> TYPE: DNA
<213> ORGANISM: Homo sapiens

<400> SEQUENCE: 207
caatcgacat ggacaactac atgctctcga gaaacgtgga caacgccgag ggctccgaca    60
ctgactactg accgtgcggg tgctctcacc ctcccttctc                          100

<210> SEQ ID NO 208
<211> LENGTH: 100
<212> TYPE: DNA
<213> ORGANISM: Homo sapiens

<400> SEQUENCE: 208
taagaatgat ttagactgac ctgtcctttt ttatctgcgc atgcgagaac atcaccttcc    60
tctgtacact tggaaatgcc tctggcttgt tgcagccctc                          100

<210> SEQ ID NO 209
<211> LENGTH: 100
<212> TYPE: DNA
<213> ORGANISM: Homo sapiens

<400> SEQUENCE: 209
agtcagagga tgggtccggc aaaggtgcgg ccctggtcac cgctgttgcc tgccgccttg    60
cgcagttgac tcgtgtctga ggaaacctcc aggctgagga                          100

<210> SEQ ID NO 210
<211> LENGTH: 100
<212> TYPE: DNA
<213> ORGANISM: Homo sapiens

<400> SEQUENCE: 210
ccctgagatg ggagccgtct tcccagtcca ccgtccccat cgtgggcatt gttgctggcc    60
tggctgtcct agcagttgtg gtcatcggag ctgtggtcgc                          100

<210> SEQ ID NO 211
<211> LENGTH: 100
<212> TYPE: DNA
<213> ORGANISM: Homo sapiens

<400> SEQUENCE: 211
cccgtgagct ggaaggaaca gatttaatat ctagggctg ggtatcccca catcactcat    60 ttgggggtc aagggacccg ggcaatatag tattctgctc                           100

<210> SEQ ID NO 212
<211> LENGTH: 100
<212> TYPE: DNA
<213> ORGANISM: Homo sapiens

<400> SEQUENCE: 212
aagagctcag attgaaaagg agggagctac tctcaggctg caatgtgaaa cagctgccct    60
gtgtgggact gagtggcaag tccctttgtg acttcaagaa                          100

<210> SEQ ID NO 213
<211> LENGTH: 100
<212> TYPE: DNA
<213> ORGANISM: Homo sapiens

<400> SEQUENCE: 213
tatgcatttt ttgtgcaaac ttgtcgggag gagcataaga agaagcaccc agatgcttca    60
gtcaacttct cagagttttc taagaagtgc tcagagaggt                          100

<210> SEQ ID NO 214
<211> LENGTH: 100
<212> TYPE: DNA
<213> ORGANISM: Homo sapiens

<400> SEQUENCE: 214
tgctgcatat cgtgccaagg gcaaaagtga agcaggaaag aagggccctg gcaggccaac     60
aggctcaaag aagaagaacg aaccagaaga tgaggaggag                         100

<210> SEQ ID NO 215
<211> LENGTH: 100
<212> TYPE: DNA
<213> ORGANISM: Homo sapiens

<400> SEQUENCE: 215
ccccatggaa atcactctcc tgttgactat ttccagagct ctaggtgttt aggcagcgtg     60
tggtgtctga gaggccatag cgccatcatg ggctgatttt                         100

<210> SEQ ID NO 216
<211> LENGTH: 100
<212> TYPE: DNA
<213> ORGANISM: Homo sapiens

<400> SEQUENCE: 216
tccctacctt ggaagagggc ctgcagttgc catcacccac tgcaaccagc cagctcccgc     60
tcgaatctga tgctgtggaa tgcttaaatt accaacacta                         100

<210> SEQ ID NO 217
<211> LENGTH: 100
<212> TYPE: DNA
<213> ORGANISM: Homo sapiens

<400> SEQUENCE: 217
gcaaggtaga gaagttgtgc cgctcaatca cagacacctg cacccacaac atacttctgt     60
tacacacaag aacatttcag gaaactcagc cagcttattt                         100

<210> SEQ ID NO 218
<211> LENGTH: 100
<212> TYPE: DNA
<213> ORGANISM: Homo sapiens

<400> SEQUENCE: 218
aacaatagga agctatgtgt atcttctgtg taaagcagtg gcttcactgg aaaaatggtg     60
tggctagcat ttccctttga gtcatgatga cagatggtgt                         100

<210> SEQ ID NO 219
<211> LENGTH: 100
<212> TYPE: DNA
<213> ORGANISM: Homo sapiens

<400> SEQUENCE: 219
gaggttccta taattgtctc tgagtaaccc tttggaatgg agagggtgtt ggtcagtcta     60
caaactgaac actgcagttc tgcgcttttt accagtgaaa                         100

<210> SEQ ID NO 220
<211> LENGTH: 100
<212> TYPE: DNA
<213> ORGANISM: Homo sapiens

<400> SEQUENCE: 220
tccacccaga tttcttcagc cagaggtctc agactgaaaa ggacttctca gagaagcatt      60
cgaccctggt gaatgatgcc tataagaccc tcctggcccc                            100

<210> SEQ ID NO 221
<211> LENGTH: 100
<212> TYPE: DNA
<213> ORGANISM: Homo sapiens

<400> SEQUENCE: 221
gcctactact actattctgc aaacgaggaa ttcagaccag agatgctcca aggaaagaaa      60
gtgattgtca caggggccag caaagggatc ggaagagaga                            100

<210> SEQ ID NO 222
<211> LENGTH: 100
<212> TYPE: DNA
<213> ORGANISM: Homo sapiens

<400> SEQUENCE: 222
ggcattctct aaaaatctca agcttggaat ccacgaagac tccactaacc gccgccgcct      60
gtctgagctg ctgcgctatc atacctccca gtctggagat                            100

<210> SEQ ID NO 223
<211> LENGTH: 100
<212> TYPE: DNA
<213> ORGANISM: Homo sapiens

<400> SEQUENCE: 223
gtggcactca agcccgccag ggggacccca gcaccggccc catcattgag gaggttgatt      60
gaatggccct tcgtgataag tcagctgtga ctgtcagggc                            100

<210> SEQ ID NO 224
<211> LENGTH: 100
<212> TYPE: DNA
<213> ORGANISM: Homo sapiens

<400> SEQUENCE: 224
ccaccaactc accgtgtgtg tcccagctgc cccatcttcc ccagcgcata cctgttcctc      60
ttctcattct ctccccgccg cctgtttcct caccttctct                            100

<210> SEQ ID NO 225
<211> LENGTH: 100
<212> TYPE: DNA
<213> ORGANISM: Homo sapiens

<400> SEQUENCE: 225
tgttccagga gcaccagttt gaggctctgg gcctgctgat tctgctccgg ctgtggcggg      60
tggcccggat catcaatggg attatcatct cagttaagac                            100

<210> SEQ ID NO 226
<211> LENGTH: 100
<212> TYPE: DNA
<213> ORGANISM: Homo sapiens

<400> SEQUENCE: 226
ctattataag atgctctgaa aactcttcag acactgaggg gcaccagagg agcagactac      60
aagaatggca cacgctatgg aaaactcctg gacaatcagt                            100

<210> SEQ ID NO 227
<211> LENGTH: 100
<212> TYPE: DNA
<213> ORGANISM: Homo sapiens

<400> SEQUENCE: 227
tggatggaca tcaggcaacg ggaagacgtc caagccttaa acatcagtgt gccgtatggt    60
ccaattcctg tggactttca gcggaaaatc cgccagagct    100

<210> SEQ ID NO 228
<211> LENGTH: 100
<212> TYPE: DNA
<213> ORGANISM: Homo sapiens

<400> SEQUENCE: 228
actttacacc tacccctcac cggaaagcta gacccgcttc agggccagga gtggcgtttc    60
cgcacaggat ttcctaagac gagagggatt tagccaagag    100

<210> SEQ ID NO 229
<211> LENGTH: 100
<212> TYPE: DNA
<213> ORGANISM: Homo sapiens

<400> SEQUENCE: 229
gtcagtgttg ggggcctgct tgggaattc accttcttct tctctcccag ctgaacccga    60
ggctaaagaa gatgaggcaa gagaaaatgt accccaaggt    100

<210> SEQ ID NO 230
<211> LENGTH: 100
<212> TYPE: DNA
<213> ORGANISM: Homo sapiens

<400> SEQUENCE: 230
tgagatgatc cagcagacct tcaatctctt cagcacagag gactcatctg ctgcttggga    60
acagagcctc ctagaaaaat tttccactga actttaccag    100

<210> SEQ ID NO 231
<211> LENGTH: 100
<212> TYPE: DNA
<213> ORGANISM: Homo sapiens

<400> SEQUENCE: 231
ctaatcagct ctcagtgatc aacccactct tgttatgggt ggtctctgtc actttgaatg    60
ccaggctggc ttctcgtcta gcagtattca gataccoctt    100

<210> SEQ ID NO 232
<211> LENGTH: 100
<212> TYPE: DNA
<213> ORGANISM: Homo sapiens

<400> SEQUENCE: 232
aaataccaca agatcatttt gtgacctcac agatgagtgg agaagcacac acgaggccta    60
tgtcaccgtc ctagaaggat tcagcgggaa cacaacgttg    100

<210> SEQ ID NO 233
<211> LENGTH: 100
<212> TYPE: DNA
<213> ORGANISM: Homo sapiens

```
<400> SEQUENCE: 233
cccgggcagc catctgactc caatagagag agagagttct tcacctttaa gtagtaacca        60
gtctgaacct ggcagcatcg ctttaaactc gtatcactcc                            100

<210> SEQ ID NO 234
<211> LENGTH: 100
<212> TYPE: DNA
<213> ORGANISM: Homo sapiens

<400> SEQUENCE: 234
atcggaatcc cgacacctgt cctcatctgg aacaaggtaa aaagggggtca ctatggagtt       60 caaaggacag aactcctgcc tggtgaccgg gacaacctgg                             100

<210> SEQ ID NO 235
<211> LENGTH: 100
<212> TYPE: DNA
<213> ORGANISM: Homo sapiens

<400> SEQUENCE: 235
ggcatctcca acatcatcat ccaacgaaga ctcagctgca aatggttctg ctgaaacatc        60
tgccttggac acagggttct cgctcaacct ttcagagctg                            100

<210> SEQ ID NO 236
<211> LENGTH: 100
<212> TYPE: DNA
<213> ORGANISM: Homo sapiens

<400> SEQUENCE: 236
gggaccaaag gcggccagga tataactgac ttcaccatgc aatttgtgtc ttcctaaaga        60
gagctgtacc cagagagtcc tgtgctgaat gtggactcaa                            100

<210> SEQ ID NO 237
<211> LENGTH: 100
<212> TYPE: DNA
<213> ORGANISM: Homo sapiens

<400> SEQUENCE: 237
tgcttctgcc acgtgctgct gggtctcagt cctccacttc ccgtgtcctc tggaagttgt        60
caggagcaat gttgcgcttg tacgtgttgg taatgggagt                            100

<210> SEQ ID NO 238
<211> LENGTH: 100
<212> TYPE: DNA
<213> ORGANISM: Homo sapiens

<400> SEQUENCE: 238
gacactcgct gcctgggtgc gactgcacag cagttccaca ggcacaagca gctgatccga        60
ttcctgaaac ggctcgacag gaacctctgg ggcctggcgg                            100

<210> SEQ ID NO 239
<211> LENGTH: 100
<212> TYPE: DNA
<213> ORGANISM: Homo sapiens

<400> SEQUENCE: 239
aataacccag cttgcgtcct gcacacttgt ggcttccgtg cacacattaa caactcatgg        60
ttctagctcc cagtcgccaa gcgttgccaa ggcgttgaga                            100
```

<210> SEQ ID NO 240
<211> LENGTH: 100
<212> TYPE: DNA
<213> ORGANISM: Homo sapiens

<400> SEQUENCE: 240
cccacgtgtc agaacagcag ctataaaagc catgttgcag ctccatgaaa gaggactgaa     60
attacaccaa acaatttata atcaggcctg taaattactc                          100

<210> SEQ ID NO 241
<211> LENGTH: 100
<212> TYPE: DNA
<213> ORGANISM: Homo sapiens

<400> SEQUENCE: 241
gtgttggccg aggtcctcac gggcatccct gcaatggata caaccgaag cccggtttac      60 ctgaaggact tactcctcag tgatattcca agcagcaccg                          100

<210> SEQ ID NO 242
<211> LENGTH: 100
<212> TYPE: DNA
<213> ORGANISM: Homo sapiens

<400> SEQUENCE: 242
ctgtgcgagt gtaccggatg cttccacctc tcaccaagaa ccagagaaaa gaaagaaagt     60
cgaagtccag ccgagatgct aagagcaagg ccaagaggaa                          100

<210> SEQ ID NO 243
<211> LENGTH: 100
<212> TYPE: DNA
<213> ORGANISM: Homo sapiens

<400> SEQUENCE: 243
gggcactgtt taaaggaaag ttccgagaag gcatcgacaa gccggaccct cccacctgga     60
agacgcgcct gcggtgcgct ttgaacaaga gcaatgactt                          100

<210> SEQ ID NO 244
<211> LENGTH: 100
<212> TYPE: DNA
<213> ORGANISM: Homo sapiens

<400> SEQUENCE: 244
atggatggga ctcttatgtc ataacttctg ttactccttt ggcccatagc taaggtcatc     60
cttccccaca ggggtggctt tgggattgga tgatacagct                          100

<210> SEQ ID NO 245
<211> LENGTH: 100
<212> TYPE: DNA
<213> ORGANISM: Homo sapiens

<400> SEQUENCE: 245
gaggtgacaa agagccaaca gagacaatag gagacttgtc aatttgtctt gatgggctac     60
agttagagtc tgaagttgtt accaatggtg aaactacatg                          100

<210> SEQ ID NO 246
<211> LENGTH: 100
<212> TYPE: DNA
<213> ORGANISM: Homo sapiens

<400> SEQUENCE: 246
gtctggtctt acccatgttc ctagcaaccc tgagatgatt ttcttccatt taccaaagca    60
gccgggtcag tgctttctca cgttgccgta ttcttcaggt    100

<210> SEQ ID NO 247
<211> LENGTH: 100
<212> TYPE: DNA
<213> ORGANISM: Homo sapiens

<400> SEQUENCE: 247
ctgaatgcag agaaccacag aactaagatc actgtcgtct tcctgaaaga tgagaagtac    60
cattctttgc ctatcatcat taaaggcagc gttggtggac    100

<210> SEQ ID NO 248
<211> LENGTH: 100
<212> TYPE: DNA
<213> ORGANISM: Homo sapiens

<400> SEQUENCE: 248
gtgagggctt gtcattacca gacggttcac cagcctctct tggtttcctt ccttggaaga    60
gaatgtctga tctaaatgtg gagaaactgt agtctcagga    100

<210> SEQ ID NO 249
<211> LENGTH: 100
<212> TYPE: DNA
<213> ORGANISM: Homo sapiens

<400> SEQUENCE: 249
gagaacacca agctctggta tgctccaaat cgcaccatca ccgttgatga caagatgtcc    60
ctccggctcc actaccggat gaggttctat ttcaccaatt    100

<210> SEQ ID NO 250
<211> LENGTH: 100
<212> TYPE: DNA
<213> ORGANISM: Homo sapiens

<400> SEQUENCE: 250
ccttcacatc cagatccctg tcggtgttag ttccactctt ggtctttcac gctccccttg    60
cctgtggaac attgtctggt cctagctgtg gttcccattg    100

<210> SEQ ID NO 251
<211> LENGTH: 100
<212> TYPE: DNA
<213> ORGANISM: Homo sapiens

<400> SEQUENCE: 251
cccagactgt agccatgcag ggtcctgcac ggactttaac gatgcaaaga ggcatgaaca    60
tgagtgtgaa cctgatgcca gcgccagcct acaatgtcaa    100

<210> SEQ ID NO 252
<211> LENGTH: 100
<212> TYPE: DNA
<213> ORGANISM: Homo sapiens

<400> SEQUENCE: 252
acaagtaaaa taacttgaca tgagcacctt tagatcccct tccctccatg ggctttgggc    60
cacagaatga acctttgagg cctgtaaagt ggattgtaat    100

<210> SEQ ID NO 253
<211> LENGTH: 100
<212> TYPE: DNA
<213> ORGANISM: Homo sapiens

<400> SEQUENCE: 253
cgacatcagt ttcatcgagg aaagctgaaa ataaatatgc aggagggaac cccgtttgcg    60
tgcgcccaac tcccaagtgg caaaaaggaa ttggagaatt                         100

<210> SEQ ID NO 254
<211> LENGTH: 100
<212> TYPE: DNA
<213> ORGANISM: Homo sapiens

<400> SEQUENCE: 254
atcgtgccca gtgttaacct cggctggcct tcactaaggg gactagacct ccctctcccc    60
aggagcccca gccccagagt ggtttgcaat aatcaagata                         100

<210> SEQ ID NO 255
<211> LENGTH: 100
<212> TYPE: DNA
<213> ORGANISM: Homo sapiens

<400> SEQUENCE: 255
gaggtgacat atgcacagtt ggatcactgc gttttcacac agacaaaaat cacttcccct    60
tctcagaggc ccaagacacc tccaacagat accaccatgt                         100

<210> SEQ ID NO 256
<211> LENGTH: 100
<212> TYPE: DNA
<213> ORGANISM: Homo sapiens

<400> SEQUENCE: 256
tccgaaaccg gtaaccccag acacctacat gttctgattg ggacctcagt ggtcaaaatc    60
cctttcacca tcctcctctt ctttctcctt catcgctggt                         100

<210> SEQ ID NO 257
<211> LENGTH: 100
<212> TYPE: DNA
<213> ORGANISM: Homo sapiens

<400> SEQUENCE: 257
ccggcagcac catgtcgctc atggtcatca gcatggcatg tgttgggttc ttctggctgc    60 aggggggcctg gccacatgag ggattccgca gaaaaccttc                        100

<210> SEQ ID NO 258
<211> LENGTH: 100
<212> TYPE: DNA
<213> ORGANISM: Homo sapiens

<400> SEQUENCE: 258
cagcaactcc gagagaaatg cttgttattt tctcacactg tcaacccttg gaataacagt    60
ctagctgatt gttccaccaa agaatccagc ctgctgctta                         100

<210> SEQ ID NO 259
<211> LENGTH: 100
<212> TYPE: DNA
<213> ORGANISM: Homo sapiens

<400> SEQUENCE: 259
acctatcact gcaaagattt accatcagct ccagagaagc tcattgttgg gatcctggga    60
attatctgtc ttatcttaat ggcctctgtg gtaacgatag    100

<210> SEQ ID NO 260
<211> LENGTH: 100
<212> TYPE: DNA
<213> ORGANISM: Homo sapiens

<400> SEQUENCE: 260
tatgtgagtc agcttatagg aagtaccaag aacagtcaaa cccatggaga cagaaagtag    60
aatagtggtt gccaatgtct cagggaggtt gaaataggag    100

<210> SEQ ID NO 261
<211> LENGTH: 100
<212> TYPE: DNA
<213> ORGANISM: Homo sapiens

<400> SEQUENCE: 261
caattttact ggattggact ctcttacagt gaggagcaca ccgcctggtt gtgggagaat    60
ggctctgcac tctcccagta tctatttcca tcatttgaaa    100

<210> SEQ ID NO 262
<211> LENGTH: 100
<212> TYPE: DNA
<213> ORGANISM: Homo sapiens

<400> SEQUENCE: 262
tatacagaaa aacctaagac aattaaacta cgtatggatt gggcttaact ttacctcctt    60
gaaaatgaca tggacttggg tggatggttc tccaatagat    100

<210> SEQ ID NO 263
<211> LENGTH: 100
<212> TYPE: DNA
<213> ORGANISM: Homo sapiens

<400> SEQUENCE: 263
aagtgcaatt aaatgccaaa atctcttctc ccttctccct ccatcatcga cactggtcta    60
gcctcagagt aacccctgtt aacaaactaa aatgtacact    100

<210> SEQ ID NO 264
<211> LENGTH: 100
<212> TYPE: DNA
<213> ORGANISM: Homo sapiens

<400> SEQUENCE: 264
ctgctgccag gcggcctgtg agcccagccc ctgccagtca ggctgcacca gctcctgcac    60
gccctcgtgc tgccagcagt ctagctgcca gccagcttgc    100

<210> SEQ ID NO 265
<211> LENGTH: 100
<212> TYPE: DNA
<213> ORGANISM: Homo sapiens

<400> SEQUENCE: 265
ttgcctgctg gtgttcctac aagtatttaa atgcaggagc aggaggaatt gctggtgcct    60
tcattcatga aaagcatgcc catacgatta aacctgcgag    100

<210> SEQ ID NO 266
<211> LENGTH: 100
<212> TYPE: DNA
<213> ORGANISM: Homo sapiens

<400> SEQUENCE: 266
ccaaccccgg cccctggtca ggcccctgca gctgcctcac accgcccctt gtgctcgcct    60
cataggtgtc tatttggact ctaagctcta cgggtgacag    100

<210> SEQ ID NO 267
<211> LENGTH: 100
<212> TYPE: DNA
<213> ORGANISM: Homo sapiens

<400> SEQUENCE: 267
atcttgtgta gtcttcaact ggttagtgtg aaatagttct gccacctctg acgcaccact    60
gccaatgctg tacgtactgc atttgcccct tgagccaggt    100

<210> SEQ ID NO 268
<211> LENGTH: 100
<212> TYPE: DNA
<213> ORGANISM: Homo sapiens

<400> SEQUENCE: 268
aacacatagt ggcttctccg cccttgtaag gtgttcagta gagctaaata aatgtaatag    60
ccaaacccac tctgttggta gcaattggca gccctatttc    100

<210> SEQ ID NO 269
<211> LENGTH: 100
<212> TYPE: DNA
<213> ORGANISM: Homo sapiens

<400> SEQUENCE: 269
aaaggaccca tcacttcttc tgaagaacct acactccagg ccaaatcaca aatgacggcc    60
cagaacagca aggctagttc aaaaggagca taaaggacta    100

<210> SEQ ID NO 270
<211> LENGTH: 100
<212> TYPE: DNA
<213> ORGANISM: Homo sapiens

<400> SEQUENCE: 270
gggatggaag gctgtcttct tttgaggatg atcagagaac ttgggcatag gaacaatctg    60
gcagaagttt ccagaaggag gtcacttggc attcaggctc    100

<210> SEQ ID NO 271
<211> LENGTH: 100
<212> TYPE: DNA
<213> ORGANISM: Homo sapiens

<400> SEQUENCE: 271
ttgaatgctg gagccttgga agcgaatctg atggtcctag gaggttcggg aagaccatct    60
gaggcctatg ccatctggac tgtctgctgg caatttcttt    100

<210> SEQ ID NO 272
<211> LENGTH: 100
<212> TYPE: DNA
<213> ORGANISM: Homo sapiens

<400> SEQUENCE: 272 cacccctctca gccctgccca gtcctgtggt gacctcagga gagaacgtga ccctccagtg        60
tggctcacgg ctgagattcg acaggttcat tctgactgag                              100

<210> SEQ ID NO 273
<211> LENGTH: 100
<212> TYPE: DNA
<213> ORGANISM: Homo sapiens

<400> SEQUENCE: 273
gcggcagcca atcagcgcgc ggcttctata gggcttgagt tattagacgc tgatctcaaa        60
acatccttca tcagacacga aggagaggcc aacagatgag                              100

<210> SEQ ID NO 274
<211> LENGTH: 100
<212> TYPE: DNA
<213> ORGANISM: Homo sapiens

<400> SEQUENCE: 274
agggtcatgc agctactgag gtcacagcct ggattcatac acaggtctga ctcctgagca        60
cttagccagg tggctgtaac agtgttccca gaaacacagg                              100

<210> SEQ ID NO 275
<211> LENGTH: 100
<212> TYPE: DNA
<213> ORGANISM: Homo sapiens

<400> SEQUENCE: 275
acctgtcttc cgggtctgtt cacccgtccc ctggactggc accagcacag agggtcgagt        60
gttggcacct gtcttctggg tctccatccc tccctttgtt                              100

<210> SEQ ID NO 276
<211> LENGTH: 100
<212> TYPE: DNA
<213> ORGANISM: Homo sapiens

<400> SEQUENCE: 276
gagaatgtct gcgcggagac agcatagctc tgtagaaatg agtggcagcg tatgtaacct        60
ggcattttga acccaggagc acaattttat taaaggaaaa                              100

<210> SEQ ID NO 277
<211> LENGTH: 100
<212> TYPE: DNA
<213> ORGANISM: Homo sapiens

<400> SEQUENCE: 277
gagtagtagg tggacagccg tcccacacaa gggtttgtat ctgggctaca cagattccct        60
tcagaaaagc accaatgtaa gcaactccct tacagttgct                              100

<210> SEQ ID NO 278
<211> LENGTH: 100
<212> TYPE: DNA
<213> ORGANISM: Homo sapiens

<400> SEQUENCE: 278
gagatagctt cctgaaatgt gtgaaggaaa atgatcagaa aaagaaagaa gccaaagaga        60
aaggtacctg ggttcaacta aagtgccagc ctgctccacc                              100

<210> SEQ ID NO 279
<211> LENGTH: 100
<212> TYPE: DNA
<213> ORGANISM: Homo sapiens

<400> SEQUENCE: 279
gctctgtcct ttgccgctca gaccaaaaac cttagagctg tctttgactt ctgtctttcc    60
cttccaccca cagttaacca ggaaatcctg ccatctccgc                          100

<210> SEQ ID NO 280
<211> LENGTH: 100
<212> TYPE: DNA
<213> ORGANISM: Homo sapiens

<400> SEQUENCE: 280
ggttacagcc attttgtgtg attcacttcg ggggttaagt aatgcaggat tctgcaaaca    60
aggtgtcgcc gtccaaatgt actgtcctgg catagagagc                          100

<210> SEQ ID NO 281
<211> LENGTH: 100
<212> TYPE: DNA
<213> ORGANISM: Homo sapiens

<400> SEQUENCE: 281
acatggcgcc acggccactt cctgctgccc tggaccccgc aagcccaggg acatccaaga    60
gcacccctcc tgagacccca gactcagaag cagcgagaag                          100

<210> SEQ ID NO 282
<211> LENGTH: 100
<212> TYPE: DNA
<213> ORGANISM: Homo sapiens

<400> SEQUENCE: 282
cccctggtgg accgcgacct ccgcaagacg ctaatggtgc gcgacaacct ggccttcggc    60
ggcccggagg tctgagccga cttgcaaagg ggataggcgg                          100

<210> SEQ ID NO 283
<211> LENGTH: 100
<212> TYPE: DNA
<213> ORGANISM: Homo sapiens

<400> SEQUENCE: 283
gcaaagcact atcacaagga atataggcaa atgtacagaa ctgaaattcg agtggcgagg    60
atggcaagaa aagctggcaa cttctatgta cctgcagaac                          100

<210> SEQ ID NO 284
<211> LENGTH: 100
<212> TYPE: DNA
<213> ORGANISM: Homo sapiens

<400> SEQUENCE: 284
aagattatgt cttccctgt ttccaaagag ctgagacaga agtacaatgt gcaatccatg     60
cccatccgaa aggatgatga agttcaggtt gtacgagggc                          100

<210> SEQ ID NO 285
<211> LENGTH: 100
<212> TYPE: DNA
<213> ORGANISM: Homo sapiens

<400> SEQUENCE: 285
atgggaccca ctctactgag gctttatgta gaactcatag aggaagctgg ctttgaggaa    60
tgaactaccc tgtgcttttc ttaggactaa aatctcagga                         100

<210> SEQ ID NO 286
<211> LENGTH: 100
<212> TYPE: DNA
<213> ORGANISM: Homo sapiens

<400> SEQUENCE: 286
gacggtaacc gggacccagt gtctgctcct gtcaccttcg cctcctaatc cctagccact    60
atgcgagatg actccttcaa caccttcagt gagacgggtg                         100

<210> SEQ ID NO 287
<211> LENGTH: 100
<212> TYPE: DNA
<213> ORGANISM: Homo sapiens

<400> SEQUENCE: 287
gagttttcca aaccctggat ttccttcgga gagagctaga ttctattcca ttcttggaat    60
tcagctcctt gcccttctct gtgaccccgg atcgcgaatg                         100

<210> SEQ ID NO 288
<211> LENGTH: 100
<212> TYPE: DNA
<213> ORGANISM: Homo sapiens

<400> SEQUENCE: 288
tgttgcaaaa gccaactacc actgtcaaac ttagcccgtt tacaacatgg ggaaaggcgt    60
atttcttact aatatctcaa caacgataac aatgctgtat                         100

<210> SEQ ID NO 289
<211> LENGTH: 100
<212> TYPE: DNA
<213> ORGANISM: Homo sapiens

<400> SEQUENCE: 289
cgggtgcagc gggaaaaggc taatggcaca actgtccacg taggcattca ccccagcaag    60
gtggttatca ctaggctaaa actggacaaa gactgtgaaa                         100

<210> SEQ ID NO 290
<211> LENGTH: 100
<212> TYPE: DNA
<213> ORGANISM: Homo sapiens

<400> SEQUENCE: 290
ggtgaagaat ttgttctatt atgaagatac tgtctggct aaaaagctta cagtgagtgg     60
aagatagcaa cttgtagggt tggtggctga acaggccgac                         100

<210> SEQ ID NO 291
<211> LENGTH: 100
<212> TYPE: DNA
<213> ORGANISM: Homo sapiens

<400> SEQUENCE: 291
ctggctcaag gatggcacgg tgttatgtga gctcaataat gcactgtacc ccaaggggca    60
ggtcccagta aagaagatcc aggcctccac catggccttc                         100

<210> SEQ ID NO 292
<211> LENGTH: 100
<212> TYPE: DNA
<213> ORGANISM: Homo sapiens

<400> SEQUENCE: 292
caggcgctgc aagttctccc aggagaaagc catgttcagt tcgagcgcca agatcgtgaa    60
gcccaatggc gagaagccgg acgagttcga gtccggccat                          100

<210> SEQ ID NO 293
<211> LENGTH: 100
<212> TYPE: DNA
<213> ORGANISM: Homo sapiens

<400> SEQUENCE: 293
gaagcactgg taaatgtctg ctgcattaac tcactcagac caaactttct cttatctagg    60
tccaaaagga agctgctcgg ctggaaggaa cctggtgagg                          100

<210> SEQ ID NO 294
<211> LENGTH: 100
<212> TYPE: DNA
<213> ORGANISM: Homo sapiens

<400> SEQUENCE: 294
aggtgctgca aaattaccag gaatacagtc tggccaacag catctactac tctctgaagg    60
agtccaccac tagtgagcag agtgccagga tgacagccat                          100

<210> SEQ ID NO 295
<211> LENGTH: 100
<212> TYPE: DNA
<213> ORGANISM: Homo sapiens

<400> SEQUENCE: 295
tggagagaag aatgaagagg tggtggttct gggtttgatt tgagttcacc tgtgggcagt    60
gggcagtgtc ttggtgaaag ggagcggata ctactttttg                          100

<210> SEQ ID NO 296
<211> LENGTH: 100
<212> TYPE: DNA
<213> ORGANISM: Homo sapiens

<400> SEQUENCE: 296
gcccttctgc catcaacgag gtggtgaccc aagaacatac catcaacatt cacaagcgca    60
tccatggaga gggcttcaag aagcgtgctc ctcgggcact                          100

<210> SEQ ID NO 297
<211> LENGTH: 100
<212> TYPE: DNA
<213> ORGANISM: Homo sapiens

<400> SEQUENCE: 297
gtagttgtcc actgctttcc tggatggatg ggactcttat gtcataactt ctatactcct    60
ttggcccata gctaaggtca tccttcccca caggggtggc                          100

<210> SEQ ID NO 298
<211> LENGTH: 100
<212> TYPE: DNA
<213> ORGANISM: Homo sapiens

<400> SEQUENCE: 298
ccaaaccaaa agaggcaagc aagtctgcgc tgaccccagt gagtcctggg tccaggagta    60
cgtgtatgac ctggaactga actgagctgc tcagagacag                         100

<210> SEQ ID NO 299
<211> LENGTH: 100
<212> TYPE: DNA
<213> ORGANISM: Homo sapiens

<400> SEQUENCE: 299
ccctgggtgc cccttaaccc gggcggtagc tcgttaagat ggcgaagtgt ccggtccgga    60
acacgcgaaa ccccaaatcc cgcctgcccg acctcctgac                         100

<210> SEQ ID NO 300
<211> LENGTH: 100
<212> TYPE: DNA
<213> ORGANISM: Homo sapiens

<400> SEQUENCE: 300
gcgcggttgc ggttagcggg cgcggtgcca aagctgccat ccccagctca cagctcctca    60
tatccaccct gccctcatct ttatgaattg cgtgtagacc                         100

<210> SEQ ID NO 301
<211> LENGTH: 100
<212> TYPE: DNA
<213> ORGANISM: Homo sapiens

<400> SEQUENCE: 301
gcccttcaga gctgcgggag atcattgatg agtgccgggc ccatgatccc tctgtgcggc    60
cctctgtgga tgagcagaag cgcagactta atgatgtgtt                         100

<210> SEQ ID NO 302
<211> LENGTH: 100
<212> TYPE: DNA
<213> ORGANISM: Homo sapiens

<400> SEQUENCE: 302
atgttgcatt gactagagga aagaggcatt tgttgattgt gggaaattta gcctgtttga    60
ggaaaaatca actttgggga cgagtgatcc aacactgcga                         100

<210> SEQ ID NO 303
<211> LENGTH: 100
<212> TYPE: DNA
<213> ORGANISM: Homo sapiens

<400> SEQUENCE: 303
agattgtttg cactggcgtg tggttaactg tgatcggagg aagtgcaccc gccgttttg     60 ttcagtctac ccactctcag ggtaacaatg cctcagaagc                         100

<210> SEQ ID NO 304
<211> LENGTH: 100
<212> TYPE: DNA
<213> ORGANISM: Homo sapiens

<400> SEQUENCE: 304
ccccacacac ctctcgaggc acctcccaga caccaaatgc ctcatcccca ggcaacccca    60
ctgctctggc caatgggact gtgcaagcac ccaagcagaa                         100

<210> SEQ ID NO 305
<211> LENGTH: 100
<212> TYPE: DNA
<213> ORGANISM: Homo sapiens

<400> SEQUENCE: 305
agaaaaaact taaaaatggg atgtcctaaa atgaaagctg ctcaaagtca cagaacaacc    60
gagggacaaa ggagattgga tgactgggaa gcgctggccc                         100

<210> SEQ ID NO 306
<211> LENGTH: 100
<212> TYPE: DNA
<213> ORGANISM: Homo sapiens

<400> SEQUENCE: 306
ttccaatacc cagcttgctt ccatggccaa tctaagggca gagaagaata aagtggagaa    60
accatctcct tctaccacaa atccacatat gaaccaatcc                         100

<210> SEQ ID NO 307
<211> LENGTH: 100
<212> TYPE: DNA
<213> ORGANISM: Homo sapiens

<400> SEQUENCE: 307
gggtcagtga cggacactta cctgacagcg gatccacaat attctcgtgc agtgtgtttg    60
gaatcctggt ctgggctctc gtcgttggcc ttgtagatca                         100

<210> SEQ ID NO 308
<211> LENGTH: 100
<212> TYPE: DNA
<213> ORGANISM: Homo sapiens

<400> SEQUENCE: 308
aagggagaga ctgtgaatac aacaatatca ttctccttca agggaataaa attttctaag    60
ggaaaataca aatgtgttgt tgaagctatt tctgggagcc                         100

<210> SEQ ID NO 309
<211> LENGTH: 100
<212> TYPE: DNA
<213> ORGANISM: Homo sapiens

<400> SEQUENCE: 309
tcctgaagag cgatgaaggt ggcaaagtgc tgcttccaaa gctcattgac ttttctgctc    60
agattgcaga gggaatggca tacatcgagc ggaagaacta                         100

<210> SEQ ID NO 310
<211> LENGTH: 100
<212> TYPE: DNA
<213> ORGANISM: Homo sapiens

<400> SEQUENCE: 310
aggggccaag cacctcttgt atcctggagt ccttgttccg agcagtaatc actaagaagg    60
tggctgattt ggttggtttt ctgctcctca aatatcgagc                         100

<210> SEQ ID NO 311
<211> LENGTH: 100
<212> TYPE: DNA
<213> ORGANISM: Homo sapiens

<400> SEQUENCE: 311
actgtgcccc tgaggagaaa atctgggagg agctgagtgt gttagaggtg tttgagggga    60
gggaagacag tatcttgggg gatcccaaga agctgctcac                         100

<210> SEQ ID NO 312
<211> LENGTH: 100
<212> TYPE: DNA
<213> ORGANISM: Homo sapiens

<400> SEQUENCE: 312
gccatattat actgctgccc acgcaatgag ttggtgttta cagtgttccc aaggagtggc    60
ttatcttcac agcatgcaac ccaaagcgct aattcacagg                         100

<210> SEQ ID NO 313
<211> LENGTH: 100
<212> TYPE: DNA
<213> ORGANISM: Homo sapiens

<400> SEQUENCE: 313
gtcaaaaagg gatatcaaat gaagtgatgg ggtcacaatg gggaaattga agtggtgcat    60
aacattgcca aaatagtgtg ccactagaaa tggtgtaaag                         100

<210> SEQ ID NO 314
<211> LENGTH: 100
<212> TYPE: DNA
<213> ORGANISM: Homo sapiens

<400> SEQUENCE: 314
tccaagtagg ttttgtttac cctactcccc aaatccctga gccagaagtg gggtgcttat    60
actcccaaac cttgagtgtc cagccttccc ctgttgtttt                         100

<210> SEQ ID NO 315
<211> LENGTH: 100
<212> TYPE: DNA
<213> ORGANISM: Homo sapiens

<400> SEQUENCE: 315
tggctgcagg cctgactact gcccacacca acgaggtgat ctagcagata catggcaacg    60
tgtgaactgc aacaacgcct ggtgccccag caccaacctt                         100

<210> SEQ ID NO 316
<211> LENGTH: 100
<212> TYPE: DNA
<213> ORGANISM: Homo sapiens

<400> SEQUENCE: 316
catactagag tatactgcgg cgtgttttct gtctacccat gtcatggtgg gggagattta    60
tctccgtaca tgtgggtgtc gccatgtgtg ccctgtcact                         100

<210> SEQ ID NO 317
<211> LENGTH: 100
<212> TYPE: DNA
<213> ORGANISM: Homo sapiens

<400> SEQUENCE: 317
tctgaagccc agctgcctgc ccgtgtatac ggccacctcg gatacccagg acagcatgtc    60
cctgctcttc cgcctgctca ccaagctctg gatctgctgt                         100

```
<210> SEQ ID NO 318
<211> LENGTH: 100
<212> TYPE: DNA
<213> ORGANISM: Homo sapiens

<400> SEQUENCE: 318
cccagcccct agaaacccaa gctcctcctc ggaaccgctc acctagagcc agaccaacgt      60
tactcagggc tcctcccagc ttgtaggagc tgaggtttca                          100

<210> SEQ ID NO 319
<211> LENGTH: 100
<212> TYPE: DNA
<213> ORGANISM: Homo sapiens

<400> SEQUENCE: 319
gaagagatcg tgtctgatcc catctacatc gaagtacaag gacttcctca ctttactaag      60
cagcctgaga gcatgaatgt caccagaaac acagccttca                          100

<210> SEQ ID NO 320
<211> LENGTH: 100
<212> TYPE: DNA
<213> ORGANISM: Homo sapiens

<400> SEQUENCE: 320
aagggctgcg ttacacaaaa taaacaatgg cattgtcata ggccttcctt ttactagtag      60
ggcataatgc tagggaatat gtgaagatgt ttttatgaag                          100

<210> SEQ ID NO 321
<211> LENGTH: 100
<212> TYPE: DNA
<213> ORGANISM: Homo sapiens

<400> SEQUENCE: 321
agctggcatt tcgccagctt gtacgtagct tgccactcag tgaaaataat aacattatta      60
tgagaaagtg gacttaaccg aaatggaacc aactgacatt                          100

<210> SEQ ID NO 322
<211> LENGTH: 100
<212> TYPE: DNA
<213> ORGANISM: Homo sapiens

<400> SEQUENCE: 322
cattcagcca agcctcctcc tctagcagca atttccagct gtgtaacact atcctgggca      60
aatgttttac cctgtcctcc agcctccctg cttcccttct                          100

<210> SEQ ID NO 323
<211> LENGTH: 100
<212> TYPE: DNA
<213> ORGANISM: Homo sapiens

<400> SEQUENCE: 323
tcaaactggt agctatgctt tgatgtcctg ttgaggccat cggacagaga ctggagccca      60
ggtgacagga gatggtgata ccagaagtca agggttgggg                          100

<210> SEQ ID NO 324
<211> LENGTH: 100
<212> TYPE: DNA
<213> ORGANISM: Homo sapiens
```

```
<400> SEQUENCE: 324
attcaaatgt ggctgtgatt tctgcatata tcatagatgg gatccttctg agaatactgg    60
aatagggaat taggacacca agccaattca gctgtgaacc                          100

<210> SEQ ID NO 325
<211> LENGTH: 100
<212> TYPE: DNA
<213> ORGANISM: Homo sapiens

<400> SEQUENCE: 325
ttctcaccat tctgggactt ggtagtgctg tgtcactcac aatctgtgga gctggggaag    60
aactcaaagg aaacaaggtt ccagaggatc gtgtttatga                          100

<210> SEQ ID NO 326
<211> LENGTH: 100
<212> TYPE: DNA
<213> ORGANISM: Homo sapiens

<400> SEQUENCE: 326
ctgggaagtt aaatgactgg cctggcatta tgctatgagt ttgtgccttt gctgaggaca    60
ctagaacctg gcttgcctcc cttataagca gaaacaattt                          100

<210> SEQ ID NO 327
<211> LENGTH: 100
<212> TYPE: DNA
<213> ORGANISM: Homo sapiens

<400> SEQUENCE: 327
ctgcggtgga aacaggctta ctctgacttc cctgggagtg tactttcct gcctcacagt     60 tacattggta attctggcat gtcctcaaaa atgactcatg                          100

<210> SEQ ID NO 328
<211> LENGTH: 100
<212> TYPE: DNA
<213> ORGANISM: Homo sapiens

<400> SEQUENCE: 328
tcctcctcat ctaatgctca tctgtttaat ggtgatgcct cgcgtacagg atctggttac    60
ctgtgcagtt gtgaataccc agaggttggg cagatcagtg                          100

<210> SEQ ID NO 329
<211> LENGTH: 100
<212> TYPE: DNA
<213> ORGANISM: Homo sapiens

<400> SEQUENCE: 329 tcttttcct ggccatgagg acaaaaatta ctgagtggcc cttaaagagg gaagtttgtt     60
ttcagctgtt ctcttttgcc cgtaggtggg agggtgggga                          100

<210> SEQ ID NO 330
<211> LENGTH: 100
<212> TYPE: DNA
<213> ORGANISM: Homo sapiens

<400> SEQUENCE: 330
tgaatgtgta gtgcacacgc acgggtgttt ctgtgtgcta gttgcttctt gctgctgctt    60
cctgcttgtc tgggactcac atacataacg tgatatatat                          100
```

<210> SEQ ID NO 331
<211> LENGTH: 100
<212> TYPE: DNA
<213> ORGANISM: Homo sapiens

<400> SEQUENCE: 331
tgtccctgaa agggccagca catcactggt tttctaggag ggactcttaa gttttctacc    60
tgggctgacg ttgccttgtc cggaggggct tgcagggtgg    100

<210> SEQ ID NO 332
<211> LENGTH: 100
<212> TYPE: DNA
<213> ORGANISM: Homo sapiens

<400> SEQUENCE: 332
tctctgggta gcagggtggt gtgatagcgg cagcgagggg ctcggagagg tgctcggatt    60
ctcgtagctg tgccgggact taaccaccac catgtcgagc    100

<210> SEQ ID NO 333
<211> LENGTH: 100
<212> TYPE: DNA
<213> ORGANISM: Homo sapiens

<400> SEQUENCE: 333
ttgggcattt tggaagctgg tcagctagca ggttttctgg gatgtcggga gacctagatg    60
accttatcgg gtgcaatact agctaaggta aagctagaaa    100

<210> SEQ ID NO 334
<211> LENGTH: 100
<212> TYPE: DNA
<213> ORGANISM: Homo sapiens

<400> SEQUENCE: 334
aaacatacca ctctcatggt tcatagtatt cactgtatgt atgctaggga aaagacttgc    60
tccagtctcc tcctcagttc tgtgcctgag aaccactgct    100

<210> SEQ ID NO 335
<211> LENGTH: 100
<212> TYPE: DNA
<213> ORGANISM: Homo sapiens

<400> SEQUENCE: 335
tccggggcta gtgatcgtga tccctttat ttgcaactgt aatgagaatt tttcacacta    60
acacagcgag ggactcaaca cgctgattct cctcctgcct    100

<210> SEQ ID NO 336
<211> LENGTH: 100
<212> TYPE: DNA
<213> ORGANISM: Homo sapiens

<400> SEQUENCE: 336
gggccaggca catcgggcac ctcctcccca tggactatag cgccaatgcc attgccttct    60
attcctacac cttttcctag ggggctggtc ccggctccac    100

<210> SEQ ID NO 337
<211> LENGTH: 100
<212> TYPE: DNA
<213> ORGANISM: Homo sapiens

<400> SEQUENCE: 337
acccaagcat caaagtctac tcagctaaag actaacagag gacagagaaa agtgacagtt    60
tcagctagga cgaacaggag gtgtcagact gctgaagccg    100

<210> SEQ ID NO 338
<211> LENGTH: 100
<212> TYPE: DNA
<213> ORGANISM: Homo sapiens

<400> SEQUENCE: 338
tggacatgtt ctcgagatgg gtggctgttc gcgacttttg taccagagtg aaattgttag    60
aaggagggtt tctggctgtg gttctaaatg gagccccagg    100

<210> SEQ ID NO 339
<211> LENGTH: 100
<212> TYPE: DNA
<213> ORGANISM: Homo sapiens

<400> SEQUENCE: 339
cgatgttttg gctcctataa caaccatgcc tggtctttcc ccagtgagcc agtgaagctc    60
ctggtcacag gcgacattga gaacaccagc cttgcacctg    100

<210> SEQ ID NO 340
<211> LENGTH: 100
<212> TYPE: DNA
<213> ORGANISM: Homo sapiens

<400> SEQUENCE: 340
tatgcatcct ctgtcctgat ctaggtgtct atagctgagg ggtaagaggt tgttgtagtt    60
gtcctggtgc ctccatcaga ctctccctac ttgtcccata    100

<210> SEQ ID NO 341
<211> LENGTH: 100
<212> TYPE: DNA
<213> ORGANISM: Homo sapiens

<400> SEQUENCE: 341
tgggacagaa ataacccaga gccctggaac aaactgggtc ccaatgatca atacaagttc    60
tactcagtga atgtggatta cagcaagctg aagaaggaac    100

<210> SEQ ID NO 342
<211> LENGTH: 100
<212> TYPE: DNA
<213> ORGANISM: Homo sapiens

<400> SEQUENCE: 342
tcctgcctcc accagttcaa actcaaatta aaggccatgc ctctgctcca tactttggaa    60
aggaagaacc ctcagtggct cccagcagca ctggtaaaac    100

<210> SEQ ID NO 343
<211> LENGTH: 100
<212> TYPE: DNA
<213> ORGANISM: Homo sapiens

<400> SEQUENCE: 343
acaatggaag atagaaggga caccattaga aactatccag aagaagctgg ctgcaaaagg    60
gctaagggat ccatggggcc gcaatgaagc ttggagatac    100

<210> SEQ ID NO 344
<211> LENGTH: 100
<212> TYPE: DNA
<213> ORGANISM: Homo sapiens

<400> SEQUENCE: 344
gagtttgata ccagagagcg atgggaaaat cctttgatgg gttgggcatc aacggctgat     60
cccttatcca acatggttct aaccttcagt actaaagaag                          100

<210> SEQ ID NO 345
<211> LENGTH: 100
<212> TYPE: DNA
<213> ORGANISM: Homo sapiens

<400> SEQUENCE: 345
ttactatgag gatttgacag ctaaggatat tgaagaaatt attgatgagc tcaaggctgg     60
caaaatccca aaccagggc caaggagtgg acgcttctct                           100

<210> SEQ ID NO 346
<211> LENGTH: 100
<212> TYPE: DNA
<213> ORGANISM: Homo sapiens

<400> SEQUENCE: 346
cccaagaagc attttttgca gcaccgaact caatttctcc acttcagtca acatcaaaca     60
gtgaacaaca agctgctttc caacagcaag ctccaatatc                          100

<210> SEQ ID NO 347
<211> LENGTH: 100
<212> TYPE: DNA
<213> ORGANISM: Homo sapiens

<400> SEQUENCE: 347
cgaattctct ggtggttgag atcccgccat ttcggaatca gaggataacc agccccgttc     60
acgtcagttt ctacgtctgc aacgggaaga gaaagcgaag                          100

<210> SEQ ID NO 348
<211> LENGTH: 100
<212> TYPE: DNA
<213> ORGANISM: Homo sapiens

<400> SEQUENCE: 348
acaagagggt ttcccggcca gtccaggtct acttttatgt ctccaatggg cggaggaaac     60
gcagtcctac ccagagtttc aggtttctgc ctgtgatctg                          100

<210> SEQ ID NO 349
<211> LENGTH: 100
<212> TYPE: DNA
<213> ORGANISM: Homo sapiens

<400> SEQUENCE: 349
cggatgcatc tggggatgag gttgcttact aagctttgcc agctgctgct ggatcacagc     60
tgctttctgt tgtcattgct gttgtccctc tgctacgttc                          100

<210> SEQ ID NO 350
<211> LENGTH: 100
<212> TYPE: DNA

```
<400> SEQUENCE: 350
atctccgggg gcatcaaacc tgaagatttc tcgaatggac aagacagcag gctctgtgcg      60
gggtggagat gaagtttatc tgctttgtga caaggtgcag                          100

<210> SEQ ID NO 351
<211> LENGTH: 100
<212> TYPE: DNA
<213> ORGANISM: Homo sapiens

<400> SEQUENCE: 351
gcgccgtgat ggccgcaaac tggtgccttg ggtagacact attaaagagt cagacattat      60
ttacaaaaaa attgctctaa cgagtgctaa taagctgact                          100

<210> SEQ ID NO 352
<211> LENGTH: 100
<212> TYPE: DNA
<213> ORGANISM: Homo sapiens

<400> SEQUENCE: 352
agtggggttc agataatgca cgtgtttcga atcccactgt gatatgccag gaagacagca      60
ttgaagagga gtggatgggt ttactggagt acctttcgag                          100

<210> SEQ ID NO 353
<211> LENGTH: 100
<212> TYPE: DNA
<213> ORGANISM: Homo sapiens

<400> SEQUENCE: 353
acctggagcg caccttcatc gccatcaagc cggacggcgt gcagcgcggc ctggtgggcg      60
agatcatcaa gcgcttcgag cagaagggat tccgcctcgt                          100

<210> SEQ ID NO 354
<211> LENGTH: 100
<212> TYPE: DNA
<213> ORGANISM: Homo sapiens

<400> SEQUENCE: 354
ccccagtggc atctcctcat cacgttctgt gccgtccttg ggaaaggcct gcattctgat      60
ccttccaggc ccttcgagca tggaggggca ctggggaagg                          100

<210> SEQ ID NO 355
<211> LENGTH: 100
<212> TYPE: DNA
<213> ORGANISM: Homo sapiens

<400> SEQUENCE: 355
cataagattg atttatcatt gatgcctact gaaataaaaa gaggaaaggc tggaagctgc      60
agacaggatc cctagcttgt tttctgtcag tcattcattg                          100

<210> SEQ ID NO 356
<211> LENGTH: 100
<212> TYPE: DNA
<213> ORGANISM: Homo sapiens

<400> SEQUENCE: 356
tttatgatcc agcagattat tcactgattt gacatagtct ggctgtaccc aggaatggag      60
cctgcacggt gaatggcttt gtatagaacc tctttgtcta                          100
```

<210> SEQ ID NO 357
<211> LENGTH: 100
<212> TYPE: DNA
<213> ORGANISM: Homo sapiens

<400> SEQUENCE: 357
acacattttg ggacaagtgg ggagcccaag aaagtaatta gtaagtgagt ggtcttttct    60
gtaagctaat ccacaacctg ttaccacttc ctgaatcagt                         100

<210> SEQ ID NO 358
<211> LENGTH: 100
<212> TYPE: DNA
<213> ORGANISM: Homo sapiens

<400> SEQUENCE: 358
ttctcttcct tcaccatctg cactacattt ctggctgatc ccaatcagat tcccgctaat    60
ggaagaagtt tagaatcttt caggtggaat aaagtcacat                         100

<210> SEQ ID NO 359
<211> LENGTH: 100
<212> TYPE: DNA
<213> ORGANISM: Homo sapiens

<400> SEQUENCE: 359
tgcagatggt gttcacatga accggagaca tcactcttta ggattctact ggcagcccct    60
gaattggctc aacgtttgtg gaggtggtat ttccctgaag                         100

<210> SEQ ID NO 360
<211> LENGTH: 100
<212> TYPE: DNA
<213> ORGANISM: Homo sapiens

<400> SEQUENCE: 360
ttacaccatg gtaaaggaaa ccatcattag cagttgtccc gttgtccgaa tcgcactgta    60
tttccaccct ttttgcctgt gccttgcaag tctctgctgc                         100

<210> SEQ ID NO 361
<211> LENGTH: 100
<212> TYPE: DNA
<213> ORGANISM: Homo sapiens

<400> SEQUENCE: 361
cgctgtcttc gtggcttcca cccttgttaa tgatgctcct gcctctgcct cccagcccct    60
cacccagcac agctctgcct ggacttggag agatgggagg                         100

<210> SEQ ID NO 362
<211> LENGTH: 100
<212> TYPE: DNA
<213> ORGANISM: Homo sapiens

<400> SEQUENCE: 362
agtggataaa ctagtacgag atatttatgg aggggactat gagaggtttg gactgccagg    60
ctgggctgtg gcttcaagct ttggaaacat gatgagcaag                         100

<210> SEQ ID NO 363
<211> LENGTH: 100
<212> TYPE: DNA
<213> ORGANISM: Homo sapiens

```
<400> SEQUENCE: 363
aagagatgta cttctcagtg gcagtattga actgccttta tctgtaaatt ttaaagtttg    60
actgtataaa ttatcagtcc ctcctgaagg gatctaatcc                         100

<210> SEQ ID NO 364
<211> LENGTH: 100
<212> TYPE: DNA
<213> ORGANISM: Homo sapiens

<400> SEQUENCE: 364
cctgtgaaaa catcagtttc ctgtaccaaa gtcaaaatga acgttacatc actctaacct    60
gaacagctca caatgtagct gtaaatataa aaaatgagag                         100

<210> SEQ ID NO 365
<211> LENGTH: 100
<212> TYPE: DNA
<213> ORGANISM: Homo sapiens

<400> SEQUENCE: 365
catgaagcaa taagagagat cagtaaactt cgaccatccc cagaaagaga tgccctcatt    60
cagctttcag aaattgtact cacaagagat aaatgacaac                         100

<210> SEQ ID NO 366
<211> LENGTH: 100
<212> TYPE: DNA
<213> ORGANISM: Homo sapiens

<400> SEQUENCE: 366
tggccccgtc tcctcgctgc ccacctcctc ttgcctgtgc cctgcaagcc ttctccctcg    60
gccagcgaga agatagcctt gaggtctcct ctttctgctc                         100

<210> SEQ ID NO 367
<211> LENGTH: 100
<212> TYPE: DNA
<213> ORGANISM: Homo sapiens

<400> SEQUENCE: 367
catccctaga tcctaaccct ttagtatgct ggaattctac tcttcactta ctgcattgac    60
tgttgttgat tagttattat tgcaaagcac tgtcaccggc                         100

<210> SEQ ID NO 368
<211> LENGTH: 100
<212> TYPE: DNA
<213> ORGANISM: Homo sapiens

<400> SEQUENCE: 368
atcgatgtgg gaactgggta ctatgtagag aagacagctg aggatgccaa ggacttcttc    60
aagaggaaga tagattttct aaccaagcag atggagaaaa                         100

<210> SEQ ID NO 369
<211> LENGTH: 100
<212> TYPE: DNA
<213> ORGANISM: Homo sapiens

<400> SEQUENCE: 369
atccaaccag ctcttcagga gaagcacgcc atgaaacagg ccgtcatgga aatgatgagt    60
cagaagattc agcagctcac agccctgggg gcagctcagg                         100
```

<210> SEQ ID NO 370
<211> LENGTH: 100
<212> TYPE: DNA
<213> ORGANISM: Homo sapiens

<400> SEQUENCE: 370
gtcctgaaag cagcaagaag tatgctgagg ctgtcactcg ggctaagcag attgtgtgga    60
atggtcctgt gggggtattt gaatgggaag cttttgcccg                         100

<210> SEQ ID NO 371
<211> LENGTH: 100
<212> TYPE: DNA
<213> ORGANISM: Homo sapiens

<400> SEQUENCE: 371
atcaaggttt agaacaccat gagatagtta cccctgatct ccagtcccta gctgggggct    60
ggacaggggg aagggagaga ggatttctat tcacctttaa                         100

<210> SEQ ID NO 372
<211> LENGTH: 100
<212> TYPE: DNA
<213> ORGANISM: Homo sapiens

<400> SEQUENCE: 372
ccagttgggt gtggcagatc tactgaatat caaatgatgc tcttcttccc atgtagacct    60
tcagcaaaag ccggtacttg aagccacag gctcaccttc                          100

<210> SEQ ID NO 373
<211> LENGTH: 100
<212> TYPE: DNA
<213> ORGANISM: Homo sapiens

<400> SEQUENCE: 373
gggaaatggg gggcatcacc atgcctgccg tcgggttcct gcgctgacac ctggtctgtg    60
cacctgtgtt gctcacagtt gaaaactgga cacttttgta                         100

<210> SEQ ID NO 374
<211> LENGTH: 100
<212> TYPE: DNA
<213> ORGANISM: Homo sapiens

<400> SEQUENCE: 374
tccatggaat tgctgagacg tggctcctgg ggctatttct ccctaataaa ggatgatcca    60
ggtcctcatt tccaaagtcc caatgctctg aaaaccaaaa                         100

<210> SEQ ID NO 375
<211> LENGTH: 100
<212> TYPE: DNA
<213> ORGANISM: Homo sapiens

<400> SEQUENCE: 375
gagccagaag tagccgcccg ctcagcggct caggtgccag ctctgttctg attcaccagg    60
ggtccgtcag tagtcattgc cacccgcggg gcacctccct                         100

<210> SEQ ID NO 376
<211> LENGTH: 100
<212> TYPE: DNA
<213> ORGANISM: Homo sapiens

```
<400> SEQUENCE: 376 tttttgggggg atgggctagg ggaaataagg cttgctgtttt gttctcctgg ggcgctccct    60 ccaactttttg cagattcttg caacctcctc ctgagccggg                          100

<210> SEQ ID NO 377
<211> LENGTH: 100
<212> TYPE: DNA
<213> ORGANISM: Homo sapiens

<400> SEQUENCE: 377
ctgatatgaa tgaatgctgt ctgtgtggaa caagcgtcgc aatgaggact ctctacagga    60
cccgatatgg catccctgga tctatttgtg atgactatat                          100

<210> SEQ ID NO 378
<211> LENGTH: 100
<212> TYPE: DNA
<213> ORGANISM: Homo sapiens

<400> SEQUENCE: 378
ccagttgtgg gttaagaata ggctagagca gacattgggt gtttccatgc tgtaggctgg    60
tgggggacca tgtgcctcta ggcagtgact agggtgcccc                          100

<210> SEQ ID NO 379
<211> LENGTH: 100
<212> TYPE: DNA
<213> ORGANISM: Homo sapiens

<400> SEQUENCE: 379
cccctgcctg tccccaaatt gaagatcctt ccttgcctgt ggcttgatgc ggggcgggta    60
aagggtattt taacttaggg gtagttcctg ctgtgagtgg                          100

<210> SEQ ID NO 380
<211> LENGTH: 100
<212> TYPE: DNA
<213> ORGANISM: Homo sapiens

<400> SEQUENCE: 380
cagaacctcc tcagttcctt cacagtgcaa ccctgtgtac ttggcccgca acccaatagt    60
attgtgcctc acttcacctt ccatgggcaa ctgccctccc                          100

<210> SEQ ID NO 381
<211> LENGTH: 100
<212> TYPE: DNA
<213> ORGANISM: Homo sapiens

<400> SEQUENCE: 381
acagcaccct cacggaacca gtggtgatgg cacttctcaa atactggcca aagactcaca    60
gtccaaaaga agtaatgttc ttaaacgaat tagaagagat                          100

<210> SEQ ID NO 382
<211> LENGTH: 100
<212> TYPE: DNA
<213> ORGANISM: Homo sapiens

<400> SEQUENCE: 382
ttaagaaatt tcagcagcaa agttgttatt cagtgggcac gatggactcc aaatgcctca    60
agttatgtat acctgtccca gatgtaaact tcattgtcct                          100
```

```
<210> SEQ ID NO 383
<211> LENGTH: 100
<212> TYPE: DNA
<213> ORGANISM: Homo sapiens

<400> SEQUENCE: 383
ctctggaagt gaagatgcct ccaagaaaga tggggctgtt gagtctatct cagtgccaga        60
tatggtggac aaaaacctta cgtgtcctga ggaagaggac                             100

<210> SEQ ID NO 384
<211> LENGTH: 100
<212> TYPE: DNA
<213> ORGANISM: Homo sapiens

<400> SEQUENCE: 384
cctacagaga acatggctcg tgagcatttc aaaaagcatg gggctgaaca ctactgggac        60
cttgcgctga gtgaatctgt gttagagtcc actgattgag                             100

<210> SEQ ID NO 385
<211> LENGTH: 100
<212> TYPE: DNA
<213> ORGANISM: Homo sapiens

<400> SEQUENCE: 385
actctgcgga tcgggaggac ctgtatgcct gaccgtttcc ctgcctcctg cttcagcctc        60
ccgaggccga agcctcagcc cctccagaca ggccgctgac                             100

<210> SEQ ID NO 386
<211> LENGTH: 100
<212> TYPE: DNA
<213> ORGANISM: Homo sapiens

<400> SEQUENCE: 386
cccgttgagc tggccatcta gtgcagtgtg ctctcagatt ccatgtttgt tgattgtgtg        60
tcttcacaag ccctctctg gtgctgaatt ggatttgaat                              100

<210> SEQ ID NO 387
<211> LENGTH: 100
<212> TYPE: DNA
<213> ORGANISM: Homo sapiens

<400> SEQUENCE: 387
agaacagtga gtacctagaa ctgtgccact aattaaagga aatcctaaga aggtgcattt        60
ctttacagag ctgtgtcatg ccatcctttg ggccctctgc                             100

<210> SEQ ID NO 388
<211> LENGTH: 100
<212> TYPE: DNA
<213> ORGANISM: Homo sapiens

<400> SEQUENCE: 388
gaagacctga ggaggctgcc ttgtctccat tgccgccttc tgtggaggat gcaggattac        60
cttcttatga acaggcagtg gcgctgacca gaaaacacag                             100

<210> SEQ ID NO 389
<211> LENGTH: 100
<212> TYPE: DNA
<213> ORGANISM: Homo sapiens
```

```
<400> SEQUENCE: 389
ctttggctac aacattccac taaaacatct tgcagacaga gtggccatgt atgtgcatgc    60
atatacactc tacagtgctg ttagaccttt tggctgcagt                         100

<210> SEQ ID NO 390
<211> LENGTH: 100
<212> TYPE: DNA
<213> ORGANISM: Homo sapiens

<400> SEQUENCE: 390
gtacattggc tgggataagc actatggctt tcagctctat cagagtgacc ctagtggaaa    60
ttacggggga tggaaggcca catgcattgg aaataatagc                         100

<210> SEQ ID NO 391
<211> LENGTH: 100
<212> TYPE: DNA
<213> ORGANISM: Homo sapiens

<400> SEQUENCE: 391
gaggaagaag aagccaaagc tgagcgtgag aagaaagaaa aagaacagaa agaaaaggat    60
aaatagaatc agagatttta ttactcattt ggggcaccat                         100

<210> SEQ ID NO 392
<211> LENGTH: 100
<212> TYPE: DNA
<213> ORGANISM: Homo sapiens

<400> SEQUENCE: 392
ggtcggctct accaagtaga atatgctttt aaggctatta accagggtgg ccttacatca    60
gtagctgtca gagggaaaga ctgtgcagta attgtcacac                         100

<210> SEQ ID NO 393
<211> LENGTH: 100
<212> TYPE: DNA
<213> ORGANISM: Homo sapiens

<400> SEQUENCE: 393
gatgctcacc ttgttgctct agcagagaga gactaaacat tgtcgttagt ttaccagatc    60
cgtgatgcca cttacctgtg tgtttggtaa caacaaacca                         100

<210> SEQ ID NO 394
<211> LENGTH: 100
<212> TYPE: DNA
<213> ORGANISM: Homo sapiens

<400> SEQUENCE: 394
gcggctggtg aaagatgtct tcatttctgc ggctgagaga gatgtgtaca ctggggacgc    60
actccggatc tgcatagtga ccaaagaggg catcagggag                         100

<210> SEQ ID NO 395
<211> LENGTH: 100
<212> TYPE: DNA
<213> ORGANISM: Homo sapiens

<400> SEQUENCE: 395
gttacattgg tgcagcccta gttttagggg gagtagatgt tactggacct cacctctaca    60
gcatctatcc tcatggatca actgataagt tgccttatgt                         100
```

<210> SEQ ID NO 396
<211> LENGTH: 100
<212> TYPE: DNA
<213> ORGANISM: Homo sapiens

<400> SEQUENCE: 396
actcacagag acagctattc tggaggcgtt gtcaatatgt accacatgaa ggaagatggt      60
tgggtgaaag tagaaagtac agatgtcagt gacctgctgc                          100

<210> SEQ ID NO 397
<211> LENGTH: 100
<212> TYPE: DNA
<213> ORGANISM: Homo sapiens

<400> SEQUENCE: 397
catcctgtgt cttttggagt acgatgtgta agtgcccatt gggtggcctg ttggtcactg      60
tgcagcagtc tgcttcccaa taaagcgtgc tctttcacaa                          100

<210> SEQ ID NO 398
<211> LENGTH: 100
<212> TYPE: DNA
<213> ORGANISM: Homo sapiens

<400> SEQUENCE: 398
gagctctctg cctccggtca ctcttgctgt ggtgctacgt ggaagtgaat ggagactgat      60
ctcaaatctg aactgcagct ttcgctgctg tgagttgggg                          100

<210> SEQ ID NO 399
<211> LENGTH: 100
<212> TYPE: DNA
<213> ORGANISM: Homo sapiens

<400> SEQUENCE: 399
tcccgagtga tacccatgaa ctgccagtag aggctgctat cgttccatgt gtaaggaatg      60
aactggttca aggcgcgtcc tacccagtca ttttctttac                          100

<210> SEQ ID NO 400
<211> LENGTH: 100
<212> TYPE: DNA
<213> ORGANISM: Homo sapiens

<400> SEQUENCE: 400
tatgatgact gaaagggaaa agtggaggaa acgcagctgc aactgaagcg gagactctaa      60
acccagcttg caggtaagag ctttcacctt tggtaaaaga                          100

<210> SEQ ID NO 401
<211> LENGTH: 100
<212> TYPE: DNA
<213> ORGANISM: Homo sapiens

<400> SEQUENCE: 401
gccaatgctt actgcgctag acgcttcatc ccacaatctt aaggggcagc ttctattagc      60
cagtctttac agctgagcac attctggctc agggaggtta                          100

<210> SEQ ID NO 402
<211> LENGTH: 100
<212> TYPE: DNA
<213> ORGANISM: Homo sapiens

```
<400> SEQUENCE: 402
aaatgttcta gtgtagagtc tgagacgggc aagtggttgc tccaggatta ctccctcctc      60
caaaaaagga atcaaatcca cgagtggaaa agcctttgta                           100

<210> SEQ ID NO 403
<211> LENGTH: 100
<212> TYPE: DNA
<213> ORGANISM: Homo sapiens

<400> SEQUENCE: 403
ttagattaga gtcatagcct taatagccct agttgtcatc ctgggagaca ggcaacagta      60
gagatatttg agagcctaaa gagaggtttg gcctgtgggt                           100

<210> SEQ ID NO 404
<211> LENGTH: 100
<212> TYPE: DNA
<213> ORGANISM: Homo sapiens

<400> SEQUENCE: 404
agggctttgc ccctttctg taagtctctt gggatcctgt gtagaagctg ttctcattaa       60
acaccaaaca gttaagtcca ttctctggta ctagctacaa                           100

<210> SEQ ID NO 405
<211> LENGTH: 100
<212> TYPE: DNA
<213> ORGANISM: Homo sapiens

<400> SEQUENCE: 405
cagtctacat ttgtactctt tgtgatgcca cccgtctgga agcctctcaa aatcttgtct      60
tccactctat aaccagaagc catgctgaga acctggaacg                           100

<210> SEQ ID NO 406
<211> LENGTH: 100
<212> TYPE: DNA
<213> ORGANISM: Homo sapiens

<400> SEQUENCE: 406
tcgtcctgca tgtctctaac attaatagaa ggcatggctc ctgctgcaac cgctgtgaat      60
gctgctgaga acctccctct atggggatgg ctattttatt                           100

<210> SEQ ID NO 407
<211> LENGTH: 100
<212> TYPE: DNA
<213> ORGANISM: Homo sapiens

<400> SEQUENCE: 407
tggtatgtat ccaagtccct gctgaccact aatgttctag ctgatggtga gcggcacagt      60
cccacttccc catctcccca agtaggtggt gttagaaaac                           100

<210> SEQ ID NO 408
<211> LENGTH: 100
<212> TYPE: DNA
<213> ORGANISM: Homo sapiens

<400> SEQUENCE: 408
taggagttga atccttctcc ctgcctacct gcagcatctc ctttccctttt aaaatgacca     60 tgtagtggca agcagccttt tactcttctg ttagctctgg                           100
```

<210> SEQ ID NO 409
<211> LENGTH: 100
<212> TYPE: DNA
<213> ORGANISM: Homo sapiens

<400> SEQUENCE: 409
gatattgtgg ttgataactg tgccatctgc aggaaccaca ttatggatct ttgcatagaa    60
tgtcaagcta accaggcgtc cgctacttca gaagagtgta                         100

<210> SEQ ID NO 410
<211> LENGTH: 100
<212> TYPE: DNA
<213> ORGANISM: Homo sapiens

<400> SEQUENCE: 410
gatggcttct atgaggctga gctctgcccg gaccgctgca tccacagttt ccagaacctg    60
ggaatccagt gtgtgaagaa gcgggacctg gagcaggcta                         100

<210> SEQ ID NO 411
<211> LENGTH: 100
<212> TYPE: DNA
<213> ORGANISM: Homo sapiens

<400> SEQUENCE: 411
tgtgtccagg ctcttgtctg aacaccgcag cccctccttc gctccttcca gagctcagca    60
tgtcacggca aggactgccg cattggtgat ggagggccag                         100

<210> SEQ ID NO 412
<211> LENGTH: 100
<212> TYPE: DNA
<213> ORGANISM: Homo sapiens

<400> SEQUENCE: 412
caccaaccag tactctttta accatgcatc ctgcttctgt ccaggaccag acaacagtac    60
gaactgtagc atcagctaca actgccattg aaattcgtag                         100

<210> SEQ ID NO 413
<211> LENGTH: 100
<212> TYPE: DNA
<213> ORGANISM: Homo sapiens

<400> SEQUENCE: 413
aaccctcgac ccgaaaccct caccagataa actacagttt gtttaggagg ccctgacctt    60
catggtgtct ttgaagccca accactcggt ttccttcgga                         100

<210> SEQ ID NO 414
<211> LENGTH: 100
<212> TYPE: DNA
<213> ORGANISM: Homo sapiens

<400> SEQUENCE: 414
gcattcttgt tagctttgct tttctcccca tatcccaagg cgaagcgctg agattcttcc    60
atctaaaaaa ccctcgaccc gaaaccctca ccagataaac                         100

<210> SEQ ID NO 415
<211> LENGTH: 100
<212> TYPE: DNA
<213> ORGANISM: Homo sapiens

<400> SEQUENCE: 415 tttcttttc cctcctttat gacctttggg acattgggaa tacccagcca actctccacc    60
atcaatgtaa ctccatggac attgctgctc ttggtggtgt                         100

<210> SEQ ID NO 416
<211> LENGTH: 100
<212> TYPE: DNA
<213> ORGANISM: Homo sapiens

<400> SEQUENCE: 416
ataaaaatca ctattttgtg tgctccgcgt gctatagctt ttggggcggc cctgcccagt    60
ccccgtgccc acgggctcc ctctcccggt ggtgaaagtg                          100

<210> SEQ ID NO 417
<211> LENGTH: 100
<212> TYPE: DNA
<213> ORGANISM: Homo sapiens

<400> SEQUENCE: 417
gggaggaggg aggatgcgct gtggggttgt ttttgccata agcgaacttt gtgcctgtcc    60
tagaagtgaa aattgttcag tccaagaaac tgatgttatt                         100

<210> SEQ ID NO 418
<211> LENGTH: 100
<212> TYPE: DNA
<213> ORGANISM: Homo sapiens

<400> SEQUENCE: 418
ctttccacac agttgttgct gcctattgtg gtgccgcctc aggttagggg ctctcagcca    60
tctctaacct ctgccctcgc tgctcttgga attgcgcccc                         100

<210> SEQ ID NO 419
<211> LENGTH: 100
<212> TYPE: DNA
<213> ORGANISM: Homo sapiens

<400> SEQUENCE: 419
ttgacagact caagagaaac tacccaggta ttacacaagc caaaatggga gcaaggcctt    60
ctctccagac tatcgtaacc tggtgcctta ccaagttgtg                         100

<210> SEQ ID NO 420
<211> LENGTH: 100
<212> TYPE: DNA
<213> ORGANISM: Homo sapiens

<400> SEQUENCE: 420
tgacctgtcc tagtaacaaa actcgcaaaa attgtcacca cagtggaagc caggtgcctt    60
taatccactg taacctcaca actccaagtc cacagaatat                         100

<210> SEQ ID NO 421
<211> LENGTH: 100
<212> TYPE: DNA
<213> ORGANISM: Homo sapiens

<400> SEQUENCE: 421
aattcagatc atctcagaag tctggaggga aatctggcga aaccttcgtt tgagggactg    60
atgtgagtgt atgtccacct cactggtggc accgagaaac                         100

<210> SEQ ID NO 422
<211> LENGTH: 100
<212> TYPE: DNA
<213> ORGANISM: Homo sapiens

<400> SEQUENCE: 422
ccccagagcc caaggtgcac cgagcccaag tgcccatatg aacctctctg ccctagccga      60
gggacaaact gtcttgaagc cagaaggtgg agaagccaga                           100

<210> SEQ ID NO 423
<211> LENGTH: 100
<212> TYPE: DNA
<213> ORGANISM: Homo sapiens

<400> SEQUENCE: 423
acctgtaagc tatgtctaat gtgccagaaa ctcgtccagc ccagtgagct gcatccaatg      60
gcgtgtaccc atgtattgca caaggagtgt atcaaattct                           100

<210> SEQ ID NO 424
<211> LENGTH: 100
<212> TYPE: DNA
<213> ORGANISM: Homo sapiens

<400> SEQUENCE: 424
cttctgtcct ctttggatga gatcagtgtc cacaagtggc cgacatggaa catgctgagc      60
agtggctcct ctgaatgttc actttattag tcatgtatat                           100

<210> SEQ ID NO 425
<211> LENGTH: 100
<212> TYPE: DNA
<213> ORGANISM: Homo sapiens

<400> SEQUENCE: 425
ctcaggatcg gaatgcgggg tcgagagctg atgggcggca ttgggaaaac catgatgcag      60
agtggcggca cctttggcac attcatggcc attgggatgg                           100

<210> SEQ ID NO 426
<211> LENGTH: 100
<212> TYPE: DNA
<213> ORGANISM: Homo sapiens

<400> SEQUENCE: 426
cactcagggt ctgaggcagc tagtagccgg agggtcacca tgaagttcaa tcccttcgtt      60
acctcggacc gcagtaaaaa ccgcaaacgt cacttcaatg                           100

<210> SEQ ID NO 427
<211> LENGTH: 100
<212> TYPE: DNA
<213> ORGANISM: Homo sapiens

<400> SEQUENCE: 427
agaagaaagc attcatggga ccactgaaga aagaccgaat tgcaaaggaa gaaggagctt      60
aatgccagga acagattttg cagttggtgg ggtctcaata                           100

<210> SEQ ID NO 428
<211> LENGTH: 100
<212> TYPE: DNA
<213> ORGANISM: Homo sapiens

```
<400> SEQUENCE: 428
cttgcaactg cggctttcct tctcccacaa tccttcgcgc tcttcctttc caacttggac       60
gctgcagaat ggctcccgca aagaagggtg gcgagaagaa                            100

<210> SEQ ID NO 429
<211> LENGTH: 100
<212> TYPE: DNA
<213> ORGANISM: Homo sapiens

<400> SEQUENCE: 429
acctcacctc agcttgagag agccagttgt gtgcatctct ttccagtttt gcatccagtg       60
acgtctgctt ggcatcttga gattgttatg gtgagagtat                            100

<210> SEQ ID NO 430
<211> LENGTH: 100
<212> TYPE: DNA
<213> ORGANISM: Homo sapiens

<400> SEQUENCE: 430
gcgggttcgg gtcggtgaca cgcagacctg agggagctgg gcccgccttt tccgcccgcg       60
ccccaggccc ttgcagatcg agatttgcgt cctagagtgg                            100

<210> SEQ ID NO 431
<211> LENGTH: 100
<212> TYPE: DNA
<213> ORGANISM: Homo sapiens

<400> SEQUENCE: 431
cccctggggt ccctcacaca gagacaccat cagccggagt ggtataatct tacggagtcc       60
ccggccagac tttcggccta gggaacctttt tctcagcaga                            100

<210> SEQ ID NO 432
<211> LENGTH: 100
<212> TYPE: DNA
<213> ORGANISM: Homo sapiens

<400> SEQUENCE: 432
atgaagaaag tcaggggggac tgcaaaggcc aatgttggtg ctggcaaaaa gccgaaggag       60
taaaggtgct gcaatgatgt tagctgtggc cactgtggat                            100

<210> SEQ ID NO 433
<211> LENGTH: 100
<212> TYPE: DNA
<213> ORGANISM: Homo sapiens

<400> SEQUENCE: 433
taaaatgtcc aggttgctac aagatcacca cggttttcag ccatgctcag acagtggttc       60
tttgtgtagg ttgttcaaca gtgttgtgcc agcctacagg                            100

<210> SEQ ID NO 434
<211> LENGTH: 100
<212> TYPE: DNA
<213> ORGANISM: Homo sapiens

<400> SEQUENCE: 434
gaatggaagg gttatgtggt ccgaatcagt ggtgggaacg acaaacaagg tttccccatg       60
aagcagggtg tcttgaccca tggccgtgtc cgcctgctac                            100
```

<210> SEQ ID NO 435
<211> LENGTH: 100
<212> TYPE: DNA
<213> ORGANISM: Homo sapiens

<400> SEQUENCE: 435
tggagtgaca ctacactcta gaatttccac tttggagaat actcagttcc aacttgtgat    60
tcctgataga acagacttta cttttctagc ccagcattga                         100

<210> SEQ ID NO 436
<211> LENGTH: 100
<212> TYPE: DNA
<213> ORGANISM: Homo sapiens

<400> SEQUENCE: 436
tggaggatga tgaagatgat ccagactata atcctgctga cccagagagt gactcagctg    60
actaatggac tgtccccatc tgcagagagg cttgactgcc                         100

<210> SEQ ID NO 437
<211> LENGTH: 100
<212> TYPE: DNA
<213> ORGANISM: Homo sapiens

<400> SEQUENCE: 437
agtaattttt aaagccttgc tctgttgtgt cctgttgccg gctctggcct tcctgtgact    60
gactgtgaag tggcttctcc gtacgattgt ctctgaaaca                         100

<210> SEQ ID NO 438
<211> LENGTH: 100
<212> TYPE: DNA
<213> ORGANISM: Homo sapiens

<400> SEQUENCE: 438
caagatgaac aggtcgactt tcaagaattc atatccctgg tagccattgc gctgaaggct    60
gcccattacc acacccacaa agagtaggta gctctctgaa                         100

<210> SEQ ID NO 439
<211> LENGTH: 100
<212> TYPE: DNA
<213> ORGANISM: Homo sapiens

<400> SEQUENCE: 439
gttaacttcc aggagttcct cattctggtg ataaagatgg gcgtggcagc ccacaaaaaa    60
agccatgaag aaagccacaa agagtagctg agttactggg                         100

<210> SEQ ID NO 440
<211> LENGTH: 100
<212> TYPE: DNA
<213> ORGANISM: Homo sapiens

<400> SEQUENCE: 440
acctgagccc ctatccttga gctcagacat ctccttaaat aagtcacagt tagatgactg    60
cccaagggac tctggttgct atatctcatc aggaaattca                         100

<210> SEQ ID NO 441
<211> LENGTH: 100
<212> TYPE: DNA
<213> ORGANISM: Homo sapiens

<400> SEQUENCE: 441
gatctccacc gaataaacga actgatacag ggaaatatgc agaggtgtaa acttgtgatg    60
gatcaaatca gtgaagccag agactccatg cttaaggttt                         100

<210> SEQ ID NO 442
<211> LENGTH: 100
<212> TYPE: DNA
<213> ORGANISM: Homo sapiens

<400> SEQUENCE: 442
cggttcttct gcctgacctt caaatgccca tgttggcctt ttacagcagt gccacggcac    60
caagcgagct gccacatctc acactctaaa gggtttgaac                         100

<210> SEQ ID NO 443
<211> LENGTH: 100
<212> TYPE: DNA
<213> ORGANISM: Homo sapiens

<400> SEQUENCE: 443
aactggaacc acagaggata cagaggcaaa gaagaggaaa agagcagagc gctttgggat    60
tgcctgatga aaagttcctg atactttctg ttctccagtg                         100

<210> SEQ ID NO 444
<211> LENGTH: 100
<212> TYPE: DNA
<213> ORGANISM: Homo sapiens

<400> SEQUENCE: 444
agttcttctc atgtaagtaa taacatgagt acaccagttt tgcctgctcc gacagcagcc    60
ccaggaaata cgggaatggt tcagggacca agttctggta                         100

<210> SEQ ID NO 445
<211> LENGTH: 100
<212> TYPE: DNA
<213> ORGANISM: Homo sapiens

<400> SEQUENCE: 445
gagagaagga agaagcccga ggaaaggaaa agcctgaggt gacagacagg gcaggtggta    60
acaaaaccgt tgaacctccc attagccaag tgggaaatgt                         100

<210> SEQ ID NO 446
<211> LENGTH: 100
<212> TYPE: DNA
<213> ORGANISM: Homo sapiens

<400> SEQUENCE: 446
tgattatttt gaaggggcca cttctcaacg aaaaggtgat aatgtgcctc aggttaatgg    60
tgaaaataca gagagacatg ctcagccacc acctatacca                         100

<210> SEQ ID NO 447
<211> LENGTH: 100
<212> TYPE: DNA
<213> ORGANISM: Homo sapiens

<400> SEQUENCE: 447
gtcactctgg aatatagacc cgtgatcgac aaaactttga acgaggctga ctgtgccacc    60
gtcccgccag ccattcgctc ctactgatga gacaagatgt                         100

<210> SEQ ID NO 448
<211> LENGTH: 100
<212> TYPE: DNA
<213> ORGANISM: Homo sapiens

<400> SEQUENCE: 448
aggcagaggc agctggagcg ccgttctctc ctgctgggac accgcttggg ctttggtatt    60
gactgagtgg ctgacagtta tcttccaacc ccaactggct                         100

<210> SEQ ID NO 449
<211> LENGTH: 100
<212> TYPE: DNA
<213> ORGANISM: Homo sapiens

<400> SEQUENCE: 449
ggcagacacc aacatggatc tcatggggga ttggatattg taattataga gcaggaagat    60
gacagtgatc gtcatttggc acaacatctt aacaacgacc                         100

<210> SEQ ID NO 450
<211> LENGTH: 100
<212> TYPE: DNA
<213> ORGANISM: Homo sapiens

<400> SEQUENCE: 450
agacagttat gatctcaagt caaccctgag cagtatgggg atgagtgatg ccttcagcca    60
aagcaaagct gatttctcag gaatgtcttc agcaagaaac                         100

<210> SEQ ID NO 451
<211> LENGTH: 100
<212> TYPE: DNA
<213> ORGANISM: Homo sapiens

<400> SEQUENCE: 451
tggttagaag ccatcagagg tgcaagggct tagaaaagac cctggccaga cctgactcca    60
ctcttaaacc tgggtcttct ccttggcggt gctgtcagcg                         100

<210> SEQ ID NO 452
<211> LENGTH: 100
<212> TYPE: DNA
<213> ORGANISM: Homo sapiens

<400> SEQUENCE: 452
aaggatcgaa gttgctgaaa ggcttcacct ggacagtaac cccttgaagt ggagtgtggc    60
agacgttgtg cggttcatca gatccactga ctgtgctcca                         100

<210> SEQ ID NO 453
<211> LENGTH: 100
<212> TYPE: DNA
<213> ORGANISM: Homo sapiens

<400> SEQUENCE: 453
ggttatgtaa gcaaagctga actgtaaatc ttcaggaata tgtattaaga ttgtggaatg    60
ggtgtaagac aattggtagg gggtgaaagt gggtttgatt                         100

<210> SEQ ID NO 454
<211> LENGTH: 100
<212> TYPE: DNA
<213> ORGANISM: Homo sapiens

<400> SEQUENCE: 454
acgagcgtta gagtgccgcc ttagacggag gcaggagttt cgttagaaag cggacgctgt    60
tctaaaaaag gtctcctgca gatctgtctg ggctgtgatg                          100

<210> SEQ ID NO 455
<211> LENGTH: 100
<212> TYPE: DNA
<213> ORGANISM: Homo sapiens

<400> SEQUENCE: 455
gaagcagagg aggatgggtc tgaacgactt tattcagaag attgccaata actcctatgc    60
atgcaaacac cctgaagttc agtccatctt gaagatctcc                          100

<210> SEQ ID NO 456
<211> LENGTH: 100
<212> TYPE: DNA
<213> ORGANISM: Homo sapiens

<400> SEQUENCE: 456
ggatatgctg tgtgaaccgt cgtgtgagtg tggtatgcct gatcacagat ggattttgtt    60
ataagcatca atgtgacact tgcaggacac tacaacgtgg                          100

<210> SEQ ID NO 457
<211> LENGTH: 100
<212> TYPE: DNA
<213> ORGANISM: Homo sapiens

<400> SEQUENCE: 457
agcaccccaa ggacactgtg atcaacccga gaatgttctg ggttcaactc aagcatctcc    60
cttgcacctc cagggtcctg cgtggactct gggttccatc                          100

<210> SEQ ID NO 458
<211> LENGTH: 100
<212> TYPE: DNA
<213> ORGANISM: Homo sapiens

<400> SEQUENCE: 458
tcgctcataa agaagttttt gggatgggag agaatccaga ccatcttggg gcagccaggc    60
ccttgccttc atttttacag aggtagcaca actgattcca                          100

<210> SEQ ID NO 459
<211> LENGTH: 100
<212> TYPE: DNA
<213> ORGANISM: Homo sapiens

<400> SEQUENCE: 459
tttattcctg acgattccct tgctgcctac ccttttctct cctctggttc tcaacctcaa    60
cgagttcaaa tcagttgtcc tttttagctc ccgtggaact                          100

<210> SEQ ID NO 460
<211> LENGTH: 100
<212> TYPE: DNA
<213> ORGANISM: Homo sapiens

<400> SEQUENCE: 460
aacaaatatt gattgagggc gctgcatgtg ctgggtacat ttcttggcac ttgggaatca    60
gtagtcaagc gaaacccttg cctttgagag tttatggtct                          100

<210> SEQ ID NO 461
<211> LENGTH: 100
<212> TYPE: DNA
<213> ORGANISM: Homo sapiens

<400> SEQUENCE: 461
gcaggataga gtgggacagt tcctgagacc agccaacctg ggggctttag ggacctgctg    60
tttcctagcg cagccatgtg attaccctct gggtctcagt                          100

<210> SEQ ID NO 462
<211> LENGTH: 100
<212> TYPE: DNA
<213> ORGANISM: Homo sapiens

<400> SEQUENCE: 462
aactcattaa aacttgtgca gtgttgctgg agctggcctg gtgtctccaa atgaccatga    60
aaatacacac gtataatgga gatcattctc tgtgggtatg                          100

<210> SEQ ID NO 463
<211> LENGTH: 100
<212> TYPE: DNA
<213> ORGANISM: Homo sapiens

<400> SEQUENCE: 463
atcttcttca gtccctagcc aggaataccc atttgatttc cagggtgcca tctaatcctg    60
ggctgtacat gtggatatgg acttgaggcc cacctctgtg                          100

<210> SEQ ID NO 464
<211> LENGTH: 100
<212> TYPE: DNA
<213> ORGANISM: Homo sapiens

<400> SEQUENCE: 464
tccagcccct tgccctctcc tcacacgtag atcatttttt ttttgcaggg tgctgcctat    60
gggccctctg ctccccaatg ccttagagag aggaggggac                          100

<210> SEQ ID NO 465
<211> LENGTH: 100
<212> TYPE: DNA
<213> ORGANISM: Homo sapiens

<400> SEQUENCE: 465
agtttctagg atgaaacact cctccatggg atttgaacat atgaaagtta tttgtagggg    60
aagagtcctg aggggcaaca cacaagaacc aggtcccctc                          100

<210> SEQ ID NO 466
<211> LENGTH: 100
<212> TYPE: DNA
<213> ORGANISM: Homo sapiens

<400> SEQUENCE: 466
gatattgcta actgatcaca gattctttcc cacctcacaa tccttccgaa tgtgctccag    60
gcagcaccat ttgccatcct gcttctaacg caaacccctg                          100

<210> SEQ ID NO 467
<211> LENGTH: 100
<212> TYPE: DNA
<213> ORGANISM: Homo sapiens

<400> SEQUENCE: 467
attctagacc aaagacacag gcagaccaag tccccaggcc ccgcctggaa ggaagtcgtt    60
cctcaactct ccccaaggca cctgtctcca atcagagccc                         100

<210> SEQ ID NO 468
<211> LENGTH: 100
<212> TYPE: DNA
<213> ORGANISM: Homo sapiens

<400> SEQUENCE: 468
attaacatga ttttcctggt tgttacatcc agggcatggc agtggcctca gccttaaact    60
tttgttccta ctcccaccct cagcgaactg ggcagcacgg                         100

<210> SEQ ID NO 469
<211> LENGTH: 100
<212> TYPE: DNA
<213> ORGANISM: Homo sapiens

<400> SEQUENCE: 469
cggcctcagc agcgagaggt gctgcggcgc tgcgtagaag tatcaatcag ccggttgctt    60
ttgtgagaag aattccttgg actgcggcgt cgagtcagct                         100

<210> SEQ ID NO 470
<211> LENGTH: 100
<212> TYPE: DNA
<213> ORGANISM: Homo sapiens

<400> SEQUENCE: 470
caatggccag ggttttacct acttcctgcc agtctttccc aaaggaaact cattccaaat    60
acttcttttt tccctggag tccgagaagg aaaatggaat                          100

<210> SEQ ID NO 471
<211> LENGTH: 100
<212> TYPE: DNA
<213> ORGANISM: Homo sapiens

<400> SEQUENCE: 471
ctcgtgggac tctagaggga gtcagtctgc aacagtaagt ggtgagttct tctgtccagc    60
gtcagtattt tgatggtggc tttagacttg ccagataaca                         100

<210> SEQ ID NO 472
<211> LENGTH: 100
<212> TYPE: DNA
<213> ORGANISM: Homo sapiens

<400> SEQUENCE: 472
ccctccctgt cgcccactcc tccctcctct ggctatccta ccctgtctgt gggctctttt    60
actaccagcc tatgctgtgg gactgtcatg gcatttagtt                         100

<210> SEQ ID NO 473
<211> LENGTH: 100
<212> TYPE: DNA
<213> ORGANISM: Homo sapiens

<400> SEQUENCE: 473
ttaactgtat ctggagccag gacctgaact cgcacctcct acctcttcat gtttacatat    60
acccagtatc tttgcacaaa ccaggggttg ggggagggtc                         100

<210> SEQ ID NO 474
<211> LENGTH: 100
<212> TYPE: DNA
<213> ORGANISM: Homo sapiens

<400> SEQUENCE: 474
gggggcaatg atgagcatat gaattttttc tcactctagc aattcccttt tctaaatgac    60
acagcattta aactcaaatc tggattcaga taacagcacc                         100

<210> SEQ ID NO 475
<211> LENGTH: 100
<212> TYPE: DNA
<213> ORGANISM: Homo sapiens

<400> SEQUENCE: 475
caaggatttg ggaatcttct tgaagggctg acacgcgaga ttctgagaga gcaaccggac    60
aatataccag cttttgcagc agcctatttt gagagccttc                         100

<210> SEQ ID NO 476
<211> LENGTH: 100
<212> TYPE: DNA
<213> ORGANISM: Homo sapiens

<400> SEQUENCE: 476
gtattgccca ctcatttgta taagtgcgct tcggtacagc acgggtcctg ctcccgcgat    60
gtggaagtgt cacacggcac ctgtacaaaa agactggcta                         100

<210> SEQ ID NO 477
<211> LENGTH: 100
<212> TYPE: DNA
<213> ORGANISM: Homo sapiens

<400> SEQUENCE: 477
gagcaatgac aaagaggatc tgtgtcgtga atttcgaagc atgcagagaa atggaaagct    60
tatctgcacc agagaaaata accctgttcg aggcccatat                         100

<210> SEQ ID NO 478
<211> LENGTH: 100
<212> TYPE: DNA
<213> ORGANISM: Homo sapiens

<400> SEQUENCE: 478
agtgcctgcg tgtgtccact cgtgggtgtg gtttgtgtgc aagagctgag gatttggcga    60
tgcttgggag gggtagttgt gggtacagac ggtgtggggg                         100

<210> SEQ ID NO 479
<211> LENGTH: 100
<212> TYPE: DNA
<213> ORGANISM: Homo sapiens

<400> SEQUENCE: 479
cccctccttg ctctgcaggc accttagtgg ctttttttcct cctgtgtaca gggaagagag    60
gggtacattt ccctgtgctg acggaagcca acttggcttt                         100

<210> SEQ ID NO 480
<211> LENGTH: 100
<212> TYPE: DNA
<213> ORGANISM: Homo sapiens

```
<400> SEQUENCE: 480
tactcatggc ccacagtaga atatccaaaa cgccttggct ttcaggcctg gcctttccta      60
cagggagctc agtaacctgg acggctctaa ggctggaatg                           100

<210> SEQ ID NO 481
<211> LENGTH: 100
<212> TYPE: DNA
<213> ORGANISM: Homo sapiens

<400> SEQUENCE: 481
ctgattttaa tcttcgaatc atgacactga gtgcagagga ggtggcattc cgacagcagg      60
acatacatgt tggtgtgaag actgggacga cactgggtag                           100

<210> SEQ ID NO 482
<211> LENGTH: 100
<212> TYPE: DNA
<213> ORGANISM: Homo sapiens

<400> SEQUENCE: 482
aagtgcctgc agcatgtctc ccaggcacct ggccatccct ggggcccagt caccacctac      60
tgccactccc tcagccctgt ggagaacaca gcagagacca                           100

<210> SEQ ID NO 483
<211> LENGTH: 100
<212> TYPE: DNA
<213> ORGANISM: Homo sapiens

<400> SEQUENCE: 483
tttcctgtgg tttatggcaa tatgaatgga gcttattact ggggtgaggg acagcttact      60
ccatttgacc agattgtttg gctaacacat cccgaagaat                           100

<210> SEQ ID NO 484
<211> LENGTH: 100
<212> TYPE: DNA
<213> ORGANISM: Homo sapiens

<400> SEQUENCE: 484
actgtgccca agtgggtcca agtggctgtg acatctacgt atggctccac acctccaatg      60
ctgcctggga gccagggtga gagtctgggt ccaggcctgg                           100

<210> SEQ ID NO 485
<211> LENGTH: 100
<212> TYPE: DNA
<213> ORGANISM: Homo sapiens

<400> SEQUENCE: 485
cccggggaag acacagagac tcgtacctgc gctgtttgtg ccgccgctgc ctctgggccc      60
tcccagcaca cgcatggtct cttcaccgct gccctcgagt                           100

<210> SEQ ID NO 486
<211> LENGTH: 100
<212> TYPE: DNA
<213> ORGANISM: Homo sapiens

<400> SEQUENCE: 486
ggggtagcgg ggtcaggaca atcatctcag tcctgcatct tttcttctgc tttcttccct      60
ccaagagcaa aacctgggca aggggactta ctgagtgggg                           100
```

<210> SEQ ID NO 487
<211> LENGTH: 100
<212> TYPE: DNA
<213> ORGANISM: Homo sapiens

<400> SEQUENCE: 487
ttgtcagtga aactactttg gattttaacc tcttagagga agaaaaaagg ttagggaagt    60
gtcaactctg gatgaaggtg atgtgtttgc ctctcagtct                        100

<210> SEQ ID NO 488
<211> LENGTH: 100
<212> TYPE: DNA
<213> ORGANISM: Homo sapiens

<400> SEQUENCE: 488
ttctgccttg tgaattcgta gtccaatcag ctgaaattaa atcacttggg agggacgcat    60
agaaggagct ctaggaacac agtgccagtg cagaagtttc                        100

<210> SEQ ID NO 489
<211> LENGTH: 100
<212> TYPE: DNA
<213> ORGANISM: Homo sapiens

<400> SEQUENCE: 489
ccctctgctc ccgcccggca ccagccctcc agtagatcct ttcacgacct tggcctctaa    60
ggcttcaccc acactggact ttacagaaag ataacgccat                        100

<210> SEQ ID NO 490
<211> LENGTH: 100
<212> TYPE: DNA
<213> ORGANISM: Homo sapiens

<400> SEQUENCE: 490
cttgccctcc ctgggtcgca gacgaggtcg gcctcgtcat tccccgcaga ccgccgcgcg    60
tccctcttgt gcggttcacc acagttgtat ttaagtgatc                        100

<210> SEQ ID NO 491
<211> LENGTH: 100
<212> TYPE: DNA
<213> ORGANISM: Homo sapiens

<400> SEQUENCE: 491
cagccagcct gctcgaaact ttagtcggcc tgatggctta gaggactctg aggatagcaa    60
agaagatgag aatgtgccta ctgctcctga tcctccaagt                        100

<210> SEQ ID NO 492
<211> LENGTH: 100
<212> TYPE: DNA
<213> ORGANISM: Homo sapiens

<400> SEQUENCE: 492
ttccaaggaa tgcactaagc cttcagtctt tttagactga cagtactggc agctaaaata    60
ttgtactgta tcttctcttg agcccagtat gtaggaaata                        100

<210> SEQ ID NO 493
<211> LENGTH: 100
<212> TYPE: DNA
<213> ORGANISM: Homo sapiens

<400> SEQUENCE: 493
tatgctgaaa aaccagctac taacactgaa gataaaatac cctcatcaac ttgatcagaa    60
agtcctggag aaacaactgc cgggctccat gacaattcaa                          100

<210> SEQ ID NO 494
<211> LENGTH: 100
<212> TYPE: DNA
<213> ORGANISM: Homo sapiens

<400> SEQUENCE: 494
accagtcttc aggatatcga cagcagatta tctccaggtg gatcactggc agacgcatgg    60
gcacatcaag aaggcactca tccgaaagac agaaatgtag                          100

<210> SEQ ID NO 495
<211> LENGTH: 100
<212> TYPE: DNA
<213> ORGANISM: Homo sapiens

<400> SEQUENCE: 495
tgtaagtgcc caccgcggga tgccgggaag gggcattatt tgtgcactga gaacaccgcg    60
cagcgtgact gtgagttgct cataccgtgc tgctatctgg                          100

<210> SEQ ID NO 496
<211> LENGTH: 100
<212> TYPE: DNA
<213> ORGANISM: Homo sapiens

<400> SEQUENCE: 496
ccaggcctgt gttgccagag ctggcagtgt gagctgtagg cagggacggg gagggactgt    60
cgctgtgatc agagtgggtt aagctgacca ggaacaccca                          100

<210> SEQ ID NO 497
<211> LENGTH: 100
<212> TYPE: DNA
<213> ORGANISM: Homo sapiens

<400> SEQUENCE: 497
ggcccacctg tccatgatgc ctccgccacc cgccctcctg ctcgctgagg ccacccacaa    60
ggcctccgcc ctctgtccca acggggccct ggacctgccc                          100

<210> SEQ ID NO 498
<211> LENGTH: 100
<212> TYPE: DNA
<213> ORGANISM: Homo sapiens

<400> SEQUENCE: 498
gtgttcggtg accgcagcac tggggaaacg atccgctccc aaaacgttat ggctgcagct    60
tcgattgcca atattgtaaa aagttctctt ggtccagttg                          100

<210> SEQ ID NO 499
<211> LENGTH: 100
<212> TYPE: DNA
<213> ORGANISM: Homo sapiens

<400> SEQUENCE: 499
cctctgaaaa cggccctctt gaagggggat atgaatggag atttgaaggt ctgcaagaac    60
ctgactcgtc tgactgtgtg tggaggagtc caggccatgg                          100

```
<210> SEQ ID NO 500
<211> LENGTH: 100
<212> TYPE: DNA
<213> ORGANISM: Homo sapiens

<400> SEQUENCE: 500
acctcaacca ggacttcagt ggatttcagc ttctagtgga tgttgcactc aaacgggctg      60
cagagatgga gcttcaggca aaacttacag cttaacccat                           100

<210> SEQ ID NO 501
<211> LENGTH: 100
<212> TYPE: DNA
<213> ORGANISM: Homo sapiens

<400> SEQUENCE: 501
ccccgggatc agttttggct cgtccatcag tgatctgcca taccactgtg actgcattga      60
aagatgtccc tttctctctc tgccagtcgg tcggtgtggg                           100

<210> SEQ ID NO 502
<211> LENGTH: 100
<212> TYPE: DNA
<213> ORGANISM: Homo sapiens

<400> SEQUENCE: 502
cctaactctg cccaccctcc tgtaccgtcg acaagaatgt cccttaggt cgcgctcttg       60 cacacacggt tttggcagct gacttggttc tgaagccatg                           100

<210> SEQ ID NO 503
<211> LENGTH: 100
<212> TYPE: DNA
<213> ORGANISM: Homo sapiens

<400> SEQUENCE: 503
gaatgacaga agcaaaggac ttgttactaa gcagatttaa gggtcagtgg gggaaggcta      60
tcaacccatt gtcagatcag catcaggctg ttatcaagtc                           100

<210> SEQ ID NO 504
<211> LENGTH: 100
<212> TYPE: DNA
<213> ORGANISM: Homo sapiens

<400> SEQUENCE: 504
acccatcatc catctgccca caaacctggc caaatgtgat acaacctgaa aacctgatgg      60
actaaaggag tactatttaa caattgattg cctttgcact                           100

<210> SEQ ID NO 505
<211> LENGTH: 100
<212> TYPE: DNA
<213> ORGANISM: Homo sapiens

<400> SEQUENCE: 505
cgctggtggt ggcgatctgt gctgagtgtt ggctccaccg gcctcttcat cttcctctac      60
tcagttttct attatgcccg gcgctccaac atgtctgggg                           100

<210> SEQ ID NO 506
<211> LENGTH: 100
<212> TYPE: DNA
<213> ORGANISM: Homo sapiens
```

```
<400> SEQUENCE: 506
gaggagcaga agaaactcga ggagctaaaa gcgaaggccg cggggaaggg gcccttggcc      60
acaggtggaa ttaagaaatc tggcaaaaag taagctgttc                          100

<210> SEQ ID NO 507
<211> LENGTH: 100
<212> TYPE: DNA
<213> ORGANISM: Homo sapiens

<400> SEQUENCE: 507
ctctccctat tcacaaccag tgcacagttt gacacagtgg cctcaggttc acagtgcacc      60
atgtcactgt gctatcctac gaaatcattt gtttctaagt                          100

<210> SEQ ID NO 508
<211> LENGTH: 100
<212> TYPE: DNA
<213> ORGANISM: Homo sapiens

<400> SEQUENCE: 508
aggccaatgc cagggccatc cacaggctcc ggaagcagct ggtgtggcag gttcaggaga      60
agtggcacct ggtggaggac ctgtcgcgac tgctgccgga                          100

<210> SEQ ID NO 509
<211> LENGTH: 100
<212> TYPE: DNA
<213> ORGANISM: Homo sapiens

<400> SEQUENCE: 509
tcatttacat aagtattttc tgtgggaccg actctcaagg cactgtgtat gccctgcaag      60
ttggctgtct atgagcattt agagatttag aagaaaaatt                          100

<210> SEQ ID NO 510
<211> LENGTH: 100
<212> TYPE: DNA
<213> ORGANISM: Homo sapiens

<400> SEQUENCE: 510
aggagaataa atgttggagg ggtaatacac aaaaacaaag gcatatttga tgaagtaccc      60
tgtgttatgt gaacacaatt tccccttctg ttaagactat                          100

<210> SEQ ID NO 511
<211> LENGTH: 100
<212> TYPE: DNA
<213> ORGANISM: Homo sapiens

<400> SEQUENCE: 511
gctctgtgaa ggcaatgagt gtcacttccc tctgctctaa taaagcaata aataatagct      60
aaagggctga ctttcacttc gaactcttgg ccacggcttt                          100

<210> SEQ ID NO 512
<211> LENGTH: 100
<212> TYPE: DNA
<213> ORGANISM: Homo sapiens

<400> SEQUENCE: 512
ggtggttagc tatacgggaa atggtaagta gtgttgtctt cagtatctta atttgtttct      60
gcaactgtgc actcctccct tggtggcacc ctatgggtgt                          100
```

<210> SEQ ID NO 513
<211> LENGTH: 100
<212> TYPE: DNA
<213> ORGANISM: Homo sapiens

<400> SEQUENCE: 513
ttaactttgt aagatgcaaa gaggttggat caagtttaaa tgactgtgct gccccttca    60 catcaaagaa ctactgacaa cgaaggccgc gcctgccttt                         100

<210> SEQ ID NO 514
<211> LENGTH: 100
<212> TYPE: DNA
<213> ORGANISM: Homo sapiens

<400> SEQUENCE: 514
gcctggagga agttttggaa agagttcaag tgtctgtata cctatggtc ttctccatcc    60 tcacaccttc tgcctttgtc ctgctccctt ttaagccagg                         100

<210> SEQ ID NO 515
<211> LENGTH: 100
<212> TYPE: DNA
<213> ORGANISM: Homo sapiens

<400> SEQUENCE: 515
agtcagagag ccggcactct cagttgccct ctggttgagt tgggggggcag ctctgggggc  60 cgtggcttgt gccatggctc tgctgaccca acaaacagag                         100

<210> SEQ ID NO 516
<211> LENGTH: 100
<212> TYPE: DNA
<213> ORGANISM: Homo sapiens

<400> SEQUENCE: 516
ccctcaaagg aggaaattgc tcagaagacc tcttatgtat cctgaaaagg gctccattca   60
agaagtcatg ggcctacctc caagtggcaa agcatctaaa                         100

<210> SEQ ID NO 517
<211> LENGTH: 100
<212> TYPE: DNA
<213> ORGANISM: Homo sapiens

<400> SEQUENCE: 517
tctggctcgg ataagagatg ggacatcatt cagtcactag ttggatggca caaggctctt   60
cacagacgca tctgtagcag agtggatctt gtactaactt                         100

<210> SEQ ID NO 518
<211> LENGTH: 100
<212> TYPE: DNA
<213> ORGANISM: Homo sapiens

<400> SEQUENCE: 518
tacttcctgt gccttgccag tgggattcct tgtgtgtctc atgtctgggt ccatgatagt   60
tgccatgcca accagctcca gaactaccgt aattatctgt                         100

<210> SEQ ID NO 519
<211> LENGTH: 100
<212> TYPE: DNA
<213> ORGANISM: Homo sapiens

```
<400> SEQUENCE: 519 tctccctcc accagccagg atcctccttc tagctcatct gtagatacta gtagtagtca      60
accaaagcct ttcagacgag taagacttca gacaacattg                          100

<210> SEQ ID NO 520
<211> LENGTH: 100
<212> TYPE: DNA
<213> ORGANISM: Homo sapiens

<400> SEQUENCE: 520
gcctgcgtcg cttccggagg cgcagcgggc gatgacgtag agggacgtgc cctctatatg     60
aggttgggga gcggctgagt cggccttttc cgcccgctcc                          100

<210> SEQ ID NO 521
<211> LENGTH: 100
<212> TYPE: DNA
<213> ORGANISM: Homo sapiens

<400> SEQUENCE: 521
gccagtgtcc catatgttcc tcctgacagt ttgatgtgtc cattctgggc ctctcagtgc     60
ttagcaagta gataatgtaa gggatgtggc agcaaatgga                          100

<210> SEQ ID NO 522
<211> LENGTH: 100
<212> TYPE: DNA
<213> ORGANISM: Homo sapiens

<400> SEQUENCE: 522
cacccgcttt gacatgggta gccttcggag ggagggtttt cagccacgaa gtactgatgc     60
aggggtatag cttgccctca cttgctcaaa aacaactacc                          100

<210> SEQ ID NO 523
<211> LENGTH: 100
<212> TYPE: DNA
<213> ORGANISM: Homo sapiens

<400> SEQUENCE: 523
ctgggaaacc ttcatgcctc tctgatggtt actgcccacc cttaccccac ccctcagctc     60
agcctggtat ggaaagcaag gtgcacgttg gtctttgatt                          100

<210> SEQ ID NO 524
<211> LENGTH: 100
<212> TYPE: DNA
<213> ORGANISM: Homo sapiens

<400> SEQUENCE: 524
tctgcagagg catccggatc ccagcaagcg agctttagca gggaagtcac ttcaccatca     60
acattcctgc cccagatggc tttgtgattc cctccagtga                          100

<210> SEQ ID NO 525
<211> LENGTH: 100
<212> TYPE: DNA
<213> ORGANISM: Homo sapiens

<400> SEQUENCE: 525
gtgctaccaa agggatacaa caagcccttt aggaagcagt acctctcgcc tggaggatct     60
gtgccatctt ggattgagaa ttgcagatgt gacagaatgg                          100
```

<210> SEQ ID NO 526
<211> LENGTH: 100
<212> TYPE: DNA
<213> ORGANISM: Homo sapiens

<400> SEQUENCE: 526
ctgctattcg ggtaatcttc acagaaatga ctgagagaag aatctgcagt ttactgaggg    60
catttcagtt cctcctacca cctcaacagg actttgtcca                         100

<210> SEQ ID NO 527
<211> LENGTH: 100
<212> TYPE: DNA
<213> ORGANISM: Homo sapiens

<400> SEQUENCE: 527
ctctatacca ataagtcagt caccttgctc ctctccagag gcaaagtgga agagatcctg    60
caagacacat ctatcctttc acagtgttcc caagggaact                         100

<210> SEQ ID NO 528
<211> LENGTH: 100
<212> TYPE: DNA
<213> ORGANISM: Homo sapiens

<400> SEQUENCE: 528
agttgatgaa cccatcatgc tggttttttct ctgagcacaa agttttaggc tgtacacagc   60
cagccttggg aatctcgttg agcgttcggc gtggatccac                         100

<210> SEQ ID NO 529
<211> LENGTH: 100
<212> TYPE: DNA
<213> ORGANISM: Homo sapiens

<400> SEQUENCE: 529
ccccagacca acccttccct ccctttcccc acctcttaca gtgtttggac aggagggtat    60
ggtgctgctc tgtgtagcaa gtactttggc ttatgaaaga                         100

<210> SEQ ID NO 530
<211> LENGTH: 100
<212> TYPE: DNA
<213> ORGANISM: Homo sapiens

<400> SEQUENCE: 530
tactaatcag gcatctgacc tgcactgtca tccctgcct ggactttgc gatggactct     60 ttgggggaaa aactaacgct ttttaattat tgtgaaagca                         100

<210> SEQ ID NO 531
<211> LENGTH: 100
<212> TYPE: DNA
<213> ORGANISM: Homo sapiens

<400> SEQUENCE: 531
tcgactgctc agatctcaga atcaagacaa acccgaattg aaaagaagat tgaagcccac    60
tttgatgcca gatcaattgc aacagttgag atggtcatag                         100

<210> SEQ ID NO 532
<211> LENGTH: 100
<212> TYPE: DNA
<213> ORGANISM: Homo sapiens

<400> SEQUENCE: 532
caaaaaagaa tgaacacccc tgactctgga gtggtgtata ctgccacatc agtgtttgag    60
tcagtcccca gaggagaggg gaaccctcct ccatcttttt                          100

<210> SEQ ID NO 533
<211> LENGTH: 100
<212> TYPE: DNA
<213> ORGANISM: Homo sapiens

<400> SEQUENCE: 533
taagctagag gtcatggtca ctgaaattac tttccaaagt ggaagacaaa atgaaacagg    60
aactgaggga atatttaaga tcccacagaa gcgtaaaaat                          100

<210> SEQ ID NO 534
<211> LENGTH: 100
<212> TYPE: DNA
<213> ORGANISM: Homo sapiens

<400> SEQUENCE: 534
ttggatccat ttccatcggt ccttacagcc gctcgtcaga ctccagcagc caagatggtg    60
aagcagatcg agagcaagac tgcttttcag gaagccttgg                          100

<210> SEQ ID NO 535
<211> LENGTH: 100
<212> TYPE: DNA
<213> ORGANISM: Homo sapiens

<400> SEQUENCE: 535
tcatctactg ccaagtagga gaaaagcctt attggaaaga tccaaataat gacttcagaa    60
aaaacttgaa agtaacagca gtgcctacac tacttaagta                          100

<210> SEQ ID NO 536
<211> LENGTH: 100
<212> TYPE: DNA
<213> ORGANISM: Homo sapiens

<400> SEQUENCE: 536
ctcagttgca gcactgagtg gtcaaaatac atttctgggc cacctcaggg aacccatgca    60
tctgcctggc atttaggcag cagagcccct gaccgtcccc                          100

<210> SEQ ID NO 537
<211> LENGTH: 100
<212> TYPE: DNA
<213> ORGANISM: Homo sapiens

<400> SEQUENCE: 537
tgttgcatgg aagggatagt ttggctccct tggaggctat gtaggcttgt cccgggaaag    60
agaactgtcc tgcagctgaa atggactgtt ctttactgac                          100

<210> SEQ ID NO 538
<211> LENGTH: 100
<212> TYPE: DNA
<213> ORGANISM: Homo sapiens

<400> SEQUENCE: 538
tttatggcca aactattttg aattttgttg tccggccctc agtgccctgc cctctccctt    60
accaggacca cagctctgtt ccttcggcct ctggtcctct                          100

```
<210> SEQ ID NO 539
<211> LENGTH: 100
<212> TYPE: DNA
<213> ORGANISM: Homo sapiens

<400> SEQUENCE: 539
ccgccacgtg cgggcgctgg tgcttgagct gtgctgtaac gacgagagcg gcgaggatgt      60
cgaggttccc tatgtccgat acaccatccg ctgaccccgt                          100

<210> SEQ ID NO 540
<211> LENGTH: 100
<212> TYPE: DNA
<213> ORGANISM: Homo sapiens

<400> SEQUENCE: 540
tgcagatctt cgtgaagacc ctgactggta agaccatcac tctcgaagtg gagccgagtg      60
acaccattga gaatgtcaag gcaaagatcc aagacaagga                          100

<210> SEQ ID NO 541
<211> LENGTH: 100
<212> TYPE: DNA
<213> ORGANISM: Homo sapiens

<400> SEQUENCE: 541
acgctggctc cctatccaca ctgtggaaac catcatgatt agtgtcattt ctatgctggc      60
agaccctaat ggagactcac ctgctaatgt tgatgctgcg                          100

<210> SEQ ID NO 542
<211> LENGTH: 100
<212> TYPE: DNA
<213> ORGANISM: Homo sapiens

<400> SEQUENCE: 542
ctgctctgct gactggggaa gtcatcgtgc cacccagaac ctgagtgcgg gcctctcaga      60
gctccttcgt ccgtgggtct gccggggact gggccttgtc                          100

<210> SEQ ID NO 543
<211> LENGTH: 100
<212> TYPE: DNA
<213> ORGANISM: Homo sapiens

<400> SEQUENCE: 543
gggggtccca aagagtttga tgaggccctc cacacctgcg gcccaatcca aggtggggtg      60
gaagcttggg gaagacccat tccttcccag aggggcctgc                          100

<210> SEQ ID NO 544
<211> LENGTH: 100
<212> TYPE: DNA
<213> ORGANISM: Homo sapiens

<400> SEQUENCE: 544
tgacgcggat gcggcatgtg atcagctaca gcttgtcacc gttcgagcag cgcgcctatc      60
cgcacgtctt cactaaagga atccccaatg ttctgcgccg                          100

<210> SEQ ID NO 545
<211> LENGTH: 100
<212> TYPE: DNA
<213> ORGANISM: Homo sapiens
```

<400> SEQUENCE: 545
tctattcctt atatggagtt gttgaacaca gtggtactat gaggtcgggg cattacactg        60
cctatgccaa ggcaagaacc gcaaatagtc atctctctaa                             100

<210> SEQ ID NO 546
<211> LENGTH: 100
<212> TYPE: DNA
<213> ORGANISM: Homo sapiens

<400> SEQUENCE: 546 cctttcact aaggaagaag agctagagtc ggagaatgcc ccagtgtgtg accgatgtcg         60
gcagaaaact cgaagtacca aaaagttgac agtacaaaga                             100

<210> SEQ ID NO 547
<211> LENGTH: 100
<212> TYPE: DNA
<213> ORGANISM: Homo sapiens

<400> SEQUENCE: 547
aggagcacac tgtagacagc tgcatcagtg acatgaaaac agaaaccagg gaggtcctga        60
ccccaacgag cacttctgac aatgagacca gagactcctc                             100

<210> SEQ ID NO 548
<211> LENGTH: 100
<212> TYPE: DNA
<213> ORGANISM: Homo sapiens

<400> SEQUENCE: 548
agagcagagg ggcagcgata gactctgggg atggagcagg acggggacgg gaggggccgg        60
ccacctgtct gtaaggagac tttgttgctt cccctgcccc                             100

<210> SEQ ID NO 549
<211> LENGTH: 100
<212> TYPE: DNA
<213> ORGANISM: Homo sapiens

<400> SEQUENCE: 549
ggtgtggaaa gacttttctg ggctcagagg tgaaactgac ccttgtgtat cagcagcatt        60
tctgactgac tgagagagtg tagtgattaa cagagttgtg                             100

<210> SEQ ID NO 550
<211> LENGTH: 100
<212> TYPE: DNA
<213> ORGANISM: Homo sapiens

<400> SEQUENCE: 550
ttataaagag aaatcactaa tggactctac tggtttgagt gcttctgagc tggatgaccg        60
accgcctgta tgtttgtgta attaattgcc ataataaact                             100

<210> SEQ ID NO 551
<211> LENGTH: 100
<212> TYPE: DNA
<213> ORGANISM: Homo sapiens

<400> SEQUENCE: 551
aactgttgcc tgtcagtgtt tacaaactag tgcgttgacg gcaccgtgtc caagttttta       60
gaacccttgt tagccagacc gaggtgtcct ggtcaccgtt                              100

<210> SEQ ID NO 552
<211> LENGTH: 100
<212> TYPE: DNA
<213> ORGANISM: Homo sapiens

<400> SEQUENCE: 552
caggctctcc tgttgctttg ccatggagcc aggtcagctc tctgtctgtt ctgctgggta    60
acaaggtttg gcagttcctg tttctctggg cttaagtcaa                         100

<210> SEQ ID NO 553
<211> LENGTH: 100
<212> TYPE: DNA
<213> ORGANISM: Homo sapiens

<400> SEQUENCE: 553
gtagtctctg gcaccctgtc cgtctccagc cagccagctc atttcacttt acaccctcat    60
ggactgagat tatactcacc ttttatgaaa gcactgcatg                         100

<210> SEQ ID NO 554
<211> LENGTH: 100
<212> TYPE: DNA
<213> ORGANISM: Homo sapiens

<400> SEQUENCE: 554
ctggatggtg gtgcatccgt gaatgcgctg atcgtttctt ccagttagag tcttcatctg    60
tccgacaagt tcactcgcct cggttgcgga cctaggacca                         100

<210> SEQ ID NO 555
<211> LENGTH: 100
<212> TYPE: DNA
<213> ORGANISM: Homo sapiens

<400> SEQUENCE: 555
gctcattttt aaaccaaatg aacagaccat gagctggctt caggggaagt gctattcaca    60
ggaccatatc caccaccctc ttaaattcct aaacaatatc                         100

<210> SEQ ID NO 556
<211> LENGTH: 100
<212> TYPE: DNA
<213> ORGANISM: Homo sapiens

<400> SEQUENCE: 556
atgatcacag gtgattcaca cgtacacaca taaacacacc caccagtgca gcctgaagta    60
actcccacag aaaccatcat cgtctttgta catcgtatgt                         100

<210> SEQ ID NO 557
<211> LENGTH: 100
<212> TYPE: DNA
<213> ORGANISM: Homo sapiens

<400> SEQUENCE: 557
tatcagatca caaactccta gagtctacat gcaagactag taaagtctta tggagtctta    60
tgatggattt ttaacttccc gtggaaaaaa aaataaaggc                         100

<210> SEQ ID NO 558
<211> LENGTH: 100
<212> TYPE: DNA
<213> ORGANISM: Homo sapiens

```
<400> SEQUENCE: 558
agagctccaa ccttcacatc caccagcggg ttcacaagaa agatcctcgc taactgacat        60
tagcccattc aggtcttcac agcgctcata ctgtaaaaac                             100

<210> SEQ ID NO 559
<211> LENGTH: 100
<212> TYPE: DNA
<213> ORGANISM: Homo sapiens

<400> SEQUENCE: 559
cagacggttc cccacagcat cctcagacag ctctgtgatg tagcttttag gaggcactca        60
ggtgtcacgg ctagactgca gctatgagac agatctggct                             100
```

COMPOSITIONS AND METHODS FOR DIAGNOSING LUNG CANCERS USING GENE EXPRESSION PROFILES

STATEMENT REGARDING FEDERALLY SPONSORED RESEARCH OR DEVELOPMENT

This invention was made with government support under Grant No. CA010815 awarded by the National Institutes of Health. The government has certain rights in the invention.

BACKGROUND OF THE INVENTION

Lung cancer is the most common worldwide cause of cancer mortality. In the United States, lung cancer is the second most prevalent cancer in both men and women and will account for more than 174,000 new cases per year and more than 162,000 cancer deaths. In fact, lung cancer accounts for more deaths each year than from breast, prostate and colorectal cancers combined.

The high mortality (80-85% in five years), which has shown little or no improvement in the past 30 years, emphasizes the fact that new and effective tools to facilitate early diagnosis prior to metastasis to regional nodes or beyond the lung are needed.

High risk populations include smokers, former smokers, and individuals with markers associated with genetic predispositions. Because surgical removal of early stage tumors remains the most effective treatment for lung cancer, there has been great interest in screening high-risk patients with low dose spiral CT (LDCT). This strategy identifies non-calcified pulmonary nodules in approximately 30-70% of high risk individuals but only a small proportion of detected nodules are ultimately diagnosed as lung cancers (0.4 to 2.7%). Currently, the only way to differentiate subjects with lung nodules of benign etiology from subjects with malignant nodules is an invasive biopsy, surgery, or prolonged observation with repeated scanning Even using the best clinical algorithms, 20-55% of patients selected to undergo surgical lung biopsy for indeterminate lung nodules, are found to have benign disease and those that do not undergo immediate biopsy or resection require sequential imaging studies. The use of serial CT in this group of patients runs the risk of delaying potential curable therapy, along with the costs of repeat scans, the not-insignificant radiation doses, and the anxiety of the patient.

Ideally, a diagnostic test would be easily accessible, inexpensive, demonstrate high sensitivity and specificity, and result in improved patient outcomes (medically and financially). Others have shown that classifiers which utilize epithelial cells have high accuracy. However, harvesting these cells requires an invasive bronchoscopy. See, Silvestri et al, N Engl J Med. 2015 Jul. 16; 373(3): 243-251, which is incorporated herein by reference.

Efforts are in progress to develop non-invasive diagnostics using sputum, blood or serum and analyzing for products of tumor cells, methylated tumor DNA, single nucleotide polymorphism (SNPs) expressed messenger RNA or proteins. This broad array of molecular tests with potential utility for early diagnosis of lung cancer has been discussed in the literature. Although each of these approaches has its own merits, none has yet passed the exploratory stage in the effort to detect patients with early stage lung cancer, even in high-risk groups, or patients which have a preliminary diagnosis based on radiological and other clinical factors. A simple blood test, a routine event associated with regular clinical office visits, would be an ideal diagnostic test.

SUMMARY OF THE INVENTION

In one aspect, a composition or kit for diagnosing or evaluating a lung cancer in a mammalian subject includes ten (10) or more polynucleotides or oligonucleotides, wherein each polynucleotide or oligonucleotide hybridizes to a different gene, gene fragment, gene transcript or expression product in a patient sample. Each gene, gene fragment, gene transcript or expression product is selected from the genes of Table I or Table II. In one embodiment, at least one polynucleotide or oligonucleotide is attached to a detectable label. In one embodiment, the composition or kit includes polynucleotides or oligonucleotides which detect the gene, gene fragment, gene transcript or expression product of each of the 559 genes in Table I. In another embodiment, the composition or kit includes polynucleotides or oligonucleotides which detect the gene, gene fragment, gene transcript or expression product of each of the 100 genes in Table II.

In another aspect, a composition or kit for diagnosing or evaluating a lung cancer in a mammalian subject includes ten (10) or more ligands, wherein each ligand hybridizes to a different gene expression product in a patient sample. Each gene expression product is selected from the genes of Table I or Table II. In one embodiment, at least one ligand is attached to a detectable label. In one embodiment, the composition or kit includes ligands which detect the expression products of each of the 559 genes in Table I. In another embodiment, the composition or kit includes ligands which detect the expression products of each of the 100 genes in Table II.

The compositions described herein enable detection of changes in expression in the genes in the subject's gene expression profile from that of a reference gene expression profile. The various reference gene expression profiles are described below. In one embodiment, the composition provides the ability to distinguish a cancerous tumor from a non-cancerous nodule.

In another aspect, a method for diagnosing or evaluating a lung cancer in a mammalian subject involves identifying changes in the expression of three or more genes in the sample of a subject, said genes selected from the genes of Table I or Table II, and comparing that subject's gene expression levels with the levels of the same genes in a reference or control, wherein changes in expression of said gene expression correlates with a diagnosis or evaluation of a lung cancer. In one embodiment, the changes in expression of said gene expression provides the ability to distinguish a cancerous tumor from a non-cancerous nodule.

In another aspect, a method for diagnosing or evaluating a lung cancer in a mammalian subject involves identifying a gene expression profile in the blood of a subject, the gene expression profile comprising 10 or more gene expression products of 10 or more informative genes as described herein. The 10 or more informative genes are selected from the genes of Table I or Table II. In one embodiment, the gene expression profile contains all 559 genes of Table I. In another embodiment, the gene expression profile contains all 100 genes of Table II. The subject's gene expression profile is compared with a reference gene expression profile from a variety of sources described below. Changes in expression of the informative genes correlate with a diagnosis or evaluation of a lung cancer. In one embodiment, the changes in expression of said gene expression provides the ability to distinguish a cancerous tumor from a non-cancerous nodule.

In another aspect, a method of detecting lung cancer in a patient is provided. The method includes obtaining a sample from the patient; and detecting a change in expression in at least 10 genes selected from Table I or Table II in the patient sample as compared to a control by contacting the sample with a composition comprising oligonucleotides, polynucleotides or ligands specific for each different gene transcript or expression product of the at least 10 gene of Table I or Table II and detecting binding between the oligonucleotide, polynucleotide or ligand and the gene product or expression product.

In yet another aspect, a method of diagnosing lung cancer in a subject is provided. The method includes obtaining a blood sample from a subject; detecting a change in expression in at least 10 genes selected from Table I or Table II in the patient sample as compared to a control by contacting the sample with a composition comprising oligonucleotides, polynucleotides or ligands specific for each different gene transcript or expression product of the at least 10 gene of Table I or Table II and detecting binding between the oligonucleotide, polynucleotide or ligand and the gene product or expression product; and diagnosing the subject with cancer when changes in expression of the subject's genes from those of the reference are detected.

In another aspect, a method of diagnosing and treating lung cancer in a subject having a neoplastic growth is provided. The method includes obtaining a blood sample from a subject; detecting a change in expression in at least 10 genes selected from Table I or Table II in the patient sample as compared to a control by contacting the sample with a composition comprising oligonucleotides, polynucleotides or ligands specific for each different gene transcript or expression product of the at least 10 gene of Table I or Table II and detecting binding between the oligonucleotide, polynucleotide or ligand and the gene product or expression product; diagnosing the subject with cancer when changes in expression of the subject's genes from those of the reference are detected; and removing the neoplastic growth. Other appropriate treatments may also be provided.

Other aspects and advantages of these compositions and methods are described further in the following detailed description of the preferred embodiments thereof.

BRIEF DESCRIPTION OF THE DRAWINGS

FIG. 1 is a table showing patient characteristics for the samples used in Example 1.

DETAILED DESCRIPTION OF THE INVENTION

Figure 2A:
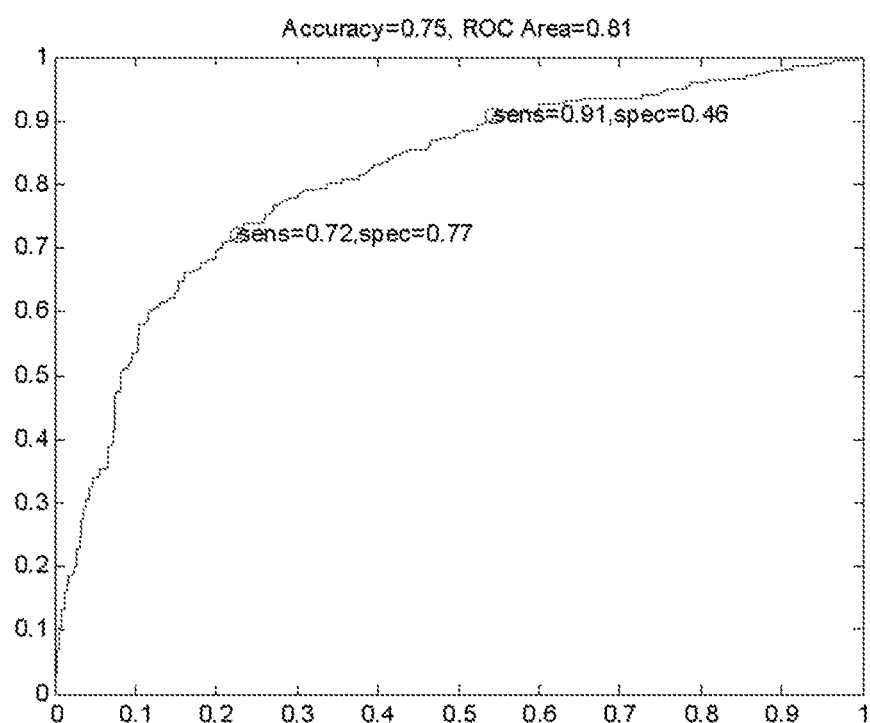
FIGS. 2A and 2B are graphs showing the cross validated support vector machine classifier (CV SVM) of all 610 samples (FIG. 2A, Accuracy=0.75, ROC Area=0.81. According to the curve, when the sensitivity is 0.91, the specificity is 0.46; when the sensitivity is 0.72, the specificity is 0.77) and a balanced set of 556 samples (FIG. 2B, Accuracy=0.76, ROC Area=0.81, According to the curve, when the sensitivity is 0.90, the specificity is 0.48; when the sensitivity is 0.76, the specificity is 0.77), using the 559 Classifier. The full and balanced sets show similar performance.

The methods and compositions described herein apply gene expression technology to blood screening for the detection and diagnosis of lung cancer. The compositions and methods described herein provide the ability to distinguish a cancerous tumor from a non-cancerous nodule, by determining a characteristic RNA expression profile of the genes of the blood of a mammalian, preferably human, subject. The profile is compared with the profile of one or more subjects of the same class (e.g., patients having lung cancer or a non-cancerous nodule) or a control to provide a useful diagnosis.

These methods of lung cancer screening employ compositions suitable for conducting a simple and cost-effective and non-invasive blood test using gene expression profiling that could alert the patient and physician to obtain further studies, such as a chest radiograph or CT scan, in much the same way that the prostate specific antigen is used to help diagnose and follow the progress of prostate cancer. The application of these profiles provides overlapping and confirmatory diagnoses of the type of lung disease, beginning with the initial test for malignant vs. non-malignant disease.

"Patient" or "subject" as used herein means a mammalian animal, including a human, a veterinary or farm animal, a domestic animal or pet, and animals normally used for clinical research. In one embodiment, the subject of these methods and compositions is a human.

"Control" or "Control subject" as used herein refers to the source of the reference gene expression profiles as well as the particular panel of control subjects described herein. In one embodiment, the control or reference level is from a single subject. In another embodiment, the control or reference level is from a population of individuals sharing a specific characteristic. In yet another embodiment, the control or reference level is an assigned value which correlates with the level of a specific control individual or population, although not necessarily measured at the time of assaying the test subject's sample. In one embodiment, the control subject or reference is from a patient (or population) having a non-cancerous nodule. In another embodiment, the control subject or reference is from a patient (or population) having a cancerous tumor. In other embodiments, the control subject can be a subject or population with lung cancer, such as a subject who is a current or former smoker with malignant disease, a subject with a solid lung tumor prior to surgery for removal of same; a subject with a solid lung tumor following surgical removal of said tumor; a subject with a solid lung tumor prior to therapy for same; and a subject with a solid lung tumor during or following therapy for same. In other embodiments, the controls for purposes of the compositions and methods described herein include any of the following classes of reference human subject with no lung cancer. Such non-healthy controls (NHC) include the classes of smoker with non-malignant disease, a former smoker with non-malignant disease (including patients with lung nodules), a non-smoker who has chronic obstructive pulmonary disease (COPD), and a former smoker with COPD. In still other embodiments, the control subject is a healthy non-smoker with no disease or a healthy smoker with no disease.

"Sample" as used herein means any biological fluid or tissue that contains immune cells and/or cancer cells. The most suitable sample for use in this invention includes whole blood. Other useful biological samples include, without limitation, peripheral blood mononuclear cells, plasma, saliva, urine, synovial fluid, bone marrow, cerebrospinal fluid, vaginal mucus, cervical mucus, nasal secretions, sputum, semen, amniotic fluid, bronchoscopy sample, bronchoalveolar lavage fluid, and other cellular exudates from a patient having cancer. Such samples may further be diluted with saline, buffer or a physiologically acceptable diluent. Alternatively, such samples are concentrated by conventional means.

As used herein, the term "cancer" refers to or describes the physiological condition in mammals that is typically characterized by unregulated cell growth. More specifically, as used herein, the term "cancer" means any lung cancer. In one embodiment, the lung cancer is non-small cell lung cancer (NSCLC). In a more specific embodiment, the lung cancer is lung adenocarcinoma (AC or LAC). In another more specific embodiment, the lung cancer is lung squamous cell carcinoma (SCC or LSCC). In another embodiment, the lung cancer is a stage I or stage II NSCLC. In still another embodiment, the lung cancer is a mixture of early and late stages and types of NSCLC.

The term "tumor," as used herein, refers to all neoplastic cell growth and proliferation, whether malignant or benign, and all pre-cancerous and cancerous cells and tissues. The term "nodule" refers to an abnormal buildup of tissue which is benign. The term "cancerous tumor" refers to a malignant tumor.

By "diagnosis" or "evaluation" it is meant a diagnosis of a lung cancer, a diagnosis of a stage of lung cancer, a diagnosis of a type or classification of a lung cancer, a diagnosis or detection of a recurrence of a lung cancer, a diagnosis or detection of a regression of a lung cancer, a prognosis of a lung cancer, or an evaluation of the response of a lung cancer to a surgical or non-surgical therapy. In one embodiment, "diagnosis" or "evaluation" refers to distinguishing between a cancerous tumor and a benign pulmonary nodule.

As used herein, "sensitivity" (also called the true positive rate), measures the proportion of positives that are correctly identified as such (e.g., the percentage of sick people who are correctly identified as having the condition).

As used herein, "specificity" (also called the true negative rate) measures the proportion of negatives that are correctly identified as such (e.g., the percentage of healthy people who are correctly identified as not having the condition).

By "change in expression" is meant an upregulation of one or more selected genes in comparison to the reference or control; a downregulation of one or more selected genes in comparison to the reference or control; or a combination of certain upregulated genes and down regulated genes.

By "therapeutic reagent" or "regimen" is meant any type of treatment employed in the treatment of cancers with or without solid tumors, including, without limitation, chemotherapeutic pharmaceuticals, biological response modifiers, radiation, diet, vitamin therapy, hormone therapies, gene therapy, surgical resection, etc.

By "informative genes" as used herein is meant those genes the expression of which changes (either in an up-regulated or down-regulated manner) characteristically in the presence of lung cancer. A statistically significant number of such informative genes thus form suitable gene expression profiles for use in the methods and compositions. Such genes are shown in Table I and Table II below. Such genes make up the "expression profile".

The term "statistically significant number of genes" in the context of this invention differs depending on the degree of change in gene expression observed. The degree of change in gene expression varies with the type of cancer and with the size or spread of the cancer or solid tumor. The degree of change also varies with the immune response of the individual and is subject to variation with each individual. For example, in one embodiment of this invention, a large change, e.g., 2-3 fold increase or decrease in a small number of genes, e.g., in about 10 to 20 genes, is statistically significant. In another embodiment, a smaller relative change in about 15 more genes is statistically significant.

Thus, the methods and compositions described herein contemplate examination of the expression profile of a "statistically significant number of genes" ranging from 5 to about 559 genes in a single profile. In one embodiment, the genes are selected from Table I. In another embodiment, the genes are selected from Table II. In one embodiment, the gene profile is formed by a statistically significant number of 5 or more genes. In one embodiment, the gene profile is formed by a statistically significant number of 10 or more genes. In another embodiment, the gene profile is formed by a statistically significant number of 15 or more genes. In another embodiment, the gene profile is formed by a statistically significant number of 20 or more genes. In another embodiment, the gene profile is formed by a statistically significant number of 25 or more genes. In another embodiment, the gene profile is formed by a statistically significant number of 30 or more genes. In another embodiment, the gene profile is formed by a statistically significant number of 35 or more genes. In another embodiment, the gene profile is formed by a statistically significant number of 40 or more genes. In another embodiment, the gene profile is formed by a statistically significant number of 45 or more genes. In another embodiment, the gene profile is formed by a statistically significant number of 50 or more genes. In another embodiment, the gene profile is formed by a statistically significant number of 60 or more genes. In another embodiment, the gene profile is formed by a statistically significant number of 65 or more genes. In another embodiment, the gene profile is formed by a statistically significant number of 70 or more genes. In another embodiment, the gene profile is formed by a statistically significant number of 75 or more genes. In another embodiment, the gene profile is formed by a statistically significant number of 80 or more genes. In another embodiment, the gene profile is formed by a statistically significant number of 85 or more genes. In another embodiment, the gene profile is formed by a statistically significant number of 90 or more genes. In another embodiment, the gene profile is formed by a statistically significant number of 95 or more genes. In another embodiment, the gene profile is formed by a statistically significant number of 100 or more genes. In another embodiment, the gene profile is formed by a statistically significant number of 200 or more genes. In another embodiment, the gene profile is formed by a statistically significant number of 300 or more genes. In another embodiment, the gene profile is formed by a statistically significant number of 350 or more genes. In still another embodiment, the gene profile is formed by 400 or more genes. In still another embodiment, the gene profile is formed by 539 genes. In still another embodiment, the gene profile is formed by 559 genes. In still other embodiments, the gene profiles examined as part of these methods contain, as statistically significant numbers of genes, from 10 to 559 genes, and any numbers therebetween. In another embodiment, the gene profile is formed by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, or all 559 genes of Table I. In another embodiment, the gene profile is formed by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all 100 genes of Table II.

Table I and Table II below refer to a collection of known genes useful in discriminating between a subject having a lung cancer, e.g., NSCLC, and subjects having benign (non-malignant) lung nodules. The sequences of the genes identified in Table I and Table II are publicly available. One skilled in the art may readily reproduce the compositions and methods described herein by use of the sequences of the genes, all of which are publicly available from conventional sources, such as GenBank. The GenBank accession number for each gene is provided.

The term "microarray" refers to an ordered arrangement of hybridizable array elements, preferably polynucleotide or oligonucleotide probes, on a substrate.

The term "polynucleotide," when used in singular or plural form, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene", "differential gene expression" and their synonyms, which are used interchangeably, refer to a gene whose expression is activated to a higher or lower level in a subject suffering from a disease, specifically cancer, such as lung cancer, relative to its expression in a control subject, such as a subject having a benign nodule. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects, non-health controls and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is a statistically significant ($p<0.05$) difference in gene expression between the subject and control samples.

The term "over-expression" with regard to an RNA transcript is used to refer to the level of the transcript determined by normalization to the level of reference mRNAs, which might be all measured transcripts in the specimen or a particular reference set of mRNAs.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

In the context of the compositions and methods described herein, reference to "10 or more", "at least 10" etc. of the genes listed in Table I or Table II means any one or any and all combinations of the genes listed. For example, suitable gene expression profiles include profiles containing any number between at least 5 through 559 genes from Table I. In another example, suitable gene expression profiles include profiles containing any number between at least 5 through 100 genes from Table II. In one embodiment, gene profiles formed by genes selected from a table are used in rank order, e.g., genes ranked in the top of the list demonstrated more significant discriminatory results in the tests, and thus may be more significant in a profile than lower ranked genes. However, in other embodiments the genes forming a useful gene profile do not have to be in rank order and may be any gene from the table. As used herein, the term "100 Classifier" or "100 Biomarker Classifier" refers to the 100 genes of Table II. As used herein, the term "559 Classifier" or "559 Biomarker Classifier" refers to the 559 genes of Table I. However, subsets of the genes of Table I or Table II, as described herein, are also useful, and, in another embodiment, the terms may refer to those subsets as well.

As used herein, "labels" or "reporter molecules" are chemical or biochemical moieties useful for labeling a nucleic acid (including a single nucleotide), polynucleotide, oligonucleotide, or protein ligand, e.g., amino acid or antibody. "Labels" and "reporter molecules" include fluorescent agents, chemiluminescent agents, chromogenic agents, quenching agents, radionucleotides, enzymes, substrates, cofactors, inhibitors, magnetic particles, and other moieties known in the art. "Labels" or "reporter molecules" are capable of generating a measurable signal and may be covalently or noncovalently joined or bound to an oligonucleotide or nucleotide (e.g., a non-natural nucleotide) or ligand.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

I. GENE EXPRESSION PROFILES

The inventors have shown that the gene expression profiles of the whole blood of lung cancer patients differ significantly from those seen in patients having non-cancerous lung nodules. For example, changes in the gene expression products of the genes of Table I and/or Table II can be observed and detected by the methods of this invention in the normal circulating blood of patients with early stage solid lung tumors.

The gene expression profiles described herein provide new diagnostic markers for the early detection of lung cancer and could prevent patients from undergoing unnecessary procedures relating to surgery or biopsy for a benign nodule. Since the risks are very low, the benefit to risk ratio is very high. In one embodiment, the methods and compositions described herein may be used in conjunction with clinical risk factors to help physicians make more accurate decisions about how to manage patients with lung nodules. Another advantage of this invention is that diagnosis may occur early since diagnosis is not dependent upon detecting circulating tumor cells which are present in only vanishing small numbers in early stage lung cancers.

In one aspect, a composition is provided for classifying a nodule as cancerous or benign in a mammalian subject. In one embodiment, the composition includes at least 10 polynucleotides or oligonucleotides or ligands, wherein each polynucleotide or oligonucleotide or ligand hybridizes to a different gene, gene fragment, gene transcript or expression product in a sample selected from the genes of Table I or Table II. In another embodiment, the composition includes at least 100 polynucleotides or oligonucleotides or ligands, wherein each polynucleotide or oligonucleotide or ligand hybridizes to a different gene, gene fragment, gene transcript or expression product in a sample selected from the genes of Table I. In one embodiment, the polynucleotide or oligonucleotide or ligand hybridizes to an mRNA.

TABLE I

| Rank | Sequence ID# | Gene | Class Name |
| --- | --- | --- | --- |
| 1 | PLEKHG4 | NM_015432.3 | Endogenous |
| 2 | SLC25A20 | NM_000387.5 | Endogenous |
| 3 | LETM2 | NM_144652.3 | Endogenous |
| 4 | GLIS3 | NM_001042413.1 | Endogenous |
| 5 | LOC100132797 | XR_036994.1 | Endogenous |
| 6 | ARHGEF5 | NM_005435.3 | Endogenous |
| 7 | TCF7L2 | NM_030756.4 | Endogenous |

TABLE I-continued

| Rank | Sequence ID# | Gene | Class Name |
|---|---|---|---|
| 8 | SFRS2IP | NM_004719.2 | Endogenous |
| 9 | CFD | NM_001928.2 | Endogenous |
| 10 | AZI2 | NM_022461.4 | Endogenous |
| 11 | STOM | NM_004099.5 | Endogenous |
| 12 | CD1A | NM_001763.2 | Endogenous |
| 13 | PANK2 | NM_153640.2 | Endogenous |
| 14 | CNIH4 | NM_014184.3 | Endogenous |
| 15 | EVI2A | NM_014210.3 | Endogenous |
| 16 | BATF | NM_006399.3 | Endogenous |
| 17 | TCP1 | NM_030752.2 | Endogenous |
| 18 | BX108566 | BX108566.1 | Endogenous |
| 19 | ANXA1 | NM_000700.2 | Endogenous |
| 20 | PSMA3 | NM_152132.2 | Endogenous |
| 21 | IRF4 | NM_002460.1 | Endogenous |
| 22 | STAG3 | NM_012447.3 | Endogenous |
| 23 | NDUFS4 | NM_002495.2 | Endogenous |
| 24 | HAT1 | NM_003642.3 | Endogenous |
| 25 | ANXA1 b | NM_000700.1 | Endogenous |
| 26 | LOC148137 | NM_144692.1 | Endogenous |
| 27 | LDHA | NM_001165416.1 | Endogenous |
| 28 | PSME3 | NM_005789.3 | Endogenous |
| 29 | REPS1 | NM_001128617.2 | Endogenous |
| 30 | CDH5 | NM_001795.3 | Endogenous |
| 31 | NAT5 | NM_181528.3 | Endogenous |
| 32 | PLAC8 | NM_001130715.1 | Endogenous |
| 33 | GSTO1 | NM_004832.2 | Endogenous |
| 34 | DGUOK | NM_080916.2 | Endogenous |
| 35 | OLR1 | NM_002543.3 | Endogenous |
| 36 | MYST4 | NM_012330.3 | Endogenous |
| 37 | TIMM8B | ENST00000504148.1 | Endogenous |
| 38 | LY96 | NM_015364.4 | Endogenous |
| 39 | CCDC72 | NM_015933.4 | Endogenous |
| 40 | ATP5I | NM_007100.2 | Endogenous |
| 41 | WDR91 | NM_014149.3 | Endogenous |
| 42 | MAGEA3 | NM_005362.3 | Endogenous |
| 43 | AK093878 | AK093878.1 | Endogenous |
| 44 | EYA3 | NM_001990.3 | Endogenous |
| 45 | ACAA2 | NM_006111.2 | Endogenous |
| 46 | ETFDH | NM_004453.3 | Endogenous |
| 47 | CCT6A | NM_001762.3 | Endogenous |
| 48 | HSCB | NM_172002.3 | Endogenous |
| 49 | EMR4 | NM_001080498.2 | Endogenous |
| 50 | USP5 | NM_003481.2 | Endogenous |
| 51 | SIK1 | NM_173354.3 | Endogenous |
| 52 | SYNJ1 | NM_003895.3 | Endogenous |
| 53 | KLRB1 | NM_002258.2 | Endogenous |
| 54 | CLK2 | XM_941392.1 | Endogenous |
| 55 | SNORA56 | NR_002984.1 | Endogenous |
| 56 | TP53BP1 | NM_005657.2 | Endogenous |
| 57 | RBX1 | NM_014248.3 | Endogenous |
| 58 | CNPY2 | NM_014255.5 | Endogenous |
| 59 | RELA | NM_021975.2 | Endogenous |
| 60 | LOC732371 | XM_001133019.1 | Endogenous |
| 61 | TMEM218 | NM_001080546.2 | Endogenous |
| 62 | LOC91431 | NM_001099776.1 | Endogenous |
| 63 | GZMB | NM_004131.3 | Endogenous |
| 64 | CAMP | NM_004345.4 | Endogenous |
| 65 | RBM16 | NM_014892.4 | Endogenous |
| 66 | MID1IP1 | NM_021242.5 | Endogenous |
| 67 | LOC399942 | XM_934471.1 | Endogenous |
| 68 | COMMD6 | NM_203497.3 | Endogenous |
| 69 | PPP6C | NM_002721.4 | Endogenous |
| 70 | BCOR | NM_017745.5 | Endogenous |
| 71 | PDCD10 | NM_145859.1 | Endogenous |
| 72 | HLA-DMB | NM_002118.3 | Endogenous |
| 73 | DNAJB1 | NM_006145.2 | Endogenous |
| 74 | KYNU | NM_001032998.1 | Endogenous |
| 75 | TM2D2 | NM_078473.2 | Endogenous |
| 76 | FAM179A | NM_199280.2 | Endogenous |
| 77 | FAM43A | NM_153690.4 | Endogenous |
| 78 | QTRTD1 | NM_024638.3 | Endogenous |
| 79 | MARCKSL1 | NM_023009.5 | Endogenous |
| 80 | FAM193A | NM_003704.3 | Endogenous |
| 81 | AK026725 | AK026725.1 | Endogenous |
| 82 | SERPINB10 | NM_005024.1 | Endogenous |
| 83 | OSBP | ILMN_1706376.1 | Endogenous |
| 84 | ST6GAL1 | NM_003032.2 | Endogenous |
| 85 | NDUFAF2 | NM_174889.4 | Endogenous |

TABLE I-continued

| Rank | Sequence ID# | Gene | Class Name |
|---|---|---|---|
| 86 | UBE2I | NM_194259.2 | Endogenous |
| 87 | CTAG1B | NM_001327.2 | Endogenous |
| 88 | TRAF6 | NM_145803.1 | Endogenous |
| 89 | REPIN1 | NM_014374.3 | Endogenous |
| 90 | LAMA5 | NM_005560.4 | Endogenous |
| 91 | TBC1D12 | NM_015188.1 | Endogenous |
| 92 | TGIF1 b | NM_173208.1 | Endogenous |
| 93 | LOC728533 | XR_015610.3 | Endogenous |
| 94 | CLN8 | NM_018941.3 | Endogenous |
| 95 | COX7B | NM_001866.2 | Endogenous |
| 96 | DYNC2LI1 | NM_016008.3 | Endogenous |
| 97 | ANP32B | NM_006401.2 | Endogenous |
| 98 | PTGDR2 | NM_004778.1 | Endogenous |
| 99 | MRPS16 | NM_016065.3 | Endogenous |
| 100 | NIPBL | NM_133433.3 | Endogenous |
| 101 | PPP2R5C | NM_178588.1 | Endogenous |
| 102 | DPF2 | NM_006268.4 | Endogenous |
| 103 | RAB10 | NM_016131.4 | Endogenous |
| 104 | MYADM | NM_001020820.1 | Endogenous |
| 105 | CCND3 | NM_001760.2 | Endogenous |
| 106 | CC2D1B | NM_032449.2 | Endogenous |
| 107 | HLA-G | NM_002127.4 | Endogenous |
| 108 | CKS2 | NM_001827.1 | Endogenous |
| 109 | HPSE | NM_006665.5 | Endogenous |
| 110 | UBE2G1 | NM_003342.4 | Endogenous |
| 111 | MED16 | NM_005481.2 | Endogenous |
| 112 | LOC339674 | XM_934917.1 | Endogenous |
| 113 | RNF114 | NM_018683.3 | Endogenous |
| 114 | KIR2DS3 | NM_012313.1 | Endogenous |
| 115 | AMD1 | NM_001634.4 | Endogenous |
| 116 | S100A8 | NM_002964.4 | Endogenous |
| 117 | NFATC4 | NM_001136022.2 | Endogenous |
| 118 | RPL39L | NM_052969.1 | Endogenous |
| 119 | LOC399753 | XM_930634.1 | Endogenous |
| 120 | FKBP1A | NM_054014.3 | Endogenous |
| 121 | CHMP5 | NM_016410.5 | Endogenous |
| 122 | CABC1 | NM_020247.4 | Endogenous |
| 123 | HLA-B | NM_005514.6 | Endogenous |
| 124 | TRIM39 | NM_021253.3 | Endogenous |
| 125 | LOC645914 | XM_928884.1 | Endogenous |
| 126 | CD79A | NM_021601.3 | Endogenous |
| 127 | GLRX | ILMN_1737308.1 | Endogenous |
| 128 | RPL26L1 | NM_016093.2 | Endogenous |
| 129 | USP21 | NM_012475.4 | Endogenous |
| 130 | CD70 | NM_001252.2 | Endogenous |
| 131 | SPINK5 | NM_006846.3 | Endogenous |
| 132 | HUWE1 | NM_031407.6 | Endogenous |
| 133 | STK38 | NM_007271.3 | Endogenous |
| 134 | SEMG1 | NM_003007.2 | Endogenous |
| 135 | NDUFA4 | NM_002489.3 | Endogenous |
| 136 | MYADM b | NM_001020820.1 | Endogenous |
| 137 | SGK1 b | NM_005627.3 | Endogenous |
| 138 | SLAMF8 | NM_020125.2 | Endogenous |
| 139 | LOC653773 | XM_938755.1 | Endogenous |
| 140 | RPS24 | NM_001026.4 | Endogenous |
| 141 | LOC338799 | NR_002809.2 | Endogenous |
| 142 | MAP3K7 | NM_145333.1 | Endogenous |
| 143 | KLRD1 | NM_002262.3 | Endogenous |
| 144 | LOC732111 | XM_001134275.1 | Endogenous |
| 145 | CD69 | NM_001781.2 | Endogenous |
| 146 | DDIT4 | NM_019058.2 | Endogenous |
| 147 | C1orf222 | NM_001003808.1 | Endogenous |
| 148 | PFAS | NM_012393.2 | Endogenous |
| 149 | USP9Y | NM_004654.3 | Endogenous |
| 150 | COLEC12 | NM_130386.2 | Endogenous |
| 151 | VPS37C | NM_017966.4 | Endogenous |
| 152 | SAP130 | NM_024545.3 | Endogenous |
| 153 | CDC42EP2 | NM_006779.3 | Endogenous |
| 154 | LOC643319 | XM_927980.1 | Endogenous |
| 155 | ASF1B | NM_018154.2 | Endogenous |
| 156 | AK094576 | AK094576.1 | Endogenous |
| 157 | BANP | NM_079837.2 | Endogenous |
| 158 | TBK1 | NM_013254.2 | Endogenous |
| 159 | GNS | NM_002076.3 | Endogenous |
| 160 | IL1R2 | NM_173343.1 | Endogenous |
| 161 | CLEC4C | NM_203503.1 | Endogenous |
| 162 | TM9SF1 | NM_006405.6 | Endogenous |
| 163 | PTGDR | NM_000953.2 | Endogenous |

TABLE I-continued

| Rank | Sequence ID# | Gene | Class Name |
|---|---|---|---|
| 164 | GOLGA3 | NM_005895.3 | Endogenous |
| 165 | CLEC4A | NM_194448.2 | Endogenous |
| 166 | TSC1 | NM_000368.4 | Endogenous |
| 167 | SFMBT1 | NM_001005158.2 | Endogenous |
| 168 | GLT25D1 | NM_024656.2 | Endogenous |
| 169 | LOC100130229 | XM_001717158.1 | Endogenous |
| 170 | PHF8 | NM_015107.2 | Endogenous |
| 171 | PUM1 | NM_001020658.1 | Endogenous |
| 172 | SMARCC1 | NM_003074.3 | Endogenous |
| 173 | AK126342 | AK126342.1 | Endogenous |
| 174 | ACSL5 | NM_203379.1 | Endogenous |
| 175 | TGIF1 | NM_003244.2 | Endogenous |
| 176 | BF375676 | BF375676.1 | Endogenous |
| 177 | SPA17 | NM_017425.3 | Endogenous |
| 178 | FLNB | NM_001457.3 | Endogenous |
| 179 | FAM105B | NM_138348.4 | Endogenous |
| 180 | CPPED1 | NM_018340.2 | Endogenous |
| 181 | TRIM32 | NM_012210.3 | Endogenous |
| 182 | RNF34 | NM_025126.3 | Endogenous |
| 183 | SLC45A3 | NM_033102.2 | Endogenous |
| 184 | P2RY10 | NM_198333.1 | Endogenous |
| 185 | AKR1C3 | NM_003739.4 | Endogenous |
| 186 | NME1-NME2 | NM_001018136.2 | Endogenous |
| 187 | AMPD3 | NM_000480.2 | Endogenous |
| 188 | HSP90AB1 | NM_007355.3 | Endogenous |
| 189 | RBM4B | NM_031492.3 | Endogenous |
| 190 | DMBT1 | NM_007329.2 | Endogenous |
| 191 | TMCO1 | NM_019026.3 | Endogenous |
| 192 | CASP2 | NM_032983.3 | Endogenous |
| 193 | C1orf103 | NM_018372.3 | Endogenous |
| 194 | ARHGAP17 | NM_018054.5 | Endogenous |
| 195 | IFNA17 | NM_021268.2 | Endogenous |
| 196 | CTSZ | NM_001336.3 | Endogenous |
| 197 | DBI | NM_001079862.1 | Endogenous |
| 198 | TXNRD1 b | NM_182743.2 | Endogenous |
| 199 | KIAA0460 | NM_015203.4 | Endogenous |
| 200 | PDGFD | NM_033135.3 | Endogenous |
| 201 | ATG5 | NM_004849.2 | Endogenous |
| 202 | ITFG2 | NM_018463.3 | Endogenous |
| 203 | HERC1 | NM_003922.3 | Endogenous |
| 204 | MEN1 | NM_130799.2 | Endogenous |
| 205 | IFI27L2 | NM_032036.2 | Endogenous |
| 206 | LOC729887 | XR_040891.2 | Endogenous |
| 207 | PI4K2A | NM_018425.3 | Endogenous |
| 208 | RAG1 | NM_000448.2 | Endogenous |
| 209 | CREB5 | NM_182898.3 | Endogenous |
| 210 | SLC6A12 | NM_003044.4 | Endogenous |
| 211 | CDKN1A | NM_000389.2 | Endogenous |
| 212 | AW173314 | AW173314.1 | Endogenous |
| 213 | SAP130 b | NM_024545.3 | Endogenous |
| 214 | ABCA5 | NM_018672.4 | Endogenous |
| 215 | SLC25A37 | NM_016612.2 | Endogenous |
| 216 | MYLIP | NM_013262.3 | Endogenous |
| 217 | GATA2 | NM_001145662.1 | Endogenous |
| 218 | ATP5L | NM_006476.4 | Endogenous |
| 219 | RPS27L | NM_015920.3 | Endogenous |
| 220 | DB338252 | DB338252.1 | Endogenous |
| 221 | FRAT2 | NM_012083.2 | Endogenous |
| 222 | CCL4 | NM_002984.2 | Endogenous |
| 223 | CD79B | NM_000626.2 | Endogenous |
| 224 | MBD1 | NM_015844.2 | Endogenous |
| 225 | TIAM1 | NM_003253.2 | Endogenous |
| 226 | HSD11B1 | NM_181755.1 | Endogenous |
| 227 | TPR | NM_003292.2 | Endogenous |
| 228 | EID2B | NM_152361.2 | Endogenous |
| 229 | PDSS1 | NM_014317.3 | Endogenous |
| 230 | C9orf164 | NM_182635.1 | Endogenous |
| 231 | ARHGEF18 | NM_015318.3 | Endogenous |
| 232 | TXNRD1 | NM_001093771.2 | Endogenous |
| 233 | HNRNPAB | NM_004499.3 | Endogenous |
| 234 | TTN | NM_133378.4 | Endogenous |
| 235 | EP300 | NM_001429.2 | Endogenous |
| 236 | CCDC97 | NM_052848.1 | Endogenous |
| 237 | HK3 | NM_002115.2 | Endogenous |
| 238 | CRKL | NM_005207.3 | Endogenous |
| 239 | NCOA5 | NM_020967.2 | Endogenous |
| 240 | AK124143 | AK124143.1 | Endogenous |
| 241 | LBA1 | NM_014831.2 | Endogenous |

TABLE I-continued

| Rank | Sequence ID# | Gene | Class Name |
|---|---|---|---|
| 242 | SLC9A3R1 | NM_004252.3 | Endogenous |
| 243 | CRY2 | NM_021117.3 | Endogenous |
| 244 | ATG4B | NM_178326.2 | Endogenous |
| 245 | CD97 | NM_078481.3 | Endogenous |
| 246 | TTC9 | NM_015351.1 | Endogenous |
| 247 | BMPR2 | NM_001204.6 | Endogenous |
| 248 | LPIN2 | NM_014646.2 | Endogenous |
| 249 | UBA1 | NM_003334.3 | Endogenous |
| 250 | SETD1B | XM_037523.11 | Endogenous |
| 251 | PRPF8 | NM_006445.3 | Endogenous |
| 252 | RNASE2 | NM_002934.2 | Endogenous |
| 253 | KIAA0101 | NM_014736.4 | Endogenous |
| 254 | ARG1 | NM_000045.3 | Endogenous |
| 255 | UBTF | NM_001076683.1 | Endogenous |
| 256 | MFSD1 | NM_022736.2 | Endogenous |
| 257 | IDO1 | NM_002164.3 | Endogenous |
| 258 | MS4A6A | NM_022349.3 | Endogenous |
| 259 | C22orf30 | NM_173566.2 | Endogenous |
| 260 | HNRNPK | NM_031263.2 | Endogenous |
| 261 | ARL8B | NM_018184.2 | Endogenous |
| 262 | SETD2 | NM_014159.6 | Endogenous |
| 263 | NCAPG | NM_022346.4 | Endogenous |
| 264 | EEF1B2 | NM_001037663.1 | Endogenous |
| 265 | TRIM39 b | NM_172016.2 | Endogenous |
| 266 | EHD4 | NM_139265.3 | Endogenous |
| 267 | IRF1 | NM_002198.1 | Endogenous |
| 268 | LOC100129022 | XM_001716591.1 | Endogenous |
| 269 | TRAF3IP2 | NM_147686.3 | Endogenous |
| 270 | PSMA6 | NM_002791.2 | Endogenous |
| 271 | RHOG | NM_001665.3 | Endogenous |
| 272 | CN312986 | CN312986.1 | Endogenous |
| 273 | PSMB8 | NM_004159.4 | Endogenous |
| 274 | ZNF239 | NM_001099283.1 | Endogenous |
| 275 | CLPTM1 | NM_001294.3 | Endogenous |
| 276 | NADK | NM_023018.4 | Endogenous |
| 277 | C8orf76 | NM_032847.2 | Endogenous |
| 278 | LIF | NM_002309.3 | Endogenous |
| 279 | EGR1 | NM_001964.2 | Endogenous |
| 280 | ARG1 b | NM_000045.2 | Endogenous |
| 281 | MERTK | NM_006343.2 | Endogenous |
| 282 | RHOU | NM_021205.5 | Endogenous |
| 283 | PFDN5 b | NM_145897.2 | Endogenous |
| 284 | MAGEA1 | NM_004988.4 | Endogenous |
| 285 | SEC24C | NM_198597.2 | Endogenous |
| 286 | SLC11A1 | NM_000578.3 | Endogenous |
| 287 | TCF20 | NM_181492.2 | Endogenous |
| 288 | AHCYL1 | NM_001242676.1 | Endogenous |
| 289 | TPT1 | NM_003295.3 | Endogenous |
| 290 | KIR2DL5A | XM_001126354.1 | Endogenous |
| 291 | IRAK2 | NM_001570.3 | Endogenous |
| 292 | C17orf51 | XM_944416.1 | Endogenous |
| 293 | C14orf156 | NM_031210.5 | Endogenous |
| 294 | ATP2C1 | NM_014382.3 | Endogenous |
| 295 | SOCS1 | NM_003745.1 | Endogenous |
| 296 | JAK1 | NM_002227.1 | Endogenous |
| 297 | RSL24D1 | NM_016304.2 | Endogenous |
| 298 | AP2S1 | NM_021575.3 | Endogenous |
| 299 | PHRF1 | NM_020901.3 | Endogenous |
| 300 | GPI | NM_000175.2 | Endogenous |
| 301 | NCR1 | NM_004829.5 | Endogenous |
| 302 | AKAP4 | NM_139289.1 | Endogenous |
| 303 | CD160 | NM_007053.3 | Endogenous |
| 304 | DDX23 | NM_004818.2 | Endogenous |
| 305 | GNL3 | NM_014366.4 | Endogenous |
| 306 | NFKB2 | NM_002502.2 | Endogenous |
| 307 | CSK | NM_004383.2 | Endogenous |
| 308 | PELP1 | NM_014389.2 | Endogenous |
| 309 | KLRF1 b | NM_016523.2 | Endogenous |
| 310 | CS | NM_004077.2 | Endogenous |
| 311 | PHCA | NM_018367.6 | Endogenous |
| 312 | LOC644315 | XR_017529.2 | Endogenous |
| 313 | NUDT18 | NM_024815.3 | Endogenous |
| 314 | XCL2 | NM_003175.3 | Endogenous |
| 315 | KLRC1 | NM_002259.3 | Endogenous |
| 316 | ARHGAP18 | NM_033515.2 | Endogenous |
| 317 | CTDSP2 | NM_005730.3 | Endogenous |
| 318 | P2RY5 | NM_005767.5 | Endogenous |
| 319 | CREB1 | NM_004379.3 | Endogenous |

TABLE I-continued

| Rank | Sequence ID# | Gene | Class Name |
|---|---|---|---|
| 320 | RHOB | NM_004040.3 | Endogenous |
| 321 | DCAF7 | NM_005828.4 | Endogenous |
| 322 | NUP153 | NM_005124.3 | Endogenous |
| 323 | AFTPH | NM_017657.4 | Endogenous |
| 324 | EWSR1 | NM_005243.3 | Endogenous |
| 325 | LYN | NM_002350.1 | Endogenous |
| 326 | CYBB | NM_000397.3 | Endogenous |
| 327 | TMEM70 | NM_017866.5 | Endogenous |
| 328 | PPP1R3E | XM_927029.1 | Endogenous |
| 329 | PSMB1 | NM_002793.3 | Endogenous |
| 330 | RERE b | NM_012102.3 | Endogenous |
| 331 | RXRA | NM_002957.5 | Endogenous |
| 332 | GZMA | NM_006144.3 | Endogenous |
| 333 | ERLIN1 | NM_006459.3 | Endogenous |
| 334 | KRTAP10-3 | NM_198696.2 | Endogenous |
| 335 | SAMSN1 | NM_022136.3 | Endogenous |
| 336 | LRRC47 | NM_020710.2 | Endogenous |
| 337 | MARCKS | NM_002356.6 | Endogenous |
| 338 | HOPX | NM_139211.4 | Endogenous |
| 339 | KLRF1 | NM_016523.1 | Endogenous |
| 340 | NFAT5 | NM_138713.3 | Endogenous |
| 341 | SLC15A2 | NM_021082.3 | Endogenous |
| 342 | STK16 | NM_003691.2 | Endogenous |
| 343 | KIR_Activating_Subgroup_2 | NM_014512.1 | Endogenous |
| 344 | TBCE | NM_001079515.2 | Endogenous |
| 345 | BAG3 | NM_004281.3 | Endogenous |
| 346 | SFRS4 | NM_005626.4 | Endogenous |
| 347 | AW270402 | AW270402.1 | Endogenous |
| 348 | CCL3L1 | NM_021006.4 | Endogenous |
| 349 | HERC3 | NM_014606.2 | Endogenous |
| 350 | RPL34 | NM_000995.3 | Endogenous |
| 351 | ALAS1 | NM_000688.4 | Endogenous |
| 352 | CCR9 | NM_031200.1 | Endogenous |
| 353 | CORO1C | ILMN_1745954.1 | Endogenous |
| 354 | FAIM3 | NM_005449.4 | Endogenous |
| 355 | SFPQ | NM_005066.2 | Endogenous |
| 356 | HOOK3 | NM_032410.3 | Endogenous |
| 357 | CD36 | NM_000072.3 | Endogenous |
| 358 | IL7 | NM_000880.2 | Endogenous |
| 359 | CBLL1 | NM_024814.3 | Endogenous |
| 360 | HVCN1 | NM_032369.3 | Endogenous |
| 361 | HMGB1 | NM_002128.4 | Endogenous |
| 362 | SIN3A | NM_015477.2 | Endogenous |
| 363 | CASP3 | NM_032991.2 | Endogenous |
| 364 | BQ189294 | BQ189294.1 | Endogenous |
| 365 | NDRG2 | NM_016250.2 | Endogenous |
| 366 | BX400436 | BX400436.2 | Endogenous |
| 367 | IFNAR2 | NM_000874.3 | Endogenous |
| 368 | MS4A6A b | NM_152851.2 | Endogenous |
| 369 | KLRC2 | NM_002260.3 | Endogenous |
| 370 | S100A12 b | NM_005621.1 | Endogenous |
| 371 | ATM | NM_000051.3 | Endogenous |
| 372 | NLRP3 | NM_001079821.2 | Endogenous |
| 373 | HAVCR2 | NM_032782.3 | Endogenous |
| 374 | C4B | NM_001002029.3 | Endogenous |
| 375 | CTSW | NM_001335.3 | Endogenous |
| 376 | TMEM170B | NM_001100829.2 | Endogenous |
| 377 | EIF4ENIF1 | NM_019843.2 | Endogenous |
| 378 | CCL3 | NM_002983.2 | Endogenous |
| 379 | CHCHD3 | NM_017812.2 | Endogenous |
| 380 | CST7 | NM_003650.3 | Endogenous |
| 381 | SFRS15 | NM_020706.2 | Endogenous |
| 382 | STIP1 | NM_006819.2 | Endogenous |
| 383 | MPDU1 | NM_004870.3 | Endogenous |
| 384 | DHX16 b | NM_001164239.1 | Endogenous |
| 385 | INTS4 | NM_033547.3 | Endogenous |
| 386 | USP16 | NM_001032410.1 | Endogenous |
| 387 | IFNAR1 | NM_000629.2 | Endogenous |
| 388 | ITCH | NM_001257138.1 | Endogenous |
| 389 | FOXK2 | NM_004514.3 | Endogenous |
| 390 | LOC642812 | XR_036892.1 | Endogenous |
| 391 | KIAA1967 | NM_021174.5 | Endogenous |
| 392 | LOC440928 | XM_942885.1 | Endogenous |
| 393 | NDUFV2 | NM_021074.4 | Endogenous |
| 394 | IL4 | NM_000589.2 | Endogenous |
| 395 | CIAPIN1 | NM_020313.3 | Endogenous |
| 396 | CXCL2 | NM_002089.3 | Endogenous |
| 397 | TXN | NM_003329.3 | Endogenous |

TABLE I-continued

| Rank | Sequence ID# | Gene | Class Name |
|---|---|---|---|
| 398 | PRG2 | NM_002728.4 | Endogenous |
| 399 | MS4A2 | NM_000139.3 | Endogenous |
| 400 | YPEL1 | NM_013313.4 | Endogenous |
| 401 | POLR2A | NM_000937.4 | Endogenous |
| 402 | C19orf10 | NM_019107.3 | Endogenous |
| 403 | IGFBP7 | NM_001553.2 | Endogenous |
| 404 | ITGAE | NM_002208.4 | Endogenous |
| 405 | CXCR5 b | NM_001716.3 | Endogenous |
| 406 | BID | NM_001196.2 | Endogenous |
| 407 | LOC100133273 | XR_039238.1 | Endogenous |
| 408 | FNBP1 | NM_015033.2 | Endogenous |
| 409 | IFNGR1 | NM_000416.1 | Endogenous |
| 410 | STAT6 | NM_003153.4 | Endogenous |
| 411 | CR2 | NM_001006658.2 | Endogenous |
| 412 | CCL3L3 | NM_001001437.3 | Endogenous |
| 413 | RFWD2 | NM_022457.6 | Endogenous |
| 414 | SP2 | NM_003110.5 | Endogenous |
| 415 | BAT2D1 | NM_015172.3 | Endogenous |
| 416 | CX3CL1 | NM_002996.3 | Endogenous |
| 417 | GPATCH3 | NM_022078.2 | Endogenous |
| 418 | CASP1 | NM_033294.3 | Endogenous |
| 419 | NAGK | NM_017567.4 | Endogenous |
| 420 | IER5 | NM_016545.4 | Endogenous |
| 421 | PHLPP2 | NM_015020.3 | Endogenous |
| 422 | RPL31 | NM_000993.4 | Endogenous |
| 423 | SPEN | NM_015001.2 | Endogenous |
| 424 | TMSB4X | NM_021109.3 | Endogenous |
| 425 | IL8RB | NM_001557.3 | Endogenous |
| 426 | XPC | NR_027299.1 | Endogenous |
| 427 | SNX11 | NM_152244.1 | Endogenous |
| 428 | SPN | NM_003123.3 | Endogenous |
| 429 | ANKHD1 | NM_017747.2 | Endogenous |
| 430 | CCR6 | NM_031409.2 | Endogenous |
| 431 | DZIP3 | NM_014648.3 | Endogenous |
| 432 | MRPL27 | NM_148571.1 | Endogenous |
| 433 | SREBF1 | NM_001005291.2 | Endogenous |
| 434 | CD14 | NM_000591.2 | Endogenous |
| 435 | TNFSF8 | NM_001244.3 | Endogenous |
| 436 | C3 | NM_000064.2 | Endogenous |
| 437 | FAM50B | NM_012135.1 | Endogenous |
| 438 | RASSF5 | NM_182664.2 | Endogenous |
| 439 | BU743228 | BU743228.1 | Endogenous |
| 440 | NFATC1 | NM_172389.1 | Endogenous |
| 441 | DOCK5 | NM_024940.6 | Endogenous |
| 442 | PACS1 | NM_018026.3 | Endogenous |
| 443 | CYP1B1 | NM_000104.3 | Endogenous |
| 444 | CLIC3 | ILMN_1796423.1 | Endogenous |
| 445 | PSMA4 | NM_002789.3 | Endogenous |
| 446 | ZNF341 | NM_032819.4 | Endogenous |
| 447 | PRPF3 | NM_004698.2 | Endogenous |
| 448 | PSMA6 b | NM_002791.2 | Endogenous |
| 449 | LOC648927 | XR_038906.2 | Endogenous |
| 450 | KCTD12 | NM_138444.3 | Endogenous |
| 451 | LOC440389 | XM_498648.3 | Endogenous |
| 452 | U2AF2 | NM_007279.2 | Endogenous |
| 453 | CLEC5A | NM_013252.2 | Endogenous |
| 454 | PRRG4 | NM_024081.5 | Endogenous |
| 455 | TNFRSF9 | NM_001561.5 | Endogenous |
| 456 | NDUFB3 | NM_002491.2 | Endogenous |
| 457 | BCL6 | NM_001130845.1 | Endogenous |
| 458 | SGK1 | NM_005627.3 | Endogenous |
| 459 | CIP29 | NM_033082.3 | Endogenous |
| 460 | CD160 b | NM_007053.2 | Endogenous |
| 461 | ARCN1 | NM_001655.4 | Endogenous |
| 462 | LOC151162 | NR_024275.1 | Endogenous |
| 463 | GPR65 | NM_003608.3 | Endogenous |
| 464 | CCR1 | NM_001295.2 | Endogenous |
| 465 | TFCP2 | NM_005653.4 | Endogenous |
| 466 | SGK | NM_005627.3 | Endogenous |
| 467 | RNF214 | NM_207343.3 | Endogenous |
| 468 | TMC8 | NM_152468.4 | Endogenous |
| 469 | RBM14 | NM_006328.3 | Endogenous |
| 470 | USP34 | NM_014709.3 | Endogenous |
| 471 | BACH2 | NM_021813.3 | Endogenous |
| 472 | LILRA5 | NM_021250.3 | Endogenous |
| 473 | C5orf21 | NM_032042.5 | Endogenous |
| 474 | LOC441073 | XR_018937.2 | Endogenous |
| 475 | TAX1BP1 | NM_001079864.2 | Endogenous |

TABLE I-continued

| Rank | Sequence ID# | Gene | Class Name |
|---|---|---|---|
| 476 | TNFSF13 | NM_003808.3 | Endogenous |
| 477 | PIM2 | NM_006875.3 | Endogenous |
| 478 | RNF19B | NM_153341.3 | Endogenous |
| 479 | EPHX2 | NM_001979.5 | Endogenous |
| 480 | LILRA5 b | NM_181879.2 | Endogenous |
| 481 | ABCF1 | NM_001025091.1 | Endogenous |
| 482 | C4orf27 | NM_017867.2 | Endogenous |
| 483 | PSMB7 | NM_002799.2 | Endogenous |
| 484 | LPCAT4 | NM_153613.2 | Endogenous |
| 485 | TRIM21 | NM_003141.3 | Endogenous |
| 486 | LOC728835 | XM_001133190.1 | Endogenous |
| 487 | NFKB1 | NM_003998.3 | Endogenous |
| 488 | CR2 b | NM_001006658.1 | Endogenous |
| 489 | HMGB2 | NM_002129.3 | Endogenous |
| 490 | IL1B | NM_000576.2 | Endogenous |
| 491 | C20orf52 | NM_080748.2 | Endogenous |
| 492 | DNAJB6 | NM_058246.3 | Endogenous |
| 493 | PFDN5 | NM_145897.2 | Endogenous |
| 494 | RPS6 | NM_001010.2 | Endogenous |
| 495 | LEF1 | NM_016269.4 | Endogenous |
| 496 | DKFZp761P0423 | XM_291277.4 | Endogenous |
| 497 | LOC647340 | XR_018104.1 | Endogenous |
| 498 | FTHL16 | XR_041433.1 | Endogenous |
| 499 | COX6C | NM_004374.2 | Endogenous |
| 500 | BCL10 | NM_003921.2 | Endogenous |
| 501 | CD48 | NM_001778.2 | Endogenous |
| 502 | ZMIZ1 | NM_020338.3 | Endogenous |
| 503 | GZMH | NM_033423.4 | Endogenous |
| 504 | TRRAP | NM_003496.3 | Endogenous |
| 505 | SH2D3C | NM_170600.2 | Endogenous |
| 506 | UBC | NM_021009.3 | Endogenous |
| 507 | TXNDC17 | NM_032731.3 | Endogenous |
| 508 | ATP5J2 | NM_004889.3 | Endogenous |
| 509 | KIAA1267 | NM_015443.3 | Endogenous |
| 510 | RFX1 | NM_002918.4 | Endogenous |
| 511 | WDR1 | NM_005112.4 | Endogenous |
| 512 | LOC100129697 | XM_001732822.2 | Endogenous |
| 513 | TOMM7 | NM_019059.2 | Endogenous |
| 514 | ARHGAP26 | NM_015071.4 | Endogenous |
| 515 | HSPA6 | NM_002155.4 | Endogenous |
| 516 | FLJ10357 | NM_018071.4 | Endogenous |
| 517 | ITGAL | NM_002209.2 | Endogenous |
| 518 | BX089765 | BX089765.1 | Endogenous |
| 519 | RERE | NM_001042682.1 | Endogenous |
| 520 | C15orf39 | NM_015492.4 | Endogenous |
| 521 | BX436458 | BX436458.2 | Endogenous |
| 522 | RWDD1 | NM_001007464.2 | Endogenous |
| 523 | TMBIM6 | NM_003217.2 | Endogenous |
| 524 | SLC6A6 | NM_003043.5 | Endogenous |
| 525 | KIAA0174 | NM_014761.3 | Endogenous |
| 526 | IL16 | NM_004513.4 | Endogenous |
| 527 | EGLN1 | NM_022051.1 | Endogenous |
| 528 | LOC391126 | XR_017684.2 | Endogenous |
| 529 | TAPBP | NM_003190.4 | Endogenous |
| 530 | NUMB | NM_001005744.1 | Endogenous |
| 531 | CENTD2 | NM_001040118.2 | Endogenous |
| 532 | CLSTN1 | NM_001009566.2 | Endogenous |
| 533 | PSMA4 b | NM_002789.4 | Endogenous |
| 534 | LOC648000 | XM_371757.4 | Endogenous |
| 535 | COX7C | NM_001867.2 | Endogenous |
| 536 | PIK3CD | NM_005026.3 | Endogenous |
| 537 | UQCRQ | NM_014402.4 | Endogenous |
| 538 | IDS | NM_006123.4 | Endogenous |
| 539 | C19orf59 | NM_174918.2 | Endogenous |
| 540 | MYL12A | NM_006471.3 | Housekeeping |
| 541 | EIF2B4 | NM_015636.3 | Housekeeping |
| 542 | DGUOK b | NM_080916.2 | Housekeeping |
| 543 | PSMC1 | NM_002802.2 | Housekeeping |
| 544 | CHFR | NM_018223.2 | Housekeeping |
| 545 | ARPC2 | NM_005731.2 | Housekeeping |
| 546 | ATP5B | NM_001686.3 | Housekeeping |
| 547 | RPL3 | NM_001033853.1 | Housekeeping |
| 548 | ZNF143 | NM_003442.5 | Housekeeping |
| 549 | PSMD7 | NM_002811.4 | Housekeeping |
| 550 | TBP | NM_003194.4 | Housekeeping |
| 551 | DHX16 | NM_003587.4 | Housekeeping |
| 552 | TUG1 | NR_002323.2 | Housekeeping |
| 553 | GUSB | NM_000181.3 | Housekeeping |

TABLE I-continued

| Rank | Sequence ID# | Gene | Class Name |
|---|---|---|---|
| 554 | HDAC3 | NM_003883.3 | Housekeeping |
| 555 | SDHA | NM_004168.3 | Housekeeping |
| 556 | PGK1 | NM_000291.3 | Housekeeping |
| 557 | STAMBP | NM_006463.4 | Housekeeping |
| 558 | MTCH1 | NM_014341.2 | Housekeeping |
| 559 | TUBB | NM_178014.2 | Housekeeping |

TABLE II

| Rank | Sequence ID# | Gene | Class Name |
|---|---|---|---|
| 1 | TPR | NM_003292.2 | Endogenous |
| 2 | DNAJB1 | NM_006145.2 | Endogenous |
| 3 | PDCD10 | NM_145859.1 | Endogenous |
| 4 | PSMB7 | NM_002799.2 | Endogenous |
| 5 | MERTK | NM_006343.2 | Endogenous |
| 6 | AFTPH | NM_017657.4 | Endogenous |
| 7 | BCOR | NM_017745.5 | Endogenous |
| 8 | RASSF5 | NM_182664.2 | Endogenous |
| 9 | SNX11 | NM_152244.1 | Endogenous |
| 10 | ANP32B | NM_006401.2 | Endogenous |
| 11 | C4B | NM_001002029.3 | Endogenous |
| 12 | NME1-NME2 | NM_001018136.2 | Endogenous |
| 13 | DGUOK | NM_080916.2 | Endogenous |
| 14 | CYP1B1 | NM_000104.3 | Endogenous |
| 15 | MPDU1 | NM_004870.3 | Endogenous |
| 16 | MED16 | NM_005481.2 | Endogenous |
| 17 | FAM179A | NM_199280.2 | Endogenous |
| 18 | CPPED1 | NM_018340.2 | Endogenous |
| 19 | LOC648927 | XR_038906.2 | Endogenous |
| 20 | ANKHD1 | NM_017747.2 | Endogenous |
| 21 | CN312986 | CN312986.1 | Endogenous |
| 22 | PHCA | NM_018367.6 | Endogenous |
| 23 | CD1A | NM_001763.2 | Endogenous |
| 24 | NCOA5 | NM_020967.2 | Endogenous |
| 25 | SLC6A12 | NM_003044.4 | Endogenous |
| 26 | LOC728533 | XR_015610.3 | Endogenous |
| 27 | TRAF3IP2 | NM_147686.3 | Endogenous |
| 28 | TBCE | NM_001079515.2 | Endogenous |
| 29 | CCT6A | NM_001762.3 | Endogenous |
| 30 | P2RY5 | NM_005767.5 | Endogenous |
| 31 | RNASE2 | NM_002934.2 | Endogenous |
| 32 | CLN8 | NM_018941.3 | Endogenous |
| 33 | REPS1 | NM_001128617.2 | Endogenous |
| 34 | TPT1 | NM_003295.3 | Endogenous |
| 35 | LOC100129022 | XM_001716591.1 | Endogenous |
| 36 | KLRC1 | NM_002259.3 | Endogenous |
| 37 | AZI2 | NM_022461.4 | Endogenous |
| 38 | FAM193A | NM_003704.3 | Endogenous |
| 39 | PLAC8 | NM_001130715.1 | Endogenous |
| 40 | LDHA | NM_001165416.1 | Endogenous |
| 41 | GPATCH3 | NM_022078.2 | Endogenous |
| 42 | RBM14 | NM_006328.3 | Endogenous |
| 43 | KYNU | NM_001032998.1 | Endogenous |
| 44 | PPP2R5C | NM_178588.1 | Endogenous |
| 45 | S100A12 b | NM_005621.1 | Endogenous |
| 46 | SFMBT1 | NM_001005158.2 | Endogenous |
| 47 | CCR6 | NM_031409.2 | Endogenous |
| 48 | TRIM39 | NM_021253.3 | Endogenous |
| 49 | AK126342 | AK126342.1 | Endogenous |
| 50 | SLC45A3 | NM_033102.2 | Endogenous |
| 51 | IL4 | NM_000589.2 | Endogenous |
| 52 | UBE2I | NM_194259.2 | Endogenous |
| 53 | PRPF3 | NM_004698.2 | Endogenous |
| 54 | NDUFB3 | NM_002491.2 | Endogenous |
| 55 | CRKL | NM_005207.3 | Endogenous |
| 56 | IDO1 | NM_002164.3 | Endogenous |
| 57 | PUM1 | NM_001020658.1 | Endogenous |
| 58 | BCL10 | NM_003921.2 | Endogenous |
| 59 | TMBIM6 | NM_003217.2 | Endogenous |
| 60 | C17orf51 | XM_944416.1 | Endogenous |
| 61 | BANP | NM_079837.2 | Endogenous |
| 62 | HAVCR2 | NM_032782.3 | Endogenous |
| 63 | BAG3 | NM_004281.3 | Endogenous |
| 64 | DBI | NM_001079862.1 | Endogenous |
| 65 | C4orf27 | NM_017867.2 | Endogenous |
| 66 | TSC1 | NM_000368.4 | Endogenous |
| 67 | LPCAT4 | NM_153613.2 | Endogenous |
| 68 | SAMSN1 | NM_022136.3 | Endogenous |
| 69 | SNORA56 | NR_002984.1 | Endogenous |
| 70 | ARG1 | NM_000045.3 | Endogenous |
| 71 | IL1R2 | NM_173343.1 | Endogenous |
| 72 | CCND3 | NM_001760.2 | Endogenous |
| 73 | USP9Y | NM_004654.3 | Endogenous |
| 74 | ATP2C1 | NM_014382.3 | Endogenous |
| 75 | PSMB1 | NM_002793.3 | Endogenous |
| 76 | NDUFAF2 | NM_174889.4 | Endogenous |
| 77 | VPS37C | NM_017966.4 | Endogenous |
| 78 | HAT1 | NM_003642.3 | Endogenous |
| 79 | LOC732371 | XM_001133019.1 | Endogenous |
| 80 | LOC148137 | NM_144692.1 | Endogenous |
| 81 | CCR1 | NM_001295.2 | Endogenous |
| 82 | CCDC97 | NM_052848.1 | Endogenous |
| 83 | PPP6C | NM_002721.4 | Endogenous |
| 84 | GPI | NM_000175.2 | Endogenous |
| 85 | PIM2 | NM_006875.3 | Endogenous |
| 86 | STAT6 | NM_003153.4 | Endogenous |
| 87 | BATF | NM_006399.3 | Endogenous |
| 88 | EIF4ENIF1 | NM_019843.2 | Endogenous |
| 89 | HSP90AB1 | NM_007355.3 | Endogenous |
| 90 | U2AF2 | NM_007279.2 | Endogenous |
| 91 | CYBB | NM_000397.3 | Endogenous |
| 92 | WDR1 | NM_005112.4 | Endogenous |
| 93 | PSMB8 | NM_004159.4 | Endogenous |
| 94 | TBC1D12 | NM_015188.1 | Endogenous |
| 95 | LOC648000 | XM_371757.4 | Endogenous |
| 96 | XCL2 | NM_003175.3 | Endogenous |
| 97 | PTGDR | NM_000953.2 | Endogenous |
| 98 | ACSL5 | NM_203379.1 | Endogenous |
| 99 | CASP1 | NM_033294.3 | Endogenous |
| 100 | UBTF | NM_001076683.1 | Endogenous |

In one embodiment, a novel gene expression profile or signature can identify and distinguish patients having cancerous tumors from patients having benign nodules. See for example the genes identified in Table I and Table II which may form a suitable gene expression profile. In another embodiment, a portion of the genes of Table I form a suitable profile. In yet another embodiment, a portion of the genes of Table II form a suitable profile. As discussed herein, these profiles are used to distinguish between cancerous and non-cancerous tumors by generating a discriminant score based on differences in gene expression profiles as exemplified below. The validity of these signatures was established on samples collected at different locations by different groups in a cohort of patients with undiagnosed lung nodules. See Example 7 and FIGS. 2A-2B and FIG. 6. The lung cancer signatures or gene expression profiles identified herein (i.e., Table I or Table II) may be further optimized to reduce the numbers of gene expression products necessary and increase accuracy of diagnosis.

In one embodiment, the composition includes 10 to 559 polynucleotides or oligonucleotides or ligands, wherein each polynucleotide or oligonucleotide or ligand hybridizes to a different gene, gene fragment, gene transcript or expression product in a sample selected from the genes of Table I. In another embodiment, the composition includes 10 to 100 polynucleotides or oligonucleotides or ligands, wherein each polynucleotide or oligonucleotide or ligand hybridizes to a different gene, gene fragment, gene transcript or expression product in a sample selected from the genes of Table II. In another embodiment, the composition includes 10 to 559 polynucleotides or oligonucleotides or ligands, wherein each polynucleotide or oligonucleotide or ligand hybridizes to a different gene, gene fragment, gene transcript or expression product in a sample selected from the genes of Table I. In another embodiment, the composition includes 10 to 100 polynucleotides or oligonucleotides or ligands, wherein each polynucleotide or oligonucleotide or ligand hybridizes to a different gene, gene fragment, gene transcript or expression product in a sample selected from the genes of Table II. In another embodiment, the composition includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, or 559 polynucleotides or oligonucleotides or ligands, wherein each polynucleotide or oligonucleotide or ligand hybridizes to a different gene, gene fragment, gene transcript or expression product in a sample selected from the genes of Table I. In another embodiment, the composition includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 polynucleotides or oligonucleotides or ligands, wherein each polynucleotide or oligonucleotide or ligand hybridizes to a different gene, gene fragment, gene transcript or expression product in a sample selected from the genes of Table II. In one embodiment, the composition includes at least 3 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 5 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 10 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 15 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 20 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 25 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 30 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 35 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 40 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 45 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 50 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 55 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 60 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 65 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 70 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 75 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 80 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 85 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 90 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 95 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 100 polynucleotides or oligonucleotides or ligands, wherein each polynucleotide or oligonucleotide or ligand hybridizes to a different gene, gene fragment, gene transcript or expression product in a sample selected from the genes of Table I or Table II. In one embodiment, the composition includes at least 150 polynucleotides or oligonucleotides or ligands, wherein each polynucleotide or oligonucleotide or ligand hybridizes to a different gene, gene fragment, gene transcript or expression product in a sample selected from the genes of Table I. In one embodiment, the composition includes at least 200 polynucleotides or oligonucleotides or ligands, wherein each polynucleotide or oligonucleotide or ligand hybridizes to a different gene, gene fragment, gene transcript or expression product in a sample selected from the genes of Table I. In one embodiment, the composition includes at least 250 polynucleotides or oligonucleotides or ligands, wherein each polynucleotide or oligonucleotide or ligand hybridizes to a different gene, gene fragment, gene transcript or expression product in a sample selected from the genes of Table I. In one embodiment, the composition includes at least 300 polynucleotides or oligonucleotides or ligands, wherein each polynucleotide or oligonucleotide or ligand hybridizes to a different gene, gene fragment, gene transcript or expression product in a sample selected from the genes of Table I. In one embodiment, the composition includes at least 350 polynucleotides or oligonucleotides or ligands, wherein each polynucleotide or oligonucleotide or ligand hybridizes to a different gene, gene fragment, gene transcript or expression product in a sample selected from the genes of Table I. In one embodiment, the composition includes at least 400 polynucleotides or oligonucleotides or ligands, wherein each polynucleotide or oligonucleotide or ligand hybridizes to a different gene, gene fragment, gene transcript or expression product in a sample selected from the genes of Table I. In one embodiment, the composition includes at least 450 polynucleotides or oligonucleotides or ligands, wherein each polynucleotide or oligonucleotide or ligand hybridizes to a different gene, gene fragment, gene transcript or expression product in a sample selected from the genes of Table I. In one embodiment, the composition includes at least 500 polynucleotides or oligonucleotides or ligands, wherein each polynucleotide or oligonucleotide or ligand hybridizes to a different gene, gene fragment, gene transcript or expression product in a sample selected from the genes of Table I. In one embodiment, the composition includes polynucleotides or oligonucleotides or ligands capable of hybridizing to each different gene, gene fragment, gene transcript or expression product listed in Table I. In another embodiment, the composition includes polynucleotides or oligonucleotides or ligands capable of hybridizing to each different gene, gene fragment, gene transcript or expression product listed in Table II.

In yet another embodiment, the expression profile is formed by the first 3 genes in rank order of Table I or Table II. In yet another embodiment, the expression profile is formed by the first 5 genes in rank order of Table I or Table II. In yet another embodiment, the expression profile is formed by the first 10 genes in rank order of Table I or Table II. In yet another embodiment, the expression profile is formed by the first 15 genes in rank order of Table I or Table II. In yet another embodiment, the expression profile is formed by the first 20 genes in rank order of Table I or Table II. In another embodiment, the expression profile is formed by the first 25 genes in rank order of Table I or Table II. In yet another embodiment, the expression profile is formed by the first 30 genes in rank order of Table I or Table II. In another embodiment, the expression profile is formed by the first 35 genes in rank order of Table I or Table II. In another embodiment, the expression profile is formed by the first 40 genes in rank order of Table I or Table II. In another embodiment, the expression profile is formed by the first 45 genes in rank order of Table I or Table II. In yet another embodiment, the expression profile is formed by the first 50 genes in rank order of Table I or Table II. In yet another embodiment, the expression profile is formed by the first 55 genes in rank order of Table I or Table II. In yet another embodiment, the expression profile is formed by the first 60 genes in rank order of Table I or Table II. In yet another embodiment, the expression profile is formed by the first 65 genes in rank order of Table I or Table II. In yet another embodiment, the expression profile is formed by the first 70 genes in rank order of Table I or Table II. In yet another embodiment, the expression profile is formed by the first 75 genes in rank order of Table I or Table II. In yet another embodiment, the expression profile is formed by the first 80 genes in rank order of Table I or Table II. In yet another embodiment, the expression profile is formed by the first 85 genes in rank order of Table I or Table II. In yet another embodiment, the expression profile is formed by the first 90 genes in rank order of Table I or Table II. In yet another embodiment, the expression profile is formed by the first 95 genes in rank order of Table I or Table II. In another embodiment, the expression profile is formed by the first 100 genes in rank order of Table I or Table II. In another embodiment, the expression profile is formed by the first 150 genes in rank order of Table I. In another embodiment, the expression profile is formed by the first 200 genes in rank order of Table I. In another embodiment, the expression profile is formed by the first 250 genes in rank order of Table I. In another embodiment, the expression profile is formed by the first 300 genes in rank order of Table I. In another embodiment, the expression profile is formed by the first 350 genes in rank order of Table I. In another embodiment, the expression profile is formed by the first 400 genes in rank order of Table I. In yet another embodiment, the expression profile is formed by the first 539 genes in rank order of Table I.

As discussed below, the compositions described herein can be used with the gene expression profiling methods which are known in the art. Thus, the compositions can be adapted accordingly to suit the method for which they are intended to be used. In one embodiment, at least one polynucleotide or oligonucleotide or ligand is attached to a detectable label. In certain embodiments, each polynucleotide or oligonucleotide is attached to a different detectable label, each capable of being detected independently. Such reagents are useful in assays such as the nCounter, as described below.

In another embodiment, the composition comprises a capture oligonucleotide or ligand, which hybridizes to at least one polynucleotide or oligonucleotide or ligand. In one embodiment, such capture oligonucleotide or ligand may include a nucleic acid sequence which is specific for a portion of the oligonucleotide or polynucleotide or ligand which is specific for the gene of interest. The capture ligand may be a peptide or polypeptide which is specific for the ligand to the gene of interest. In one embodiment, the capture ligand is an antibody, as in a sandwich ELISA.

The capture oligonucleotide also includes a moiety which allows for binding with a substrate. Such substrate includes, without limitation, a plate, bead, slide, well, chip or chamber. In one embodiment, the composition includes a capture oligonucleotide for each different polynucleotide or oligonucleotide which is specific to a gene of interest. Each capture oligonucleotide may contain the same moiety which allows for binding with the same substrate. In one embodiment, the binding moiety is biotin.

Thus, a composition for such diagnosis or evaluation in a mammalian subject as described herein can be a kit or a reagent. For example, one embodiment of a composition includes a substrate upon which the ligands used to detect and quantitate mRNA are immobilized. The reagent, in one embodiment, is an amplification nucleic acid primer (such as an RNA primer) or primer pair that amplifies and detects a nucleic acid sequence of the mRNA. In another embodiment, the reagent is a polynucleotide probe that hybridizes to the target sequence. In another embodiment, the target sequences are illustrated in Table III. In another embodiment, the reagent is an antibody or fragment of an antibody. The reagent can include multiple said primers, probes or antibodies, each specific for at least one gene, gene fragment or expression product of Table I or Table II. Optionally, the reagent can be associated with a conventional detectable label.

In another embodiment, the composition is a kit containing the relevant multiple polynucleotides or oligonucleotide probes or ligands, optional detectable labels for same, immobilization substrates, optional substrates for enzymatic labels, as well as other laboratory items. In still another embodiment, at least one polynucleotide or oligonucleotide or ligand is associated with a detectable label. In certain embodiments, the reagent is immobilized on a substrate. Exemplary substrates include a microarray, chip, microfluidics card, or chamber.

In one embodiment, the composition is a kit designed for use with the nCounter Nanostring system, as further discussed below.

II. GENE EXPRESSION PROFILING METHODS

Methods of gene expression profiling that were used in generating the profiles useful in the compositions and methods described herein or in performing the diagnostic steps using the compositions described herein are known and well summarized in U.S. Pat. No. 7,081,340. Such methods of gene expression profiling include methods based on hybridization analysis of polynucleotides, methods based on sequencing of polynucleotides, and proteomics-based methods. The most commonly used methods known in the art for the quantification of mRNA expression in a sample include northern blotting and in situ hybridization; RNAse protection assays; nCounter® Analysis; and PCR-based methods, such as RT-PCR. Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

In certain embodiments, the compositions described herein are adapted for use in the methods of gene expression profiling described herein, and those known in the art.

A. Patient Sample

The "sample" or "biological sample" as used herein means any biological fluid or tissue that contains immune cells and/or cancer cells. In one embodiment, a suitable sample is whole blood. In another embodiment, the sample may be venous blood. In another embodiment, the sample may be arterial blood. In another embodiment, a suitable sample for use in the methods described herein includes peripheral blood, more specifically peripheral blood mononuclear cells. Other useful biological samples include, without limitation, plasma or serum. In still other embodiment, the sample is saliva, urine, synovial fluid, bone marrow, cerebrospinal fluid, vaginal mucus, cervical mucus, nasal secretions, sputum, semen, amniotic fluid, bronchoalveolar lavage fluid, and other cellular exudates from a subject suspected of having a lung disease. Such samples may further be diluted with saline, buffer or a physiologically acceptable diluent. Alternatively, such samples are concentrated by conventional means. It should be understood that the use or reference throughout this specification to any one biological sample is exemplary only. For example, where in the specification the sample is referred to as whole blood, it is understood that other samples, e.g., serum, plasma, etc., may also be employed in another embodiment.

In one embodiment, the biological sample is whole blood, and the method employs the PaxGene Blood RNA Workflow system (Qiagen). That system involves blood collection (e.g., single blood draws) and RNA stabilization, followed by transport and storage, followed by purification of Total RNA and Molecular RNA testing. This system provides immediate RNA stabilization and consistent blood draw volumes. The blood can be drawn at a physician's office or clinic, and the specimen transported and stored in the same tube. Short term RNA stability is 3 days at between 18-25° C. or 5 days at between 2-8° C. Long term RNA stability is 4 years at −20 to −70° C. This sample collection system enables the user to reliably obtain data on gene expression in whole blood. In one embodiment, the biological sample is whole blood. While the PAXgene system has more noise than the use of PBMC as a biological sample source, the benefits of PAXgene sample collection outweighs the problems. Noise can be subtracted bioinformatically by the person of skill in the art.

In one embodiment, the biological samples may be collected using the proprietary PaxGene Blood RNA System (PreAnalytiX, a Qiagen, BD company). The PAXgene Blood RNA System comprises two integrated components: PAXgene Blood RNA Tube and the PAXgene Blood RNA Kit. Blood samples are drawn directly into PAXgene Blood RNA Tubes via standard phlebotomy technique. These tubes contain a proprietary reagent that immediately stabilizes intracellular RNA, minimizing the ex-vivo degradation or up-regulation of RNA transcripts. The ability to eliminate freezing, batch samples, and to minimize the urgency to process samples following collection, greatly enhances lab efficiency and reduces costs. Thereafter, the miRNA is detected and/or measured using a variety of assays.

B. Nanostring Analysis

A sensitive and flexible quantitative method that is suitable for use with the compositions and methods described herein is the nCounter® Analysis system (NanoString Technologies, Inc., Seattle Wash.). The nCounter Analysis System utilizes a digital color-coded barcode technology that is based on direct multiplexed measurement of gene expression and offers high levels of precision and sensitivity (<1 copy per cell). The technology uses molecular "barcodes" and single molecule imaging to detect and count hundreds of unique transcripts in a single reaction. Each color-coded barcode is attached to a single target-specific probe (i.e., polynucleotide, oligonucleotide or ligand) corresponding to a gene of interest, i.e., a gene of Table I. Mixed together with controls, they form a multiplexed CodeSet. In one embodiment, the CodeSet includes all 559 genes of Table I. In another embodiment, the CodeSet includes all 100 genes of Table II. In another embodiment, the CodeSet includes at least 3 genes of Table I or Table II. In another embodiment, the CodeSet includes at least 5 genes of Table I or Table II. In another embodiment, the CodeSet includes at least 10 genes of Table I or Table II. In another embodiment, the CodeSet includes at least 15 genes of Table I or Table II. In another embodiment, the CodeSet includes at least 20 genes of Table I or Table II. In another embodiment, the CodeSet includes at least 25 genes of Table I or Table II. In another embodiment, the CodeSet includes at least 30 genes of Table I or Table II. In yet another embodiment, the CodeSet includes at least 40 genes of Table I or Table II. In yet another embodiment, the CodeSet includes at least 50 genes of Table I or Table II. In another embodiment, the CodeSet includes at least 60 genes of Table I or Table II. In another embodiment, the CodeSet includes at least 70 genes of Table I or Table II. In yet another embodiment, the CodeSet includes at least 80 genes of Table I or Table II. In yet another embodiment, the CodeSet includes at least 90 genes of Table I or Table II. In another embodiment, the CodeSet includes at least 100 genes of Table I. In another embodiment, the CodeSet includes at least 200 genes of Table I. In another embodiment, the CodeSet includes at least 300 genes of Table I. In yet another embodiment, the CodeSet includes at least 400 genes of Table I. In yet another embodiment, the CodeSet includes at least 500 genes of Table I. In yet another embodiment, the CodeSet is formed by the first 539 genes in rank order of Table I. In yet another embodiment, the CodeSet includes any subset of genes of Table I, as described herein. In another embodiment, the CodeSet includes any subset of genes of Table II, as described herein.

The NanoString platform employs two ~50 base probes per mRNA that hybridizes in solution. The Reporter Probe carries the signal; the Capture Probe allows the complex to be immobilized for data collection. The probes are mixed with the patient sample. After hybridization, the excess probes are removed and the probe/target complexes aligned and immobilized to a substrate, e.g., in the nCounter Cartridge.

The target sequences utilized in the Examples below for each of the genes of Table I and Table II are shown in Table III below, and are reproduced in the sequence listing. These sequences are portions of the published sequences of these genes. Suitable alternatives may be readily designed by one of skill in the art.

Sample Cartridges are placed in the Digital Analyzer for data collection. Color codes on the surface of the cartridge are counted and tabulated for each target molecule.

A benefit of the use of the NanoString nCounter system is that no amplification of mRNA is necessary in order to perform the detection and quantification. However, in alternate embodiments, other suitable quantitative methods are used. See, e.g., Geiss et al, Direct multiplexed measurement of gene expression with color-coded probe pairs, Nat Biotechnol. 2008 March; 26(3):317-25. doi: 10.1038/nbt1385. Epub 2008 Feb. 17, which is incorporated herein by reference in its entirety.

TABLE III

| Sequence ID# | Gene | Position | Target Sequence |
|---|---|---|---|
| 1 | ABCA5 | NM_018672.4 | 6839-6938 | AAGGAAGACTGTGTGTAGAATCTTACGTAATAGTCTGATTCTTTGACTCTGTGGCTAGAATGACAGTTATCTATGGAGGTGGTAGAATTAAGCCATACCT |
| 2 | ABCF1 | NM_001025091.1 | 2875-2974 | CCTAAACAAACAAGAGGTGACCACCTTATTGTGAGGTTCCATCCAGCCAAGTTTATGTGGCCTATTGTCTCAGGACTCTCATCACTCAGAAGCCTGCCTC |
| 3 | ACAA2 | NM_006111.2 | 1605-1704 | CTCACTGTGACCCATCCTTACTCTACTTGGCCAGGCCACAGTAAAACAAGTGACCTTCAGAGCAGCTGCCACAACTGGCCATGCCCTGCCATTGAAACAG |
| 4 | PHCA | NM_018367.6 | 3324-3423 | AGCCAATAGTGATTTGTTTGCATATCACCTAATGTGAAAAGTGCTCATCTGTGAACTCTACAGCAAATTATATTTTAGAAAATACTTTGTGAGGCCGGGC |

TABLE III-continued

| Sequence ID# | Gene | Position | Target Sequence |
|---|---|---|---|
| 5 | ACSL5 | NM_203379.1 | 2701-2800 | CTATCACTCATGTCAATCATATC TATGAGACAAATGTCTCCGATGC TCTTCTGCGTAAATTAAATTGTG TACTGAAGGGAAAAGTTTGATCA TACCAAAC |
| 6 | CABC1 | NM_020247.4 | 2536-2635 | TTCTAGAGTGAGATTTGTGTTTT CTGCCCTTTTCCTCTCCAGCCGA TGGGCTGGAGCTGGGAGAGGTGC TGAGCTAACAGTGCCAACAAGT GCTCCTTAA |
| 7 | CD97 | NM_078481.3 | 3186-3285 | GCCAGTACTCGGGACAGACTAA GGGCGCTTGTCCCATCCTGGACT TTTCCTCTCATGTCTTTGCTGCA GAACTGAAGAGACTAGGCGCTGG GGCTCAGCT |
| 8 | AFTPH | NM_017657.4 | 2741-2840 | CTACCACCCGTCCAGTTTGACTG GAGTAGCAGTGGCCTTACTAACC CTTTAGATGGTGTGGATCCGGAG TTGTATGAGTTAACAACTTCTAA GCTGGAAA |
| 9 | AHCYL1 | NM_001242676.1 | 2401-2500 | CTACCCGGCAGGTAGGTTAGATG TGGGTGGTGCATGTTAATTTCCC TTAGAAGTTCCAAGCCCTGTTTC CTGCGTAAAGGTGGTATGTCCAG TTCAGAGA |
| 10 | AK026725 | AK026725.1 | 1869-1968 | AATGAAATTACTGTAGAGTCAGC AAAGAAGTAGAGAAGAAAAAAC ACCAAGAATGAGGAGAACCTAG CAAGGGCAGGCTTTTGGAAGCA AGAGGTAGATA |
| 11 | AK093878 | AK093878.1 | 1554-1653 | AGAATTTCTTGGTAGCTTTACAC CGAAAATGCGTGTAACTAAAT ACCAGACATCTTGACCATTCAGC TAGAACCCTGGCAGCAACAGAG CTATTTAATT |
| 12 | AK094576 | AK094576.1 | 1765-1864 | CCCCTCCAGCCAGCCCTGCGTGG TTGTGGCCCCACTGCAGAAACGC CTCCGCTTAACACTCCAGCCTCT CTTCTATTCGGTCAGGCCACAGC TGCTGACT |
| 13 | AK124143 | AK124143.1 | 2252-2351 | GTACCTGGTAGAAATTGTGTCTT GGAATGACCCTTTCGAGTTATTG ACATGGCTCTGATGAATAGAACA TGAGCCCCAAAACTAAATCCAA AAGGAATTT |
| 14 | AK126342 | AK126342.1 | 2906-3005 | CTTATTGATTAGTGAATGTAGCT TAAGCCTTTGTATGTGTCCTCAG GGGGCAGACCGACTTTAAGAGG GACCAGATAACGTTTGAATGGA GGGATTATAT |
| 15 | AKAP4 | NM_139289.1 | 417-516 | CTGTAAGTGTCCTCAACTGGCTT CTCAGTGATCTCCAAGAAGTATGC CTTGGGTTCCAACATGCACTGA GCCCCTCAACCTCTACCTGTAAA CATAAAGT |
| 16 | AKR1C3 | NM_003739.4 | 1097-1196 | GAGGACGTCTCTATGCCGGTGAC TGGACATATCACCTCTACTTAAA TCCGTCCTGTTTAGCGACTTCAG TCAACTACAGCTGAGTCCATAGG CCAGAAAG |
| 17 | ALAS1 | NM_000688.4 | 1616-1715 | GGGGATCGGGATGGAGTCATGC CAAAAATGGACATCATTTCTGGA ACACTTGGCAAAGCCTTTGGTTG TGTTGGAGGGTACATCGCCAGCA CGAGTTCTC |
| 18 | AMD1 | NM_001634.4 | 572-671 | ACCACCCTCTTGCTGAAAGCACT GGTTCCCTGTTGAAGCTTGCTA GGGATTACAGTGGGTTTGACTCA ATTCAAAGCTTCTTTTATTCTCG TAAGAATT |
| 19 | AMPD3 | NM_000480.2 | 3389-3488 | GTGATGCTCAGGGGCTGTCAAAG TGACTGCGTTCATCAGTTTTACA CTGGGGCTGCTACATAATATTTT CATTTGAACGAAGAACTTCAAAA AGCACAGG |
| 20 | ANKHD1 | NM_017747.2 | 7665-7764 | CTTGGAACCCTATGATAAAAGTT ATCCAAATTCAACTGAATGCAC TGATGCCCAGCAGATTTGGCCTG GCACGTGGGCACCTCATATTGGA AACATGCA |
| 21 | ANP32B | NM_006401.2 | 661-760 | CACCTTGGAACCTTTGAAAAAGT TAGAATGTCTGAAAAGCCTGGAC CTCTTTAACTGTGAGGTTACCAA CCTGAATGACTACCGAGAGAGT GTCTTCAAG |
| 22 | ANXA1b | NM_000700.1 | 516-615 | GAAATCAGAGACATTAACAGGG TCTACAGAGAGGAACTGAAGAG AGATCTGGCCAAAGACATAACCT CAGACACATCTGGAGATTTTCGG AACGCTTTGC |
| 23 | ANXA1 | NM_000700.2 | 1191-1290 | TGGATGAAACAAAGGAGATTA TGAGAAAATCCTGGTGGCTCTTT GTGGAGGAAACTAAACATTCCCT TGATGGTCTCAAGCTATGATCAG AAGACTTTA |
| 24 | AP2S1 | NM_021575.3 | 746-845 | CGAGTAACCGTGCCGTTGTCGTG TGATGCCATAAGCGTCTGTGCGT GGAGTCCCCAATAAACCTGTGGT CCTGCCTGGCCTTGCCGTCAAAA AAAAAAA |
| 25 | CENTD2 | NM_001040118.2 | 4923-5022 | AAACTCCAGAACAGCAGAAAGC GGGTGCTGTAGAGGAGCACTCA GCTCACGGGGAGGGAGCTCTTG GCTGAGCTTCTACAGGGCTGAGA GCTGCGCTTTG |
| 26 | ARCN1 | NM_001655.4 | 3437-3536 | CACTTTTAGCTGGTTGAAAAGTA CCACTCCCACTCTGAACATCTG CCGTCCCTGCAAAGAGTGTACTG TGCTTGAAGCAGAGCACTCACAC ATAAATGG |
| 27 | ARG1b | NM_000045.2 | 506-605 | AAGGAACTAAAAGGAAAGATTC CCGATGTGCCAGGATTCTCCTGG GTGACTCCCTGTATATCTGCCAA GGATATTGTGTATATTGGCTTGA GAGACGTGG |
| 28 | ARG1 | NM_000045.3 | 989-1088 | TTCGGACTTGCTCGGAGGGTAA TCACAAGCCTATTGACTACCTTA ACCCACCTAAGTAAATGTGGAA ACATCCGATATAAATCTCATAGT TAATGGCAT |
| 29 | ARHGAP17 | NM_018054.5 | 3027-3126 | CATGTATGGTCTGTGTCTCCCCA GTCCCCTCAGAACCATGCCCATG GATGGTGACTGCTGGCTCTGTCA CCTCATCAAACTGGATGTGACCC ATGCCGCC |

TABLE III-continued

| Sequence ID# | Gene | Position | Target Sequence |
|---|---|---|---|
| 30 | ARHGAP18 | NM_033515.2 2499-2598 | TTTTTGACCAAAAAGATAACAAATACCAGGTATGGCAAGTTGTGAAGACAGCACATTAAAACATACCTAATTTCACAGTATTCCTGTCACGACAGAATGT |
| 31 | ARHGAP26 | NM_015071.4 6088-6187 | TCCCTGAGCTTTCCCAGTAGCCTCCAGTTTCCTTTGTAAGACCCAGGGATCACTTAGCCATAGCCTGAATCTTTTAGGGGTATTAAGGTCAGCCTCTCAC |
| 32 | ARHGEF18 | NM_015318.3 5128-5227 | GATTACAACATTTTCCTCACTGCGGGATATTTCTGACCCGCTTTAGAACTTAAGACCTGATTCTAGCAATAAACGTGTCCGAGATGAGCGGTGAAAAAAA |
| 33 | FLJ10357 | NM_018071.4 5402-5501 | GAATGTGTCTCCTCCACAGTGGCTCCCAGAGGTTCCACACACTCTCTGAAGCTCCTTCTCCCACACTGCACCTACTCCTTGAGGCTGAACTGGTCACAGA |
| 34 | ARHGEF5 | NM_005435.3 5151-5250 | GGGGGACCATTGGGGCCTGAGCCAAGGAACTTTCCTTCTACTGCCTTATAGTGCTTAAACATTCTCCGCCTCCAGGGTGCAGATTCAGAGCTGGCCAGAG |
| 35 | ARL8B | NM_018184.2 2491-2590 | ACCATTACAAAGAATGTGGCAACTTGCTTGTGCCTAAAAGGAGGAATTGGAACTAGAATGTGTGACTCTGTGGGGACTGCATAGGTTTGTTAATTGACCT |
| 36 | ARPC2 | NM_005731.2 951-1050 | ACGGGGAAGACGTTTTCATCCCGCTAATCTTGGGAATAAGAGGAGGAAGCGGCTGGCAACTGAAGGCTGGAACACTTGCTACTGGATAATCGTAGCTTTT |
| 37 | ASF1B | NM_018154.2 1476-1575 | CTGTCTCCGGGCCAGGGTCAGGGACCCTCTGCCTCTGGCAGCCTTAACCTGTCCTCTGCTAGGACCAGGGTGATTTCAAGCCAGGGAAGCAACTGGGACC |
| 38 | ATG4B | NM_178326.2 106-205 | GGACGCAGCTACTCTGACCTACGACACTCTCCGGTTTGCTGAGTTTGAAGATTTTCCTGAGACCTCAGAGCCCGTTTGGATACTGGGTAGAAAATACAGC |
| 39 | ATG5 | NM_004849.2 1105-1204 | TGCAGTGGCTGAGTGAACATCTGAGCTACCCGGATAATTTTCTTCATATTAGTATCATCCCACAGCCAACAGATTGAAGGATCAACTATTTGCCTGAACA |
| 40 | ATM | NM_000051.3 31-130 | ACGCTAAGTCGCTGGCCATTGGTGGACATGGCGCAGGCGCGTTTGCTCCGACGGGCCGAATGTTTTGGGGCAGTGTTTTGAGCGCGGAGACCGCGTGATA |
| 41 | ATP2C1 | NM_014382.3 4070-4169 | TAAAAAGTCCCCAAACCCAAACAAATGGTTTATGAACCAGAGTATATGTGGAAGATTCTTTGCTGGTCTTGCTCTGTGTGCATCTGAAGCTTCTTTGGCC |
| 42 | ATP5B | NM_001686.3 1626-1725 | CTATATGGTGGGACCCATTGAAGAAGCTGTGGCAAAAGCTGATAAAGCTGGCTGAAGAGCATTCATCGTGAGGGGTCTTTGTCCTCTGTACTGTCTCTCTC |
| 43 | ATP5I | NM_007100.2 256-355 | TTGCCAGAGAATTGGCAGAAGATGACAGCATATTAAAGTGAGTGACCCTGCGACCCACTCTTTGGACCAGCAGCGGATGAATAAAGCTTCCTGTGTTGTG |
| 44 | ATP5J2 | NM_004889.3 267-366 | GCTGGCATGCTACGTGCTCTTTAGCTACTCCTTTTCCTACAAGCATCTCAAGCACGAGCGGCTCCGCAAATACCACTGAAGAGGACACACTCTGCACCCC |
| 45 | ATP5L | NM_006476.4 196-295 | GGGACGGGGTCCTGCAGCGGGTCCTTCCGGCGGGTGACATTCAGCCGGCGGTTCGGGGCGACGGACTCTCCATTCCAGAACCATGGCCCAATTTGTCCGT |
| 46 | AW173314 | AW173314.1 419-518 | AGCAGAAGGCAGGGGAGTCCACACAGGGCAAGCAGCAACCAGGCTTCTGAGGACAGGAAAGGAGGGAGCATCTGGTGGGAAGCTGGCGAGGAGGGGCTGG |
| 47 | AW270402 | AW270402.1 203-302 | GATATCTCACACACGGAATAATCATTAAGAAACAACCACTGTTGAGCAAAGTTGATAGGCAGTAAGGAAATAAAGTGGACATAAACACAGCAGTACTAAT |
| 48 | AZI2 | NM_022461.4 3031-3130 | GAATTGGTGTCAGATGCTGGAATTTATTCTGACCAATGAACACAGCTGACTCAGGGGAGTACAATCTCCTGCCAAGTAATAGAACCAAACCCAATATGCA |
| 49 | BACH2 | NM_021813.3 8696-8795 | TCCAGAACCAGTCTGATGCAAGTGCACCTCTAATATATGCCTTACAAACTCCAGAGGCCATATTCAAAACAGGGTCTTCTCAGTGTATGCAAGGGGCTGC |
| 50 | BAG3 | NM_004281.3 2304-2403 | CCCCACCACCTGTTAGCTGTGGTTGTGCACTGTCTTTTGTAGCTCTGGACTGGAGGGGTAGATGGGGAGTCAATTACCCATCACATAAATATGAAACATT |
| 51 | BANP | NM_079837.2 2125-2224 | GGAGCCCTTTGCTGTGTGCTCTGTCCAGTGTCATGAGGCAGGTGTTTGCAAAGCCAGCTCTCGGTTCCGATGGGGTATTGCTGACCTACTTTTCTAGGGG |
| 52 | BATF | NM_006399.3 294-393 | CCTGGCAAACAGGACTCATCTGATGATGTGAGAAGAGTTCAGAGGAGGGAGAAAAATCGTATTGCCGCCCAGAAGAGCCGACAGAGGCAGACACAGAAGG |
| 53 | BCL10 | NM_003921.2 1251-1350 | TGAAAATACCATCTTCTCTTCAACTACACTTCCCAGACCTGGGGACCCAGGGGCTCCTCCTTTGCCACCAGATCTACAGTTAGAAGAAGAAGGAACTTGT |
| 54 | BCL6 | NM_001130845.1 3401-3500 | CCTCACGGTGCCTTTTTCACGGAAGTTTTCAATGATGGGCAGCGTGCACCATCCCTTTTTGAAGTGTAGGCAGACACAGGGACTTGAAGTTGTTACTA |

TABLE III-continued

| Sequence ID# | Gene | Position | Target Sequence |
|---|---|---|---|
| 55 | BCOR | NM_017745.5 | 5794-5893 | ATACAAAGCTCTGATGACAGGCCATGACTGTAGAGTGGTCAGAACTGTGTGGTTGTTTGAGGGAGCGAATTCGGGGAAGGCACTTGGTGATATAACTTT |
| 56 | BF375676 | BF375676.1 | 141-240 | TGTATTTCTGTGCAATGAGAGAGGCTCTTTATGGTGGTGCTACAAACAAGCTCATCTTTGGAACTGGCACTCTGCTTGCTGTCCAGCCAAATATCCAGAA |
| 57 | BID | NM_001196.2 | 1876-1975 | AAGCACGACAGTGGATGCTGGGTCCATATCACACACATTGCTGTGAACAGGAAACTCCTGTGACCACAACATGAGGCCACTGGAGACGCATATGAGTAAG |
| 58 | BMPR2 | NM_001204.6 | 1164-1263 | CAGCGGCCCTGGCGGGTGCCCTGGCTACCATGGACCATCCTGCTGGTCAGCACTGCGGCTGCTTCGCAGAATCAAGAACGGCTATGTGCGTTTAAAGATC |
| 59 | BQ189294 | BQ189294.1 | 416-515 | GCTGGAGTGATTGGCCCTGATGACCATGGAGAAAAGAGAGTAGGGAGAACAGTATAACCAGAAGTCAGGGGGGTCTCCTGGAATCCCTCCTCACAATACC |
| 60 | BU743228 | BU743228.1 | 154-253 | CCCTGTGGGCCTTGCAGGCCAGTCCAGGCAGGTCTTTCACACTGTTGTCCCACATAACAGAAAAAGCTGAGCAGACAGGGTAGGAAACACACTTGCATCT |
| 61 | BX089765 | BX089765.1 | 106-205 | TTAAGCAACTTGCTCCAGTGACGCAGCTGGTAAGCAGCAGAGCTGGGATTAAAACCCAGGCATTCGATTCCACCACCTACACACTTAGCCATTCCGCCC |
| 62 | BX108566 | BX108566.1 | 365-464 | ATTTAGGGTGAGAGCTTCACAGCTGAAAATCTCCTTTAAAGAAAACGCGGCCCAAATGTGCTGGGAGGAGAAGCCAGTGGATCTAGGAGGGGGCCCGGCG |
| 63 | BX400436 | BX400436.2 | 1-100 | ATATTTTGGAGAGGGAAGTTGGCTCACTGTTGTAGAGGACCTGAACAAGGTGTTCCCACCCGAGGTCGCTGTGTTTGAGCCATCAGAAGCAGAGATCTCC |
| 64 | BX436458 | BX436458.2 | 518-617 | ATGCAGACAATTTGCCTGTGAGATGAGGAAAATTCTCTGGAAGATTTAGGCCCTGAGAGCTGAAAAGGGACCCTAAACATTACCTGGTGACAACTGCCCT |
| 65 | C15orf39 | NM_015492.4 | 3535-3634 | CCTGAGCTTTTAACGTGAGGGTCTTTATTGGATAGGACTACTCCCTATTTCTTGCCTAGAGAACACACATGGGCTTTGGAGCCCGACAGACCTGGGCTTG |
| 66 | C17orf51 | XM_944416.1 | 4909-5008 | AAGGATGGGGTGGATTGACCAAGCTGGGCCAGAGGTGCGAGGAGCTGATCTGCGAGCCCTGTGTGCCTGTGAGTCCTTGGCGGAGTGGCCGTGCGTGGTG |
| 67 | C3 | NM_000064.2 | 4397-4496 | CATCTACCTGGACAAGGTCTCACACTCTGAGGATGACTGTCTAGCTTTCAAAGTTCACCAATACTTTAATGTAGAGCTTATCCAGCCTGGAGCAGTCAAG |
| 68 | C4B | NM_001002029.3 | 4438-4537 | GAGTCCAGGGTGCACTACACCGTGTGCATCTGGCGGAACGGCAAGGTGGGGCTGTCTGGCATGGCCATCGCGGACGTCACCCTCCTGAGTGGATTCCACG |
| 69 | C4orf27 | NM_017867.2 | 682-781 | GAACCGTGAAGATGAAACAGAGAGATAAGAAAGTTGTGACAAAGACCTTTCATGGTGCAGGCTTGGTTGTTCCAGTAGATAAAAATGATGTTGGGTACCG |
| 70 | C8orf76 | NM_032847.2 | 1029-1128 | TAAAAGATGAAGTTCACCCAGAGGTGAAGTGTGTTGGCTCCGTAGCCCTGACTGCCTTGGTGACTGTATCCTCAGAAGAATTTGAAGACAAGTGGTTCAG |
| 71 | C9orf164 | NM_182635.1 | 529-628 | CGCTGGCCATGGGGAAGCCACCTCCAGGGCAGTCCCAGGGACTGAATTGGAAGTTGTCCCAAGTCACTTCAGGTCCAACTGGGACAGCAGAGGTAACCCC |
| 72 | CAMP | NM_004345.4 | 623-722 | TTGTCCAGAGAATCAAGGATTTTTGCGGAATCTTGTACCCAGGACAGAGTCCTAGTGTGTGCCCTACCCTGGCTCAGGCTTCTGGGCTCTGAGAAATAA |
| 73 | CASP1 | NM_033294.3 | 219-318 | ATTTATCCAATAATGGACAAGTCAAGCCGCACACGTCTTGCTCTCATTATCTGCAATGAAGAATTTGACAGTATTCCTAGAAGAACTGGAGCTGAGGTTG |
| 74 | CASP2 | NM_032983.3 | 3347-3446 | CCCACCACTCTTGACTCAGGTGGTGTCCTTCTTCCTCAAGTCTTGACAATTCCCGGGCCCTTCAGTCCCTGAGCAGTCTACTTCTGTGTCTGTCACCACA |
| 75 | CASP3 | NM_032991.2 | 686-785 | ACTCCACAGCACCTGGTTATTATTCTTGGCGAAATTCAAAGGATGGCTCCTGGTTCATCCAGTCGCTTTGTGCCATGCTGAAACAGTATGCCGACAAGCT |
| 76 | CBLL1 | NM_024814.3 | 1967-2066 | ATGAGGGGGAAAAAAACTTATGTGTAGTCAATCTTTTAAGCTTTGACTGTTTTGGGAAGGAAGAGTACCTCTTATCGAGGTAGTATAAAACACATAGGGT |
| 77 | CC2D1B | NM_032449.2 | 4183-4282 | TTGCATAAGCACAGCTCAAGAACTGAGCTTTGTATGTGTCCTTTTGGGGGATAACAGGGCTGGACCATGCTTCCCTGCCCTTAAACGCAGAGCTTTTAGT |
| 78 | KIAA1967 | NM_021174.5 | 201-300 | GGGAGAGGGCCCACACAGTCTCCTCGCCGGCACCGGCCTCCTCCATTTTTCCGGGCCTTGCGTGGAGGGTTTTGGCGGATGTTTTGAACGAAGGAATGT |
| 79 | CCDC97 | NM_052848.1 | 2867-2966 | ATCCAGAGTGAGACAGCATTGGAGGGACAAGTGTGCATGCAGATGTCCTCAGACGGGAAGGTTTGAGAAGGGTCAGATGGTAGGCGGGCCTAACAAGGGC |

TABLE III-continued

| Sequence ID# | Gene | Position | Target Sequence |
|---|---|---|---|
| 80 | CCL3 | NM_002983.2 | 160-259 | CAGTTCTCTGCATCACTTGCTGC TGACACGCCGACCGCCTGCTGCT TCAGCTACACCTCCCGGCAGATT CCACAGAATTTCATAGCTGACTA CTTTGAGA |
| 81 | CCL3L1 | NM_021006.4 | 422-521 | GGGAGCCTGAGCCTTGGGAACAT GCGTGTGACCTCTACAGCTACCT CTTCTATGGACTGGTTATTGCCA AACAGCCACACTGTGGGACTCTT CTTAACTTA |
| 82 | CCL3L3 | NM_001001437.3 | 402-501 | GGGGAGGAGCAGGAGCCTGAGC CTTGGGAACATGCGTGTGACCTC CACAGCTACCTCTTCTATGGACT GGTTATTGCCAAACAGCCACACT GTGGGACTC |
| 83 | CCL4 | NM_002984.2 | 36-135 | TTCTGCAGCCTCACCTCTGAGAA AACCTCTTTGCCACCAATACCAT GAAGCTCTGCGTGACTGTCCTGT CTCTCCTCATGCTAGTAGCTGCC TTCTGCTC |
| 84 | CCND3 | NM_001760.2 | 1216-1315 | GGCCAGCCATGTCTGCATTTCGG TGGCTAGTCAAGCTCCTCCTCCC TGCATCTGACCAGCAGCGCCTTT CCCAACTCTAGCTGGGGGTGGGC CAGGCTGA |
| 85 | CCR1 | NM_001295.2 | 536-635 | CATCATTTGGGCCCTGGCCATCT TGGCTTCCATGCCAGGCTTATAC TTTTCCAAGAACCAATGGGAATT CACTCACCACACCTGCAGCCTTC ACTTTCCT |
| 86 | CCR6 | NM_031409.2 | 936-1035 | CTTTAACTGCGGGATGCTGCTCC TGACTTGCATTAGCATGGACCGG TACATCGCCATTGTACAGGCGAC TAAGTCATTCCGGCTCCGATCCA GAACACTA |
| 87 | CCR9 | NM_031200.1 | 1096-1195 | CCCTGTTCTCTATGTTTTTGTGG GTGAGAGATTCCGCCGGGATCTC GTGAAAACCCTGAAGAACTTGGG TTGCATCAGCCAGGCCCAGTGGG TTTCATTT |
| 88 | CCT6A | NM_001762.3 | 281-380 | GCCCAAGGGCACCATGAAGATG CTCGTTTCTGGCGCTGGAGACAT CAAACTTACTAAAGACGGCAAT GTGCTGCTTCACGAAATGCAAAT TCAACACCCA |
| 89 | CD14 | NM_000591.2 | 886-985 | GCCCAAGCACACTCGCCTGCCTT TTCCTGCGAACAGGTTCGCGCCT TCCCGGCCCTTACCAGCCTAGAC CTGTCTGACAATCCTGGACTGGG CGAACGCG |
| 90 | CD160b | NM_007053.2 | 501-600 | TTGATGTTCACCATAAGCCAAGT CACACCGTTGCACAGTGGGACCT ACCAGTGTTGTGCCAGAAGCCAG AAGTCAGGTATCCGCCTTCAGGG CCATTTTT |
| 91 | CD160 | NM_007053.3 | 1286-1385 | AAAGGAAGACAGCCAGATCCAG TGATTGACTTGGCATGAAAATGA GAAAATGCAGACAGACCTCAAC ATTCAACAACATCCATACAGCAC TGCTGGAGGA |
| 92 | CD1A | NM_001763.2 | 1816-1915 | CCTGTTTTAGATATCCCTTACTC CAGAGGGCCTTCCCTGACTTACA AGTGGGAAGCAGTCTCTTCCTGG TCTGAACTCCCGCCACATTTTAG CCGTACTT |
| 93 | CD36 | NM_000072.3 | 1619-1718 | TAAAGAATCTGAAGAGGAACTA TATTGTGCCTATTCTTTGGCTTA ATGAGACTGGGACCATTGGTGAT GAGAAGGCAAACATGTTCAGAAG TCAAGTAAC |
| 94 | CD48 | NM_001778.2 | 271-370 | AATTTAAAGGCAGGGTCAGACTT GATCCTCAGAGTGGCGCACTGTA CATCTCTAAGGTCCAGAAAGAG GACAACAGCACCTACATCATGA GGGTGTTGAA |
| 95 | CD69 | NM_001781.2 | 1360-1459 | TATACAGTGTCTTACAGAGAAAA GACATAAGCAAAGACTATGAGG AATATTTGCAAGACATAGAATAG TGTTGGAAAATGTGCAATATGTG ATGTGGCAA |
| 96 | CD70 | NM_001252.2 | 191-290 | CCTATGGGTGCGTCCTGCGGGCT GCTTTGGTCCCATTGGTCGCGGG CTTGGTGATCTGCCTCGTGGTGT GCATCCAGCGCTTCGCACAGGCT CAGCAGCA |
| 97 | CD79A | NM_021601.3 | 617-716 | TGAAGATGAAAACCTTTATGAAG GCCTGAACCTGGACGACTGCTCC ATGTATGAGGACATCTCCCGGGG CCTCCAGGGCACCTACCAGGATG TGGGCAGC |
| 98 | CD79B | NM_000626.2 | 350-449 | GAAGCTGGAAAAGGGCCGCATG GAAGAGTCCCAGAACGAATCTCT CGCCACCCTCACCATCCAAGGCA TCCGGTTTGAGGACAATGGCATC TACTTCTGT |
| 99 | CDC42EP2 | NM_006779.3 | 1779-1878 | AGGGCTTTGTGGAGGACAGGCCT TGCCCTCAAGAACGTCGTACCTG ACGCTGAGCCTGTCATGAGAATG CAACAGGAGCAAAACCAAGTGTT GCTGTGACA |
| 100 | CDH5 | NM_001795.3 | 3406-3505 | TCTCCCCTTCTCTGCCTCACCTG GTCGCCAATCCATGCTCTCTTTC TTTTCTCTGTCTACTCCTTATCC CTTGGTTTAGAGGAACCCAAGAT GTGGCCTT |
| 101 | CDKN1A | NM_000389.2 | 1976-2075 | CATGTGTCCTGGTTCCCGTTTCT CCACCTAGACTGTAAACCTCTCG AGGGCAGGGACCACACCCTGTAC TGTTCTGTGTCTTTCACAGCTCC TCCCACAA |
| 102 | CFD | NM_001928.2 | 860-959 | CTGGTTGGTCTTTATTGAGCACC TACTATATGCAGAAGGGGAGGC CGAGGTGGGAGGATCATTGGAT CTCAGGAGTTCGAGATCAGCATG GGCCACGTAG |
| 103 | CHCHD3 | NM_017812.2 | 1173-1272 | TCCACCCTAACAAAGTAGGATGG GGTTGGGGGCTAAATTAATTGGA GTGGGGCAGGAGAGAGCCAGA AAACATAGATCCGAGGGCAGCA GTGCTGGGTG |
| 104 | CHFR | NM_018223.2 | 2836-2935 | CGCCGCTCCCTCATGCTGCCCGG GCCCTTCCTCAAGACCCCTACAG AGCCTGAGGGGCACCTTGGCTTC CGCCTGTGCTAGCTTTGCCATGT CATCTGGA |

TABLE III-continued

| Sequence ID# | Gene | Position | Target Sequence |
|---|---|---|---|
| 105 | CHMP5 | NM_016410.5 | 1148-1247 | ACTAAGGAAATGGAATCTTAAAAGTCTATGACAGTGTAACTCTACAGTCTCAAAATGACCTGATAAATTGATAAGACAAAGATGAGATTATTGGGGCTGT |
| 106 | CIAPIN1 | NM_020313.3 | 1816-1915 | GCATGTCTTGTAAAGAGAGGGGATGTGCATTTGTGTGTGATGTTGGATAGTCATCCACGCTCAGTTTTGGACCATTGGAGGAACTTAGTGTCACGCACAAA |
| 107 | CKS2 | NM_001827.1 | 228-327 | AGACTTGGTGTCCAACAGAGTCTAGGCTGGGTTCATTACATGATTCATGAGCCAGAACCACATATTCTTCTCTTTAGACGACCTCTTCCAAAAGATCAAC |
| 108 | CLEC4A | NM_194448.2 | 389-488 | ATTTCTACTGAATCAGCATCTTGGCAAGACAGTGAGAAAGACTGTGCTAGAATGGAGGCTCACCTGCTGGTGATAAACACTCAAGAAGAGCAGGATTTCA |
| 109 | CLEC4C | NM_203503.1 | 571-670 | TACGAGAGTATCAACAGTATCATCCAAGCCTGACCTGCGTCATGGAAGGAAAGGACATAGAAGATTGGAGCTGCTGCCCAACCCCTTGGACTTCATTTCA |
| 110 | CLEC5A | NM_013252.2 | 3251-3350 | CCCCATCCAACCCTTAGACTCACGAACAAATCCACCTGAGATCAGCAGAGCCACCCTAGATCAGCTGAAACTCTAAGCACAAAAATAAAAACTTATACT |
| 111 | CLIC3 | ILMN_1796423.1 | 99-198 | CGTACGCCGCTACCTGGACAGCGCGATGCAGGAGAAAGAGTTCAAATACACGTGTCCGACAGCGCCGAGATCCTGGCGGCCTACCGGCCCGCCGTGCAC |
| 112 | CLK2 | XM_941392.1 | 552-651 | GATTATAGCCGGGATCGGGGAGATGCCTACTATGACACAGACTATCGGCATTCCTATGAATATCAGCGGGAGAACAGCAGTTACCGCAGCCAGCGCAGCA |
| 113 | CLN8 | NM_018941.3 | 4486-4585 | GGCGCCAGAGCTGGGCTCTTCAACACGGCATTTAGCGCAGAAAGTCGTGGTTCAGGCAGTATGGGCCGCTGTGACAAAACACCTAAGACTGGGTAGTTTA |
| 114 | CLPTM1 | NM_001294.3 | 2389-2488 | TCTGTGTTTCCAGCCATCTCGCCCTGCCAGCCCAGCACCACTGGAATCATGGTGAAGCTGATGCAGCGTTGCCGAGGGGGTGGGTTGGGCGGGGGTGGG |
| 115 | CLSTN1 | NM_0010095 6.2 | 4990-5089 | TTGAATACTGTTCTGTGACCCTGACTGCTAGTTCTGAGGACACTGGTGGCTGTGCTATGTGTGGCCATCCTCCATGTCCCGTCCCTGTAGCTGCTCTGTT |
| 116 | CN312986 | CN312986.1 | 491-590 | AGGAAACTAAGACATGGAAAGGTTAGGTAACTTGCCCAAGGTCGCACAGCTAGTAAGTGGCAGACATCCAGATGTTCTGCTCTGCTCTTAACTCTCACCA |
| 117 | CNIH4 | NM_014184.3 | 526-625 | AATGACTGAAGCTGGAGAAGCCGTGGTTGAAGTCAGCCTACACTACAGTGCACAGTTGAGGAGCCAGAGACTTCTTAAATCATCCTTAGAACCGTGACCA |
| 118 | CNPY2 | NM_014255.5 | 1038-1137 | TTGCAGTAAGCGAACAGATCTTTGTGACCATGCCCTGCACATATCGCATGATGAGCTATGAACCACTGGAGCAGCCCACACTGGCTTGATGGATCACCCC |
| 119 | COLEC12 | NM_130386.2 | 901-1000 | ACACAAGCCAGGCTATCCAGCGAATCAAGAACGACTTTCAAAATCTGCAGCAGGTTTTTCTTCAAGCCAAGAAGGACACGGATTGGCTGAAGGAGAAAGT |
| 120 | GLT25D1 | NM_024656.2 | 3067-3166 | CTGTGTGCCAGGCCTCACAGACTCCCAGTTGGGTTGAAGAATGGTTGACTGAGTTTGATTCTTCCTGTACCCTCGGTCGTCGAGCTGTGTGCGGACAAC |
| 121 | COMMD6 | NM_203497.3 | 32-131 | CTCTCGAGTCCGGGCCGCAAGTCCCAGACGCTGCCCATGGAGGCGTCCAGCGAGCCGCCGCTGGATGCTAAGTCCGATGTCACCAACCAGCTTGTAGATT |
| 122 | CORO1C | ILMN_1745954.1 | 98-197 | AAGTAAAGTTGTTGATGGTGGTGAAACACCGTAGGGCATGTGGTTCAAAGAGAAGCAGGAGGGCAAGGGAAAGTTACCCTGATCTTAGTTTGTAGCTTAT |
| 123 | COX6C | NM_004374.2 | 70-169 | GAAGTTTTGCCAAAACCTCGGATGCGTGGCCTTCTGGCCAGGCGTCTGCGAAATCATATGGCTGTAGCATTCGTGCTATCCCTGGGGGTTGCAGCTTTGT |
| 124 | COX7B | NM_001866.2 | 160-259 | CAGAGCCACCAGAAACGTACACCTGATTTTCATGACAAATACGGTAATGCTGTATTAGCTAGTGGAGCCACTTTCTGTATTGTTACATGGACATATGTAG |
| 125 | COX7C | NM_001867.2 | 1-100 | CAAGGTCGTGAAAAAAAAGGTCTTGGTGAGGTGCCGCCATTTCATCTGTCCTCATTCTCTGCGCCTTTCGCAGAGCTTCCAGCAGCGGTATGTTGGGCCA |
| 126 | CPPED1 | NM_018340.2 | 2494-2593 | TGTATTTGTTTCTTTACAACAGGTGTAGGTATAGGAGGTCAAGAAAAGGAGTTCGGTAAAGGGCATAGCTAATAACAACCACACATTGGGCCAGGCACAG |
| 127 | CR2 b | NM_001006658.1 | 486-585 | GGTGTCAAGCAAATAATATGTGGGGGCCGACACGACTACCAACCTGTGTAAGTGTTTTCCCTCTCGAGTGTCCAGCACTTCCTATGATCCACAATGGACA |
| 128 | CR2 | NM_001006658.2 | 3581-3680 | AGCCCAGTTTCACTGCCATATACTCTTCAAGGACTTTCTGAAGCCTCACTTATGAGATGCCTGAAGCCAGGCCATGGCTATAAACAATTACATGGCTCTA |
| 129 | CREB1 | NM_004379.3 | 4856-4955 | TTTGATGGTAGGTCAGCAGCAGTGCTAGTCTCTGAAAGCACAATACCAGTCAGGCAGCCTATCCCATCAGATGTCATCTGGCTGAAGTTTATCTCTGTCT |

TABLE III-continued

| Sequence ID# | Gene | Position | Target Sequence |
|---|---|---|---|
| 130 | CREB5 | NM_182898.3 | 7898-7997 ACCTACTCACCTTTTTCCCTTCT AAGTTCTGCTAAATCACATCTGC CTCATAGAGAAAGGAATGTTGCC TTTGAGAACTGTCTTGGAGAACA GATAAGCT |
| 131 | CRKL | NM_005207.3 | 4901-5000 TTCTAAAGGAGCAGAAGGACAG GTCTCTGAGACAGGATCGTTGTC CCTACAGGAGGAACAGTGGCCTT GCTTCTTAGACGGTCTTCACTGT GTGTTTTAA |
| 132 | CRY2 | NM_021117.3 | 4013-4112 CAGCTCAGGTGGCCCTGAGGGCT CCCTCGGAACAGTGCCTCAAATC CTGACCCAAGGGCCAGCATGGG GAAGAGATGGTTGCAGGCAAAA TGCACTTTAT |
| 133 | CS | NM_004077.2 | 2080-2179 CCTCCTAGCAAGACCTGTTGGTT AGCTGGACATGCTTTGGCAATTT TTTTATACTACCAAGTGACCATA AAGGCATGGCATTTGTTGTGACT GGCACCCA |
| 134 | CSK | NM_004383.2 | 2501-2600 TCTAGGGACCCCTCGCCCCAGCC TCATTCCCCATTCTGTGTCCCAT GTCCCGTGTCTCCTCGGTCGCCC CGTGTTTGCGCTTGACCATGTTG CACTGTTT |
| 135 | CST7 | NM_003650.3 | 618-717 CAACCACACCTTGAAGCAGACTC TGAGCTGCTACTCTGAAGTCTGG GTCGTGCCCTGGCTCCAGCACTT CGAGGTGCCTGTTCTCCGTTGTC ACTGACCC |
| 136 | CTAG1B | NM_001327.2 | 286-385 GCGGGGCCAGGGGGCCGGAGAG CCGCCTGCTTGAGTTCTACCTCG CCATGCCTTTCGCGACACCCATG GAAGCAGAGCTGGCCCGCAGGA GCCTGGCCCA |
| 137 | CTDSP2 | NM_005730.3 | 4685-4784 GAGGTCGGGCCAGCTGCCCCATT CTTTTAACGTTGTAGGGCCTGCC CATGGAGCGGACCCTCCTCTTTG GGCCTCGTGAGCTTTTTTGCTTA TCATGTTC |
| 138 | CTSW | NM_001335.3 | 1076-1175 TGCACCGAGGGAGCAATACCTGT GGGCATCACCAAGTTCCCGCTCAC TGCCCGTGTGCAGAAACCGGATA TGAAGCCCGAGTCTCCTGCCCT CCCTGAAC |
| 139 | CTSZ | NM_001336.3 | 1174-1273 CACTGGCTGCGAGTGTTCCTGAG AGTTGAAAGTGGGATGACTTATG ACACTTGCACAGCATGGCTCTGC CTCACAATGATGCAGTCAGCCAC CTGGTGAA |
| 140 | CX3CL1 | NM_002996.3 | 141-240 AGCACCACGGTGTGACGAAATG CAACATCACGTGCACGAAGATGA ACATCAAAGATACCTGTAGCTTT GCTCATCCACTATCAACAGAACC AGGCATCATG |
| 141 | CXCL2 | NM_002089.3 | 855-954 ATCACATGTCAGCCACTGTGATA GAGGCTGAGGAATCCAAGAAAA TGGCCAGTGAGATCAATGTGACG GCAGGGAAATGTATGTGTGTCTA TTTTGTAAC |
| 142 | IL8RB | NM_001557.3 | 410-509 ACCTCAAAAATGGAAGATTTTAA CATGGAGAGTGACAGCTTTGAA GATTTCTGAAAGGTGAAGATCT TAGTAATTACAGTTACAGCTCTA CCCTGCCCC |
| 143 | CXCR5b | NM_001716.3 | 2619-2718 ACGTCCCTTTTTTCTCTGAGTAT CTCCTCGCAAGCTGGGTAATCGA TGGGGGAGTCTGAAGCAGATGCA AAGAGGCAAGAGGCTGGATTTT GAATTTTCT |
| 144 | CYBB | NM_000397.3 | 3787-3886 ACTGGAGAGGGTACCTCAGTTAT AAGGAGTCTGAGAATATTGGCCC TTTCTAACCTATGTGCATAATTA AAACCAGCTTCATTTGTTGCTCC GAGAGTGT |
| 145 | CYP1B1 | NM_000104.3 | 2361-2460 CTTACACCAAACTACTGAATGAA GCAGTATTTTGGTAACCAGGCCA TTTTTGGTGGGAATCCAAGATTG GTCTCCCATATGCAGAAATAGAC AAAAGTA |
| 146 | DB338252 | DB338252.1 | 436-535 GTTCTTGGTCTGTATGTGTAGGT GGAGGGAGGCAAAGTTGTGGTA ATAAAGTGGGAAGGCCCGGGAA GAACAGCTAACTGTATAGGGGT GAAATGACGCT |
| 147 | DBI | NM_001079862.1 | 241-340 CATAAATACAGAACGGCCCGGG ATGTTGGACTTCACGGGCAAGGC CAAGTGGGATGCCTGGAATGAG CTGAAAGGGACTTCCAAGGAAG ATGCCATGAAA |
| 148 | DCAF7 | NM_005828.4 | 6155-6254 TTAACACTGTGCTGTGAAACAAC TATGGGGAATCTCCATTGAAGGC TACTTCATGGGCACCTGAAAGTG GAGTGTTATAGCTATGACTTTCT ATTTCTTG |
| 149 | DDIT4 | NM_019058.2 | 1414-1513 GACCTGTTGTAGGCAGCTATCTT ACAGACGCATGAATGTAAGAGT AGGAAGGGGTGGGTGTCAGGGA TCACTTGGGATCTTTGACACTTG AAAAATTACA |
| 150 | DDX23 | NM_004818.2 | 2811-2910 ATTGCACTGGGCCATCAGCTCAT GCCAGGCTATGGGGCAGCCAG TTGGCATTGCTCCCCAGACTGA CAGAAACCTGGCCGCCGGATGG GACCTCCTTT |
| 151 | DGUOK | NM_080916.2 | 573-672 ACATCGAGTGGCATATCTATCAG GACTGGCATTCTTTTCTCCTGTG GGAGTTTGCCAGCCGGATCACAT TACATGGCTTCATCTACCTCCAG GCTTCTCC |
| 152 | DGUOKb | NM_080916.2 | 903-1002 TTGTAAAGAATCTGTAACCAATA CCATGAAGTTCAGGCTGTGATCT GGGCTCCCTGACTTTCTGAAGCT AGAAAAATGTTGTGTCTCCCAAC CACCTTTC |
| 153 | DHX16b | NM_001164239.1 | 2491-2590 CCCGTGTCAACTTCTTTCTCCCT GGCGGTGACCACCTGGTTCTGCT AAATGTTTACACACAGTGGGCTG AGAGTGGTTACTCTTCCCAGTGG TGCTATGA |
| 154 | DHX16 | NM_003587.4 | 3189-3288 ACCAAAGAGTTCATGAGACAGG TACTGGAGATTGAGAGCAGTTGG CTTCTGGAGGTGGCTCCCATTA TTATAAGGCCAAGGAGCTAGAA GATCCCCATG |

TABLE III-continued

| Sequence ID# | Gene | | Position | Target Sequence |
|---|---|---|---|---|
| 155 | DKFZp761P04 23 | XM_291277.4 | 4192-4291 | CTCCTGCAGCTTCTGTGAGCCAA GCCCCAGCCTGCACCGTCGCTGC CCCTTCCCTGCCTAACCCTTTCC TGTCTCGCCTTGGAAGCACCCAT GTCTCCCT |
| 156 | DMBT1 | NM_007329.2 | 3713-3812 | CACAATGGCTGGCTCTCCCACAA CTGTGGCCATCATGAAGACGCTG GTGTCATCTGCTCAGCTTCCCAG TCCCAGCCGACACCCAGCCCAGA CACTTGGC |
| 157 | DNAJB1 | NM_006145.2 | 1904-2003 | GACCTCTGGCTCCAGTGAAGCTG AATGTCCTCACTTTGTGGGTCAC ACTCTTTACATTTCTGTAAGGCA ATCTTGGCACACGTGGGGCTTAC CAGTGGCC |
| 158 | DNAJB6 | NM_058246.3 | 2087-2186 | CTTCCCTGCATGCTCCCTCCCAG TGACTTTCCTTCCCTTTCACATG AGGATCTGCCGTTCATGTTGCTT TCTCCTTTGTCCTCTTGGACTTG AGGGCATT |
| 159 | DOCK5 | NM_024940.6 | 7201-7300 | AAAGAGATTTCCATTTCTGCTGC CAGAGCTGGTATTTGCCTGCCTG ATTCTCTGTGTTTCCTGTTTCAC CGCCACCCTTTCAGGAGAGAACT ACACCAGT |
| 160 | DPF2 | NM_006268.4 | 2249-2348 | TCTCAGCTCATGGGGAAGCCACA TAGACATCCCTTTCTTCCCTTGC ACGCTCGCTAGCAGCTGGTAAGG TCTTCACACCCTGATTCCTCAAG TTTTCTGC |
| 161 | DYNC2LI1 | NM_016008.3 | 351-450 | TTTGGGAACTCGGTGGAGGAACC TCTTTATTGGACTTAATCAGCAT ACCCATCACAGGTGACACCTTAC GGACGTTTTCTCTTGTTCTCGTT CTGGATCT |
| 162 | DZIP3 | NM_014648.3 | 4323-4422 | CCCAGTGTCTTGCCCAGTAGATA CAAGATAAATATTGCCAGAATCA GATATCAGGAAGTAGTAAGAAA AGGAGTTAATATGCAAACTAAAT CACTCGCTC |
| 163 | EEF1B2 | NM_001037663.1 | 699-798 | GGATACGGAATTAAGAAACTTC AAATACAGTGTGTAGTTGAAGAT GATAAAGTTGGAACAGATATGCT GGAGGAGCAGATCACTGCTTTTG AGGACTATG |
| 164 | EGLN1 | NM_022051.1 | 3976-4075 | AGCAGCATGGACGACCTGATAC GCCACTGTAACGGGAAGCTGGG CAGCTACAAAATCAATGGCCGG ACGAAAGCCATGGT |
| 165 | EGR1 | NM_001964.2 | 1506-1605 | GAGGCATACCAAGATCCACTTGC GGCAGAAGGACAAGAAAGCAGA CAAAAGTGTTGTGGCCTCTTCGG CCACCTCCTCTCTCTCTTCCTAC CCGTCCCCG |
| 166 | EHD4 | NM_139265.3 | 2605-2704 | TCAAACATTAAATATCCCGAGGT CTCCTTGGTGGGTGGCAGGATTT AAATTCAATCAAATCCTGTCCTA GTGTGTGCAGTGTCTTCGGCCCT GTGGACAC |
| 167 | EID2B | NM_152361.2 | 628-727 | GCCAGTTTAGTTAACTCAGTCAT TAGGGGAATGCAAACTGGAAG GGAATACGGCAATGTGCAATTG AAGGAGGAAGCACACTCCGAAA TGGAAACAGAC |
| 168 | EIF2B4 | NM_015636.3 | 1497-1596 | GTCTCTAATGAGCTAGATGACCC TGATGATCTGCAATGTAAGCGGG GAGAACATGTTGCGCTGGCTAAC TGGCAGAACCACGCATCCCTACG GTTGTTGA |
| 169 | EIF4ENIF1 | NM_019843.2 | 3051-3150 | CACACTGGGCAGGACCCTGCTTC ATCTCGGGTTGGTTTATGGGCTT TTACTTTGGAGCACTCTGTGTGA AGCTGTTTGGTGGAACCCATGCA TCTGGTGT |
| 170 | EMR4 | NM_001080498.2 | 1719-1818 | GGGAAGACGATTGGATCAATCA TTGCATACTCATTCACCATCATC AACACCCTTCAGGGAGTGTTGCT CTTTGTGGTACACTGTCTCCTTA ATCGCCAGG |
| 171 | EP300 | NM_001429.2 | 716-815 | CCAGCCAGGCCCAACAGAGCAG TCCTGGATTAGGTTTGATAAATA GCATGGTCAAAAGCCCAATGAC ACAGGCAGGCTTGACTTCTCCCA ACATGGGAT |
| 172 | EPHX2 | NM_001979.5 | 1909-2008 | CATCCTTCCACCTGCTGGGGCAC CATTCTTAGTATACAGAGGTGGC CTTACACATCTTGCATGGATG GCAGCATTGTTCTGAAGGGGTTT GCAGAAAA |
| 173 | ERLIN1 | NM_006459.3 | 3197-3296 | TGATGGCCCTGGAGGCGGGGCT GAGGAACAGGGAAATGCCGCTG TGAAGTCTTAAAGCACTTCTGCT TAAACTCCCATGTGTGAGGAGTG TGCCTCCCTG |
| 174 | ETFDH | NM_004453.3 | 1904-2003 | TGACCTCTTGTCATCTGTGGCTC TGAGTGGTACTAATCATGAACAT GACCAGCCGGCACACTTAACCTT AAGGGATGACAGTATACCTGTAA ATAGAAAT |
| 175 | EVI2A | NM_014210.3 | 1410-1509 | GAGAGAGCTAAACTGTGTAATTT AATGGTATCTTCCTTGCTGGATG TGGCAGAATCCACACCAGCTTAT CAACCAACACAGCTAATTTTAGA ATAGATCC |
| 176 | EWSR1 | NM_005243.3 | 2248-2347 | AAAAATGGATAAAGGCGAGCAC CGTCAGGAGCGCAGAGATCGGC CCTACTAGATGCAGAGACCCCGC AGAGCTGCATTGACTACCAGATT TATTTTTAA |
| 177 | EYA3 | NM_001990.3 | 1551-1650 | GATTCCTGGTTAGGAACTGCATT AAAGTCCTTACTTCTCATCCAGT CCAGAAAGAATTGTGTGAATGTT CTGATCACTACCACCCAGCTGGT TCCAGCCC |
| 178 | C5orf21 | NM_032042.5 | 4058-4157 | TTAGAACAAGTAGAATGGGAAA GGAGTGACTGATAAATCTAAGAT TCAAAATAGTCCCGTCGAAACTT AAAGGCCAGATTATTGCTTTGGA GCTTTCTAT |
| 179 | FAM179A | NM_199280.2 | 3306-3405 | ACTCTTAGACTCAGAGTCCTTGG GAGGCAGCCGCAAGGCCACTGA CAGAGGGGTGGCCCCTGACAGC AAGACAACTGGCAGCTCATACCC TTTTCAGCTG |
| 180 | FAM193A | NM_003704.3 | 4523-4622 | CCCTGACTTGTAGCCAGCTTGTG TAAGATCCCTTGCAGAACGAGA |

TABLE III-continued

| Sequence ID# | Gene | | Position | Target Sequence |
|---|---|---|---|---|
| | | | | AAGTTAAAAACAAGCCCACCCA GTACTCACACCATCAAGTCTGTT ATAGAGTGTA |
| 181 | FAM43A | NM_153690.4 | 2741-2840 | AGACCCTGAAATGTTGCCAAAT TCTTCAAATAACTGTTTGGGGGG TGGGGGGAGATGAAAGAGAGTC GCGTTTTGTTTACAGTTAAAGAC ATCCAATAT |
| 182 | FAM50B | NM_012135.1 | 1273-1372 | TTCTGAGTATTTTAGTGTTGCCA CCTGGATTTGCTGCATTGCTCTG CTGAGCTGTATTGAAACCATGAC TGGGCCCACTGTCAGACAGAAAT TAGAATAG |
| 183 | FAIM3 | NM_005449.4 | 1689-1788 | CAGGCTCTAGATCACATGGCATC AGGCTGGGCAGAGGCATAGCT ATTGTCTCGGGCATCCTTCCCAG GGTTGGGTCTTACACAAATAGAA GGTCTTGC |
| 184 | FKBP1A | NM_054014.3 | 301-400 | AGAAACAAGCCCTTTAAGTTTAT GCTAGGCAAGCAGGAGGTGATC CGAGGCTGGGAAGAAGGGGTTG CCCAGATGAGTGTGGGTCAGAG AGCCAAACTGA |
| 185 | FLNB | NM_001457.3 | 9148-9247 | CAGACCTGAGCTGGCTTTGGAAT GAGGTTAAAGTGTCAGGGACGTT GCCTGAGCCCAAATGTGTAGTGT GGTCTGGGCAGGCAGACCTTTAG GTTTTGCT |
| 186 | FNBP1 | NM_015033.2 | 5237-5336 | TGTGTGTTGCACTAATTCTAAAC TTTGGAGGCATTTGCTGTGTGA GGCCGATCGCCACTGTAAAGGTC CTAGAGTTGCCTGTTTGTCTCTG GAGATGGA |
| 187 | FOXK2 | NM_004514.3 | 4387-4486 | TTTTTTGCCGTAGGCACCATTCT GCATCTTGAACCCAGACTGAAGT GTGCCTCTCACAGATGGAAGGTG CACACGCTCCTGTCTCCTCCTCA CTCTGCCA |
| 188 | FRAT2 | NM_012083.2 | 1769-1868 | CTTGTCCTCCCAGCTGAGCTTTC TTATTCCACCCTTTCTGGTGTCT ATAGGAATGCATGAGAGACCCTG GACGTTTTTCTGCTCTCTTCTGG CCCTCCAT |
| 189 | FTHL16 | XR_041433.1 | 255-354 | GGACTCAGAGGCCGCCATCAAC CGCCAGATCAACCTAGAGCTCTG TGCCTCCTACGTTTACCTGTCCA TGTCTTACTGCTTTGACCGTGAT GATGTGGCT |
| 190 | GATA2 | NM_001145662.1 | 2573-2672 | GTCCAGTTGATTGTACGTAGCCA CAGGAGCCCTGCTATGAAGGA ATAAAACCTACACACAAGGTTG GAGCTTTGCAATTCTTTTGGAA AAGAGCTGGG |
| 191 | GLIS3 | NM_001042413.1 | 548-647 | ACTCGCGCTGGCCGGCCGGGGG AAGGGACCCGCACGCCGGGCTTT GTTGTGGAAATCCCGGTTACCTG GCTTATAACCCACACCATGGATA ACTTATTGG |
| 192 | GLRX | ILMN_1737308.1 | 119-218 | AAAGCATAGTTGGTCTTGGTGTC ATATGGATCAGAGGCACAAGTG CAGAGGCTGTGGTCATGCGGAA CACTCTGTTATTTAAGATGGCTA TCCAGATAAT |
| 193 | GNL3 | NM_014366.4 | 1733-1832 | TACAGCAGGTGAACAGTCTACA AGGTCTTTTATCTTGGATAAAAT CATTGAAGAGGATGATGCTTATG ACTTCAGTACAGATTATGTGTAA CAGAACAAT |
| 194 | GNS | NM_002076.3 | 4988-5087 | CCTGTGTTTGCATCCTCTGTTCC TATTCTGCCCTTGCTCTGTGTCA TCTCAGTCATTTGACTTAGAAGA TGCCCTTCAAAAGGACCCTGTTC ACTGCTGC |
| 195 | GOLGA3 | NM_005895.3 | 8961-9060 | CTCACTGACCGGAAGGTCCAGGT GAATCTCGTCATAAGTGATCTCA GGCTCTCACAGGATCCGGAGGG AAATGTGTTAGAGGGTCTGGAA AATTCAGTGC |
| 196 | GPATCH3 | NM_022078.2 | 1686-1785 | AGTCTGGGAGCAGCAGTCTTCGT GGCTGGTTCAGGGTGTTTTGTTC CGAGCCTGCCTGCCTGCCGGTTC TATACCTCAGGGGCATTTTTACA AAAAGCCC |
| 197 | GPI | NM_000175.2 | 1696-1795 | CAGTGCTCAAGTGACCTCTCACG ACGCTTCTACCAATGGGCTCATC AACTTCATCAAGCAGCAGCGCG AGGCCAGAGTCCAATAAACTCGT GCTCATCTG |
| 198 | GPR65 | NM_003608.3 | 1899-1998 | TATGATTTTTCTCACTCTTTCTT TGGACTCCAGGGTGTCAGCCATC AGGTCTCCTAATTTTGTGTACCG GTCTCCAACAACCCCAGCTACTG AATACTGC |
| 199 | GSTO1 | NM_004832.2 | 897-996 | AGAGCTCTACTTACAGAACAGCC CTGAGGCCTGTGACTATGGGCTC TGAAGGGGCAGGAGTCAGCAA TAAAGCTATGTCTGATATTTTCC TTCACTAAT |
| 200 | GUSH | NM_000181.3 | 2032-2131 | GGTATCCCCACTCAGTAGCCAAG TCACAATGTTTGGAAAACAGCCT GTTTACTTGAGCAAGACTGATAC CACCTGCGTGTCCCTTCCTCCCC GAGTCAGG |
| 201 | GZMA | NM_006144.3 | 636-735 | GCCTCCGAGGTGGAAGAGACTC GTGCAATGGAGATTCTGGAAGCC CTTTGTTGTGCGAGGGTGTTTTC CGAGGGGTCACTTCCTTTGGCCT TGAAAATAA |
| 202 | GZMB | NM_004131.3 | 541-640 | ACACTACAAGAGGTGAAGATGA CAGTGCAGGAAGATCGAAAGTG CGAATCTGACTTACGCCATTATT ACGACAGTACCATTGAGTTGTGC GTGGGGACC |
| 203 | GZMH | NM_033423.4 | 718-817 | GGCCCCTCGTGTGTAAGGACGTA GCCCAAGGTATTCTCTCCTATGG AAACAAAAAGGGACACCTCCA GGAGTCTACATCAAGGTCTCACA CTTCCTGCC |
| 204 | HAT1 | NM_003642.3 | 1235-1334 | AACCAAATAGAAATAAGCATGC AACATGAACAGCTGGAAGAGAG TTTTCAGGAACTAGTGGAAGATT ACCGGCGTGTTATTGAACGACTT GCTCAAGAGT |
| 205 | HAVCR2 | NM_032782.3 | 956-1055 | TATATGAAGTGGAGGAGCCCAA TGAGTATTATTGCTATGTCAGCA GCAGGCAGCAACCCTCACAACCT |

TABLE III-continued

| Sequence ID# | Gene | Position | Target Sequence |
|---|---|---|---|
| | | | TTGGGTTGTCGCTTTGCAATGCCATAGATCCA |
| 206 | HDAC3 | NM_003883.3 | 1765-1864 | AAGATGAAGAGAGAGAGATTTGGAAGGGGCTCTGGCTCCCTAACACCTGAATCCCAGATGATGGGAAGTATGTTTTCAAGTGTGGGGAGGATATGAAAAT |
| 207 | HERC1 | NM_003922.3 | 14664-14763 | CAATCGACATGGACAACTACATGCTCTCGAGAAACGTGGACAACGCCGAGGGCTCCGACACTGACTACTGACCGTGCGGGTGCTCTCACCCTCCCTTCTC |
| 208 | HERC3 | NM_014606.2 | 3796-3895 | TAAGAATGATTTAGACTGACCTGTCCTTTTTTATCTGCGCATGCGAGAACATCACCTTCCTCTGTACACTTGGAAATGCCTCTGGCTTGTTGCAGCCCTC |
| 209 | HK3 | NM_002115.2 | 2785-2884 | AGTCAGAGGATGGGTCCGGCAAAGGTGCGGCCCTGGTCACGCTGTTGCCTGCCGCCTTGCGCAGTTGACTCGTGTCTGAGGAAACCTCCAGGCTGAGGA |
| 210 | HLA-B | NM_005514.6 | 938-1037 | CCCTGAGATGGGAGCCGTCTTCCCAGTCCACCGTCCCCATCGTGGGCATTGTTGCTGGCCTGGCTGTCCTAGCAGTTGTGGTCATCGGAGCTGTGGTCGC |
| 211 | HLA-DMB | NM_002118.3 | 21-120 | CCCGTGAGCTGGAAGGAACAGATTTAATATCTAGGGGCTGGGTATCCCCACATCACTCATTTGGGGGGTCAAGGGACCCGGGCAATATAGTATTCTGCTC |
| 212 | HLA-G | NM_002127.4 | 1181-1280 | AAGAGCTCAGATTGAAAGGAGGGAGCTACTCTCAGGCTGCAATGTGAAACAGCTGCCCTGTGTGGGACTGAGTGGCAAGTCCCTTTGTACTTCAAGAA |
| 213 | HMGB1 | NM_002128.4 | 209-308 | TATGCATTTTTTGTGCAAACTTGTCGGGAGGAGCATAAGAAGCACCCAGATGCTTCAACTTCTCAGAGTTTTCTAAGAAGTGCTCAGAGAGGT |
| 214 | HMGB2 | NM_002129.3 | 670-769 | TGCTGCATATCGTGCCAAGGGCAAAAGTGAGTCAGGAAAGAAGGGCCCTGGCAGGCCAACAGGCTCAAAGAAGAAGAACGAACCAGAAGATGAGGAGGAG |
| 215 | HNRNPAB | NM_004499.3 | 1246-1345 | CCCCATGGAAATCACTCTCCTGTTGACTATTCCAGAGCTCTAGGTGTTTAGGCAGCGTGTGGTGTCTGAGAGGCCATAGCGCCATCATGGGCTGATTTT |
| 216 | HNRNPK | NM_031263.2 | 538-637 | TCCCTACCTTGGAAGAGGGCCTGCAGTTGCCATCACCCACTGCAACCAGCCAGCTCCCGCTCGAATCTGATGCTGTGGAATGCTTAAATTACCAACACTA |
| 217 | HOOK3 | NM_032410.3 | 2391-2490 | GCAAGGTAGAGAAGTTGTGCCGCTCAATCACAGACACCTGCACCCACAACATACTTCTGTTACACACAAGAACATTTCAGGAAACTCAGCCAGCTTATTT |
| 218 | HOPX | NM_139211.4 | 590-689 | AACAATAGGAAGCTATGTGTATCTTCTGTGTAAAGCAGTGGCTTCACTGGAAAAATGGTGTGGCTAGCATTTCCCTTTGAGTCATGATGACAGATGGTGT |
| 219 | HPSE | NM_006665.5 | 3920-4019 | GAGGTTCCTATAATTGTCTCTGAGTAACCCTTTGGAATGGAGAGGGTGTTGGTCAGTCTACAAACTGAACACTGCAGTTCTGCGCTTTTTACCAGTGAAA |
| 220 | HSCB | NM_172002.3 | 343-442 | TCCACCCAGATTTCTTCAGCCAGAGGTCTCAGACTGAAAAGGACTTCTCAGAGAAGCATTCGACCCTGGTGAATGATGCCTATAAGACCCTCCTGGCCCC |
| 221 | HSD11B1 | NM_181755.1 | 156-255 | GCCTACTACTACTATTCTGCAAACGAGGAATTCAGACCAGAGATGCTCCAAGGAAAGAAAGTGATTGTCACAGGGGCCAGCAAAGGGATCGGAAGAGAGA |
| 222 | HSP90AB1 | NM_007355.3 | 1531-1630 | GGCATTCTCTAAAAATCTCAAGCTTGGAATCCACGAAGACTCCACTAACCGCCGCCGCCTGTCTGAGCTGCTGCGCTATCATACCTCCCAGTCTGGAGAT |
| 223 | HSPA6 | NM_002155.4 | 1990-2089 | GTGGCACTCAAGCCCGCCAGGGGGACCCCAGCACCGGCCCCATCATTGAGGAGGTTGATTGAATGGCCCTTCGTGATAAGTCAGCTGTGACTGTCAGGGC |
| 224 | HUWE1 | NM_031407.6 | 13637-13736 | CCACCAACTCACCGTGTGTGTCCCAGCTGCCCCATCTTCCCCAGCGCATACCTGTTCCTCTTCTCATTCTCTCCCCGCCGCCTGTTTCCTCACCTTCTCT |
| 225 | HVCN1 | NM_032369.3 | 747-846 | TGTTCCAGGAGCACCAGTTTGAGGCTCTGGGCCTGCTGATTCTGCTCCGGCTGTGGCGGGTGGCCCGGATCATCAATGGGATTATCATCTCAGTTAAGAC |
| 226 | IDO1 | NM_002164.3 | 51-150 | CTATTATAAGATGCTCTGAAAACTCTTCAGACACTGAGGGGCACCAGAGGAGCAGACTACAAGAATGGCACACGCTATGGAAAACTCCTGGACAATCAGT |
| 227 | IDS | NM_006123.4 | 1016-1115 | TGGATGGACATCAGGCAACGGGAAGACGTCCAAGCCTTAAACATCAGTGTGCCGTATGGTCCAATTCCTGTGGACTTTCAGCGGAAAATCCGCCAGAGCT |
| 228 | IER5 | NM_016545.4 | 1802-1901 | ACTTTACACCTACCCCTCACCGGAAAGCTAGACCCGCTTCAGGGCCAGGAGTGGCGTTTCCGCACAGGATTTCCTAAGACGAGAGGGATTTAGCCAAGAG |
| 229 | IFI27L2 | NM_032036.2 | 305-404 | GTCAGTGTTGGGGGCCTGCTTGGGGAATTCACCTCTTCTTCTCTCCAGCTGAACCCGAGGCTAAAGAAGATGAGGCAAGAGAAAATGTACCCCAAGGT |

TABLE III-continued

| Sequence ID# | Gene | | Position | Target Sequence |
|---|---|---|---|---|
| 230 | IFNA17 | NM_021268.2 | 292-391 | TGAGATGATCCAGCAGACCTTCAATCTCTTCAGCACAGAGGACTCATCTGCTGCTTGGGAACAGAGCCTCCTAGAAAAATTTTCCACTGAACTTTACCAG |
| 231 | IFNAR1 | NM_000629.2 | 3124-3223 | CTAATCAGCTCTCAGTGATCAACCCACTCTTGTTATGGGTGGTCTCTGTCACTTTGAATGCCAGGCTGGCTTCTCGTCTAGCAGTATTCAGATACCCCTT |
| 232 | IFNAR2 | NM_000874.3 | 632-731 | AAATACCACAAGATCATTTTGTGACCTCACAGATGAGTGGAGAAGCACACACGAGGCCTATGTCACCGTCCTAGAAGGATTCAGCGGGAACACAACGTTG |
| 233 | IFNGR1 | NM_000416.1 | 1141-1240 | CCCGGGCAGCCATCTGACTCCAATAGAGAGAGAGAGTTCTTCACCTTTAAGTAGTAACCAGTCTGAACCTGGCAGCATCGCTTTAAACTCGTATCACTCC |
| 234 | IGFBP7 | NM_001553.2 | 584-683 | ATCGGAATCCCGACACCTGTCCTCATCTGGAACAAGGTAAAAAGGGGTCACTATGGAGTTCAAAGGACAGAACTCCTGCCTGGTGACCGGGACAACCTGG |
| 235 | IL16 | NM_004513.4 | 1263-1362 | GGCATCTCCAACATCATCATCCAACGAAGACTCAGCTGCAAATGGTTCTGCTGAAACATCTGCCTTGGACACAGGGTTCTCGCTCAACCTTTCAGAGCTG |
| 236 | IL1B | NM_000576.2 | 841-940 | GGGACCAAAGGCGGCCAGGATATAACTGACTTCACCATGCAATTTGTGTCTTCCTAAAGAGAGCTGTACCCAGAGAGTCCTGTGCTGAATGTGGACTCAA |
| 237 | IL1R2 | NM_173343.1 | 114-213 | TGCTTCTGCCACGTGCTGCTGGGTCTCAGTCCTCCACTTCCCGTGTCCTCTGGAAGTTGTCAGGAGCAATGTTGCGCTTGTACGTGTTGGTAATGGGAGT |
| 238 | IL4 | NM_000589.2 | 626-725 | GACACTCGCTGCCTGGGTGCGACTGCACAGCAGTTCCACAGGCACAAGCAGCTGATCCGATTCCTGAAACGGCTCGACAGGAACCTCTGGGCCTGGCGG |
| 239 | IL7 | NM_000880.2 | 39-138 | AATAACCCAGCTTGCGTCCTGCACACTTGTGGCTTCCGTGCACACATTAACAACTCATGGTTCTAGCTCCCAGTCGCCAAGCGTTGCCAAGGCGTTGAGA |
| 240 | INTS4 | NM_033547.3 | 652-751 | CCCACGTGTCAGAACAGCAGCTATAAAAGCCATGTTGCAGCTCCATGAAAGAGGACTGAAATTACACCAAACAATTTATAATCAGGCCTGTAAATTACTC |
| 241 | IRAK2 | NM_001570.3 | 1286-1385 | GTGTTGGCCGAGGTCCTCACGGGCATCCCTGCAATGGATAACAACCGAAGCCCGGTTTACCTGAAGGACTTACTCCTCAGTGATATTCCAAGCAGCACCG |
| 242 | IRF1 | NM_002198.1 | 511-610 | CTGTGCGAGTGTACCGGATGCTTCCACCTCTCACCAAGAACCAGAGAAAAGAAAGAAAGTCGAAGTCCAGCCGAGATGCTAAGAGCAAGGCCAAGAGGAA |
| 243 | IRF4 | NM_002460.1 | 326-425 | GGGCACTGTTTAAAGGAAAGTTCCGAGAAGGCATCGACAAGCCGGACCCTCCCACCTGGAAGACGCGCCTGCGGTGCGCTTTGAACAAGAGCAATGACTT |
| 244 | KIAA0174 | NM_014761.3 | 2187-2286 | ATGGATGGGACTCTTATGTCATAACTTCTGTTACTCCTTTGGCCCATAGCTAAGGTCATCCTTCCCCACAGGGGTGGCTTTGGGATTGGATGATACAGCT |
| 245 | ITCH | NM_001257138.1 | 439-538 | GAGGTGACAAAGAGCCAACAGAGACAATAGGAGACTTGTCAATTTGTCTTGATGGGCTACAGTTAGAGTCTGAAGTTGTTACCAATGGTGAAACTACATG |
| 246 | ITFG2 | NM_018463.3 | 1985-2084 | GTCTGGTCTTACCCATGTTCCTAGCAACCCTGAGATGATTTCTTCCATTTACCAAAGCAGCCGGGTCAGTGCTTTCTCACGTTGCCGTATTCTTCAGGT |
| 247 | ITGAE | NM_002208.4 | 3406-3505 | CTGAATGCAGAGAACCACAGAACTAAGATCACTGTCGTCTTCCTGAAAGATGAGAAGTACCATTCTTTGCCTATCATCATTAAAGGCAGCGTTGGTGGAC |
| 248 | ITGAL | NM_002209.2 | 3906-4005 | GTGAGGGCTTGTCATTACCAGACGGTTCACCAGCCTCTCTTGGTTTCCTTCCTTGGAAGAGAATGTCTGATCTAAATGTGGAGAAACTGTAGTCTCAGGA |
| 249 | JAK1 | NM_002227.1 | 286-385 | GAGAACACCAAGCTCTGGTAGCTCCAAATCGCACCATCACCGTTGATGACAAGATGTCCCTCCGGCTCACTACCGGATGAGGTTCTATTTCACCAATT |
| 250 | KIAA1267 | NM_015443.3 | 4402-4501 | CCTTCACATCCAGATCCCTGTCGGTGTTAGTTCCACTCTTGGTCTTTCACGCTCCCCTTGCCTGTGGAACATTGTCTGGTCCTAGCTGTGGTTCCCATTG |
| 251 | MYST4 | NM_012330.3 | 6541-6640 | CCCAGACTGTAGCCATGCAGGGTCCTGCACGGACTTTAACGATGCAAAGAGGCATGAACATGAGTGTGAACCTGATGCCAGCGCCAGCCTACAATGTCAA |
| 252 | KCTD12 | NM_138444.3 | 4208-4307 | ACAAGTAAAATAACTTGACATGAGCACCTTTAGATCCCTTCCCCTCCATGGGCTTTGGGCCACAGAATGAACCTTTGAGGCCTGTAAAGTGGATTGTAAT |
| 253 | KIAA0101 | NM_014736.4 | 236-335 | CGACATCAGTTTCATCGAGGAAAGCTGAAAATAAATATGCAGGAGGGAACCCCGTTTGCGTGCGCCCAACTCCCAAGTGGCAAAAGGAATTGGAGAATT |
| 254 | SETD1B | XM_037523.11 | 7779-7878 | ATCGTGCCCAGTGTTAACCTCGGCTGGCCTTCACTAAGGGGACTAGACCTCCCTCTCCCAGGAGCCCCAGCCCCAGAGTGGTTTGCAATAATCAAGATA |

TABLE III-continued

| Sequence ID# | Gene | Position | Target Sequence |
|---|---|---|---|
| 255 | KIR2DL5A | XM_001126355.1 | 265-364 | GAGGTGACATATGCACAGTTGGATCACTGCGTTTTCACACAGACAAAATCACTTCCCCTTCTCAGAGGCCCAAGACACCTCCAACAGATACCACCATGT |
| 256 | KIR_Activating_Subgroup_2 | NM_014512.1 | 719-818 | TCCGAAACCGGTAACCCCAGACACCTACATGTTCTGATTGGGACCTCAGTGGTCAAATCCCTTTCACCATCCTCCTCTTCTTTCTCCTTCATCGCTGGT |
| 257 | KIR2DS3 | NM_012313.1 | 1-100 | CCGGCAGCACCATGTCGCTCATGGTCATCAGCATGGCATGTGTTGGGTTCTTCTGGCTGCAGGGGCCTGGCCACATGAGGGATTCCGCAGAAAACCTTC |
| 258 | KLRB1 | NM_002258.2 | 357-456 | CAGCAACTCCGAGAGAAATGCTTGTTATTTTCTCACACTGTCAACCCTTGGAATAACAGTCTAGCTGATTGTTCCACCAAAGAATCCAGCCTGCTGCTTA |
| 259 | KLRC1 | NM_002259.3 | 336-435 | ACCTATCACTGCAAAGATTTACCATCAGCTCCAGAAGCTCATTGTTGGGATCTGGGAATTATCTGTCTTATCTTAATGGCCTCTGTGGTAACGATAG |
| 260 | KLRC2 | NM_002260.3 | 943-1042 | TATGTGAGTCAGCTTATAGGAAGTACCAAGAACAGTCAAACCCATGGAGACAGAAAGTAGAATAGTGGTTGCCAATGTCTCAGGGAGGTTGAAATAGGAG |
| 261 | KLRD1 | NM_002262.3 | 597-696 | CAATTTTACTGGATTGGACTCTCTTACAGTGAGGAGCACACCGCCTGGTTGTGGAGAATGGCTCTGCACTCTCCCAGTATCTATTTCCATCATTTGAAA |
| 262 | KLRF1 | NM_016523.1 | 544-643 | TATACAGAAAAACCTAAGACAATTAAAACTACGTATGATTGGGCTTAACTTTACCTCCTTGAAAATGACATGGACTTGGGTGGATGGTTCTCCAATAGAT |
| 263 | KLRF1b | NM_016523.2 | 849-948 | AAGTGCAATTAAATGCCAAAATCTCTTCTCCCTTCCCTCCATCATCGACACTGGTCTAGCCTCAGAGTAACCCCTGTTAACAAACTAAAATGTACACT |
| 264 | KRTAP10-3 | NM_198696.2 | 213-312 | CTGCTGCCAGGCGGCCTGTGAGCCCAGCCCCTGCCAGTCAGGCTGCACCAGCTCCTGCACGCCCTCGTGCTGCCAGCAGTCTAGCTGCCAGCCAGCTTGC |
| 265 | KYNU | NM_001032998.1 | 936-1035 | TTGCCTGCTGGTGTTCCTACAAGTATTTAAATGCAGGAGCAGGAGGAATTGCTGGTGCCTTCATTCATGAAAAGCATGCCCATACGATTAAACCTGCGAG |
| 266 | LAMA5 | NM_005560.4 | 11163-11262 | CCAACCCCGGCCCCTGGTCAGGCCCTGCAGCTGCCTCACACCGCCCCTTGTGCTCGCCTCATAGGTGTCTATTTGGACTCTAAGCTCTACGGGTGACAG |
| 267 | LDHA | NM_001165416.1 | 1348-1447 | ATCTTGTGTAGTCTTCAACTGGTTAGTGTGAAATAGTTCTGCCACCTCTGACGCACCACTGCCAATGCTGTACGTACTGCATTTGCCCCTTGAGCCAGGT |
| 268 | LEF1 | NM_016269.4 | 3136-3235 | AACACATAGTGGCTTCTCCGCCCTTGTAAGGTGTTCAGTAGAGCTAAATAAATGTAATAGCCAAACCCACTCTGTTGGTAGCAATTGGCAGCCCTATTTC |
| 269 | LETM2 | NM_144652.3 | 1331-1430 | AAAGGACCCATCACTTCTTCTGAAGAACCTACACTCCAGGCCAAATCACAAATGACGGCCCAGAACAGCAAGGCTAGTTCAAAAGGAGCATAAAGGACTA |
| 270 | LIF | NM_002309.3 | 1241-1340 | GGGATGGAAGGCTGTCTTCTTTTGAGGATGATCAGAGAACTTGGGCATAGGAACAATCTGGCAGAAGTTTCCAGAAGGAGGTCACTTGGCATTCAGGCTC |
| 271 | LILRA5 | NM_021250.3 | 1044-1143 | TTGAATGCTGGAGCCTTGGAAGCGAATCTGATGGTCCTAGGAGGTTCGGGAAGACCATCTGAGGCCTATGCCATCTGGACTGTCTGCTGGCAATTTCTTT |
| 272 | LILRA5b | NM_181879.2 | 546-645 | CACCCTCTCAGCCCTGCCCAGTCCTGTGGTGACCTCAGGAGAGAACGTGACCCTCCAGTGTGGCTCACGGCTGAGATTCGACAGGTTCATTCTGACTGAG |
| 273 | LOC338799 | NR_002809.2 | 471-570 | GCGGCAGCCAATCAGCGCGCGGCTTCTATAGGGCTTGAGTTATTAGACGCTGATCTCAAAACATCCTTCATCAGACACGAAGGAGAGGCCAACAGATGAG |
| 274 | LOC100129022 | XM_001716591.1 | 568-667 | AGGGTCATGCAGCTACTGAGGTCACAGCCTGGATTCATACACAGGTCTGACTCCTGAGCACTTAGCCAGGTGGCTGTAACAGTGTTCCCAGAAACACAGG |
| 275 | LOC100129697 | XM_001732822.2 | 1148-1247 | ACCTGTCTTCCGGGTCTGTTCACCCGTCCCTGGACTGGCACCAGCACAGAGGGTCGAGTGTTGGCACCTGTCTTCTGGGTCTCCATCCCTCCCTTTGTT |
| 276 | LOC100130229 | XM_001717158.1 | 1469-1568 | GAGAATGTCTGCGCGGAGACAGCATAGCTCTGTAGAAATGAGTGGCAGCGTATGTAACCTGGCATTTTGAACCCAGGAGCACAATTTTATTAAAGGAAAA |
| 277 | LOC100132797 | XR_036994.1 | 15-114 | GAGTAGTAGGTGGACAGCCGTCCCACACAAGGGTTTGTATCTGGGCTACACAGATTCCCTTCAGAAAAGCACCAATGTAAGCAACTCCCTTACAGTTGCT |
| 278 | LOC100133273 | XR_039238.1 | 342-441 | GAGATAGCTTCCTGAAATGTGTGAAGGAAAATGATCAGAAAAAGAAAGAAGCCAAAGAGAAAGGTACCTGGGTTCACTAAAGTGCCAGCCTGCTCCACC |
| 279 | LOC148137 | NM_144692.1 | 3367-3466 | GCTCTGTCCTTTGCCGCTCAGACCAAAAACCTTAGAGCTGTCTTTGACTTCTGTCTTTCCCTTCCACCC |

TABLE III-continued

| Sequence ID# | Gene | Position | Target Sequence |
|---|---|---|---|
| 280 | LOC 151162 | NR_024275.1 5062-5161 | GGTTACAGCCATTTTGTGTGATTCACTTCGGGGGTTAAGTAATGCAGGATTCTGCAAACAAGGTGTCGCCGTCCAAATGTACTGTCCTGGCATAGAGAGC |
| 281 | C1orf222 | NM_001003808.1 2561-2660 | ACATGGCGCCACGGCCACTTCCTGCTGCCCTGGACCCCGCAAGCCCAGGGACATCCAAGAGCACCCCTCCTGAGACCCCAGACTCAGAAGCAGCGAGAAG |
| 282 | LOC 339674 | XM_934917.1 376-475 | CCCCTGGTGGACCGCGACCTCCGCAAGACGCTAATGGTGCGCGACAACCTGGCCTTCGGCGGCCCGGAGGTCTGAGCCGACTTGCAAAGGGGATAGGCGG |
| 283 | LOC 648000 | XM_371757.4 210-309 | GCAAAGCACTATCACAAGGAATATAGGCAAATGTACAGAACTGAAATTCGAGTGGCGAGGATGGCAAGAAAAGCTGGCAACTTCTATGTACCTGCAGAAC |
| 284 | LOC 391126 | XR_017684.2 82-181 | AAGATTATGTCTTCCCCTGTTTCCAAAGAGCTGAGACAGAAGTACAATGTGCAATCCATGCCCATCCGAAAGGATGATGAAGTTCAGGTTGTACGAGGGC |
| 285 | LOC 399753 | XM_930634.1 1448-1547 | ATGGGACCCACTCTACTGAGGCTTTATGTAGAACTCATAGAGGAAGCTGGCTTTGAGGAATGAACTACCCTGTGCTTTTCTTAGGACTAAAATCTCAGGA |
| 286 | LOC 399942 | XM_934471.1 21-120 | GACGGTAACCGGGACCCAGTGTCTGCTCCTGTCACCTTCGCCTCCTAATCCCTAGCCACTATGCGAGATGACTCCTTCAACACCTTCAGTGAGACGGGTG |
| 287 | LOC 440389 | XM_498648.3 552-651 | GAGTTTTCCAAACCCTGGATTTCCTTCGGAGAGAGCTAGATTCTATTCCATTCTTGGAATTCAGCTCCTTGCCCTTCTCTGTGACCCCGGATCGCGAATG |
| 288 | LOC 440928 | XM_942885.1 1533-1632 | TGTTGCAAAAGCCAACTACCACTGTCAAACTTAGCCGTTTACAACATGGGGAAAGGCGTATTTCTTACTAATATCTCAACAACGATAACAATGCTGTAT |
| 289 | LOC 441073 | XR_018937.2 287-386 | CGGGTGCAGCGGGAAAAGGCTAATGGCACAACTGTCCACGTAGGCATTCACCCCAGCAAGGTGGTTATCACTAGGCTAAAACTGGACAAAGACTGTGAAA |
| 290 | LOC 642812 | XR_036892.1 591-690 | GGTGAAGAATTTGTTCTATTATGAAGATACTGTCTGGGCTAAAAAGCTTACAGTGAGTGGAAGATAGCAACTTGTAGGGTTGGTGGCTGAACAGGCCGAC |
| 291 | LOC 643319 | XM_927980.1 255-354 | CTGGCTCAAGGATGGCACGGTGTTATGTGAGCTCAATAATGCACTGTACCCCAAGGGGCAGGTCCCAGTAAAGAAGATCCAGGCCTCCACCATGGCCTTC |
| 292 | LOC 644315 | XR_017529.2 38-137 | CAGGCGCTGCAAGTTCTCCCAGGAGAAAGCCATGTTCAGTTCGAGCGCCAAGATCGTGAAGCCCAATGGCGAGAAGCCGGACGAGTTCGAGTCCGGCCAT |
| 293 | LOC 645914 | XM_928884.1 13-112 | GAAGCACTGGTAAATGTCTGCTGCATTAACTCACTCAGACCAAACTTTCTCTTATCTAGGTCCAAAGGAAGCTGCTCGGCTGGAAGGAACCTGGTGAGG |
| 294 | LOC 647340 | XR_018104.1 670-769 | AGGTGCTGCAAAATTACCAGGAATACAGTCTGGCCAACAGCATCTACTACTCTCTGAAGGAGTCCACCACTAGTGAGCAGAGTGCCAGGATGACAGCCAT |
| 295 | LOC 648927 | XR_038906.2 1638-1737 | TGGAGAGAAGAATGAAGAGGTGGTGGTTCTGGGTTTGATTTGAGTTCACCTGTGGGCAGTGGGCAGTGTCTTGGTGAAAGGGAGCGGATACTACTTTTTG |
| 296 | LOC 653773 | XM_938755.1 38-137 | GCCCTTCTGCCATCAACGAGGTGGTGACCCAAGAACATACCATCAACATTCACAAGCGCATCCATGGAGAGGGCTTCAAGAAGCGTGCTCCTCGGGCACT |
| 297 | LOC 728533 | XR_015610.3 1861-1960 | GTAGTTGTCCACTGCTTTCCTGGATGGATGGGACTCTTATGTCATAACTTCTATACTCCTTTGGCCCATAGCTAAGGTCATCCTTCCCCACAGGGGTGGC |
| 298 | LOC 728835 | XM_001133190.1 510-609 | CCAAACCAAAAGAGGCAAGCAAGTCTGCGCTGACCCCAGTGAGTCCTGGGTCCAGGAGTACGTGTATGACCTGGAACTGAACTGAGCTGCTCAGAGACAG |
| 299 | LOC 729887 | XR_040891.2 625-724 | CCCTGGGTGCCCCTTAACCCGGGCGGTAGCTCGTTAAGATGGCGAAGTGTCCGGTCCGGAACACGCGAAACCCCAAATCCCGCCTGCCCGACCTCCTGAC |
| 300 | LOC 732111 | XM_001134275.1 765-864 | GCGCGGTTGCGGTTAGCGGGCGCGGTGCCAAAGCTGCCATCCCCAGCTCACAGCTCCTCATATCCACCCTGCCCTCATCTTTATGAATTGCGTGTAGACC |
| 301 | LOC 732371 | XM_001133019.1 182-281 | GCCCTTCAGAGCTGCGGGAGATCATTGATGAGTGCCGGGCCCATGATCCCTCTGTGCGGCCCTCTGTGGATGAGCAGAAGCCAGACTTAATGATGTGTT |
| 302 | LOC 91431 | NM_001099776.1 2666-2765 | ATGTTGCATTGACTAGAGGAAAGAGGCATTTGTTGATTGTGGGAAATTTAGCCTGTTTGAGGAAAAATCAACTTTGGGACGAGTGATCCAACACTGCGA |
| 303 | P2RY5 | NM_005767.5 2026-2125 | AGATTGTTTGCACTGGCGTGTGGTTAACTGTGATCGGAGGAAGTGCACCCGCCGTTTTTGTTCAGTCTACCCCTCTCAGGGTAACAATGCCTCAGAAGC |
| 304 | LPCAT4 | NM_153613.2 1560-1659 | CCCCACACACCTCTCGAGGCACCTCCCAGACACCAAATGCCTCATCCCCAGGCAACCCCACTGCTCTGG |

TABLE III-continued

| Sequence ID# | Gene | NM | Position | Target Sequence |
|---|---|---|---|---|
| | | | | CCAATGGGACTGTGCAAGCACCCAAGCAGAA |
| 305 | LPIN2 | NM_014646.2 | 5620-5719 | AGAAAAAACTTAAAAATGGGATGTCCTAAAATGAAAGCTGCTCAAAGTCACAGAACAACCGAGGGACAAAGGAGATTGGATGACTGGGAAGCGCTGGCCC |
| 306 | C1orf103 | NM_018372.3 | 1543-1642 | TTCCAATACCCAGCTTGCTTCCATGGCCAATCTAAGGGCAGAGAAGAATAAAGTGGAGAAACCATCTCCTTCTACCACAAATCCACATATGAACCAATCC |
| 307 | LRRC47 | NM_020710.2 | 2461-2560 | GGGTCAGTGACGGACACTTACCTGACAGCGGATCCACAATATTCTGTGCAGTGTGTTTGGAATCCTGGTCTGGGCTCTCGTCGTTGGCCTTGTAGATCA |
| 308 | LY96 | NM_015364.4 | 439-538 | AAGGGAGAGACTGTGAATACAACAATATCATTCTCCTTCAAGGGAATAAAATTTTCTAAGGGAAAATACAAATGTGTTGTTGAAGCTATTTCTGGGAGCC |
| 309 | LYN | NM_002350.1 | 1286-1385 | TCCTGAAGAGCGATGAAGGTGGCAAAGTGCTGCTTCCAAAGCTCATTGACTTTTCTGCTCAGATTGCAGAGGGAATGGCATACATCGAGCGGAAGAACTA |
| 310 | MAGEA1 | NM_004988.4 | 477-576 | AGGGGCCAAGCACCTCTTGTATCCTGGAGTCCTTGTTCCGAGCAGTAATCACTAAGAAGGTGGCTGATTTGGTTGGTTTTCTGCTCCTCAAATATCGAGC |
| 311 | MAGEA3 | NM_005362.3 | 850-949 | ACTGTGCCCCTGAGGAGAAAATCTGGGAGGAGCTGAGTGTGTTAGAGGTGTTTGAGGGGAGGAAGACAGTATCTTGGGGGATCCCAAGAAGCTGCTCAC |
| 312 | MAP3K7 | NM_145333.1 | 671-770 | GCCATATTATACTGCTGCCCACGCAATGGTTGGTGTTTACAGTGTTCCCAAGGAGTGGCTTATCTTCACAGCATGCAACCCAAAGCGCTAATTCACAGG |
| 313 | MARCKS | NM_002356.6 | 1800-1899 | GTCAAAAAGGGATATCAAATGAAGTGATGGGGTCACACATGGGGAAATTGAAGTGGTGCATAACATTGCCAAAAATAGTGTGCCACTAGAAATGGTGTAAAG |
| 314 | MARCKSL1 | NM_023009.5 | 1117-1216 | TCCAAGTAGGTTTTGTTTACCCTACTCCCCAAATCCCTGAGCCAGAAGTGGGTGCTTATACTCCCAAACCTTGAGTGTCCAGCCTTCCCCTGTTGTTTT |
| 315 | MBD1 | NM_015844.2 | 2380-2479 | TGGCTGCAGGCCTGACTACTGCCCACACCAACGAGGTGATCTAGCAGATACATGGCAACGTGTGAACTGCAACAACGCCTGGTGCCCCAGCACCAACCTT |
| 316 | C19orf59 | NM_174918.2 | 1062-1161 | CATACTAGAGTATACTGCGGCGTGTTTTCTGTCTACCCATGTCATGGTGGGGGAGATTTATCTCCGTACATGTGGGTGTCGCCATGTGTGCCCTGTCACT |
| 317 | MED16 | NM_005481.2 | 2152-2251 | TCTGAAGCCCAGCTGCCTGCCCGTGTATACGGCCACCTCGGATACCCAGGACAGCATGTCCCTGCTCTTCCGCCTGCTCACCAAGCTCTGGATCTGCTGT |
| 318 | MEN1 | NM_130799.2 | 2222-2321 | CCCAGCCCCTAGAAACCCAAGCTCCTCCTCGGAACCGCTCACCTAGAGCCAGACCAACGTTACTCAGGGCTCCTCCCAGCTTGTAGGAGCTGAGGTTTCA |
| 319 | MERTK | NM_006343.2 | 666-765 | GAAGAGATCGTGTCTGATCCCATCTACATCGAAGTACAAGGACTTCCTCACTTTACTAAGCAGCCTGAGAGCATGAATGTCACCAGAAACACAGCCTTCA |
| 320 | MFSD1 | NM_022736.2 | 2023-2122 | AAGGGCTGCGTTACACAAAATAAACAATGGCATTGTCATAGGCCTTCCTTTTACTAGTAGGGCATAATGCTAGGGAATATGTGAAGATGTTTTTATGAAG |
| 321 | MID1IP1 | NM_021242.5 | 3472-3571 | AGCTGGCATTTCGCCAGCTTGTACGTAGCTTGCCACTCAGTGAAAATAATAACATTATTATGAGAAAGTGGACTTAACCGAAATGGAACCAACTGACATT |
| 322 | MPDU1 | NM_004870.3 | 1226-1325 | CATTCAGCCAAGCCTCCTCCTCTAGCAGCAATTTCCAGCTGTGTAACACTATCCTGGGCAAATGTTTTACCCTGTCCTCCAGCCTCCCTGCTTCCCTTCT |
| 323 | MRPL27 | NM_148571.1 | 2189-2288 | TCAAACTGGTAGCTATGCTTTGATGTCCTGTTGAGGCCATCGGACAGAGACTGGAGCCCAGGTGACAGGAGATGGTGATACCAGAAGTCAAGGGTTGGGG |
| 324 | MRPS16 | NM_016065.3 | 1811-1910 | ATTCAAATGTGGCTGTGATTTCTGCATATATCATGAGTGGGATCCTTCTGAGAATACTGGAATAGGGAATTAGGCACCAAGCCAATTCAGCTGTGAACC |
| 325 | MS4A2 | NM_000139.3 | 662-761 | TTCTCACCATTCTGGGACTTGGTAGTGCTGTGTCACTCACAATCTGTGGAGCTGGGAAGAACTCAAAGGAAACAAGGTTCCAGAGGATCGTGTTTATGA |
| 326 | MS4A6A | NM_022349.3 | 1290-1389 | CTGGGAAGTTAAATGACTGGCCTGGCATTATGCTATGAGTTTGTGCCTTTGCTGAGGACACTAGAACCTGGCTTGCCTCCCTTATAAGCAGAAACAATTT |
| 327 | MS4A6Ab | NM_152851.2 | 880-979 | CTGCGGTGGAAACAGGCTTACTCTGACTTCCCTGGGAGTGTACTTTTCCTGCCTCACAGTTACATTGGTAATTCTGGCATGTCCTCAAAAATGACTCATG |
| 328 | MTCH1 | NM_014341.2 | 2081-2180 | TCCTCCTCATCTAATGCTCATCTGTTTAATGGTGATGCCTCGCGTACAGGATCTGGTTACCTGTGCAGTTGTGAATACCCAGAGGTTGGGCAGATCAGTG |

TABLE III-continued

| Sequence ID# | Gene | Position | Target Sequence |
|---|---|---|---|
| 329 | MYADM | NM_001020820.1 | 2656-2755 | TCTTTTTCCTGGCCATGAGGACAAAAATTACTGAGTGGCCCTTAAAGAGGGAAGTTTGTTTTCAGCTGTTCTCTTTTGCCCGTAGGTGGGAGGGTGGGA |
| 330 | MYADMb | NM_001020820.1 | 2789-2888 | TGAATGTGTAGTGCACACGCACGGGTGTTTCTGTGTGCTAGTTGCTTCTTGCTGCTGCTTCCTGCTTGTCTGGGACTCACATACATAACGTGATATATAT |
| 331 | C19orf10 | NM_019107.3 | 649-748 | TGTCCCTGAAAGGGCCAGCACATCACTGGTTTTCTAGGAGGGACTCTTAAGTTTTCTACCTGGGCTGACGTTGCCTTGTCCGGAGGGGCTTGCAGGGTGG |
| 332 | MYL12A | NM_006471.3 | 305-404 | TCTCTGGGTAGCAGGGTGGTGTGATAGCGGCAGCGAGGGGCTCGGAGAGGTGCTCGGATTCTCGTAGCTGTGCCGGGACTTAACCACCACCATGTCGAGC |
| 333 | MYLIP | NM_013262.3 | 2701-2800 | TTGGGCATTTTGGAAGCTGGTCAGCTAGCAGGTTTTCTGGGATGTCGGGAGACCTAGATGACCTTATCGGGTGCAATACTAGCTAAGGTAAAGCTAGAAA |
| 334 | NAT5 | NM_181528.3 | 735-834 | AAACATACCACTCTCATGGTTCATAGTATTCACTGTATGTATGCTAGGGAAAAGACTTGCTCCAGTCTCCTCCTCAGTTCTGTGCCTGAGAACCACTGCT |
| 335 | NADK | NM_023018.4 | 2449-2548 | TCCGGGGCTAGTGATCGTGATCCCTTTTATTTGCAACTGTAATGAGAATTTTTCACACTAACACAGCGAGGGACTCAACACGCTGATTCTCCTCCTGCCT |
| 336 | NAGK | NM_017567.4 | 1362-1461 | GGGCCAGGCACATCGGGCACCTCCTCCCCATGGACTATAGCGCCAATGCCATTGCCTTCTATTCCTACACCTTTTCCTAGGGGGCTGGTCCCGGCTCCAC |
| 337 | NCAPG | NM_022346.4 | 3080-3179 | ACCCAAGCATCAAAGTCTACTCAGCTAAAGACTAACAGAGGACAGAGAAAAGTGACAGTTTCAGCTAGGACGAACAGGAGGTGTCAGACTGCTGAAGCCG |
| 338 | NCOA5 | NM_020967.2 | 2837-2936 | TGGACATGTTCTCGAGATGGGTGGCTGTTCGCGACTTTTGTACCAGAGTGAAATTGTTAGAAGGAGGGTTTCTGGCTGTGGTTCTAAATGGAGCCCCAGG |
| 339 | NCR1 | NM_004829.5 | 603-702 | CGATGTTTTGGCTCCTATAACAACCATGCCTGGTCTTTCCCCAGTGAGCCAGTGAAGCTCCTGGTCACAGGCGACATTGAGAACACCAGCCTTGCACCTG |
| 340 | NDRG2 | NM_016250.2 | 1516-1615 | TATGCATCCTCTGTCCTGATCTAGGTGTCTATAGCTGAGGGGTAAGAGGTTGTTGTAGTTGTCCTGGTGCCTCCATCAGACTCTCCCTACTTGTCCCATA |
| 341 | NDUFA4 | NM_002489.3 | 262-361 | TGGGACAGAAATAACCCAGAGCCCTGGAACAAACTGGGTCCCAATGATCAATACAAGTTCTACTCAGTGAATGTGGATTACAGCAAGCTGAAGAAGGAAC |
| 342 | NDUFAF2 | NM_174889.4 | 486-585 | TCCTGCCTCCACCAGTTCAAACTCAAATTAAAGGCCATGCCTCTGCTCCATACTTTGGAAAGGAAGAACCCTCAGTGGCTCCCAGCAGCACTGGTAAAAC |
| 343 | NDUFB3 | NM_002491.2 | 383-482 | ACAATGGAAGATAGAAGGGACACCATTAGAAACTATCCAGAAGAAGCTGGCTGCAAAAGGGCTAAGGGATCCATGGGGCCGCAATGAAGCTTGGAGATAC |
| 344 | NDUFS4 | NM_002495.2 | 326-425 | GAGTTTGATACCAGAGAGCGATGGGAAAATCCTTTGATGGGTTGGGCATCAACGGCTGATCCCTTATCCAACATGGTTCTAACCTTCAGTACTAAAGAAG |
| 345 | NDUFV2 | NM_021074.4 | 687-786 | TTACTATGAGGATTTGACAGCTAAGGATATTGAAGAATTATTGATGAGCTCAAGGCTGGCAAAATCCCAAAACCAGGGCCAAGGAGTGGACGCTTCTCT |
| 346 | NFAT5 | NM_138713.3 | 3857-3956 | CCCAAGAAGCATTTTTTGCAGCACCGAACTCAATTTCTCCACTTCAGTCAACATCAAACAGTGAACAACAAGCTGCTTTCCAACAGCAAGCTCCAATATC |
| 347 | NFATC1 | NM_172389.1 | 1985-2084 | CGAATTCTCTGGTGGTTGAGATCCCGCCATTTCGGAATCAGAGGATAACCAGCCCCGTTCACGTCAGTTTCTACGTCTGCAACGGGAAGAGAAAGCGAAG |
| 348 | NFATC4 | NM_001136022.2 | 2297-2396 | ACAAGAGGGTTTCCCGGCCAGTCCAGGTCTACTTTTATGTCTCCAATGGGCGGAGGAAACGCAGTCCTACCCAGAGTTCAGGTTTCTGCCTGTGATCTG |
| 349 | NFKB1 | NM_003998.3 | 3606-3705 | CGGATGCATCTGGGGATGAGGTTGCTTACTAAGCTTTGCCAGCTGCTGCTGGATCACAGCTGCTTTTCTGTTGTCATTGCTGTTGTCCCTCTGCTACGTTC |
| 350 | NFKB2 | NM_002502.2 | 826-925 | ATCTCCGGGGGCATCAAACCTGAAGATTTCTCGAATGGACAAGACAGCAGGCTCTGTGCGGGGTGGAGATGAAGTTTATCTGCTTTGTGACAAGGTGCAG |
| 351 | NIPBL | NM_133433.3 | 8755-8854 | GCGCCGTGATGGCCGCAAACTGGTGCCTTGGGTAGACACTATTAAAGAGTCAGACATTATTTACAAAAAATTGCTCTAACGAGTGCTAATAAGCTGACT |
| 352 | NLRP3 | NM_001079821.2 | 416-515 | AGTGGGGTTCAGATAATGCACGTGTTTCGAATCCCACTGTGATATGCCAGGAAGACAGCATTGAAGAGGAGTGGATGGGTTACTGGAGTACCTTTCGAG |
| 353 | NME1-NME2 | NM_001018136.2 | 484-583 | ACCTGGAGCGCACCTTCATCGCCATCAAGCCGGACGGCGTGCAGCGCGGCCTGGTGGGCGAGATCATCAAGCGCTTCGAGCAGAAGGGATTCCGCCTCGT |

TABLE III-continued

| Sequence ID# | Gene | Position | Target Sequence |
|---|---|---|---|
| 354 | NUDT18 | NM_024815.3 | 1369-1468 | CCCCAGTGGCATCTCCTCATCAC GTTCTGTGCCGTCCTTGGGAAAG GCCTGCATTCTGATCCTTCCAGG CCCTTCGAGCATGGAGGGGCACT GGGGAAGG |
| 355 | NUMB | NM_001005744.1 | 2833-2932 | CATAAGATTGATTTATCATTGAT GCCTACTGAAATAAAAAGAGGA AAGGCTGGAAGCTGCAGACAGG ATCCCTAGCTTGTTTTCTGTCAG TCATTCATTG |
| 356 | NUP153 | NM_005124.3 | 5104-5203 | TTTATGATCCAGCAGATTATTCA CTGATTTGACATAGTCTGGCTGT ACCCAGGAATGGAGCCTGCACG GTGAATGGCTTTGTATAGAACCT CTTTGTCTA |
| 357 | OLR1 | NM_002543.3 | 1524-1623 | ACACATTTTGGGACAAGTGGGG AGCCCAAGAAAGTAATTAGTAA GTGAGTGGTCTTTTCTGTAAGCT AATCCACAACCTGTTACCACTTC CTGAATCAGT |
| 358 | OSBP | ILMN_1706376.1 | 130-229 | TTCTCTTCCTTCACCATCTGCAC TACATTTCTGGCTGATCCCAATC AGATTCCCGCTAATGGAAGAAGT TTAGAATCTTTCAGGTGGAATAA AGTCACAT |
| 359 | FAM105B | NM_138348.4 | 2537-2636 | TGCAGATGGTGTTCACATGAACC GGAGACATCACTCTTTAGGATTC TACTGGCAGCCCCTGAATTGGCT CAACGTTTGTGGAGGTGGTATTT CCCTGAAG |
| 360 | P2RY10 | NM_198333.1 | 972-1071 | TTACACCATGGTAAAGGAAACC ATCATTAGCAGTTGTCCCGTTGT CCGAATCGCACTGTATTTCCACC CTTTTTGCCTGTGCCTTGCAAGT CTCTGCTGC |
| 361 | PACS1 | NM_018026.3 | 3830-3929 | CGCTGTCTTCGTGGCTTCCACCC TTGTTAATGATGCTCCTGCCTCT GCCTCCCAGCCCCTCACCCAGCA CAGCTCTGCCTGGACTTGGAGAG ATGGGAGG |
| 362 | PANK2 | NM_153640.2 | 824-923 | AGTGGATAAACTAGTACGAGAT ATTTATGAGGGGACTATGAGA GGTTTGGACTGCCAGGCTGGGCT GTGGCTTCAAGCTTTGGAAACAT GATGAGCAAG |
| 363 | PDCD10 | NM_145859.1 | 901-1000 | AAGAGATGTACTTCTCAGTGGCA GTATTGAACTGCCTTTATCTGTA AATTTTAAAGTTTGACTGTATAA ATTATCAGTCCCTCCTGAAGGGA TCTAATCC |
| 364 | PDGFD | NM_033135.3 | 3394-3493 | CCTGTGAAAACATCAGTTTCCTG TACCAAAGTCAAAATGAACGTTA CATCACTCTAACCTGAACAGCTC ACAATGTAGCTGTAAATATAAAA AATGAGAG |
| 365 | PDSS1 | NM_014317.3 | 1199-1298 | CATGAAGCAATAAGAGAGATCA GTAAACTTCGACCATCCCAGAA AGAGATGCCCTCATTCAGCTTTC AGAAATTGTACTCACAAGAGAT AAATGACAAC |
| 366 | PELP1 | NM_014389.2 | 1989-2088 | TGGCCCCGTCTCCTCGCTGCCCA CCTCCTCTTGCCTGTGCCCTGCA AGCCTTCTCCCTCGGCCAGCGAG AAGATAGCCTTGAGGTCTCCTCT TTCTGCTC |
| 367 | PFAS | NM_012393.2 | 5109-5208 | CATCCCTAGATCCTAACCCTTTA GTATGCTGGAATTCTACTCTTCA CTTACTGCATTGACTGTTGTTGA TTAGTTATTATTGCAAAGCACTG TCACCGGC |
| 368 | PFDN5 | NM_145897.2 | 232-331 | ATCGATGTGGGAACTGGGTACTA TGTAGAGAAGACAGCTGAGGAT GCCAAGGACTTCTTCAAGAGGA AGATAGATTTTCTAACCAAGCAG ATGGAGAAAA |
| 369 | PFDN5b | NM_145897.2 | 331-430 | ATCCAACCAGCTCTTCAGGAGAA GCACGCCATGAAACAGGCCGTC ATGGAAATGATGAGTCAGAAGA TTCAGCAGCTCACAGCCCTGGGG GCAGCTCAGG |
| 370 | PGK1 | NM_000291.3 | 1122-1221 | GTCCTGAAAGCAGCAAGAAGTA TGCTGAGGCTGTCACTCGGGCTA AGCAGATTGTGTGGAATGGTCCT GTGGGGGTATTTGAATGGGAAG CTTTTGCCCG |
| 371 | PHF8 | NM_015107.2 | 5704-5803 | ATCAAGGTTTAGAACACCATGAG ATAGTTACCCCTGATCTCCAGTC CCTAGCTGGGGGCTGGACAGGG GGAAGGGAGAGAGGATTTCTAT TCACCTTTAA |
| 372 | PHLPP2 | NM_015020.3 | 7601-7700 | CCAGTTGGGTGTGGCAGATCTAC TGAATATCAAATGATGCTCTTCT TCCCATGTAGACCTTCAGCAAAA GCCGGTACTTGGAAGCCACAGG CTCACCTTC |
| 373 | PHRF1 | NM_020901.3 | 5239-5338 | GGGAAATGGGGGGCATCACCAT GCCTGCCGTCGGGTTCCTGCGCT GACACCTGGTCTGTGCACCTGTG TTGCTCACAGTTGAAAACTGGAC ACTTTTGTA |
| 374 | PI4K2A | NM_018425.3 | 3886-3985 | TCCATGGAATTGCTGAGACGTGG CTCCTGGGGCTATTTCTCCCTAA TAAAGGATGATCCAGGTCCTCAT TTCCAAAGTCCCAATGCTCTGAA AACCAAAA |
| 375 | PIK3CD | NM_005026.3 | 4799-4898 | GAGCCAGAAGTAGCCGCCCGCT CAGCGGCTCAGGTGCCAGCTCTG TTCTGATTCACCAGGGGTCCGTC AGTAGTCATTGCCACCCGCGGGG CACCTCCCT |
| 376 | PIM2 | NM_006875.3 | 1947-2046 | TTTTTGGGGGATGGGCTAGGGGA AATAAGGCTTGCTGTTTGTTCTC CTGGGGCGCTCCCTCCAACTTTT GCAGATTCTTGCAACCTCCTCCT GAGCCGGG |
| 377 | PLAC8 | NM_001130715.1 | 289-388 | CTGATATGAATGAATGCTGTCTG TGTGGAACAAGCGTCGCAATGA GGACTCTCTACAGGACCCGATAT GGCATCCCTGGATCTATTTGTGA TGACTATAT |
| 378 | PLEKHG4 | NM_015432.3 | 6365-6464 | CCAGTTGTGGGTTAAGAATAGGC TAGAGCAGACATTGGGTGTTTCC ATGCTGTAGGCTGGTGGGGACC |

TABLE III-continued

| Sequence ID# | Gene | Position | Target Sequence |
|---|---|---|---|
| | | | ATGTGCCTCTAGGCAGTGACTAG GGTGCCCC |
| 379 | POLR2A | NM_000937.4 | 6539-6638 | CCCCTGCCCTGTCCCAAATTGAA GATCCTTCCTTGCCTGTGGCTTG ATGCGGGGCGGGTAAAGGGTAT TTTAACTTAGGGGTAGTTCCTGC TGTGAGTGG |
| 380 | PPP1R3E | XM_927029.1 | 4342-4441 | CAGAACCTCCTCAGTTCCTTCAC AGTGCAACCCTGTGTACTTGGCC CGCAACCCAATAGTATTGTGCCT CACTTCACCTTCCATGGGCAACT GCCCTCCC |
| 381 | PPP2R5C | NM_178588.1 | 941-1040 | ACAGCACCCTCACGGAACCAGT GGTGATGGCACTTCTCAAATACT GGCCAAAGACTCACAGTCCAAA AGAAGTAATGTTCTTAAACGAAT TAGAAGAGAT |
| 382 | PPP6C | NM_002721.4 | 1536-1635 | TTAAGAAATTTCAGCAGCAAAGT TGTTATTCAGTGGGCACGATGGA CTCCAAATGCCTCAAGTTATGTA TACCTGTCCCAGATGTAAACTTC ATTGTCCT |
| 383 | PRG2 | NM_002728.4 | 257-356 | CTCTGGAAGTGAAGATGCCTCCA AGAAAGATGGGGCTGTTGAGTCT ATCTCAGTGCCAGATATGGTGGA CAAAAACCTTACGTGTCCTGAGG AAGAGGAC |
| 384 | PRPF3 | NM_004698.2 | 2116-2215 | CCTACAGAGAACATGGCTCGTGA GCATTTCAAAAAGCATGGGGCTG AACACTACTGGGACCTTGCGCTG AGTGAATCTGTGTTAGAGTCCAC TGATTGAG |
| 385 | PRPF8 | NM_006445.3 | 7091-7190 | ACTCTGCGGATCGGGAGGACCTG TATGCCTGACCGTTTCCCTGCCT CCTGCTTCAGCCTCCCGAGGCCG AAGCCTCAGCCCCTCCAGACAGG CCGCTGAC |
| 386 | C22orf30 | NM_173566.2 | 10495-10594 | CCCGTTGAGCTGGCCATCTAGTG CAGTGTGCTCTCAGATTCCATGT TTGTTGATTGTGTGTCTTCACAA GCCCCTCTCTGGTGCTGAATTGG ATTTGAAT |
| 387 | BAT2D1 | NM_015172.3 | 9620-9719 | AGAACAGTGAGTACCTAGAACT GTGCCACTAATTAAAGGAAATCC TAAGAAGGTGCATTTCTTTACAG AGCTGTGTCATGCCATCCTTTGG GCCCTCTGC |
| 388 | PRRG4 | NM_024081.5 | 761-860 | GAAGACCTGAGGAGGCTGCCTT GTCTCCATTGCCGCCTTCTGTGG AGGATGCAGGATTACCTTCTTAT GAACAGGCAGTGGCGCTGACCA GAAAACACAG |
| 389 | PSMA3 | NM_152132.2 | 422-521 | CTTTGGCTACAACATTCCACTAA AACATCTTGCAGACAGAGTGGCC ATGTATGTGCATGCATATACACT CTACAGTGCTGTTAGACCTTTTG GCTGCAGT |
| 390 | PSMA4 | NM_002789.3 | 541-640 | GTACATTGGCTGGGATAAGCACT ATGGCTTTCAGCTCTATCAGAGT GACCCTAGTGGAAATTACGGGG GATGGAAGGCCACATGCATTGG AAATAATAGC |
| 391 | PSMA4b | NM_002789.4 | 879-978 | GAGGAAGAAGAAGCCAAAGCTG AGCGTGAGAAGAAAGAAAAAGA ACAGAAAGAAAAGGATAAATAG AATCAGAGATTTTATTACTCATT TGGGGCACCAT |
| 392 | PSMA6 | NM_002791.2 | 218-317 | GGTCGGCTCTACCAAGTAGAATA TGCTTTTAAGGCTATTAACCAGG GTGGCCTTACATCAGTAGCTGTC AGAGGGAAAGACTGTGCAGTAA TTGTCACAC |
| 393 | PSMA6b | NM_002791.2 | 866-965 | GATGCTCACCTTGTTGCTCTAGC AGAGAGAGACTAAACATTGTCG TTAGTTTACCAGATCCGTGATGC CACTTACCTGTGTGTTTGGTAAC AACAAACCA |
| 394 | PSMB1 | NM_002793.3 | 687-786 | GCGGCTGGTGAAAGATGTCTTCA TTTCTGCGGCTGAGAGAGATGTG TACACTGGGGACGCACTCCGGAT CTGCATAGTGACCAAAGAGGGC ATCAGGGAG |
| 395 | PSMB7 | NM_002799.2 | 421-520 | GTTACATTGGTGCAGCCCTAGTT TTAGGGGGAGTAGATGTTACTGG ACCTCACCTCTACAGCATCTATC CTCATGGATCAACTGATAAGTTG CCTTATGT |
| 396 | PSMB8 | NM_004159.4 | 1216-1315 | ACTCACAGAGACAGCTATTCTGG AGGCGTTGTCAATATGTACCACA TGAAGGAAGATGGTTGGGTGAA AGTAGAAAGTACAGATGTCAGT GACCTGCTGC |
| 397 | PSMC1 | NM_002802.2 | 1487-1586 | CATCCTGTGTCTTTTGGAGTACG ATGTGTAAGTGCCCATTGGGTGG CCTGTTGGTCACTGTGCAGCAGT CTGCTTCCCAATAAAGCGTGCTC TTTCACAA |
| 398 | PSMD7 | NM_002811.4 | 1231-1330 | GAGCTCTCTGCCTCCGGTCACTC TTGCTGTGGTGCTACGTGGAAGT GAATGGAGACTGATCTCAAATCT GAACTGCAGCTTTCGCTGCTGTG AGTTGGGG |
| 399 | PSME3 | NM_005789.3 | 3203-3302 | TCCCGAGTGATACCCATGAACTG CCAGTAGAGGCTGCTATCGTTCC ATGTGTAAGGAATGAACTGGTTC AAGGCGCGTCCTACCCAGTCATT TTCTTTAC |
| 400 | PTGDR | NM_000953.2 | 2341-2440 | TATGATGACTGAAAGGGAAAAG TGGAGGAAACGCAGCTGCAACT GAAGCGGGAGACTCTAAACCCAG CTTGCAGGTAAGAGCTTTCACCT TTGGTAAAAGA |
| 401 | PTGDR2 | NM_004778.1 | 1836-1935 | GCCAATGCTTACTGCGCTAGACG CTTCATCCCACAATCTTAAGGGG CAGCTTCTATTAGCCAGTCTTTA CAGCTGAGCACATTCTGGCTCAG GGAGGTTA |
| 402 | PUM1 | NM_001020658.1 | 3753-3852 | AAATGTTCTAGTGTAGAGTCTGA GACGGGCAAGTGGTTGCTCCAG GATTACTCCTCCTCAAAAAAG GAATCAAATTCCACGAGTGGAAA AGCCTTTGTA |
| 403 | QTRTD1 | NM_024638.3 | 2508-2607 | TTAGATTAGAGTCATAGCCTTAA TAGCCCTAGTTGTCATCCTGGGA GACAGGCAACAGTAGAGATATT |

TABLE III-continued

| Sequence ID# | Gene | Position | Target Sequence |
|---|---|---|---|
| | | | TGAGAGCCTAAAGAGAGGTTTG GCCTGTGGGT |
| 404 | RAB10 | NM_016131.4 3593-3692 | AGGGCTTTGCCCCTTTTCTGTAA GTCTCTTGGGATCCTGTGTAGAA GCTGTTCTCATTAAACACCAAAC AGTTAAGTCCATTCTCTGGTACT AGCTACAA |
| 405 | RAG1 | NM_000448.2 2301-2400 | CAGTCTACATTTGTACTCTTTGT GATGCCACCCGTCTGGAAGCCTC TCAAAATCTTGTCTTCCACTCTA TAACCAGAAGCCATGCTGAGAAC CTGGAACG |
| 406 | RASSF5 | NM_182664.2 3061-3160 | TCGTCCTGCATGTCTCTAACATT AATAGAAGGCATGGCTCCTGCTG CAACCGCTGTGAATGCTGCTGAG AACCTCCCTCTATGGGGATGGCT ATTTTATT |
| 407 | RBM14 | NM_006328.3 2661-2760 | TGGTATGTATCCAAGTCCCTGCT GACCACTAATGTTCTAGCTGATG GTGAGCGGCACAGTCCCACTTCC CCATCTCCCCAAGTAGGTGGTGT TAGAAAAC |
| 408 | RBM4B | NM_031492.3 1557-1656 | TAGGAGTTGAATCCTTCTCCCTG CCTACCTGCAGCATCTCCTTTCC CTTTAAAATGACCATGTAGTGGC AAGCAGCCTTTTACTCTTCTGTT AGCTCTGG |
| 409 | RBX1 | NM_014248.3 158-257 | GATATTGTGGTTGATAACTGTGC CATCTGCAGGAACCACATTATGG ATCTTTGCATAGAATGTCAAGCT AACCAGGCGTCCGCTACTTCAGA AGAGTGTA |
| 410 | RELA | NM_021975.2 361-460 | GATGGCTTCTATGAGGCTGAGCT CTGCCCGGACCGCTGCATCCACA GTTTCCAGAACCTGGGAATCCAG TGTGTGAAGAAGCGGGACCTGG AGCAGGCTA |
| 411 | REPIN1 | NM_014374.3 2491-2590 | TGTGTCCAGGCTCTTGTCTGAAC ACCGCAGCCCCTTCCTTCGCTCCT TCCAGAGCTCAGCATGTCACGGC AAGGACTGCCGCATTGGTGATGG AGGGCCAG |
| 412 | REPS1 | NM_001128617.2 1289-1388 | CACCAACCAGTACTCTTTTAACC ATGCATCCTGCTTCTGTCCAGGA CCAGACAACAGTACGAACTGTA GCATCAGCTACAACTGCCATTGA AATTCGTAG |
| 413 | RERE | NM_001042682.1 5916-6015 | AACCCTCGACCCGAAACCCTCAC CAGATAAACTACAGTTTGTTTAG GAGGCCCTGACCTTCATGGTGTC TTTGAAGCCCAACCACTCGGTTT CCTTCGGA |
| 414 | REREb | NM_012102.3 7734-7833 | GCATTCTTGTTAGCTTTGCTTTT CTCCCCATATCCCAAGGCGAAGC GCTGAGATTCTTCCATCTAAAAA ACCCTCGACCCGAAACCCTCACC AGATAAAC |
| 415 | RFWD2 | NM_022457.6 2606-2705 | TTTTCTTTTCCCTCCTTTATGAC CTTTGGGACATTGGGAATACCCA GCCAACTCTCCACCATCAATGTA ACTCCATGGACATTGCTGCTCTT GGTGGTGT |
| 416 | RFX1 | NM_002918.4 4187-4286 | ATAAAAATCACTATTTTGTGTGC TCCGCGTGCTATAGCTTTTGGGG CGGCCCTGCCCAGTCCCCGTGCC CACGGGGCTCCCTCTCCCGGTGG TGAAAGTG |
| 417 | RHOB | NM_004040.3 1707-1806 | GGGAGGAGGGAGGGATGCGCTGT GGGGTTGTTTTTGCCATAAGCGA ACTTTGTGCCTGTCCTAGAAGTG AAAATTGTTCAGTCCAAGAAACT GATGTTATT |
| 418 | RHOG | NM_001665.3 1045-1144 | CTTTCCACACAGTTGTTGCTGCC TATTGTGGTGCCGCCTCAGGTTA GGGGCTCTCAGCCATCTCTAACC TCTGCCCTCGCTGCTCTTGGAAT TGCGCCCC |
| 419 | RHOU | NM_021205.5 4174-4273 | TTGACAGACTCAAGAGAAACTA CCCAGGTATTACACAAGCCAAA ATGGGAGCAAGGCCTTCTCTCCA GACTATCGTAACCTGGTGCCTTA CCAAGTTGTG |
| 420 | RNASE2 | NM_002934.2 331-430 | TGACCTGTCCTAGTAACAAAACT CGCAAAAATTGTCACCACAGTGG AAGCCAGGTGCCTTTAATCCACT GTAACCTCACAACTCCAAGTCCA CAGAATAT |
| 421 | RNF114 | NM_018683.3 2246-2345 | AATTCAGATCATCTCAGAAGTCT GGAGGGAAATCTGGCGAAACCT TCGTTTGAGGGACTGATGTGAGT GTATGTCCACCTCACTGGTGGCA CCGAGAAAC |
| 422 | RNF19B | NM_153341.3 2222-2321 | CCCCAGAGCCCAAGGTGCACCG AGCCCAAGTGCCCATATGAACCT CTCTGCCCTAGCCGAGGGACAAA CTGTCTTGAAGCCAGAAGGTGGA GAAGCCAGA |
| 423 | RNF214 | NM_207343.3 2068-2167 | ACCTGTAAGCTATGTCTAATGTG CCAGAAACTCGTCCAGCCCAGTG AGCTGCATCCAATGGCGTGTACC CATGTATTGCACAAGGAGTGTAT CAAATTCT |
| 424 | RNF34 | NM_025126.3 1619-1718 | CTTCTGTCCTCTTTGGATGAGAT CAGTGTCCACAAGTGGCCGACAT GGAACATGCTGAGCAGTGGCTCC TCTGAATGTTCACTTTATTAGTC ATGTATAT |
| 425 | C20orf52 | NM_080748.2 274-373 | CTCAGGATCGGAATGCGGGTC GAGAGCTGATGGGCGGCATTGG GAAAACCATGATGCAGAGTGGC GGCACCTTTTGGCACATTCATGGC CATTGGGATGG |
| 426 | RPL26L1 | NM_016093.2 4-103 | CACTCAGGGTCTGAGGCAGCTAG TAGCCGGAGGGTCACCATGAAG TTCAATCCCTTCGTTACCTCGGA CCGCAGTAAAAACCGCAAACGT CACTTCAATG |
| 427 | RPL3 | NM_001033853.1 1072-1171 | AGAAGAAAGCATTCATGGGACC ACTGAAGAAAGACCGAATTGCA AAGGAAGAAGGAGCTTAATGCC AGGAACAGATTTTGCAGTTGGTG GGGTCTCAATA |
| 428 | RPL31 | NM_000993.4 20-119 | CTTGCAACTGCGGCTTTCCTTCT CCCACAATCCTTCGCGCTCTTCC TTTCCAACTTGGACGCTGCAGAA |

TABLE III-continued

| Sequence ID# | Gene | Position | Target Sequence |
|---|---|---|---|
| 429 | RPL34 | NM_000995.3 | 471-570 | TGGCTCCCGCAAAGAAGGGTGGCGAGAAGAAACCTCACCTCAGCTTGAGAGAGCCAGTTGTGTGCATCTCTTTCCAGTTTTGCATCCAGTGACGTCTGCTTGGCATCTTGAGATTGTTATGGTGAGAGTAT |
| 430 | RPL39L | NM_052969.1 | 139-238 | GCGGGTTCGGGTCGGTGACACGGAGACCTGAGGGAGCTGGGCCCGCCTTTTCCGCCCGCGCCCCAGGCCCTTGCAGATCGAGATTTGCGTCCTAGAGTGG |
| 431 | KIAA0460 | NM_015203.4 | 4795-4894 | CCCCTTGGGTCCCTCACACAGAGACACCATCAGCCGGAGTGGTATAATCTTACGGAGTCCCCGGCCAGACTTTCGGCCTAGGGAACCTTTTCTCAGCAGA |
| 432 | RPS24 | NM_001026.4 | 482-581 | ATGAAGAAAGTCAGGGGACTGCAAAGGCCAATGTTGGTGCTGGCAAAAAAGCCGAAGGAGTAAAGGTGCTGCAATGATGTTAGCTGTGGCCACTGTGGAT |
| 433 | RPS27L | NM_015920.3 | 241-340 | TAAAATGTCCAGGTTGCTACAAGATCACCACGGTTTTCAGCCATGCTCAGACAGTGGTTCTTTGTGTAGGTTGTTCAACAGTGTTGTGCCAGCCTACAGG |
| 434 | RPS6 | NM_001010.2 | 172-271 | GAATGGAAGGGTTATGTGGTCCGAATCAGTGGTGGGAACGACAAACAAGGTTTCCCCATGAAGCAGGGTGTCTTGACCCATGGCCGTGTCCGCCTGCTAC |
| 435 | RSL24D1 | NM_016304.2 | 1232-1331 | TGGAGTGACACTACACTCTAGAATTTTCCACTTTGGAGAATACTCAGTTCCAACTTGTGATTCCTGATAGAACAGACTTTACTTTTCTAGCCCAGCATTGA |
| 436 | RWDD1 | NM_001007464.2 | 998-1097 | TGGAGGATGATGAAGATGATCCAGACTATAATCCTGCTGACCCAGAGAGTGACTCAGCTGACTAATGGACTGTCCCATCTGCAGAGAGGCTTGACTGCC |
| 437 | RXRA | NM_002957.5 | 5301-5400 | AGTAATTTTTAAAGCCTTGCTCTGTTGTGTCCTGTTCCGGCCTCTGGCCTTCCTGTGACTGACTGTGAAGTGGCTTCTCCGTACGATTGTCTCTGAAACA |
| 438 | S100A12 b | NM_005621.1 | 261-360 | CAAGATGAACAGGTCGACTTTCAAGAATTCATATCCCTGGTAGCCATTGCGCTGAAGGCTGCCCATTACCACACCCACAAAGAGTAGGTAGCTCTCTGAA |
| 439 | S100A8 | NM_002964.4 | 366-465 | GTTAACTTCCAGGAGTTCCTCATTCTGGTGATAAAGATGGGCGTGGCAGCCCACAAAAAAGCCATGAAGAAAGCCACAAAGAGTAGCTGAGTTACTGGG |
| 440 | SAMSN1 | NM_022136.3 | 1024-1123 | ACCTGAGCCCCTATCCTTGAGCTCAGACATCTCCTTAAATAAGTCACAGTTAGATGACTGCCCAAGGGACTCTGGTTGCTATATCTCATCAGGAAATTCA |
| 441 | SAP130 b | NM_024545.3 | 3091-3190 | GATCTCCACCGAATAAACGAACTGATACAGGGAAATATGCAGAGGTGTAAACTTGTGATGGATCAAATCAGTGAAGCCAGAGACTCCATGCTTAAGGTTT |
| 442 | SAP130 | NM_024545.3 | 3720-3819 | CGGTTCTTCTGCCTGACCTTCAAATGCCCATGTTGGCCTTTTACAGCAGTGCCACGGCACCAAGCGAGCTGCCACATCTCACACTCTAAAGGGTTTGAAC |
| 443 | CIP29 | NM_033082.3 | 622-721 | AACTGGAACCACAGAGGATACAGAGGCAAAGAAGAGGAAAGAGCAGAGCGCTTTGGGATTGCCTGATGAAAAGTTCCTGATACTTTCTTTCTCCAGTG |
| 444 | SFRS2IP | NM_004719.2 | 4203-4302 | AGTTCTTCTCATGTAAGTAATAACATGAGTACACCAGTTTGCCTGCTCCGACAGCAGCCCCAGGAAATACGGGAATGGTTCAGGGACCAAGTTCTGGTA |
| 445 | SFRS15 | NM_020706.2 | 3635-3734 | GAGAGAAGGAAGAAGCCCGAGGAAAGGAAAAGCCTGAGGTGACAGACAGGGCAGGTGGTAACAAACCGTTGAACCTCCCATTAGCCAAGTGGGAAATGT |
| 446 | RBM16 | NM_014892.4 | 4111-4210 | TGATTATTTTGAAGGGGCCACTTCTCAACGAAAGGTGATAATGTGCCTCAGGTTAATGGTGAAAATACAGAGAGACATGCTCAGCACCACCTATACCA |
| 447 | SDHA | NM_004168.3 | 2042-2141 | GTCACTCTGGAATATAGACCCGTGATCGACAAAACTTTGAACGAGGCTGACTGTGCCACCGTCCCGCCAGCCATTCGCTCCTACTGATGAGACAAGATGT |
| 448 | SEC24C | NM_198597.2 | 4194-4293 | AGGCAGAGGCAGCTGGAGCGCCGTTCTCTCCTGCTGGGACACCGCTTGGGCTTTGGTTATTGACTGAGTGGCTGACAGTTATCTTCCAACCCCAACTGGCT |
| 449 | SEMG1 | NM_003007.2 | 1291-1390 | GGCAGACACCAACATGGATCTCATGGGGGATTGGATATTGTAATTATAGAGCAGGAAGATGACAGTGATCGTCATTTGGCACAACATCTTAACAACGACC |
| 450 | SERPINB10 | NM_005024.1 | 891-990 | AGACAGTTATGATCTCAAGTCAACCCTGAGCAGTATGGGGATGAGTGATGCCTTCAGCCAAAGCAAAGCTGATTTCTCAGGAATGTCTTCAGCAAGAAAC |
| 451 | SETD2 | NM_014159.6 | 7956-8055 | TGGTTAGAAGCCATCAGAGGTGCAAGGGCTTAGAAAAGACCCTGGCCAGACCTGACTCCACTCTTAAACCTGGGTCTTCTCCTTGGCGGTGCTGTCAGCG |
| 452 | SFMBT1 | NM_001005158.2 | 2844-2943 | AAGGATCGAAGTTGCTGAAAGGCTTCACCTGGACAGTAACCCCTTGAAGTGGAGTGTGGCAGACGTTGTGCGGTTCATCAGATCCACTGACTGTGCTCCA |
| 453 | SFPQ | NM_005066.2 | 2800-2899 | GGTTATGTAAGCAAAGCTGAACTGTAAATCTTCAGGAATATGTATTAAGATTGTGGAATGGGTGTAAG |

TABLE III-continued

| Sequence ID# | Gene | Position | Target Sequence |
|---|---|---|---|
| | | | ACAATTGGTAGGGGGTGAAAGT GGGTTTGATT |
| 454 | SGK1 | NM_05627.3 1622-1721 | ACGAGCGTTAGAGTGCCGCCTTA GACGGAGGCAGGAGTTTCGTTA GAAAGCGGACGCTGTTCTAAAA AAGGTCTCCTGCAGATCTGTCTG GGCTGTGATG |
| 455 | SGK | NM_005627.3 173-272 | GAAGCAGAGGAGGATGGGTCTG AACGACTTTATTCAGAAGATTGC CAATAACTCCTATGCATGCAAAC ACCCTGAAGTTCAGTCCATCTTG AAGATCTCC |
| 456 | SGK1 b | NM_005627.3 1814-1913 | GGATATGCTGTGTGAACCGTCGT GTGAGTGTGGTATGCCTGATCAC AGATGGATTTTGTTATAAGCATC AATGTGACACTTGCAGGACACTA CAACGTGG |
| 457 | SH2D3C | NM_170600.2 2795-2894 | AGCACCCCAAGGACACTGTGATC AACCCGAGAATGTTCTGGGTTCA ACTCAAGCATCTCCCTTGCACCT CCAGGGTCCTGCGTGGACTCTGG GTTCCATC |
| 458 | SIK1 | NM_173354.3 4185-4284 | TCGCTCATAAAGAAGTTTTTGGG ATGGGAGAGAATCCAGACCATC TTGGGGCAGCCAGGCCCTTGCCT TCATTTTTACAGAGGTAGCACAA CTGATTCCA |
| 459 | SIN3A | NM_015477.2 4666-4765 | TTTATTCCTGACGATTCCCTTGC TGCCTACCCTTTTCTCTCCTCTG GTTCTCAACCTCAACGAGTTCAA ATCAGTTGTCCTTTTTAGCTCCC GTGGAACT |
| 460 | SLAMF8 | NM_020125.2 3173-3272 | AACAAATATTGATTGAGGGCGCT GCATGTGCTGGGTACATTTCTTG GCACTTGGGAATCAGTAGTCAAG CGAAACCCTTGCCTTTGAGAGTT TATGGTCT |
| 461 | SLC11A1 | NM_000578.3 2072-2171 | GCAGGATAGAGTGGGACAGTTC CTGAGACCAGCCAACCTGGGGG CTTTAGGGACCTGCTGTTTCCTA GCGCAGCCATGTGATTACCCTCT GGGTCTCAGT |
| 462 | SLC15A2 | NM_021082.3 2548-2647 | AACTCATTAAAACTTGTGCAGTG TTGCTGGAGCTGGCCTGGTGTCT CCAAATGACCATGAAAATACAC ACGTATAATGGAGATCATTCTCT GTGGGTATG |
| 463 | SLC25A20 | NM_000387.5 1511-1610 | ATCTTCTTCAGTCCCTAGCCAGG AATACCCATTTGATTTCCAGGGT GCCATCTAATCCTGGGCTGTACA TGTGGATATGGACTTGAGGCCCA CCTCTGTG |
| 464 | SLC25A37 | NM_016612.2 1217-1316 | TCCAGCCCCTTGCCCTCTCCTCA CACGTAGATCATTTTTTTTTTGC AGGGTGCTGCCTATGGGCCCTCT GCTCCCCAATGCCTTAGAGAGAG GAGGGGAC |
| 465 | SLC45A3 | NM_033102.2 2455-2554 | AGTTTCTAGGATGAAACACTCCT CCATGGGATTTGAACATATGAAA GTTATTGTAGGGGAAGAGTCCT GAGGGGCAACACACAAGAACCA GGTCCCCTC |
| 466 | SLC6A12 | NM_003044.4 3220-3319 | GATATTGCTAACTGATCACAGAT TCTTTCCCACCTCACAATCCTTC CGAATGTGCTCCAGGCAGCACCA TTTGCCATCCTGCTTCTAACGCA AACCCCTG |
| 467 | SLC6A6 | NM_003043.5 4438-4537 | ATTCTAGACCAAAGACACAGGC AGACCAAGTCCCCAGGCCCCGCC TGGAAGGAAGTCGTTCCTCAACT CTCCCAAGGCACCTGTCTCCAA TCAGAGCCC |
| 468 | SLC9A3R1 | NM_004252.3 1811-1910 | ATTAACATGATTTTCCTGGTTGT TACATCCAGGGCATGGCAGTGGC CTCAGCCTTAAACTTTTGTTCCT ACTCCCACCCTCAGCGAACTGGG CAGCACGG |
| 469 | C14orf156 | NM_031210.5 46-145 | CGGCCTCAGCAGCGAGAGGTGC TGCGGCGCTGCGTAGAACTATCA ATCAGCCGGTTGCTTTTGTGAGA AGAATTCTTGGACTGCGGCGTC GAGTCAGCT |
| 470 | SMARCC1 | NM_003074.3 5281-5380 | CAATGGCCAGGGTTTTACCTACT TCCTGCCAGTCTTTCCCAAAGGA AACTCATTCCAAATACTTCTTTT TTCCCCTGGAGTCCGAGAAGGAA AATGGAAT |
| 471 | SNORA56 | NR_002984.1 30-129 | CTCGTGGGACTCTAGAGGGAGTC AGTCTGCAACAGTAAGTGGTGA GTTCTTCTGTCCAGCGTCAGTAT TTTGATGGTGGCTTTAGACTTGC CAGATAACA |
| 472 | SNX11 | NM_152244.1 2261-2360 | CCCTCCCTGTCGCCCACTCCTCC CTCCTCTGGCTATCCTACCCTGT CTGTGGGCTCTTTTACTACCAGC CTATGCTGTGGGACTGTCATGGC ATTTAGTT |
| 473 | SOCS1 | NM_003745.1 1026-1125 | TTAACTGTATCTGGAGCCAGGAC CTGAACTCGCACCTCCTACCTCT TCATGTTTACATATACCCAGTAT CTTTGCACAAACCAGGGGTTGGG GGAGGGTC |
| 474 | SP2 | NM_003110.5 2701-2800 | GGGGGCAATGATGAGCATATGA ATTTTTTCTCACTCTAGCAATTC CCTTTTCTAAATGACACAGCATT TAAACTCAAATCTGGATTCAGAT AACAGCACC |
| 475 | SPA17 | NM_017425.3 176-275 | CAAGGATTTGGGAATCTTCTTGA AGGGCTGACACGCGAGATTCTG AGAGAGCAACCGGACAATATAC CAGCTTTTGCAGCAGCCTATTTT GAGAGCCTTC |
| 476 | SPEN | NM_015001.2 11995-12094 | GTATTGCCCACTCATTTGTATAA GTGCGCTTCGGTACAGCACGGGT CCTGCTCCCGCGATGTGGAAGTG TCACACGGCACCTGTACAAAAA GACTGGCTA |
| 477 | SPINK5 | NM_006846.3 2596-2695 | GAGCAATGACAAAGAGGATCTG TGTCGTGAATTTCGAAGCATGCA GAGAAATGGAAAGCTTATCTGC ACCAGAGAAATAACCCTGTTCG AGGCCCATAT |
| 478 | SPN | NM_003123.3 2346-2445 | AGTGCCTGCGTGTGTCCACTCGT GGGTGTGGTTTGTGTGCAAGAGC TGAGGATTTGGCGATGCTTGGGA |

TABLE III-continued

| Sequence ID# | Gene | NM_ID | Position | Target Sequence |
|---|---|---|---|---|
| | | | | GGGGTAGTTGTGGGTACAGACGGTGTGGGGG |
| 479 | SREBF1 | NM_001005291.2 | 3985-4084 | CCCCTCCTTGCTCTGCAGGCACCTTAGTGGCTTTTTTCCTCCTGTGTACAGGGAAGAGAGGGGTACATTTCCCTGTGCTGACGGAAGCCAACTTGGCTTT |
| 480 | SFRS4 | NM_005626.4 | 2080-2179 | TACTCATGGCCCACAGTAGAATATCCAAAACGCCTTGGCTTTCAGGCCTGGCCTTTCCTACAGGGAGCTCAGTAACCTGGACGGCTCTAAGGCTGGAATG |
| 481 | ST6GAL1 | NM_003032.2 | 3783-3882 | CTGATTTTAATCTTCGAATCATGACACTGAGTGCAGAGGAGGTGGCATTCCGACAGCAGGACATACATGTTGGTGTGAAGACTGGGACGACACTGGGTAG |
| 482 | STAG3 | NM_012447.3 | 3424-3523 | AAGTGCCTGCAGCATGTCTCCCAGGCACCTGGCCATCCCTGGGGCCCAGTCACCACCTACTGCCACTCCCTCAGCCCTGTGGAGAACACAGCAGAGACCA |
| 483 | STAMBP | NM_006463.4 | 1926-2025 | TTTCCTGTGGTTTATGGCAATATGAATGGAGCTTATTACTGGGGTGAGGGACAGCTTACTCCATTTGACCAGATTGTTTGGCTAACACATCCCGAAGAAT |
| 484 | STAT6 | NM_003153.4 | 3725-3824 | ACTGTGCCCAAGTGGGTCCAAGTGGCTGTGACATCTACGTATGGCTCCACACCTCCAATGCTGCCTGGGAGCCAGGGTGAGAGTCTGGGTCCAGGCCTGG |
| 485 | STIP1 | NM_006819.2 | 1906-2005 | CCCGGGGAAGACACAGAGACTCGTACCTGCGCTGTTTGTGCCGCCGCTGCCTCTGGGCCCTCCCAGCACACGCATGGTCTCTTCACCGCTGCCCTCGAGT |
| 486 | STK16 | NM_003691.2 | 1420-1519 | GGGGTAGCGGGGTCAGGACAATCATCTCCAGTCCTGCATCTTTTCTTCTGCTTTCTTCCCTCCAAGAGCAAAACCTGGGCAAGGGGACTTACTGAGTGGGG |
| 487 | STK38 | NM_007271.3 | 3269-3368 | TTGTCAGTGAAACTACTTTGGATTTTAACCTCTTAGAGGAAGAAAAAAGGTTAGGGAAGTGTCAACTCTGGATGAAGGTGATGTGTTTGCCTCTCAGTCT |
| 488 | STOM | NM_004099.5 | 2953-3052 | TTCTGCCTTGTGAATTCGTAGTCCAATCAGCTGAAATTAAATCACTTGGGAGGGACGCATAGAAGGAGCTCTAGGAACACAGTGCCAGTGCAGAAGTTTC |
| 489 | SYNJ1 | NM_003895.3 | 4746-4845 | CCCTCTGCTCCCGCCCGGCACCAGCCCTCCAGTAGATCCTTTCACGACCTTGGCCTCTAAGGCTTCACCCACACTGGACTTTACAGAAAGATAACGCCAT |
| 490 | TAPBP | NM_003190.4 | 3397-3496 | CTTGCCCTCCCTGGGTCGCAGACGAGGCTCGGCCTCGTCATTCCCCGCAGACCGCCGCGCGTCCCTCTTGTGCGGTTCACCACAGTTGTATTTAAGTGATC |
| 491 | TAX1BP1 | NM_001079864.2 | 2081-2180 | CAGCCAGCCTGCTCGAAACTTTAGTCGGCCTGATGGCTTAGAGGACTCTGAGGATAGCAAAGAAGATGAGAATGTGCCTACTGCTCCTGATCCTCCAAGT |
| 492 | TBC1D12 | NM_015188.1 | 5451-5550 | TTCCAAGGAATGCACTAAGCCTTCAGTCTTTTTAGACTGACAGTACTGGCAGCTAAAATATTGTACTGTATCTTCTCTTGAGCCCAGTATGTAGGAAATA |
| 493 | TBCE | NM_001079515.2 | 1541-1640 | TATGCTGAAAAACCAGCTACTAAACACTGAAGATAAAATACCCTCATCAACTTGATCAGAAAGTCCTGGAGAAACAACTGCCGGGCTCCATGACAATTCAA |
| 494 | TBK1 | NM_013254.2 | 1611-1710 | ACCAGTCTTCAGGATATCGACAGCAGATTATCTCCAGGTGGATCACTGGCAGACGCATGGGCACATCAAGAAGGCACTCATCCGAAAGACAGAAATGTAG |
| 495 | TBP | NM_003194.4 | 1441-1540 | TGTAAGTGCCCACCGCGGGATGCCGGGAAGGGGCATTATTTGTGCACTGAGAACACCGCGCAGCGTGACTGTGAGTTGCTCATACCGTGCTGCTATCTGG |
| 496 | TCF20 | NM_181492.2 | 6765-6864 | CCAGGCCTGTGTTGCCAGAGCTGGCAGTGTGAGCTGTAGGCAGGGACGGGGAGGGACTGTGCTGCTGTGATCAGAGTGGGTTAAGCTGACCAGGAACACCCA |
| 497 | TCF7L2 | NM_030756.4 | 2067-2166 | GGCCCACCTGTCCATGATGCCTCCGCCACCCGCCCTCCTGCTCGCTGAGGCCACCCACAAGGCCTCCGCCCTCTGTCCCAACGGGGCCCTGGACCTGCCC |
| 498 | TCP1 | NM_030752.2 | 254-353 | GTGTTCGGTGACCGCAGCACTGGGGAAACGATCCGCTCCCAAAACGTTATGGCTGCAGCTTCGATTGCCAATATTGTAAAAGTTCTCTTGGTCCAGTTG |
| 499 | TFCP2 | NM_005653.4 | 2271-2370 | CCTCTGAAAACGGCCCTCTTGAAGGGGGATATGAATGGAGATTTGAAGGTCTGCAAGAACCTGACTCGTCTGACTGTGTGTGGAGGAGTCCAGGCCATGG |
| 500 | TGIF1 | NM_003244.2 | 1041-1140 | ACCTCAACCAGGACTTCAGTGGATTTCAGCTTCTAGTGGATGTTGCACTCAAACGGGCTGCAGAGATGGAGCTTCAGGCAAAACTTACAGCTTAACCCAT |
| 501 | TGIF1b | NM_173208.1 | 691-790 | CCCCGGGATCAGTTTTGGCTCGTCCATCAGTGATCTGCCATACCACTGTGACTGCATTGAAAGATGTCCCTTTCTCTCTGCCAGTCGGTCGGTGTGGG |
| 502 | TIAM1 | NM_003253.2 | 5293-5392 | CCTAACTCTGCCCACCCTCCTGTACCGTCGACAAGAATGTCCCCTTAGGTCGCGCTCTTGCACACACGGTTTTGGCAGCTGACTTGGTTCTGAAGCCATG |
| 503 | TIMM8B | ENST00000504148.1 | 339-438 | GAATGACAGAAGCAAAGGACTTGTTACTAAGCAGATTTAAGGGTCAGTGGGGGAAGGCTATCAACCC |

TABLE III-continued

| Sequence ID# | Gene | Position | Target Sequence |
|---|---|---|---|
| | | | ATTGTCAGATCAGCATCAGGCTGTTATCAAGTC |
| 504 | TM2D2 | NM_078473.2 | 2970-3069 | ACCCATCATCCATCTGCCCACAAACCTGGCCAAATGTGATACAACCTGAAAACCTGATGGACTAAAGGAGTACTATTTAACAATTGATTGCCTTTGCACT |
| 505 | TM9SF1 | NM_006405.6 | 1996-2095 | CGCTGGTGGTGGCGATCTGTGCTGAGTGTTGGCTCCACCGGCCTCTTCATCTTCCTCTACTCAGTTTTCTATTATGCCCGGCGCTCCAACATGTCTGGGG |
| 506 | CCDC72 | NM_015933.4 | 124-223 | GAGGAGCAGAAGAAACTCGAGGAGCTAAAAGCGAAGGCCGCGGGGAAGGGGCCCTTGGCCACAGGTGGAATTAAGAAATCTGGCAAAAAGTAAGCTGTTC |
| 507 | TMBIM6 | NM_003217.2 | 2282-2381 | CTCTCCCTATTCACAACCAGTGCACAGTTTGACACAGTGGCCTCAGGTTCACAGTGCACCATGTCACTGTGCTATCCTACGAAATCATTTGTTTCTAAGT |
| 508 | TMC8 | NM_152468.4 | 2238-2337 | AGGCCAATGCCAGGGCCATCCACAGGCTCCGGAAGCAGCTGGTGTGGCAGGTTCAGGAGAAGTGGCACCTGGTGGAGGACCTGTCGCGACTGCTGCCGGA |
| 509 | TMCO1 | NM_019026.3 | 992-1091 | TCATTTACATAAGTATTTTCTGTGGGACCGACTCTCAAGGCACTGTGTATGCCCTGCAAGTTGGCTGTCTATGAGCATTTAGAGATTTAGAAGAAAAATT |
| 510 | TMEM170B | NM_001100829.2 | 7652-7751 | AGGAGAATAAATGTTGGAGGGGTAATACACAAAAACAAAGGCATATTTGATGAAGTACCCTGTGTTATGTGAACACAATTTCCCCTTCTGTTAAGACTAT |
| 511 | TMEM218 | NM_001080546.2 | 1313-1412 | GCTCTGTGAAGGCAATGAGTGTCACTTCCCTCTGCTCTAATAAAGCAATAAATAATAGCTAAAGGGCTGACTTTCACTTCGAACTCTTGGCCACGGCTTT |
| 512 | TMEM70 | NM_017866.5 | 1952-2051 | GGTGGTTAGCTATACGGGAAATGGTAAGTAGTGTTGTCTTCAGTATCTTAATTTGTTTCTGCAACTGTGCACTCCTCCCTTGGTGGCACCCTATGGGTGT |
| 513 | TMSB4X | NM_021109.3 | 286-385 | TTAACTTTGTAAGATGCAAAGAGGTTGGATCAAGTTTAAATGACTGTGCTGCCCCTTTCACATCAAAGAACTACTGACAACGAAGGCCGCGCCTGCCTTT |
| 514 | TNFRSF9 | NM_001561.5 | 1848-1947 | GCCTGGAGGAAGTTTTGGAAAGAGTTCAAGTGTCTGTATATCCTATGGTCTTCTCCATCCTCACACCTTCTGCCTTTGTCCTGCTCCCTTTTAAGCCAGG |
| 515 | TNFSF13 | NM_003808.3 | 811-910 | AGTCAGAGAGCCGGCACTCTCAGTTGCCCTCTGGTTGAGTTGGGGGCAGCTCTGGGGCCGTGGCTTGTGCCATGGCTCTGCTGACCCAACAAACAGAG |
| 516 | TNFSF8 | NM_001244.3 | 519-618 | CCCTCAAAGGAGGAAATTGCTCAGAAGACCTCTTATGTATCCTGAAAAGGGCTCCATTCAAGAAGTCATGGGCCTACCTCCAAGTGGCAAAGCATCTAAA |
| 517 | TOMM7 | NM_019059.2 | 251-350 | TCTGGCTCGGATAAGAGATGGGACATCATTCAGTCACTAGTTGGATGGCACAAGGCTCTTCACAGACGCATCTGTAGCAGAGTGGATCTTGTACTAACTT |
| 518 | TP53BP1 | NM_005657.2 | 5591-5690 | TACTTCCTGTGCCTTGCCAGTGGGATTCCTTGTGTGTCTCATGTCTGGGTCCATGATAGTTGCCATGCCAACCAGCTCCAGAACTACCGTAATTATCTGT |
| 519 | TPR | NM_003292.2 | 7194-7293 | TCTCCCCTCCACCAGCCAGGATCCTCCTTCTAGCTCATCTGTAGATACTAGTAGTAGTCAACCAAAGCCTTTCAGACGAGTAAGACTTCAGACAACATTG |
| 520 | TPT1 | NM_003295.3 | 18-117 | GCCTGCGTCGCTTCCGGAGGCGCAGCGGGCGATGACGTAGAGGGACGTGCCCTCTATATGAGGTTGGGGAGCGGCTGAGTCGGCCTTTTCCGCCCGCTCC |
| 521 | TRAF3IP2 | NM_147686.3 | 2449-2548 | GCCAGTGTCCCATATGTTCCTCCTGACAGTTTGATGTGTCCATTCTGGGCCTCTCAGTGCTTAGCAAGTAGATAATGTAAGGGATGTGGCAGCAAATGGA |
| 522 | TRAF6 | NM_145803.1 | 1840-1939 | CACCCGCTTTGACATGGGTAGCCTTCGGAGGGAGGTTTTCAGCCACGAAGTACTGATGCAGGGGTATAGCTTGCCCTCACTTGCTCAAAAACAACTACC |
| 523 | LBA1 | NM_014831.2 | 10132-10231 | CTGGGAAACCTTCATGCCTCTCTGATGGTTACTGCCCACCCTTACCCCACCCCTCAGCTCAGCTGGTATGGAAAGCAAGGTGCACGTTGGTCTTTGATT |
| 524 | TRIM21 | NM_003141.3 | 1637-1736 | TCTGCAGAGGCATCCGGATCCCAGCAAGCGAGCTTTAGCAGGGAAGTCACTTCACCATCAACATTCCTGCCCCAGATGGCTTTGTGATTCCCTCCAGTGA |
| 525 | TRIM32 | NM_012210.3 | 2681-2780 | GTGCTACCAAAGGGGATACACAAGCCCTTTAGGAAGCAGTACCTCTCGCCTGGAGGATCTGTGCCATCTTGGATTGAGAATTGCAGATGTGACAGAATGG |
| 526 | TRIM39 | NM_021253.3 | 3141-3240 | CTGCTATTCGGGTAATCTTCACAGAAATGACTGAGAGAAGAATCTGCAGTTTACTGAGGGCATTTCAGTTCCTCCTACCACCTCAACAGGACTTTGTCCA |
| 527 | TRIM39b | NM_172016.2 | 2841-2940 | CTCTATACCAATAAGTCAGTCACCTTGCTCCTCTCCAGAGGCAAAGTGGAAGAGATCCTGCAAGACACATCTCATTCACAGTGTTCCCAAGGGAACT |
| 528 | TRRAP | NM_003496.3 | 12169-12268 | AGTTGATGAACCCATCATGCTGGTTTTTCTCTGAGCACAAAGTTTTAGGCTGTACACAGCCAGCCTTGG |

TABLE III-continued

| Sequence ID# | Gene | Position | Target Sequence |
|---|---|---|---|
| | | | GAATCTCGTTGAGCGTTCGGCGT GGATCCAC |
| 529 | TSC1 | NM_000368.4 8068-8167 | CCCCAGACCAACCCTTCCCTCCC TTTCCCCACCTCTTACAGTGTTT GGACAGGAGGGTATGGTGCTGCT CTGTGTAGCAAGTACTTTGGCTT ATGAAAGA |
| 530 | TTC9 | NM_015351.1 4050-4149 | TACTAATCAGGCATCTGACCTGC ACTGTCATCCCTGCCTGGACTTT TTGCGATGGACTCTTTGGGGGAA AAACTAACGCTTTTTAATTATTG TGAAAGCA |
| 531 | TTN | NM_133378.4 850-949 | TCGACTGCTCAGATCTCAGAATC AAGACAAACCCGAATTGAAAAG AAGATTGAAGCCCACTTTGATGC CAGATCAATTGCAACAGTTGAGA TGGTCATAG |
| 532 | TUBB | NM_178014.2 2223-2322 | CAAAAAAGAATGAACACCCCTG ACTCTGGAGTGGTGTATACTGCC ACATCAGTGTTTGAGTCAGTCCC CAGAGGAGAGGGGAACCCTCCT CCATCTTTTT |
| 533 | TUG1 | NR_002323.2 7082-7181 | TAAGCTAGAGGTCATGGTCACTG AAATTACTTTTCCAAGTGGAAGA CAAAATGAAACAGGAACTGAGG GAATATTTAAGATCCCACAGAAG CGTAAAAAT |
| 534 | TXN | NM_003329.3 152-251 | TTGGATCCATTTCCATCGGTCCT TACAGCCGCTCGTCAGACTCCAG CAGCCAAGATGGTGAAGCAGATC GAGAGCAAGACTGCTTTTCAGGA AGCCTTGG |
| 535 | TXNDC17 | NM_032731.3 378-477 | TCATCTACTGCCAAGTAGGAGAA AAGCCTTATTGGAAAGATCCAAA TAATGACTTCAGAAAAAACTTGA AAGTAACAGCAGTGCCTACACTA CTTAAGTA |
| 536 | TXNRD1 | NM_001093771.2 3348-3447 | CTCAGTTGCAGCACTGAGTGGTC AAAATACATTTCTGGGCCACCTC AGGGAACCCATGCATCTGCCTGG CATTTAGGCAGCAGAGCCCCTGA CCGTCCCC |
| 537 | TXNRD1b | NM_182743.2 2438-2537 | TGTTGCATGGAAGGGATAGTTTG GCTCCCTTGGAGTGCTATGTAGGC TTGTCCCGGGAAAGAGAACTGTC CTGCAGCTGAAATGGACTGTTCT TTACTGAC |
| 538 | U2AF2 | NM_007279.2 2871-2970 | TTTATGGCCAAACTATTTTGAAT TTTGTTGTCCGGCCCTCAGTGCC CTGCCCTCTCCCTTACCAGGACC ACAGCTCTGTTCCTTCGGCCTCT GGTCCTCT |
| 539 | UBA1 | NM_003334.3 3307-3406 | CCGCCACGTGCGGGCGCTGGTGC TTGAGCTGTGCTGTAACGACGAG AGCGGCGAGGATGTCGAGGTTC CCTATGTCCGATACACCATCCGC TGACCCCGT |
| 540 | UBC | NM_021009.3 1876-1975 | TGCAGATCTTCGTGAAGACCCTG ACTGGTAAGACCATCACTCTCGA AGTGGAGCCGAGTGACACCATT GAGAATGTCAAGGCAAAGATCC AAGACAAGGA |
| 541 | UBE2G1 | NM_003342.4 685-784 | ACGCTGGCTCCCTATCCACACTG TGGAAACCATCATGATTAGTGTC ATTTCTATGCTGGCAGACCCTAA TGGAGACTCACCTGCTAATGTTG ATGCTGCG |
| 542 | UBE2I | NM_194259.2 288-387 | CTGCTCTGCTGACTGGGGAAGTC ATCGTGCCACCCAGAACCTGAGT GCGGGCCTCTCAGAGCTCCTTCG TCCGTGGGTCTGCCGGGGACTGG GCCTTGTC |
| 543 | UBTF | NM_001076683.1 2724-2823 | GGGGGTCCCAAAGAGTTTGATG AGGCCCTCCACACCTGCGGCCCA ATCCAAGGTGGGGTGGAAGCTT GGGGAAGACCCATTCCTTCCCAG AGGGGCCTGC |
| 544 | UQCRQ | NM_014402.4 97-196 | TGACGCGGATGCGGCATGTGATC AGCTACAGCTTGTCACCGTTCGA GCAGCGCGCCTATCCGCACGTCT TCACTAAAGGAATCCCCAATGTT CTGCGCCG |
| 545 | USP16 | NM_001032410.1 2487-2586 | TCTATTCCTTATATGGAGTTGTT GAACACAGTGGTACTATGAGGTC GGGGCATTACACTGCCTATGCCA AGGCAAGAACCGCAAATAGTCAT CTCTCTAA |
| 546 | USP21 | NM_012475.4 1499-1598 | CCTTTTCACTAAGGAAGAAGAGC TAGAGTCGGAGAATGCCCCAGT GTGTGACCGATGTCGGCAGAAA ACTCGAAGTACCAAAAAGTTGA CAGTACAAAGA |
| 547 | USP34 | NM_014709.3 10104-10203 | AGGAGCACACTGTAGACAGCTG CATCAGTGACATGAAAACAGAA ACCAGGGAGGTCCTGACCCCAA CGAGCACTTCTGACAATGAGACC AGAGACTCCTC |
| 548 | USP5 | NM_003481.2 2720-2819 | AGAGCAGAGGGGCAGCGATAGA CTCTGGGGATGGAGCAGGACGG GGACGGGAGGGGCCGGCCACCT GTCTGTAAGGAGACTTTGTTGCT TCCCCTGCCCC |
| 549 | USP9Y | NM_004654.3 86-185 | GGTGTGGAAAGACTTTTCTGGGC TCAGAGGTGAAACTGACCCTTGT GTATCAGCAGCATTTCTGACTGA CTGAGAGAGTGTAGTGATTAACA GAGTTGTG |
| 550 | VPS37C | NM_017966.4 2579-2678 | TTATAAAGAGAAATCACTAATGG ACTCTACTGGTTTGAGTGCTTCT GAGCTGGATGACCGACCGCCTGT ATGTTTGTGTAATTAATTGCCAT AATAAACT |
| 551 | WDR1 | NM_005112.4 2325-2424 | AACTGTTGCCTGTCAGTGTTTAC AAACTAGTGCGTTGACGGCACCG TGTCCAAGTTTTTAGAACCCTTG TTAGCCAGACCGAGGTGTCCTGG TCACCGTT |
| 552 | WDR91 | NM_014149.3 2777-2876 | CAGGCTCTCCTGTTGCTTTGCCA TGGAGCCAGGTCAGCTCTCTGTC TGTTCTGCTGGGTAACAAGGTTT GGCAGTTCCTGTTTTCTCTGGGCT TAAGTCAA |
| 553 | XCL2 | NM_003175.3 378-477 | GTAGTCTCTGGCACCCTGTCCGT CTCCAGCCAGCCAGCTCATTTCA CTTTACACCCTCATGGACTGAGA |

TABLE III-continued

| Sequence ID# | Gene | Position | Target Sequence |
|---|---|---|---|
| | | | TTATACTCACCTTTTATGAAAGC ACTGCATG |
| 554 | XPC | NR_027299.1 | 3168-3267 | CTGGATGGTGGTGCATCCGTGAA TGCGCTGATCGTTTCTTCCAGTT AGAGTCTTCATCTGTCCGACAAG TTCACTCGCCTCGGTTGCGGACC TAGGACCA |
| 555 | YPEL1 | NM_013313.4 | 3672-3771 | GCTCATTTTTAAACCAAATGAAC AGACCATGAGCTGGCTTCAGGG GAAGTGCTATTCACAGGACCATA TCCACCACCCTCTTAAATTCCTA AACAATATC |
| 556 | ZMIZ1 | NM_020338.3 | 7171-7270 | ATGATCACAGGTGATTCACACGT ACACACATAAACACACCCACCA GTGCAGCCTGAAGTAACTCCCAC AGAAACCATCATCGTCTTTGTAC ATCGTATGT |
| 557 | ZNF143 | NM_003442.5 | 2292-2391 | TATCAGATCACAAACTCCTAGAG TCTACATGCAAGACTAGTAAAGT CTTATGGAGTCTTATGATGGATT TTTAACTTCCCGTGGAAAAAAAA ATAAAGGC |
| 558 | ZNF239 | NM_001099283.1 | 1496-1595 | AGAGCTCCAACCTTCACATCCAC CAGCGGGTTCACAAGAAAGATC CTCGCTAACTGACATTAGCCCAT TCAGGTCTTCACAGCGCTCATAC TGTAAAAAC |
| 559 | ZNF341 | NM_032819.4 | 3247-3346 | CAGACGGTTCCCCACAGCATCCT CAGACAGCTCTGTGATGTAGCTT TTAGGAGGCACTCAGGTGTCACG GCTAGACTGCAGCTATGAGACA GATCTGGCT |

C. Polymerase Chain Reaction (PCR) Techniques

Another suitable quantitative method is RT-PCR, which can be used to compare mRNA levels in different sample populations, in normal and tumor tissues, to characterize patterns of gene expression, to discriminate between closely related mRNAs, and to analyze RNA structure. The first step is the isolation of mRNA from a target sample (e.g., typically total RNA isolated from human PBMC). mRNA can be extracted, for example, from frozen or archived paraffin-embedded and fixed (e.g. formalin-fixed) tissue samples.

General methods for mRNA extraction are well known in the art, such standard textbooks of molecular biology. In particular, RNA isolation can be performed using a purification kit, buffer set and protease from commercial manufacturers, according to the manufacturer's instructions. Exemplary commercial products include TRI-REAGENT, Qiagen RNeasy mini-columns, MASTERPURE Complete DNA and RNA Purification Kit (EPICENTRE®, Madison, Wis.), Paraffin Block RNA Isolation Kit (Ambion, Inc.) and RNA Stat-60 (Tel-Test). Conventional techniques such as cesium chloride density gradient centrifugation may also be employed.

The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. See, e.g., manufacturer's instructions accompanying the product GENEAMP RNA PCR kit (Perkin Elmer, Calif., USA). The derived cDNA can then be used as a template in the subsequent RT-PCR reaction.

The PCR step generally uses a thermostable DNA-dependent DNA polymerase, such as the Taq DNA polymerase, which has a 5'-3' nuclease activity but lacks a 3'-5' proofreading endonuclease activity. Thus, TAQMAN® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. In one embodiment, the target sequence is shown in Table III. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment. In a preferred embodiment, the 5' nuclease procedure is run on a real-time quantitative PCR device such as the ABI PRISM 7900® Sequence Detection System®. The system amplifies samples in a 96-well format on a thermocycler. During amplification, laser-induced fluorescent signal is collected in real-time through fiber optic cables for all 96 wells, and detected at the CCD. The system includes software for running the instrument and for analyzing the data. 5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

Real time PCR is comparable both with quantitative competitive PCR, where internal competitor for each target sequence is used for normalization, and with quantitative comparative PCR using a normalization gene contained within the sample, or a housekeeping gene for RT-PCR.

In another PCR method, i.e., the MassARRAY-based gene expression profiling method (Sequenom, Inc., San Diego, Calif.), following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derived PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated.

Still other embodiments of PCR-based techniques which are known to the art and may be used for gene expression profiling include, e.g., differential display, amplified fragment length polymorphism (iAFLP), and BeadArray™ technology (Illumina, San Diego, Calif.) using the commercially available Luminex100 LabMAP system and multiple color-coded microspheres (Luminex Corp., Austin, Tex.) in a rapid assay for gene expression; and high coverage expression profiling (HiCEP) analysis.

D. Microarrays

Differential gene expression can also be identified, or confirmed using the microarray technique. Thus, the expression profile of lung cancer-associated genes can be measured in either fresh or paraffin-embedded tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the other methods and compositions herein, the source of mRNA is total RNA isolated from whole blood of controls and patient subjects.

In one embodiment of the microarray technique, PCR amplified inserts of cDNA clones are applied to a substrate in a dense array. In one embodiment, all 559 nucleotide sequences from Table III are applied to the substrate. The microarrayed genes, immobilized on the microchip, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels. Microarray analysis can be performed by commercially available equipment, following manufacturer's protocols.

Other useful methods summarized by U.S. Pat. No. 7,081,340, and incorporated by reference herein include Serial Analysis of Gene Expression (SAGE) and Massively Parallel Signature Sequencing (MPSS). Briefly, serial analysis of gene expression (SAGE) is a method that allows the simultaneous and quantitative analysis of a large number of gene transcripts, without the need of providing an individual hybridization probe for each transcript. First, a short sequence tag (about 10 to 14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., Science 270:484 487 (1995); and Velculescu et al., Cell 88:243 51 (1997), both of which are incorporated herein by reference.

Gene Expression Analysis by Massively Parallel Signature Sequencing (MPSS), described by Brenner et al., Nature Biotechnology 18:630 634 (2000) (which is incorporated herein by reference), is a sequencing approach that combines non-gel-based signature sequencing with in vitro cloning of millions of templates on separate 5 µm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

E. Immunohistochemistry

Immunohistochemistry methods are also suitable for detecting the expression levels of the gene expression products of the informative genes described for use in the methods and compositions herein. Antibodies or antisera, preferably polyclonal antisera, and most preferably monoclonal antibodies, or other protein-binding ligands specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Protocols and kits for immunohistochemical analyses are well known in the art and are commercially available.

III. COMPOSITIONS OF THE INVENTION

The methods for diagnosing lung cancer described herein which utilize defined gene expression profiles permit the development of simplified diagnostic tools for diagnosing lung cancer, e.g., NSCLC vs. non-cancerous nodule. Thus, a composition for diagnosing lung cancer in a mammalian subject as described herein can be a kit or a reagent. For example, one embodiment of a composition includes a substrate upon which said polynucleotides or oligonucleotides or ligands or ligands are immobilized. In another embodiment, the composition is a kit containing the relevant 5 or more polynucleotides or oligonucleotides or ligands, optional detectable labels for same, immobilization substrates, optional substrates for enzymatic labels, as well as other laboratory items. In still another embodiment, at least one polynucleotide or oligonucleotide or ligand is associated with a detectable label.

In one embodiment, a composition for diagnosing lung cancer in a mammalian subject includes 5 or more PCR primer-probe sets. Each primer-probe set amplifies a different polynucleotide sequence from a gene expression product of 5 or more informative genes found in the blood of the subject. These informative genes are selected to form a gene expression profile or signature which is distinguishable between a subject having lung cancer and a subject having a non-cancerous nodule. Changes in expression in the genes in the gene expression profile from that of a reference gene expression profile are correlated with a lung cancer, such as non-small cell lung cancer (NSCLC).

In one embodiment of this composition, the informative genes are selected from among the genes identified in Table I. In another embodiment of this composition, the informative genes are selected from among the genes identified in Table II. This collection of genes is those for which the gene product expression is altered (i.e., increased or decreased) versus the same gene product expression in the blood of a reference control (i.e., a patient having a non-cancerous nodule). In one embodiment, polynucleotide or oligonucleotide or ligands, i.e., probes, are generated to 5 or more informative genes from Table I or Table II for use in the composition (the CodeSet). An example of such a composition contains probes to a targeted portion of the 559 genes of Table I. In another embodiment, probes are generated to all 559 genes from Table I for use in the composition. In another embodiment, probes are generated to the first 539 genes from Table I for use in the composition. In another embodiment, probes are generated to the first 3 genes from Table I or Table II for use in the composition. In another embodiment, probes are generated to the first 5 genes from Table I or Table II for use in the composition. In another embodiment, probes are generated to the first 10 genes from Table I or Table II for use in the composition. In another embodiment, probes are generated to the first 15 genes from Table I or Table II for use in the composition. In another embodiment, probes are generated to the first 20 genes from Table I or Table II for use in the composition. In another embodiment, probes are generated to the first 25 genes from Table I or Table II for use in the composition. In yet another embodiment, probes are generated to the first 30 genes from Table I or Table II for use in the composition. In yet another embodiment, probes are generated to the first 35 genes from Table I or Table II for use in the composition. In yet another embodiment, probes are generated to the first 40 genes from Table I or Table II for use in the composition. In yet another embodiment, probes are generated to the first 45 genes from Table I or Table II for use in the composition. In yet another embodiment, probes are generated to the first 50 genes from Table I or Table II for use in the composition. In yet another embodiment, probes are generated to the first 60 genes from Table I or Table II for use in the composition. In yet another embodiment, probes are generated to the first 65 genes from Table I or Table II for use in the composition. In yet another embodiment, probes are generated to the first 70 genes from Table I or Table II for use in the composition. In yet another embodiment, probes are generated to the first 75 genes from Table I or Table II for use in the composition. In yet another embodiment, probes are generated to the first 80 genes from Table I or Table II for use in the composition. In yet another embodiment, probes are generated to the first 85 genes from Table I or Table II for use in the composition. In yet another embodiment, probes are generated to the first 90 genes from Table I or Table II for use in the composition. In yet another embodiment, probes are generated to the first 95 genes from Table I or Table II for use in the composition. In another embodiment, probes are generated to the first 100 genes from Table I or Table II for use in the composition. In another embodiment, probes are generated to the first 200 genes from Table I for use in the composition. In yet another embodiment, probes are generated to 300 genes from Table I for use in the composition. Still other embodiments employ probes to a targeted portion of other combinations of the genes in Table I or Table II. The selected genes from the Table need not be in rank order; rather any combination that clearly shows a difference in expression between the reference control to the diseased patient is useful in such a composition.

In one embodiment of the compositions described above, the reference control is a non-healthy control (NHC) as described above. In other embodiments, the reference control may be any class of controls as described above in "Definitions".

The compositions based on the genes selected from Table I or Table II described herein, optionally associated with detectable labels, can be presented in the format of a microfluidics card, a chip or chamber, or a kit adapted for use with the Nanostring, PCR, RT-PCR or Q PCR techniques described above. In one aspect, such a format is a diagnostic assay using TAQMAN® Quantitative PCR low density arrays. In another aspect, such a format is a diagnostic assay using the Nanostring nCounter platform.

For use in the above-noted compositions the PCR primers and probes are preferably designed based upon intron sequences present in the gene(s) to be amplified selected from the gene expression profile. Exemplary target sequences are shown in Table III. The design of the primer and probe sequences is within the skill of the art once the particular gene target is selected. The particular methods selected for the primer and probe design and the particular primer and probe sequences are not limiting features of these compositions. A ready explanation of primer and probe design techniques available to those of skill in the art is summarized in U.S. Pat. No. 7,081,340, with reference to publically available tools such as DNA BLAST software, the Repeat Masker program (Baylor College of Medicine), Primer Express (Applied Biosystems); MGB assay-by-design (Applied Biosystems); Primer3 (Steve Rozen and Helen J. Skaletsky (2000) Primer3 on the WWW for general users and for biologist programmers.

In general, optimal PCR primers and probes used in the compositions described herein are generally 17-30 bases in length, and contain about 20-80%, such as, for example, about 50-60% G+C bases. Melting temperatures of between 50 and 80° C., e.g. about 50 to 70° C. are typically preferred.

In another aspect, a composition for diagnosing lung cancer in a mammalian subject contains a plurality of polynucleotides immobilized on a substrate, wherein the plurality of genomic probes hybridize to 100 or more gene expression products of 100 or more informative genes selected from a gene expression profile in the blood of the subject, the gene expression profile comprising genes selected from Table I. In another embodiment, a composition for diagnosing lung cancer in a mammalian subject contains a plurality of polynucleotides immobilized on a substrate, wherein the plurality of genomic probes hybridize to 10 or more gene expression products of 10 or more informative genes selected from a gene expression profile in the blood of the subject, the gene expression profile comprising genes selected from Table I or Table II. This type of composition relies on recognition of the same gene profiles as described above for the Nanostring compositions but employs the techniques of a cDNA array. Hybridization of the immobilized polynucleotides in the composition to the gene expression products present in the blood of the patient subject is employed to quantitate the expression of the informative genes selected from among the genes identified in Tables I or Table II to generate a gene expression profile for the patient, which is then compared to that of a reference sample. As described above, depending upon the identification of the profile (i.e., that of genes of Table I or subsets thereof, that of genes of Table II or subsets thereof), this composition enables the diagnosis and prognosis of NSCLC lung cancers. Again, the selection of the polynucleotide sequences, their length and labels used in the composition are routine determinations made by one of skill in the art in view of the teachings of which genes can form the gene expression profiles suitable for the diagnosis and prognosis of lung cancers.

In yet another aspect, a composition or kit useful in the methods described herein contain a plurality of ligands that bind to 100 or more gene expression products of 100 or more informative genes selected from a gene expression profile in the blood of the subject. In another embodiment, a composition or kit useful in the methods described herein contain a plurality of ligands that bind to 10 or more gene expression products of 10 or more informative genes selected from a gene expression profile in the blood of the subject. The gene expression profile contains the genes of Table I or Table II, as described above for the other compositions. This composition enables detection of the proteins expressed by the genes in the indicated Tables. While preferably the ligands are antibodies to the proteins encoded by the genes in the profile, it would be evident to one of skill in the art that various forms of antibody, e.g., polyclonal, monoclonal, recombinant, chimeric, as well as fragments and components (e.g., CDRs, single chain variable regions, etc.) may be used in place of antibodies. Such ligands may be immobilized on suitable substrates for contact with the subject's blood and analyzed in a conventional fashion. In certain embodiments, the ligands are associated with detectable labels. These compositions also enable detection of changes in proteins encoded by the genes in the gene expression profile from those of a reference gene expression profile. Such changes correlate with lung cancer in a manner similar to that for the PCR and polynucleotide-containing compositions described above.

For all of the above forms of diagnostic/prognostic compositions, the gene expression profile can, in one embodiment, include at least the first 25 of the informative genes of Table I or Table II. In another embodiment for all of the above forms of diagnostic/prognostic compositions, the gene expression profile can include 10 or more of the informative genes of Table I or Table II. In another embodiment for all of the above forms of diagnostic/prognostic compositions, the gene expression profile can include 15 or more of the informative genes of Table I or Table II. In another embodiment for all of the above forms of diagnostic/prognostic compositions, the gene expression profile can include 20 or more of the informative genes of Table I or Table II. In another embodiment for all of the above forms of diagnostic/prognostic compositions, the gene expression profile can include 30 or more of the informative genes of Table I or Table II. In another embodiment for all of the above forms of diagnostic/prognostic compositions, the gene expression profile can include 40 or more of the informative genes of Table I or Table II. In another embodiment for all of the above forms of diagnostic/prognostic compositions, the gene expression profile can include 50 or more of the informative genes of Table I or Table II. In another embodiment for all of the above forms of diagnostic/prognostic compositions, the gene expression profile can include 60 or more of the informative genes of Table I or Table II. In another embodiment for all of the above forms of diagnostic/prognostic compositions, the gene expression profile can include 70 or more of the informative genes of Table I or Table II. In another embodiment for all of the above forms of diagnostic/prognostic compositions, the gene expression profile can include 80 or more of the informative genes of Table I or Table II. In another embodiment for all of the above forms of diagnostic/prognostic compositions, the gene expression profile can include 90 or more of the informative genes of Table I or Table II. In another embodiment for all of the above forms of diagnostic/prognostic compositions, the gene expression profile can include all 100 of the informative genes of Table II. In one embodiment, for all of the above forms of diagnostic/prognostic compositions, the gene expression profile can include at least the first 100 of the informative genes of Table I. In another embodiment for all of the above forms of diagnostic/prognostic compositions, the gene expression profile can include 200 or more of the informative genes of Table I. In another embodiment for all of the above forms of diagnostic/prognostic compositions, the gene expression profile can include 300 or more of the informative genes of Table I. In another embodiment for all of the above forms of diagnostic/prognostic compositions, the gene expression profile can include 400 or more of the informative genes of Table I. In another embodiment for all of the above forms of diagnostic/prognostic compositions, the gene expression profile can include 500 or more of the informative genes of Table I. In another embodiment for all of the above forms of diagnostic/prognostic compositions, the gene expression profile can include 539 or more of the informative genes of Table I. In another embodiment for all of the above forms of diagnostic/prognostic compositions, the gene expression profile can include all 559 of the informative genes of Table I.

These compositions may be used to diagnose lung cancers, such as stage I or stage II NSCLC. Further these compositions are useful to provide a supplemental or original diagnosis in a subject having lung nodules of unknown etiology.

IV. DIAGNOSTIC METHODS OF THE INVENTION

All of the above-described compositions provide a variety of diagnostic tools which permit a blood-based, non-invasive assessment of disease status in a subject. Use of these compositions in diagnostic tests, which may be coupled with other screening tests, such as a chest X-ray or CT scan, increase diagnostic accuracy and/or direct additional testing.

Thus, in one aspect, a method is provided for diagnosing lung cancer in a mammalian subject. This method involves identifying a gene expression profile in the blood of a mammalian, preferably human, subject. In one embodiment, the gene expression profile includes 100 or more gene expression products of 100 or more informative genes having increased or decreased expression in lung cancer. The gene expression profiles are formed by selection of 100 or more informative genes from the genes of Table I. In another embodiment, the gene expression profile includes 10 or more gene expression products of 10 or more informative genes having increased or decreased expression in lung cancer. The gene expression profiles are formed by selection of 10 or more informative genes from the genes of Table I. In another embodiment, the gene expression profiles are formed by selection of 10 or more informative genes from the genes of Table II. In another embodiment, the gene expression profile includes 10 or more gene expression products of 5 or more informative genes having increased or decreased expression in lung cancer. The gene expression profiles are formed by selection of 5 or more informative genes from the genes of Table I. In another embodiment, the gene expression profiles are formed by selection of 5 or more informative genes from the genes of Table II. Comparison of a subject's gene expression profile with a reference gene expression profile permits identification of changes in expression of the informative genes that correlate with a lung cancer (e.g., NSCLC). This method may be performed using any of the compositions described above. In one embodiment, the method enables the diagnosis of a cancerous tumor from a benign nodule.

In another aspect, use of any of the compositions described herein is provided for diagnosing lung cancer in a subject.

The diagnostic compositions and methods described herein provide a variety of advantages over current diagnostic methods. Among such advantages are the following. As exemplified herein, subjects with cancerous tumors are distinguished from those with benign nodules. These methods and compositions provide a solution to the practical diagnostic problem of whether a patient who presents at a lung clinic with a small nodule has malignant disease. Patients with an intermediate-risk nodule would clearly benefit from a non-invasive test that would move the patient into either a very low-likelihood or a very high-likelihood category of disease risk. An accurate estimate of malignancy based on a genomic profile (i.e. estimating a given patient has a 90% probability of having cancer versus estimating the patient has only a 5% chance of having cancer) would result in fewer surgeries for benign disease, more early stage tumors removed at a curable stage, fewer follow-up CT scans, and reduction of the significant psychological costs of worrying about a nodule. The economic impact would also likely be significant, such as reducing the current estimated cost of additional health care associated with CT screening for lung cancer, i.e., $116,000 per quality adjusted life-year gained. A non-invasive blood genomics test that has a sufficient sensitivity and specificity would significantly alter the post-test probability of malignancy and thus, the subsequent clinical care.

A desirable advantage of these methods over existing methods is that they are able to characterize the disease state from a minimally-invasive procedure, i.e., by taking a blood sample. In contrast, current practice for classification of cancer tumors from gene expression profiles depends on a tissue sample, usually a sample from a tumor. In the case of very small tumors a biopsy is problematic and clearly if no tumor is known or visible, a sample from it is impossible. No purification of tumor is required, as is the case when tumor samples are analyzed. A recently published method depends on brushing epithelial cells from the lung during bronchoscopy, a method which is also considerably more invasive than taking a blood sample. Blood samples have an additional advantage, which is that the material is easily prepared and stabilized for later analysis, which is important when messenger RNA is to be analyzed.

The 559 classifier described herein showed a ROC-AUC of 0.81 over all tested samples. In one embodiment, when the sensitivity is about 90%, the specificity is about 46%. When the nodule classification accuracy is assessed by size without using a specific threshold for sensitivity, as nodules size and the cancer risk factor increases, the number of benign nodules classified as cancer increases. In one embodiment, the accuracy of the gene classifier is about 89% for nodules ≤8 mm. In another embodiment, the accuracy of the gene classifier is about 75% for nodules >8 to about ≤12 mm. In yet another embodiment, the accuracy of the gene classifier is about 68% for nodules >12 to about ≤16 mm. In another embodiment, the accuracy of the gene classifier is about 53% for >16 mm. See examples below.

In one embodiment, for nodules about <10 mm, the specificity is about 54% and the ROC-AUC to 0.85 at about 90% sensitivity. In another embodiment, for larger nodules, about >10 mm, the specificity is about 24% and the ROC-AUC about 0.71 at about 90% sensitivity.

The 100 Classifier described herein showed a ROC-AUC of 0.82 over all tested samples. In one embodiment, when the sensitivity is about 90%, the specificity is about 62%. In another embodiment, when the sensitivity is about 79%, the specificity is about 68%. In one embodiment, when the sensitivity is about 71%, the specificity is about 75%. See examples below.

These compositions and methods allow for more accurate diagnosis and treatment of lung cancer. Thus, in one embodiment, the methods described include treatment of the lung cancer. Treatment may removal of the neoplastic growth, chemotherapy and/or any other treatment known in the art or described herein.

In one embodiment, a method for diagnosing the existence or evaluating a lung cancer in a mammalian subject is provided, which includes identifying changes in the expression of 5, 10, 15 or more genes in the sample of said subject, said genes selected from the genes of Table I or the genes of Table II. The subject's gene expression levels are compare with the levels of the same genes in a reference or control, wherein changes in expression of the subject's genes from those of the reference correlates with a diagnosis or evaluation of a lung cancer.

In one embodiment, the diagnosis or evaluation comprise one or more of a diagnosis of a lung cancer, a diagnosis of a benign nodule, a diagnosis of a stage of lung cancer, a diagnosis of a type or classification of a lung cancer, a diagnosis or detection of a recurrence of a lung cancer, a diagnosis or detection of a regression of a lung cancer, a prognosis of a lung cancer, or an evaluation of the response of a lung cancer to a surgical or non-surgical therapy. In another embodiment, the changes comprise an upregulation of one or more selected genes in comparison to said reference or control or a downregulation of one or more selected genes in comparison to said reference or control.

In one embodiment, the method includes the size of a lung nodule in the subject. The specificity and sensitivity may be variable based on the size of the nodule. In one embodiment, the specificity is about 46% at about 90% sensitivity. In another embodiment, the specificity is about 54% at about 90% sensitivity for nodules <10 mm. In yet another embodiment, the accuracy is about 88% for nodules ≤8 mm, about 75% for nodules >8 mm and ≤12 mm, about 68% for nodules >12 mm and ≤16 mm, and about 53% for nodules >16 mm.

In another embodiment, the reference or control comprises three or more genes of Table I sample of at least one reference subject. The reference subject may be selected from the group consisting of: (a) a smoker with malignant disease, (b) a smoker with non-malignant disease, (c) a former smoker with non-malignant disease, (d) a healthy non-smoker with no disease, (e) a non-smoker who has chronic obstructive pulmonary disease (COPD), (f) a former smoker with COPD, (g) a subject with a solid lung tumor prior to surgery for removal of same; (h) a subject with a solid lung tumor following surgical removal of said tumor; (i) a subject with a solid lung tumor prior to therapy for same; and (j) a subject with a solid lung tumor during or following therapy for same. In one embodiment, the reference or control subject (a)-(j) is the same test subject at a temporally earlier timepoint.

The sample is selected from those described herein. In one embodiment, the sample is peripheral blood. The nucleic acids in the sample are, in some embodiments, stabilized prior to identifying changes in the gene expression levels. Such stabilization may be accomplished, e.g., using the Pax Gene system, described herein.

In one embodiment, the method of detecting lung cancer in a patient includes
  a. obtaining a sample from the patient; and
  b. detecting a change in expression in at least 10 genes selected from Table I or Table II in the patient sample as compared to a control by contacting the sample with a composition comprising oligonucleotides, polynucleotides or ligands specific for each different gene transcript or expression product of the at least 10 gene of Table I or Table II and detecting binding between the oligonucleotide, polynucleotide or ligand and the gene product or expression product.

In another embodiment, the method of diagnosing lung cancer in a subject includes
  a. obtaining a blood sample from a subject;
  b. detecting a change in expression in at least 10 genes selected from Table I or Table II in the patient sample as compared to a control by contacting the sample with a composition comprising oligonucleotides, polynucleotides or ligands specific for each different gene transcript or expression product of the at least 100 gene of Table I or Table II and detecting binding between the oligonucleotide, polynucleotide or ligand and the gene product or expression product; and
  c. diagnosing the subject with cancer when changes in expression of the subject's genes from those of the reference are detected.

In yet another embodiment, the method includes
  a. obtaining a blood sample from a subject;
  b. detecting a change in expression in at least 10 genes selected from Table I or Table II in the patient sample as compared to a control by contacting the sample with a composition comprising oligonucleotides, polynucleotides or ligands specific for each different gene transcript or expression product of the at least 10 genes of Table I or Table II and detecting binding between the oligonucleotide, polynucleotide or ligand and the gene product or expression product;
  c. diagnosing the subject with cancer when changes in expression of the subject's genes from those of the reference are detected; and
  d. removing the neoplastic growth.

V. EXAMPLES

The invention is now described with reference to the following examples. These examples are provided for the purpose of illustration only and the invention should in no way be construed as being limited to these examples but rather should be construed to encompass any and all variations that become evident as a result of the teaching provided herein.

Example 1: Patient Population—Analysis A

For development of the gene classifier described herein, blood samples and clinical information were collected from 150 subjects, 73 having a diagnosis of lung cancer and 77 having a diagnosis of benign nodule. Patient characteristics are shown in FIG. 1.

Patients with lung cancer included newly diagnosed male and female patients with early stage lung cancer. They were in moderately good health (ambulatory), although with medical illness. They were excluded if they have had previous cancers, chemotherapy, radiation, or cancer surgery. They must have had a lung cancer diagnosis within preceding 6 months, histologic confirmation, and no systemic therapy, such as chemotherapy, radiation therapy or cancer surgery as biomarker levels may change with therapy. Thus the majority of the cancer patients were early stage (i.e., Stage I and Stage II).

The "control" cohort was derived from patients with benign lung nodules (e.g. ground glass opacities, single nodules, granulomas or hamartomas). These patients were evaluated at pulmonary clinics, or underwent thoracic surgery for a lung nodule. All samples were collected prior to surgery.

Example 2: Patient Population—Analysis B

Further blood samples and clinical information were collected from 120 subjects, 60 having a diagnosis of lung cancer and 60 having a diagnosis of benign nodule. Patients with lung cancer included newly diagnosed male and female patients with early stage lung cancer. They were in moderately good health (ambulatory), although with medical illness. They were excluded if they have had previous cancers, chemotherapy, radiation, or cancer surgery. They must have had a lung cancer diagnosis within preceding 6 months, histologic confirmation, and no systemic therapy, such as chemotherapy, radiation therapy or cancer surgery as biomarker levels may change with therapy. Thus the majority of the cancer patients were early stage (i.e., Stage I and Stage II).

The "control" cohort was derived from patients with benign lung nodules (e.g. granulomas or hamartomas). These patients were evaluated at pulmonary clinics, or underwent thoracic surgery for a lung nodule. All samples were collected prior to surgery.

Example 3: Sample Collection Protocols and Processing

Blood samples were collected in the clinic by the tissue acquisition technician. Blood samples were drawn directly into PAXgene Blood RNA Tubes via standard phlebotomy technique. These tubes contain a proprietary reagent that immediately stabilizes intracellular RNA, minimizing the ex-vivo degradation or up-regulation of RNA transcripts. The ability to eliminate freezing, batch samples, and to minimize the urgency to process samples following collection, greatly enhances lab efficiency and reduces costs.

Example 4—RNA Purification and Quality Assessment

PAXgene RNA is prepared using a standard commercially available kit from Qiagen™ that allows purification of mRNA. The resulting RNA is used for mRNA profiling. The RNA quality is determined using a Bioanalyzer. Only samples with RNA Integrity numbers >3 were used.

Briefly, RNA is isolated as follows. Turn shaker-incubator on and set to 55° C. before beginning. Unless otherwise noted, all steps in this protocol including centrifugation steps, should be carried out at room temp (15-25° C.). This protocol assumes samples are stores at −80° C. Unfrozen samples that have been left a RT per the Qiagen protocol of a minimum of 2 hours should be processed in the same way.

Thaw Paxgene tubes upright in a plastic rack. Invert tubes at least 10 times to mix before starting isolation. Prepare all necessary tubes. For each sample, the following are needed: 2 numbered 1.5 ml Eppendorf tubes; 1 Eppendorf tube with the sample information (this is the final tube); 1 Lilac Paxgene spin column; 1 Red Paxgene Spin column; and 5 Processing tubes.

Centrifuge the PAXgene Blood RNA Tube for 10 minutes at 5000×g using a swing-out rotor in Qiagen centrifuge. (Sigma 4-15° C. Centrifuge., Rotor: Sigma Nr. 11140, 7/01, 5500/min, Holder: Sigma 13115, 286 g 14/D, Inside tube holder: 18010, 125 g). Note: After thawed, ensure that the blood sample has been incubated in the PAXgene Blood RNA Tube for a minimum of 2 hours at room temperature (15-25° C.), in order to achieve complete lysis of blood cells.

Under the hood—remove the supernatant by decanting into bleach. When the supernatant is decanted, take care not to disturb the pellet, and dry the rim of the tube with a clean paper towel. Discard the decanted supernatant by placing the clotted blood into a bag and then into the infectious waste and discard the fluid portion down the sink and wash down with a lot of water. Add 4 ml RNase-free water to the pellet, and close the tube using a fresh secondary Hemogard closure.

Vortex until the pellet is visibly dissolved. Weigh the tubes in the centrifuge holder again to ensure they are balanced, and centrifuge for 10 minutes at 5000×g using a swing-out rotor Qiagen centrifuge Small debris remaining in the supernatant after vortexing but before centrifugation will not affect the procedure.

Remove and discard the entire supernatant. Leave tube upside-down for 1 min to drain off all supernatant. Incomplete removal of the supernatant will inhibit lysis and dilute the lysate, and therefore affect the conditions for binding RNA to the PAXgene membrane.

Add 350 µl Buffer BM1 and pipet up and down lyse the pellet.

Pipet the re-suspended sample into a labeled 1.5 ml microcentrifuge tube. Add 300 µl Buffer BM2. Then add 40 µl proteinase K. Mix by vortexing for 5 seconds, and incubate for 10 minutes at 55° C. using a shaker-incubator at the highest possible speed, 800 rpm on Eppendorf thermomixer. (If using a shaking water bath instead of a thermomixer, quickly vortex the samples every 2-3 minutes during the incubation. Keep the vortexer next to the incubator).

Pipet the lysate directly into a PAXgene Shredder spin column (lilac tube) placed in a 2 ml processing tube, and centrifuge for 3 minutes at 24 C at 18,500×g in the TOMY Microtwin centrifuge. Carefully pipet the lysate into the spin column and visually check that the lysate is completely transferred to the spin column. To prevent damage to columns and tubes, do not exceed 20,000×g.

Carefully transfer the entire supernatant of the flow-through fraction to a fresh 1.5 ml microcentrifuge tube without disturbing the pellet in the processing tube. Discard the pellet in the processing tube.

Add 700 µl isopropanol (100%) to the supernatant. Mix by vortexing.

Pipet 690 µl sample into the PAXgene RNA spin column (red) placed in a 2 ml processing tube, and centrifuge for 1 minute at 10,000×g. Place the spin column in a new 2 ml processing tube, and discard the old processing tube containing flow-through.

Pipet the remaining sample into the PAXgene RNA spin column (red), and centrifuge for 1 minute at 18,500×g. Place the spin column in a new 2 ml processing tube, and discard the old processing tube containing flow-through. Carefully pipet the sample into the spin column and visually check that the sample is completely transferred to the spin column.

Pipet 350 µl Buffer BM3 into the PAXgene RNA spin column. Centrifuge for 15 sec at 10,000×g. Place the spin column in a new 2 ml processing tube, and discard the old processing tube containing flow-through.

Prepare DNase I incubation mix for step 13. Add 10 µl DNase I stock solution to 70 µl Buffer RDD in a 1.5 ml microcentrifuge tube. Mix by gently flicking the tube, and centrifuge briefly to collect residual liquid from the sides of the tube.

Pipet the DNase I incubation mix (80 µl) directly onto the PAXgene RNA spin column membrane, and place on the benchtop (20-30° C.) for 15 minutes. Ensure that the DNase I incubation mix is placed directly onto the membrane. DNase digestion will be incomplete if part of the mix is applied to and remains on the walls or the O-ring of the spin column.

Pipet 350 µl Buffer BM3 into the PAXgene RNA spin column, and centrifuge for 15 sec at 18,500×g. Place the spin column in a new 2 ml processing tube, and discard the old processing tube containing flow-through.

Pipet 500 µl Buffer BM4 to the PAXgene RNA spin column, and centrifuge for 15 sec at 10,000×g. Place the spin column in a new 2 ml processing tube, and discard the old processing tube containing flow-through.

Add another 500 µl Buffer BM4 to the PAXgene RNA spin column. Centrifuge for 2 minutes at 18,500×g.

Discard the tube containing the flow-through, and place the PAXgene RNA spin column in a new 2 ml processing tube. Centrifuge for 1 minute at 18,500×g.

Discard the tube containing the flow-through. Place the PAXgene RNA spin column in a labeled 1.5 ml microcentrifuge tube (final tube), and pipet 40 µl Buffer BR5 directly onto the PAXgene RNA spin column membrane. Centrifuge for 1 minute at 10,000×g to elute the RNA. It is important to wet the entire membrane with Buffer BR5 in order to achieve maximum elution efficiency.

Repeat the elution step as described, using 40 µl Buffer BR5 and the same microcentrifuge tube. Centrifuge for 1 minute at 20,000×g to elute the RNA.

Incubate the eluate for 5 minutes at 65° C. in the shaker-incubator without shaking. After incubation, chill immediately on ice. This incubation at 65° C. denatures the RNA for downstream applications. Do not exceed the incubation time or temperature.

If the RNA samples will not be used immediately, store at −20° C. or −70° C. Since the RNA remains denatured after repeated freezing and thawing, it is not necessary to repeat the incubation at 65° C.

Example 5: Measurement of RNA Levels

To provide a biomarker signature that can be used in clinical practice to diagnose lung cancer, a gene expression profile with the smallest number of genes that maintain satisfactory accuracy is provided by the use of 100 more of the genes identified in Table I as well as by the use of 10 or more of the genes identified in Table II. These gene profiles or signatures permit simpler and more practical tests that are easy to use in a standard clinical laboratory. Because the number of discriminating genes is small enough, NanoString nCounter® platforms are developed using these gene expression profiles.

A. Nanostring nCounter® Platform Gene Expression Assay Protocol

Total RNA was isolated from whole blood using the Paxgene Blood miRNA Kit, as described above, and samples were checked for RNA quality. Samples were analyzed with the Agilent 2100 Bioanalyzer on a RNA Nano chip, using the RIN score and electropherogram picture as indicators for good sample integrity. Samples were also quantitated on the Nanodrop (ND-1000 Spectrophotometer) where 260/280 and 260/230 readings were recorded and evaluated for Nanostring-compatibility. From the concentrations taken by Nanodrop, total RNA samples were normalized to contain 100 ng in 5 μL, using Nuclease-free water as diluent, into Nanostring-provided tube strips. An 8 μL aliquot of a mixture of the Nanostring nCounter Reporter CodeSet and Hybridization Buffer (70 μL Hybridization Buffer, 42 μL Reporter CodeSet per 12 assays) and 2 μL of Capture ProbeSet was added to each 5 μL RNA sample. Samples were hybridized for 19 hours at 65° C. in the Thermocycler (Eppendorf). During hybridization, Reporter Probes, which have fluorescent barcodes specific to each mRNA of interest to the user, and biotinylated Capture Probes bound to their associated target mRNA to create target-probe complexes. After hybridization was complete, samples were then transferred to the nCounter Prep Station for processing using the Standard Protocol setting (Run Time: 2 hr35 min). The Prep Station robot, during the Standard Protocol, washed samples to remove excess Reporter and Capture Probes. Samples were moved to a streptavidin-coated cartridge where purified target-probe complexes were immobilized in preparation for imaging by the nCounter Digital Analyzer. Upon completion, the cartridge was sealed and placed in the Digital Analyzer using a Field of View (FOV) setting at 555. A fluorescent microscope tabulated the raw counts for each unique barcode associated with a target mRNA. Data collected was stored in .csv files and then transferred to the Bioinformatics Facility for analysis according to the manufacturer's instructions.

Example 6: Biomarker Selection

Support Vector Machine (SVM) can be applied to gene expression datasets for gene function discovery and classification. SVM has been found to be most efficient at distinguishing the more closely related cases and controls that reside in the margins. Primarily SVM-RFE (48, 54) was used to develop gene expression classifiers which distinguish clinically defined classes of patients from clinically defined classes of controls (smokers, non-smokers, COPD, granuloma, etc). SVM-RFE is a SVM based model utilized in the art that removes genes, recursively based on their contribution to the discrimination, between the two classes being analyzed. The lowest scoring genes by coefficient weights were removed and the remaining genes were scored again and the procedure was repeated until only a few genes remained. This method has been used in several studies to perform classification and gene selection tasks. However, choosing appropriate values of the algorithm parameters (penalty parameter, kernel-function, etc.) can often influence performance.

SVM-RCE is a related SVM based model, in that it, like SVM-RFE assesses the relative contributions of the genes to the classifier. SVM-RCE assesses the contributions of groups of correlated genes instead of individual genes. Additionally, although both methods remove the least important genes at each step, SVM-RCE scores and removes clusters of genes, while SVM-RFE scores and removes a single or small numbers of genes at each round of the algorithm.

The SVM-RCE method is briefly described here. Low expressing genes (average expression less than 2× background) were removed, quantile normalization performed, and then "outlier" arrays whose median expression values differ by more than 3 sigma from the median of the dataset were removed. The remaining samples were subject to SVM-RCE using ten repetitions of 10-fold cross-validation of the algorithm. The genes were reduced by t-test (applied on the training set) to an experimentally determined optimal value which produces highest accuracy in the final result. These starting genes were clustered by K-means into clusters of correlated genes whose average size is 3-5 genes. SVM classification scoring was carried out on each cluster using 3-fold resampling repeated 5 times, and the worst scoring clusters eliminated. Accuracy is determined on the surviving pool of genes using the left-out 10% of samples (testing set) and the top-scoring 100 genes were recorded. The procedure was repeated from the clustering step to an end point of 2 clusters. The optimal gene panel was taken to be the minimal number of genes which gives the maximal accuracy starting with the most frequently selected gene. The identity of the individual genes in this panel is not fixed, since the order reflects the number of times a given gene was selected in the top 100 informative genes and this order is subject to some variation.

A. Biomarker Selection.

Genes which score highest (by SVM) in discriminating cancerous tumors from benign nodules were examined for their utility for clinical tests. Factors considered include, higher differences in expression levels between classes, and low variability within classes. When selecting biomarkers for validation an effort was made to select genes with distinct expression profiles to avoid selection of correlated genes and to identify genes with differential expression levels that were robust by alternative techniques including PCR and/or immuno-histochemistry.

B. Validation.

Three methods of validation were considered.

Cross-Validation: To minimize over-fitting within a dataset, K-fold cross-validation (K usually equal to 10) was used, when the dataset is split on K parts randomly and K−1 parts were used for training and 1 for testing. Thus, for K=10 the algorithm was trained on a random selection of 90% of the patients and 90% of the controls and then tested on the remaining 10%. This was repeated until all of the samples have been employed as test subjects and the cumulated classifier makes use of all of the samples, but no sample is tested using a training set of which it is a part. To reduce the randomization impact, K-fold separation was performed M times producing different combinations of patients and controls in each of K folds each time. Therefore, for individual dataset M*K rounds of permuted selection of training and testing sets were used for each set of genes.

Independent Validation: To estimate the reproducibility of the data and the generality of the classifier, one needs to examine the classifier that was built using one dataset and tested using another dataset to estimate the performance of the classifier. To estimate the performance, validation on the second set was performed using the classifier developed with the original dataset.

Resampling (permutation): To demonstrate dependence of the classifier on the disease state, patients and controls from the dataset were chosen at random (permuted) and the classification was repeated. The accuracy of classification using randomized samples was compared to the accuracy of the developed classifier to determine the p value for the classifier, i.e., the possibility that the classifier might have been chosen by chance. In order to test the generality of a classifier developed in this manner, it was used to classify independent sets of samples that were not used in developing the classifier. The cross-validation accuracies of the permuted and original classifier were compared on independent test sets to confirm its validity in classifying new samples.

C. Classifier Performance

Performance of each classifier was estimated by different methods and several performance measurements were used for comparing classifiers between each other. These measurements include accuracy, area under ROC curve, sensitivity, specificity, true positive rate and true negative rate. Based on the required properties of the classification of interest, different performance measurements can be used to pick the optimal classifier, e.g. classifier to use in screening of the whole population would require better specificity to compensate for small (~1%) prevalence of the disease and therefore avoid large number of false positive hits, while a diagnostic classifier of patients in hospital should be more sensitive.

For diagnosing cancerous tumors from benign nodules, higher sensitivity is more desirable than specificity, as the patients are already at high risk.

Example 7: Testing of the Classifiers

Peripheral blood samples were all collected in PAXgene RNA stabilizations tubes and RNA was extracted according to the manufacturer. Samples were tested on a Nanostring nCounter™ (as described above) against a custom panel of 559 probes (Table III). In addition, they were tested against a 100 probe subset of 559 marker panel.

For the 559 Classifier, 432 were selected based on previous microarray data, 107 probes were selected from Nanostring studies and 20 were housekeeping genes. We analyzed 610 PAXgene RNA samples (278 cancers, 332 controls) derived from 5 collection sites. For QC, a Universal RNA standard (Agilent) was included in each batch of 36 samples tested. Probe expression values were normalized using the 20 housekeeping genes as well as spike-in positive and negative controls supplied by Nanostring (included in classifier). Zscores were calculated for probe count values and served as the input to a Support Vector Machine (SVM) classifier using a polynomial kernel. Classification performance was evaluated by 10-fold cross-validation of the samples.

A. 559 Classifier

Figure 2B:
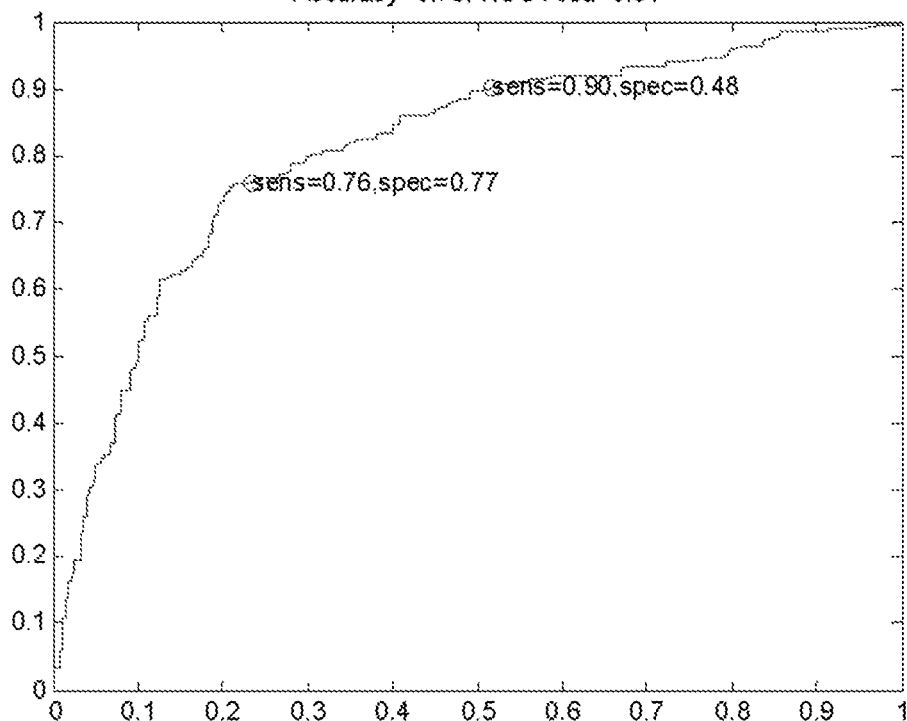

As shown in FIGS. 2A to 2B, the 559 classifier developed on all the samples showed a ROC-AUC of 0.81 (FIG. 2A). With the Sensitivity set at 90%, the specificity is 46%. When performed on a balanced set of 556 samples (278 cancer, 278 nodule), similar performance is shown (FIG. 2B). For both sets, UHR controls, post samples, and patients with other cancers were excluded.

Figures 3, 4A:
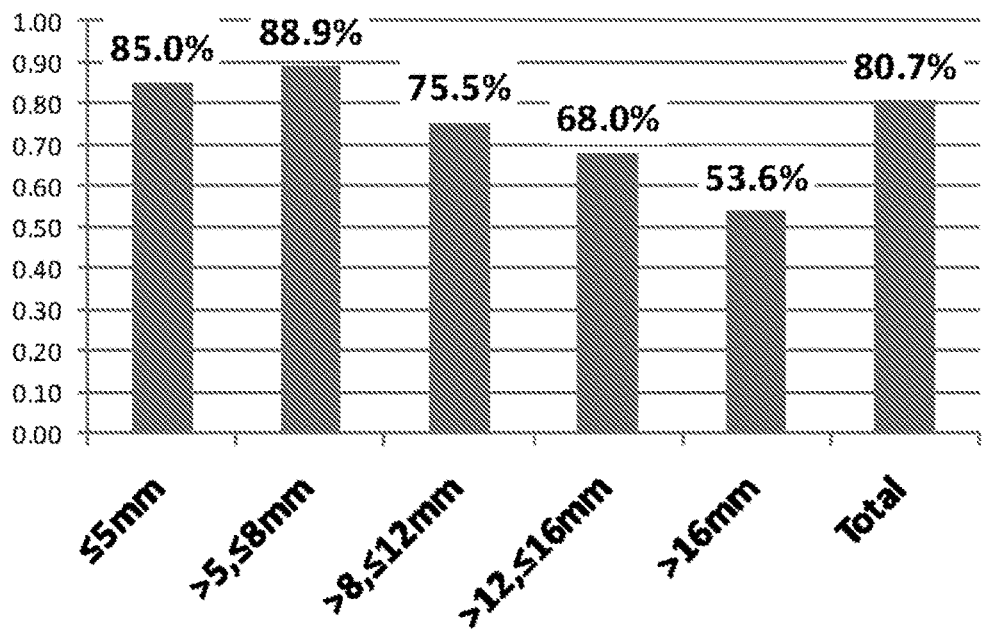
FIG. 3 is a bar graph showing sensitivity of the classifier by nodule size groups (x-axis). Data shows that larger nodules are more likely to be misclassified ($p=1.54*10^{-4}$).
FIGS. 4A to 4C show the classification of samples groups (cancer, FIG. 4B, n=204; and nodule, FIG. 4C, n=331) stratified by lesion size. Over cancers >5 mm and higher, r=0.95. For nodules of all sizes, r=0.97. The chart (FIG. 4A) shows the sensitivity and specificity of the classification of cancers and nodules based on lesion size. These numbers are shown in bar graph form below.

When nodule classification accuracy is assessed by size without using a specific threshold for sensitivity, we find that as nodules size and the cancer risk factor increases, the number of benign nodules classified as cancer increases. FIG. 3. In this analysis, nodules ≤8 mm were correctly classified 88.9% of the time, for nodules >8, ≤12 mm accuracy was 75%, for nodules >12, ≤16 mm accuracy was 68%, for nodules >16 mm accuracy is 53.6%. See Table IV below.

TABLE IV

| Nodule Size | Correct | Incorrect | Total | Specificity |
|---|---|---|---|---|
| <=5 mm | 108 | 19 | 127 | 85.0% |
| >5, <=8 mm | 88 | 11 | 99 | 88.9% |
| >8, <=12 mm | 40 | 13 | 53 | 75.5% |
| >12, <=16 mm | 17 | 8 | 25 | 68.0% |
| >16 mm | 15 | 13 | 28 | 53.6% |
| Total | 268 | 64 | 332 | 80.7% |

Figure 4B:
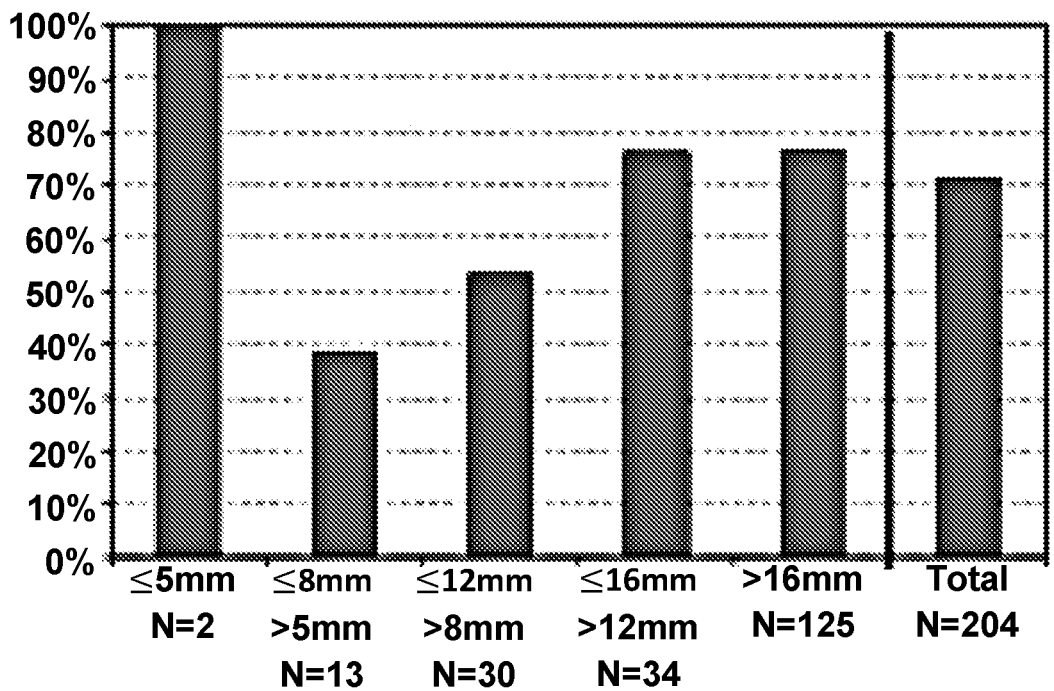
Figure 4C:
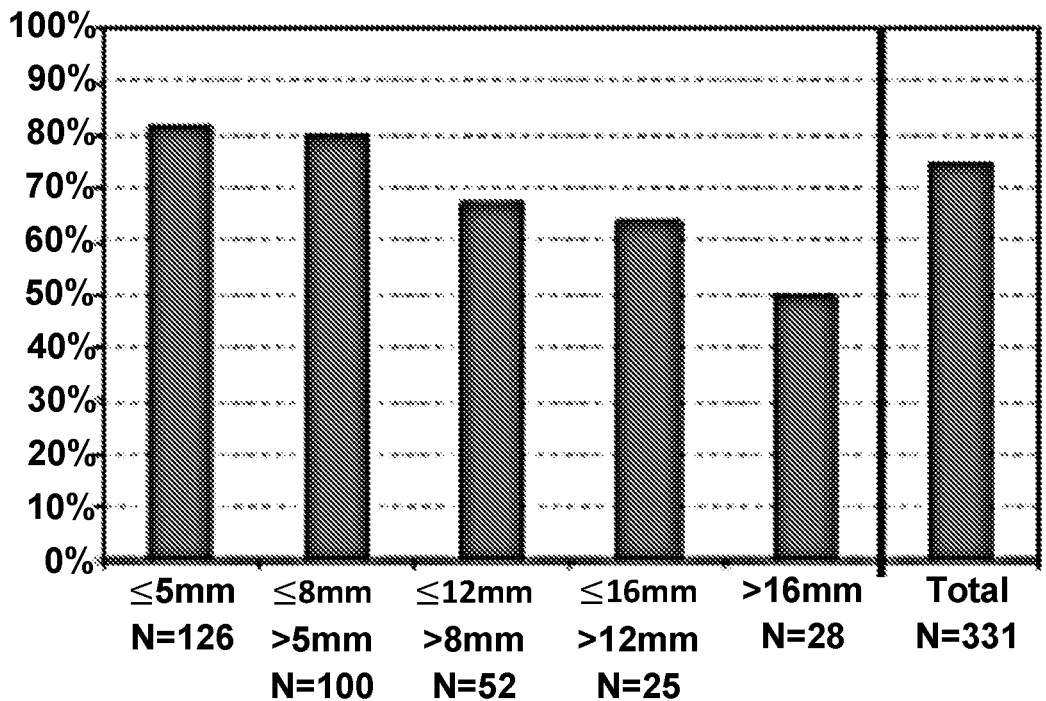

A second set of nodules was tested and the accuracy of the classifier for size groups was determined by sample group (cancer vs benign nodule). Similarly, as nodule size and the cancer risk factor increases, the number of benign nodules classified as cancer increases (FIGS. 4A to 4C). For cancers >5 mm and higher, r=0.95. For nodules of all sizes, r=0.97. The chart shows the sensitivity and specificity of the classification of cancers and nodules based on lesion size. These numbers are shown in bar graph form below.

Figure 5A:
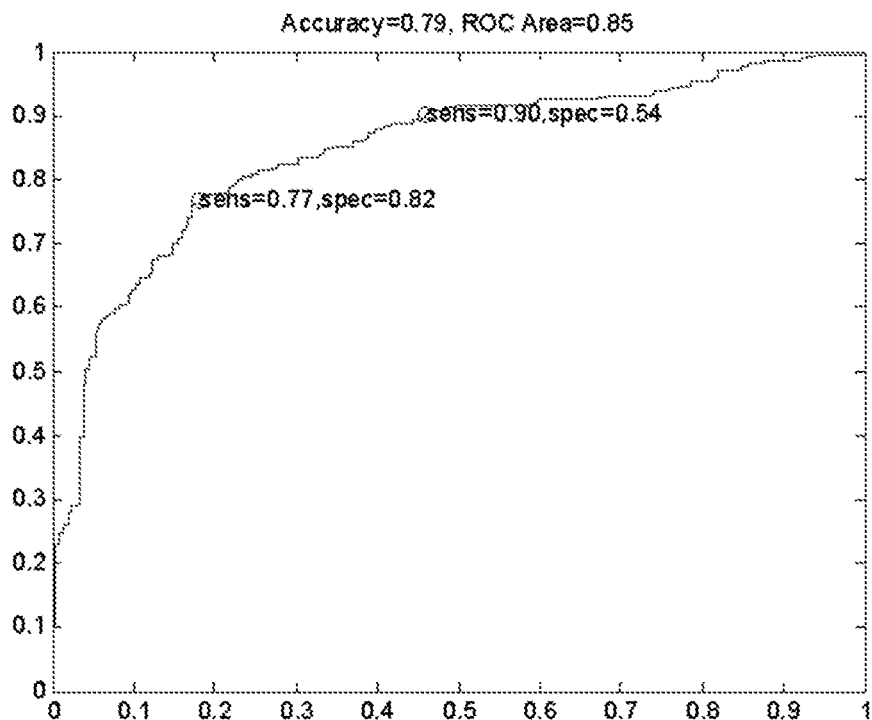
FIGS. 5A and 5B are graphs showing the cross validated support vector machine classifier (CV SVM) of all cancer samples (n=278) vs. small nodules (<10 mm) (n=244) (FIG. 5A, Accuracy=0.79, ROC Area=0.85. According to the curve, when the sensitivity is 0.90, the specificity is 0.54; when the sensitivity is 0.77, the specificity is 0.82) and 10-fold CV SVM using all cancer samples (n=278) vs. large nodules (≥10 mm) (n=88) (FIG. 5B, Accuracy=0.76, ROC Area=0.71. According to the curve, when the sensitivity is 0.90, the specificity is 0.24; when the sensitivity is 0.87, the specificity is 0.42).
Figure 5B:
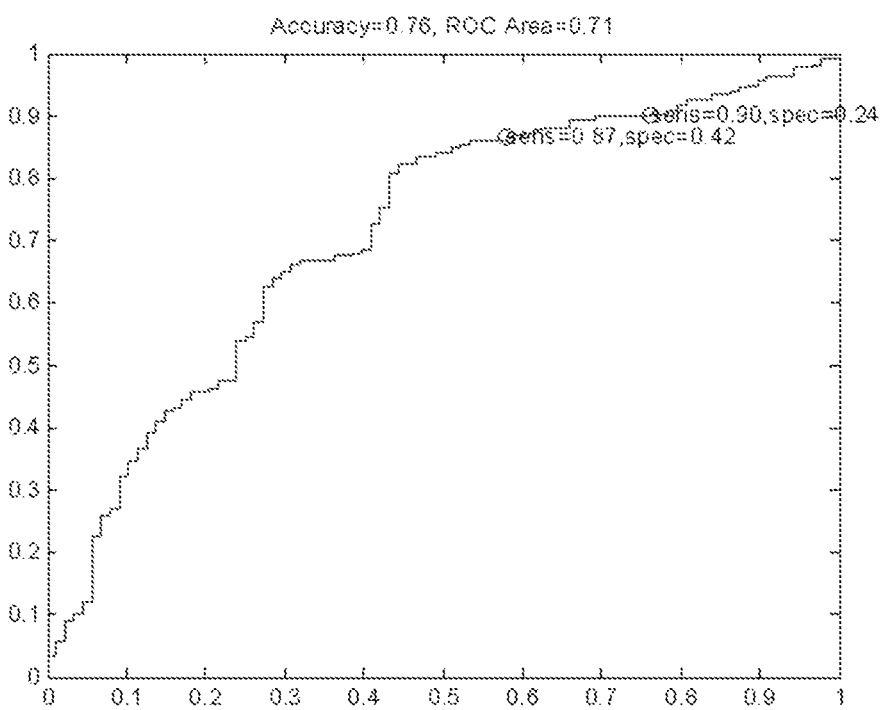

Since classification accuracy was found to be negatively correlated with benign nodule size, we reanalyzed the data using only nodules <10 mm (n=244) (FIG. 5A) and sensitivity fixed at 90%, in this case the specificity rises to 54% and the ROC-AUC to 0.85. For larger nodules, >10 mm (n=88) the specificity drops to 24% and the ROC-AUC drops to 0.71 (FIG. 5B). See Table V below.

TABLE V

| | Small ≤10 mm | Large >10 mm | All nodules |
|---|---|---|---|
| N (nodules) | 244 | 88 | 332 |
| min | 1 | 10.4 | 1 |
| max | 10 | 90 | 90 |
| mean | 6.07 | 17.8 | 8.7 |
| median | 6 | 15 | 6 |
| std | 1.73 | 10.6 | 7.13 |
| ROC Area | 0.85 | 0.71 | 0.81 |
| Specificity at 90% Sensitivity | 54% | 42% | 46% |

B. 100 Marker Classifier

Figure 6:
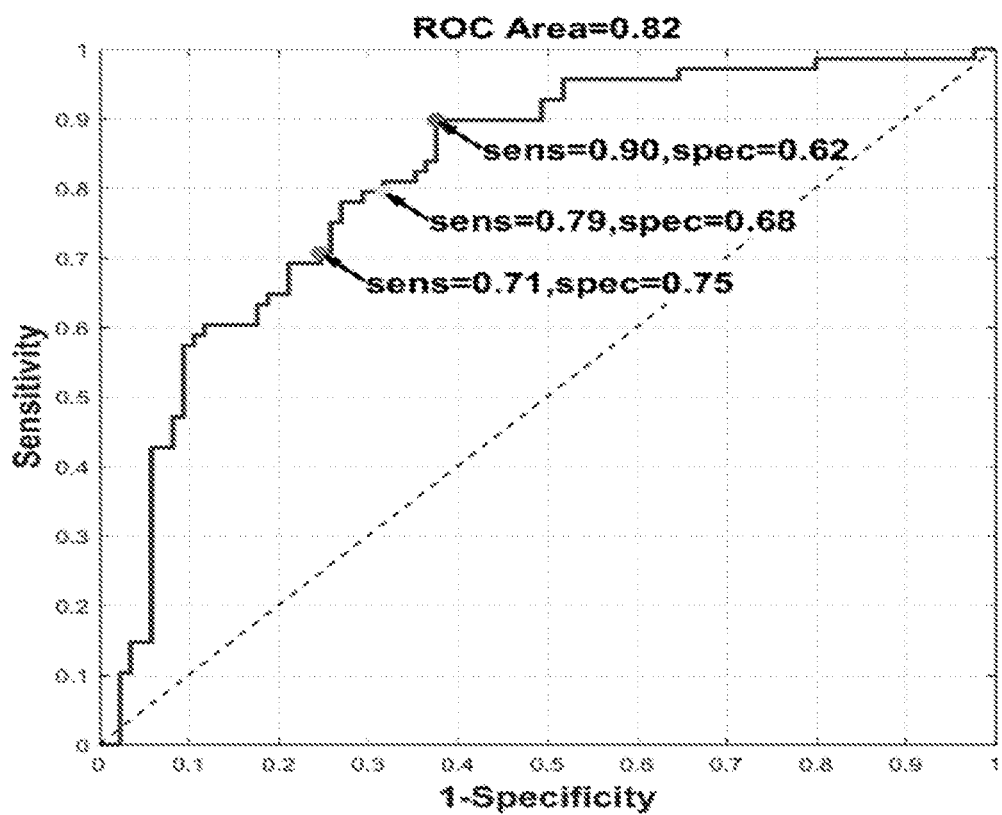
FIG. 6 is a graph showing the cross validated support vector machine classifier (CV SVM) of 25% of the data set used for the 559 Classifier, used as a testing set for the 100 Classifier. ROC Area=0.82. According to the curve, when the sensitivity is 0.90, the specificity is 0.62; when the sensitivity is 0.79, the specificity is 0.68; and when the sensitivity is 0.71, the specificity is 0.75.

We now reanalyzed the data from the 633 samples analyzed by W559 on the Nanostring platform in order to identify the minimal number of probes required to maintain performance attained with the whole panel. We used SVM-RFE for probe selection as previously described. We used 75% of the data for the training set with SVM-RFE and the tested the performance of top 100 probes (Table II) selected by this process on an independent testing set composed of 25% of the samples. Samples were randomly selected for training and testing sets Table VI below. The accuracy obtained on the testing set is shown in FIG. 6. In this analysis, at a sensitivity of 90%, specificity was 62%; at a sensitivity of 79%, specificity was 68%; and at a sensitivity of 71%, specificity was 75% (FIG. 6). In summary the ROC-AUC is 0.82 and at a sensitivity of 0.90 we achieve a specificity of 0.62.

TABLE VI

| nodules | | | cancer | | |
|---|---|---|---|---|---|
| > | <= | n | > | <= | n |
| 0 | 5 | 130 | 0 | 14 | 86 |
| 5 | 8 | 109 | 14 | 22 | 75 |
| 8 | 12.5 | 65 | 22 | 33 | 64 |
| 12.5 | | 57 | 33 | | 47 |

Each and every patent, patent application, and publication, including the priority application, U.S. Provisional Patent Application No. 62/352,865, filed Jun. 21, 2017, and publically available gene sequence cited throughout the disclosure is expressly incorporated herein by reference in its entirety. While this invention has been disclosed with reference to specific embodiments, it is apparent that other embodiments and variations of this invention are devised by others skilled in the art without departing from the true spirit and scope of the invention. The appended claims include such embodiments and equivalent variations.

The invention claimed is:

1. A substrate comprising a set of polynucleotides, oligonucleotides or ligands immobilized on the substrate, wherein the set of polynucleotides, oligonucleotides, or ligands consists of multiple polynucleotides, oligonucleotides, or ligands, wherein each polynucleotide, oligonucleotide or ligand is capable of hybridizing to a different gene or gene transcript in a group consisting of TPR, DNAJB1, PDCD10, PSMB7, MERTK, AFTPH, BCOR, RASSF5, SNX11, ANP32B, C4B, NME1-NME2, DGUOK, CYP1B1, MPDU1, MED16, FAM179A, CPPED1, LOC648927, ANKHD1, CN312986, PHCA, CD1A, NCOA5, SLC6A12, LOC728533, TRAF3IP2, TBCE, CCT6A, P2RY5, RNASE2, CLN8, REPS1, TPT1, LOC100129022, KLRC1, AZI2, FAM193A, PLACE, LDHA, GPATCH3, RBM14, KYNU, PPP2R5C, S100A12, SFMBT1, CCR6, TRIM39, AK126342, SLC45A3, IL4, UBE2I, PRPF3, NDUFB3, CRKL, IDO1, PUM1, BCL10, TMBIM6, C17orf51, BANP, HAVCR2, BAG3, DBI, C4orf27, TSC1, LPCAT4, SAMSN1, SNORA56, ARG1, IL1R2, CCND3, USP9Y, ATP2C1, PSMB1, NDUFAF2, VPS37C, HAT1, LOC732371, LOC148137, CCR1, CCDC97, PPP6C, GPI, PIM2, STAT6, BATF, EIF4ENIF1, HSP90AB1, U2AF2, CYBB, WDR1, PSMB8, TBC1D12, LOC648000, XCL2, PTGDR, ACSL5, CASP1, and UBTF, wherein the set includes a polynucleotide, oligonucleotide or ligand that is capable of hybridizing each of the recited genes or gene transcripts.

2. A set of polynucleotides, oligonucleotides or ligands, wherein the set of polynucleotides, oligonucleotides, or ligands comprises multiple polynucleotides, oligonucleotides, or ligands, wherein each polynucleotide, oligonucleotide or ligand is capable of hybridizing to a different gene or gene transcript in a group consisting of TPR, DNAJB1, PDCD10, PSMB7, MERTK, AFTPH, BCOR, RASSF5, SNX11, ANP32B, C4B, NME1-NME2, DGUOK, CYP1B1, MPDU1, MED16, FAM179A, CPPED1, LOC648927, ANKHD1, CN312986, PHCA, CD1A, NCOA5, SLC6A12, LOC728533, TRAF3IP2, TBCE, CCT6A, P2RY5, RNASE2, CLN8, REPS1, TPT1, LOC100129022, KLRC1, AZI2, FAM193A, PLACE, LDHA, GPATCH3, RBM14, KYNU, PPP2R5C, S100A12 b, SFMBT1, CCR6, TRIM39, AK126342, SLC45A3, IL4, UBE2I, PRPF3, NDUFB3, CRKL, IDO1, PUM1, BCL10, TMBIM6, C17orf51, BANP, HAVCR2, BAG3, DBI, C4orf27, TSC1, LPCAT4, SAMSN1, SNORA56, ARG1, IL1R2, CCND3, USP9Y, ATP2C1, PSMB1, NDUFAF2, VPS37C, HAT1, LOC732371, LOC148137, CCR1, CCDC97, PPP6C, GPI, PIM2, STAT6, BATF, EIF4ENIF1, HSP90AB1, U2AF2, CYBB, WDR1, PSMB8, TBC1D12, LOC648000, XCL2, PTGDR, ACSL5, CASP1, and UBTF, wherein the set includes a polynucleotide, oligonucleotide or ligand that is capable of hybridizing each of the recited genes or gene transcripts, and wherein each polynucleotide, oligonucleotide or ligand in the set is attached to a different color-coded label.

3. The set of claim 2, further comprising a capture oligonucleotide which hybridizes to at least one of the polynucleotides, oligonucleotides, or ligands in the set.

4. The set of claim 3, wherein the capture oligonucleotide is capable of hybridizing to each polynucleotide, oligonucleotide or ligand in the set.

5. The set of claim 3, wherein the capture oligonucleotide is capable of binding to a substrate.

6. The set of claim 5, further comprising the substrate to which the capture oligonucleotide is capable of binding.

7. A kit comprising the substrate of claim 1 or the set of claim 2.

8. The kit of claim 7, further comprising an apparatus comprising a tube for holding blood.

* * * * *